US011116737B1

(12) United States Patent
Tripp et al.

(10) Patent No.: US 11,116,737 B1
(45) Date of Patent: Sep. 14, 2021

(54) METHODS OF USING PROBENECID FOR TREATMENT OF CORONAVIRUS INFECTIONS

(71) Applicant: University of Georgia Research Foundation, Inc., Athens, GA (US)

(72) Inventors: Ralph A. Tripp, Watkinsville, GA (US); Jackelyn Murray, Monroe, GA (US); Robert Jeff Hogan, Watkinsville, GA (US)

(73) Assignee: UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 0 days.

(21) Appl. No.: 16/875,487

(22) Filed: May 15, 2020

Related U.S. Application Data

(60) Provisional application No. 63/023,021, filed on May 11, 2020, provisional application No. 63/008,624, filed on Apr. 10, 2020.

(51) Int. Cl.

| | |
|---|---|
| ***A61K 31/195*** | (2006.01) |
| ***A61K 31/63*** | (2006.01) |
| ***A61P 31/14*** | (2006.01) |
| ***A61P 31/12*** | (2006.01) |
| *A61K 9/00* | (2006.01) |

(52) U.S. Cl.
CPC ............ *A61K 31/195* (2013.01); *A61P 31/14* (2018.01); *A61K 9/0019* (2013.01); *A61K 9/0053* (2013.01)

(58) Field of Classification Search
CPC ....... A61K 31/195; A61K 31/63; A61P 31/63; A61P 31/12; A61P 31/14
See application file for complete search history.

(56) References Cited

U.S. PATENT DOCUMENTS

| | | | |
|---|---|---|---|
| 4,831,025 | A | 5/1989 | Godtfredsen |
| 5,972,309 | A | 10/1999 | Kallick |
| 6,180,639 | B1 | 1/2001 | Coates |
| 6,506,785 | B2 | 1/2003 | Evans |
| 6,551,584 | B2 | 4/2003 | Bandyopadhyay |
| 6,664,239 | B2 | 12/2003 | Mitchell |
| 6,740,655 | B2 | 5/2004 | Magee |
| 6,756,369 | B2 | 6/2004 | Mitchell |
| 6,878,728 | B1 | 4/2005 | Hale |
| 6,884,784 | B1 | 4/2005 | Mitchell |
| 7,094,397 | B2 | 8/2006 | Stratton |
| 7,129,241 | B2 | 10/2006 | Eggenweiler |
| 7,135,471 | B2 | 11/2006 | Eggenweiler |
| 7,312,328 | B2 | 12/2007 | Eggenweiler |
| 7,354,941 | B2 | 4/2008 | Marfat |
| 7,547,680 | B2 | 6/2009 | Kikuchi |
| 7,790,723 | B2 | 9/2010 | Eggenweiler |
| 7,795,268 | B2 | 9/2010 | Zeng |
| 7,960,403 | B2 | 6/2011 | Chan Chun Kong |
| 8,124,613 | B2 | 2/2012 | Moinet |
| 8,455,497 | B2 | 6/2013 | Hale |
| 8,557,831 | B2 | 10/2013 | Johnson |
| 8,633,201 | B2 | 1/2014 | Aicher |
| 8,691,991 | B2 | 4/2014 | Johns |
| 8,697,713 | B2 | 4/2014 | Jäkel |
| 8,946,142 | B2 | 2/2015 | Yamashita |
| 8,999,709 | B2 | 4/2015 | Fernández Miguel |
| 8,999,969 | B2 | 4/2015 | Mackman |
| 9,078,929 | B2 | 7/2015 | Kuebelbeck |
| 10,065,993 | B2 | 9/2018 | Kuebelbeck |
| 10,150,800 | B2 | 12/2018 | Roschke |
| 10,160,778 | B2 | 12/2018 | Liu |
| 10,273,252 | B2 | 4/2019 | Iwase |
| 10,675,227 | B2 | 6/2020 | Latta |
| 2002/0016293 | A1 | 2/2002 | Ratain |
| 2002/0044968 | A1 | 4/2002 | Van Lengerich |
| 2002/0111495 | A1 | 8/2002 | Magee |

(Continued)

FOREIGN PATENT DOCUMENTS

| | | |
|---|---|---|
| AP | 90A | 7/1990 |
| AU | 2009221761 A1 | 9/2009 |

(Continued)

OTHER PUBLICATIONS

Biospace.com ("XORTX Launches XRx-101, A New Program to Treat Coronavirus COVID-19 Infection." https://www.biospace.com/article/releases/xortx-launches-xrx-101-a-new-program-to-treat-coronavirus-covid-19-infection/ (Mar. 16, 2020)) (Year: 2020).*
EMedicine Health ("Medication and Drugs: Generic name: colchicine and probenecid" (2015) https://web.archive.org/web/20150919111115/https://www.emedicinehealth.com/drug-colchicine_and_probenecid/article_em.htm.) (Year: 2015).*

(Continued)

*Primary Examiner* — Jeffrey S Lundgren
*Assistant Examiner* — Chris E Simmons
(74) *Attorney, Agent, or Firm* — PABST Patent Group LLP

(57) ABSTRACT

Compositions and methods of treating a subject for a coronavirus infection are provided. The methods typically include administering the subject an effective amount of probenecid, a metabolite or analog thereof, or a pharmaceutically acceptable salt thereof. The methods can by therapeutic and/or prophylactic. The amount of probenecid or a pharmaceutically acceptable salt thereof can be effective to, for example, reduce viral replication, reduce one or more symptoms of disease, disorder, or illness associated with virus, or a combination thereof. In preferred embodiments, the virus is a Severe acute respiratory syndrome-related coronavirus such as SARS-CoV-2 or SARS-CoV, a Middle East respiratory syndrome-related coronavirus such as MERS-CoV, or a coronavirus that causes the common cold.

25 Claims, 2 Drawing Sheets

Specification includes a Sequence Listing.

(56) References Cited

U.S. PATENT DOCUMENTS

| | | | |
|---|---|---|---|
| 2002/0123520 | A1 | 9/2002 | Marfat |
| 2002/0150585 | A1 | 10/2002 | Marciani |
| 2003/0027845 | A1 | 2/2003 | Marfat |
| 2003/0049302 | A1 | 3/2003 | Pauletti |
| 2003/0144300 | A1 | 7/2003 | Magee |
| 2003/0186989 | A1 | 10/2003 | Marfat |
| 2003/0203926 | A1 | 10/2003 | Kois |
| 2003/0220330 | A1 | 11/2003 | Yoshitaka |
| 2004/0023916 | A1 | 2/2004 | Millan |
| 2004/0048903 | A1 | 3/2004 | Chambers |
| 2004/0054974 | A1 | 3/2004 | Acar |
| 2004/0067954 | A1 | 4/2004 | Eggenweiler |
| 2004/0071757 | A1 | 4/2004 | Rolf |
| 2004/0171798 | A1 | 9/2004 | Magee |
| 2004/0259863 | A1 | 12/2004 | Eggenweiler |
| 2004/0265323 | A1 | 12/2004 | McCormick |
| 2005/0059686 | A1 | 3/2005 | Eggenweiler |
| 2005/0075326 | A1 | 4/2005 | Chan Chun Kong |
| 2005/0075407 | A1 | 4/2005 | Tamarkin |
| 2005/0222160 | A1 | 10/2005 | Eggenweiler |
| 2005/0261641 | A1 | 11/2005 | Warchol |
| 2006/0009651 | A1 | 1/2006 | Chan |
| 2006/0047116 | A1 | 3/2006 | Youngman |
| 2006/0052408 | A1 | 3/2006 | Peckham |
| 2006/0058284 | A1 | 3/2006 | Yang |
| 2006/0122166 | A1 | 6/2006 | Duan |
| 2006/0122228 | A1 | 6/2006 | Zeldis |
| 2006/0142241 | A1 | 6/2006 | Yoo |
| 2006/0229336 | A1 | 10/2006 | Kazmierski |
| 2006/0233743 | A1 | 10/2006 | Kelly |
| 2006/0240037 | A1 | 10/2006 | Fey |
| 2006/0270676 | A1 | 11/2006 | Eggenweiler |
| 2006/0286041 | A1 | 12/2006 | Goeggel |
| 2007/0044693 | A1 | 3/2007 | Smyrniotis |
| 2007/0115822 | A1 | 5/2007 | Odijk et al. |
| 2007/0124152 | A1 | 5/2007 | Johns |
| 2007/0141096 | A1 | 6/2007 | Van Lengerich |
| 2007/0142365 | A1 | 6/2007 | Johns |
| 2007/0148703 | A1 | 6/2007 | Tamai |
| 2007/0211212 | A1 | 9/2007 | Bennwik |
| 2008/0066741 | A1 | 3/2008 | LeMahieu |
| 2008/0152640 | A1 | 6/2008 | Prehm |
| 2008/0194523 | A1 | 8/2008 | Johns |
| 2008/0194554 | A1 | 8/2008 | McLean |
| 2008/0214503 | A1 | 9/2008 | Johns |
| 2008/0214527 | A1 | 9/2008 | Kawasuji |
| 2008/0220441 | A1 | 9/2008 | Birnbaum |
| 2008/0234231 | A1 | 9/2008 | Johns |
| 2009/0047238 | A1 | 2/2009 | Chan Chun Kong |
| 2009/0053172 | A1 | 2/2009 | Aquino |
| 2009/0142790 | A1 | 6/2009 | Fang |
| 2009/0298948 | A1* | 12/2009 | Davis ..................... A61K 31/16 514/630 |
| 2010/0016262 | A1 | 1/2010 | Mehal |
| 2010/0048538 | A1 | 2/2010 | Soares Da Silva |
| 2010/0056548 | A1 | 3/2010 | Aicher |
| 2010/0105708 | A1 | 4/2010 | Jakel |
| 2010/0159001 | A1 | 6/2010 | Cardinal |
| 2010/0226943 | A1 | 9/2010 | Brennan |
| 2010/0285001 | A1 | 11/2010 | Land |
| 2010/0297271 | A1 | 11/2010 | Mehal |
| 2011/0105434 | A1 | 5/2011 | Exley |
| 2011/0105976 | A1 | 5/2011 | Berlin |
| 2011/0269141 | A1 | 11/2011 | Murayama |
| 2012/0082659 | A1 | 4/2012 | Land |
| 2012/0114670 | A1 | 5/2012 | Land |
| 2012/0121711 | A1 | 5/2012 | Hu |
| 2013/0020969 | A1 | 1/2013 | Leivenzon |
| 2013/0046021 | A1 | 2/2013 | Jack |
| 2013/0116312 | A2 | 5/2013 | Khan |
| 2013/0203969 | A1 | 8/2013 | Jaber |
| 2013/0289107 | A1 | 10/2013 | Brown |
| 2014/0080727 | A1 | 3/2014 | Sulem |
| 2014/0121237 | A1 | 5/2014 | Tripp |
| 2015/0072961 | A1 | 3/2015 | Yu |
| 2015/0079035 | A1 | 3/2015 | Stockwell |
| 2015/0272870 | A1 | 10/2015 | Hsin-Yung |
| 2016/0015062 | A1 | 1/2016 | Sandau |
| 2016/0258954 | A1 | 9/2016 | Lerner |
| 2016/0263200 | A1 | 9/2016 | Cunningham |
| 2016/0297748 | A1 | 10/2016 | Stockwell |
| 2017/0157038 | A1 | 6/2017 | Peyman |
| 2017/0172971 | A1 | 6/2017 | Andersson |
| 2017/0312217 | A9 | 11/2017 | Hsin-Yung |
| 2018/0200164 | A1 | 7/2018 | Latta |
| 2019/0204136 | A1 | 7/2019 | Fitzgerald |
| 2019/0234940 | A1 | 8/2019 | Lam |
| 2019/0365798 | A1 | 12/2019 | Beal |
| 2019/0374516 | A1 | 12/2019 | Michael |
| 2020/0101025 | A1 | 4/2020 | Masiz |
| 2020/0138756 | A1 | 5/2020 | Mrsny |
| 2020/0253878 | A1 | 8/2020 | Dunne |
| 2020/0397854 | A1 | 12/2020 | Berna |

FOREIGN PATENT DOCUMENTS

| | | | |
|---|---|---|---|
| AU | 2012261721 | A1 | 9/2014 |
| CA | 1302263 | C | 6/1992 |
| CN | 101584735 | A | 11/2009 |
| DE | 3812605 | A1 | 6/1990 |
| DK | 1252158 | T3 | 8/2005 |
| EP | 0082667 | A1 | 6/1983 |
| EP | 0594223 | B1 | 3/2000 |
| EP | 0526253 | B1 | 11/2002 |
| EP | 1104760 | B1 | 3/2003 |
| EP | 1229034 | B1 | 4/2005 |
| EP | 1194404 | B1 | 5/2006 |
| EP | 1624899 | B1 | 11/2010 |
| EP | 2046740 | B1 | 5/2012 |
| EP | 2317995 | B1 | 12/2016 |
| ES | 2006672 | A6 | 5/1989 |
| IE | 20000303 | A1 | 2/2003 |
| IL | 93223 | | 11/1990 |
| IN | 5520DELNP2007 | A | 8/2007 |
| IN | 9223DELNP20008 | A | 3/2009 |
| IN | 505DELNP2009 | A | 8/2010 |
| JP | 2006176427 | A | 7/2006 |
| JP | 2015151361 | A | 8/2015 |
| KR | 1020030007314 | A | 1/2003 |
| NZ | 555624 | B | 9/2009 |
| NZ | 563759 | A | 6/2010 |
| PH | 12003500817 | A1 | 9/2003 |
| WO | 1995007919 | | 3/1995 |
| WO | 1996034604 | | 11/1996 |
| WO | 9640165 | | 12/1996 |
| WO | 1998018610 | | 5/1998 |
| WO | 1998050033 | | 11/1998 |
| WO | 2000021504 | | 4/2000 |
| WO | 2000048636 | | 8/2000 |
| WO | 2000057187 | | 9/2000 |
| WO | 2000072868 | | 12/2000 |
| WO | 2001013897 | | 3/2001 |
| WO | 0157036 | | 8/2001 |
| WO | 2001057025 | | 8/2001 |
| WO | 2001057036 | | 8/2001 |
| WO | 2002030395 | | 4/2002 |
| WO | 2002051814 | | 7/2002 |
| WO | 2002060875 | | 8/2002 |
| WO | 2002060896 | | 8/2002 |
| WO | 2002060898 | | 8/2002 |
| WO | 2003039548 | | 5/2003 |
| WO | 2003074562 | A2 | 9/2003 |
| WO | 2004062600 | A2 | 7/2004 |
| WO | 2004080393 | | 9/2004 |
| WO | 2005077050 | | 8/2005 |
| WO | 2006050165 | | 5/2006 |
| WO | 2006058008 | | 6/2006 |
| WO | 2006060919 | | 6/2006 |
| WO | 2006067401 | | 6/2006 |
| WO | 2006115137 | | 11/2006 |
| WO | 2006130174 | | 12/2006 |
| WO | 2006136244 | | 12/2006 |
| WO | 2007044693 | | 4/2007 |
| WO | 2007059905 | A2 | 5/2007 |

(56) References Cited

FOREIGN PATENT DOCUMENTS

| | | | |
|---|---|---|---|
| WO | 2007065256 | A1 | 6/2007 |
| WO | 2007109547 | | 9/2007 |
| WO | 2007115822 | | 10/2007 |
| WO | 2008006547 | | 1/2008 |
| WO | 2008012511 | | 1/2008 |
| WO | 2008062905 | | 5/2008 |
| WO | 2008088233 | | 7/2008 |
| WO | 2008116165 | A2 | 9/2008 |
| WO | 2008127291 | A2 | 10/2008 |
| WO | 2008133982 | A2 | 11/2008 |
| WO | 2008133982 | A3 | 5/2009 |
| WO | 2009082818 | | 7/2009 |
| WO | 2009082819 | | 7/2009 |
| WO | 2009082819 | A1 | 7/2009 |
| WO | 2009100532 | | 8/2009 |
| WO | 2009082818 | A8 | 9/2009 |
| WO | 2009111040 | | 9/2009 |
| WO | 2011041311 | A2 | 4/2011 |
| WO | 2011041311 | A3 | 8/2011 |
| WO | 2011150067 | A1 | 12/2011 |
| WO | 2012024367 | | 2/2012 |
| WO | 2013028334 | | 2/2013 |
| WO | 2013111014 | A1 | 8/2013 |
| WO | 2013116312 | | 8/2013 |
| WO | 2013142817 | | 9/2013 |
| WO | 2014081405 | | 5/2014 |
| WO | 2014111957 | | 7/2014 |
| WO | 2014168255 | A1 | 10/2014 |
| WO | 2016029127 | A1 | 2/2016 |
| WO | 2018005445 | A1 | 1/2018 |
| WO | 2018013871 | A1 | 1/2018 |
| WO | 2019023468 | | 1/2019 |
| WO | 2019081573 | | 5/2019 |
| WO | 2019097187 | | 5/2019 |
| WO | 2019133531 | | 7/2019 |
| WO | 2019148132 | | 8/2019 |
| WO | 2019161152 | | 8/2019 |
| WO | 2019177927 | A1 | 9/2019 |
| WO | 2019204136 | | 10/2019 |
| WO | 2019204136 | A1 | 10/2019 |
| WO | 2020052677 | | 3/2020 |
| WO | 2020113028 | A1 | 6/2020 |
| WO | 2020127573 | A1 | 6/2020 |
| WO | 2020222187 | A1 | 11/2020 |
| WO | 2020229761 | A1 | 11/2020 |

OTHER PUBLICATIONS

Rosli, et al., "Repurposing drugs targeting the P2X7 receptor to limit hyperinflammation and disease during influenza virus infection," *Br J Pharmacol.* 176(19): 3834-3844 (2019). Published online Aug. 19, 2019. doi: 10.1111/bph.14787.

Bitter, et al., "Nasal Drug Delivery in Humans", Topical Applications and the Mucosa, 40:20-35 (2011).

Benemid (Probenecid) dosing, indications, interactions, adverse effects, and more, retrieved from https://reference.medscape.com/drug/probenecid-342832, on May 11, 2020.

Coronaviridae Study Group of the International Committee on Taxonomy of Viruses, "The species Severe acute respiratory syndromerelated coronavirus: classifying 2019-nCoV and naming it SARS-CoV-2", Nat. Microbiol., 5:536-544 (2020).

Dayton, et al., "The metabolism of probenecid in man," N. Y. Acad. Sci., 179:399-402 (1971).

Dayton, et al., "The effect of probenecid, phenylbutazone, and their analogues on the excretion of L-ascorbic acid in rats," J. Med. Chem., 9:941-944 (1966).

Djupesland, "Nasal drug delivery devices: characteristics and performance in a clinical perspective—a review", Drug Deliv. and Transl. Res., 3:42-62 (2013).

Evaluation of Alternative Oseltamivir (Tamiflu) Dosing Strategies, retrieved from https://clinicaltrials.gov/ct2/show/NCT00304434, on Jun. 18, 2020, last updated Sep. 23, 2009.

GenBank Accession No. AY274119.3, 11 pages, accessed Jun. 17, 2020.

GenBank Accession No. JX869059.2, 12 pages, accessed Jun. 17, 2020.

GenBank Accession No. MN908947.3, 11 pages, accessed Jun. 17, 2020.

GenBank Accession No. MN985325.1, 11 pages, accessed Jun. 17, 2020.

Ghadiri, et al., "Strategies to Enhance Drug Absorption via Nasal and Pulmonary Routes", Pharmaceutics, 11(3): 113, 20 pages (2019).

Guarino, et al., "Mass spectral identification of probenecid metabolites in rat bile," Eur. J. Pharmacol., 8:244-252 (1969).

Ibrahim, et al., "Pharmacodynamics of Pulse Dosing versus Standard Dosing: In Vitro Metronidazole Activity against Bacteroides fragilis and Bacteroides thetaiotaomicron", Antimicrobial Agents and Chemotherapy, 48(11 ):4195-4199 (2004).

Israili, et al., "Metabolites of probenecid. Chemical, physical, and pharmacological studies," J. Med. Chern., 15(7): 709-713 (1972).

Jorquera, et al., "Verdinexor (KPT-335), a Selective Inhibitor of Nuclear Export, Reduces Respiratory Syncytial Virus replication In Vitro", Journal of Virology, 93(4):e01684-18 (2019).

Nigam, et al., "The Organic Anion Transporter (OAT) Family: A Systems Biology Perspective", Physiol.Rev., 95(1):83-123 (2015).

NR-52281, SARS-Related Coronavirus 2, Isolate USA-WA1/2020 (Viruses), accessed online Apr. 10, 2020.

Perel, et al., "Studies of the renal excretion of probenecid acyl glucuronide in man," Eur. J. Clin. Pharmacol, 3:106-112 (1971).

Perwitasari, et al., "Targeting Organic Anion Transporter 3 with Probenecid as a Novel Anti-Influenza A Virus Strategy", Antimicrob. Agents Chemother., 57(1):475-83 (2013).

Perwitasari, et al., "Verdinexor, a Novel Selective Inhibitor of Nuclear Export, Reduces Influenza A Virus Replication In Vitro and In Vivo", J. of Virology, 88(17): 10288-10243 (2014).

Pharmacological Study of Oseltamivir in Healthy Volunteers (SEA002), retrieved from https://clinicaltrials.gov/ct2/show/NCT00439530, on Jun. 18, 2020, last updated Jul. 28, 2009.

Pickens, et al., "Verdinexor Targeting of CRM1 is a Promising Therapeutic Approach against RSV and Influenza Viruses", Viruses, 10(48):1-24 (2018).

Pires, et al., "Intranasal Drug Delivery: How, Why and What for", J. Pharm. Pharmaceut. Sci., 12(3):288-311 (2009).

Probenecid CAS#57-66-9, retrieved from https://www.chemsrc.com/en/cas/57-66-9_242920.html, on Apr. 10, 2020.

Probenecid Tablets—FDA Prescribing Information, side effects and uses, retrieved from https://www.drugs.com/pro/probenecid-tablets.html, on Apr. 10, 2020.

Probenecid (probenecid) dose, indications, adverse effects, interactions retrieved from https://www.pdr.net/drug-summary/Probenecid-probenecid-1984 , on May 11, 2020.

Probenecid, Science Direct, retrieved from https://www.sciencedirect.com/topics/pharmacology-toxicology-and-pharmaceutical- science/probenecid , on May 15, 2020.

Ratia, et al., "A noncovalent class of papain-like protease/ deubiquitinase inhibitors blocks SARS virus replication", Proc. Natl. Acad. Sci. USA, 105(42):16119-16124 (2008).

WHO, "Pneumonia of unknown cause—China" World Health Organization: Online Jan. 5, 2020.

Liu, et al., "Research and Development on Therapeutic Agents and Vaccines for COVID-19 and Related Human Coronavirus Diseases," ACS Cent Sci., 6(3): 315-331, and 18 pages of supplemental information (2020), Published online Mar. 12, 2020. doi: 10.1021/acscentsci.0c00272.

Wu, et al., "A new coronavirus associated with human respiratory disease in China," Nature, 579(7798): 265-269, and 19 pages of supplemental information and Erratum (2020), Published online Feb. 3, 2020. doi: 10.1038/s41586-020-2008-3.

Adelson, et al. "Treatment of urinary infections in pregnancy using single versus 10-day dosing", J Natl Med Assoc., 84(1):73-5 (1992).

Ahmed, et al. "Repositioning of drugs using open-access data portal DTome: A test case with probenecid (Review)", Int J Mol Med., (2016).

(56) References Cited

OTHER PUBLICATIONS

Chiang & Benet, "Dose-dependent kinetics of probenecid in rhesus monkeys-intravenous bolus studies", Pharmacology, 23(6):326-36 (1981).
Crone & Lassen, "The mechanism of the increased renal excretion of urate during the administration of probenecid," Acta Pharmacol Toxicol (Copenh)., 11 (3):301-6 (1955).
Cunningham, et al. "Clinical pharmacokinetics of probenecid." Clin Pharmacokinet., 6(2):135-51 (1981).
Cutler, et al., "In vitro and in vivo assessment of renal drug transporters in the disposition of mesna and dimesna", J Clin Pharmacol., 52(4):530-42 (2012).
El-Farrash, et al., "Allopurinol as a potential therapeutic agent for recurrent herpes labialis", J Med Dent Sci., 50(2):147-54 (2003).
Emanuelsson & Paalzow, "Dose-dependent pharmacokinetics of probenecid in the rat", Biopharm Drug Dispos., 9(1):59-70 (1988).
Emanuelsson & Paalzow, "Hepatic and renal clearances of probenecid in the rat," Pharmacology, 38(1):61-8 (1989).
Emanuelsson, et al., "Non-linear elimination and protein binding of probenecid", Eur J Clin Pharmacol., 32(4):395-401 (1987).
Gerk, et al., "Interactions between cimetidine, nitrofurantoin, and probenecid active transport into rat milk", J Pharmacol Exp Ther., 296(1):175-80 (2001).
Gollapudi, et al., "Probenecid reverses multidrug resistance in multidrug resistance-associated protein-overexpressing HL60/AR and H69/AR cells but not in P-glycoprotein-overexpressing HL60/Tax and P388/ADR cells", Cancer Chemother Pharmacol., 40(2):150-8 (1997).
Guerrini, et al., "Pharmacokinetics of probenecid in sheep", J Vet Pharmacol Ther., 8(2):128-35 (1985).
Gutman, et al., "Combination of probenecid-sulphadoxine-pyrimethamine for intermittent preventive treatment in pregnancy", Malar J.,11:39 (2012). doi: 10.1186/1475-2875-11-39.
He, et al., "Analysis of multimerization of the SARS coronavirus nucleocapsid protein", Biochem. and Biophys. res. Comm., 316:476-483 (2004).
Holodniy, et al. "Pharmacokinetics and tolerability of oseltamivir combined with probenecid", Antimicrob Agents Chemother. 52(9):3013-21 (2008).
Howton, "Probenecid with Oseltamivir for Human Influenza A (H5N1) Virus Infection?", N Engl J Med., 354(8):879-80 (2006).
Ilett, et al. "Transfer of probenecid and cephalexin into breast milk", Ann Pharmacother., 40(5):986-9 (2006).
Kakizaki, et al. "Probenecid: its chromatographic determination, plasma protein binding, and in vivo pharmacokinetics in dogs", J Vet Med Sci., (2006).
Krick, et al. "Dual Oxidase 2 (Duox2) Regulates Pannexin 1-mediated ATP Release in Primary Human Airway Epithelial Cells via Changes in Intracellular pH and Not H2O2 Production", J Biol Chem., 291 (12):6423-32 (2016).
Lai, et al., "Treatment of severe acute respiratory syndrome", Eur. J. Clin. Microbiol. Infect. Dis., 24:583-591 (2005).
Laskin, et al. "Effects of probenecid on the pharmacokinetics and elimination of acyclovir in humans." Antimicrob Agents Chemother., 21(5):804-7 (1982).
Lee & Loeffler, "Gout and pregnancy", J Obstet Gynaecol Br Emp., 69:299-304 (1962).
McDermott, et al., "Pharmacokinetics of zidovudine plus probenecid", J Infect Dis., 166(3):687-8 (1992).
Miranda, et al. "Alteration of zidovudine pharmacokinetics by probenecid in patients with AIDS or AIDS-related complex", Clin Pharmacol Ther., 46(5):494-500 (1989).
Momper, et al. "Pharmacokinetics of low-dose cidofovir in kidney transplant recipients with BK virus infection", Transpl Infect Dis., 15(1):34-41 (2013).
Noormohame, et al. "Renal excretion and pharmacokinetics of foscarnet in HIV sero-positive patients: effect of probenecid pre-treatment," Br J Clin Pharmacol., 43(1):112-5 (1997).
Pérez-Mazliah, et al. "Allopurinol reduces antigen-specific and polyclonal activation of human T cells", Front Immunol., 3:295 (2012).
Qi, et al. "Differential distribution of probenecid as detected by on-tissue mass spectrometry", Cell Tissue Res., 360(2):427-9 (2015).
Ramnitz, et al. "Phenotypic and Genotypic Characterization and Treatment of a Cohort With Familial Tumoral Calcinosis/Hyperostosis-Hyperphosphatemia Syndrome", J Bone Miner Res., 31 (10):1845-1854 (2016).
Rayner, et al. "Population pharmacokinetics of oseltamivir when coadministered with probenecid", J Clin Pharmacol., 48(8):935-47 (2008).
Roy, et al. "Exploration of inclusion complexes of probenecid with α and β-cyclodextrins: Enhancing the utility of the drug", Journal of Molecular Structure, (2017).
Schackis, "Hyperuricaemia and preeclampsia: is there a pathogenic link?" Med Hypotheses, 63(2):239-44 (2004).
Selen, et al. "Pharmacokinetics of probenecid following oral doses to human volunteers", J Pharm Sci.,71(11):1238-42 (1982).
Stocker, et al. "Pharmacokinetic and pharmacodynamic interaction between allopurinol and probenecid in patients with gout", J Rheumatol., 38(5):904-10 (2011).
Takeda, et al. "Characterization of organic anion transport inhibitors using cells stably expressing human organic anion transporters", Eur J Pharmacol., 11 ;419(2-3):113-20 (2011).
Vossen, et al. "Single-dose pharmacokinetics of cidofovir in continuous venovenous hemofiltration", Antimicrob Agents Chemother. 58(4):1952-5 (2014).
Vree, et al. "Capacity-limited renal glucuronidation of probenecid by humans. A pilot Vmax-finding study", Pharm Weekbl Sci., 14(5):325-31 (1992).
Wang, et al. "Renal secretion of the antiviral nucleoside analog AM188 is inhibited by probenecid, p-aminohippuric acid, and cimetidine in the isolated perfused rat kidney", Pharm Res., 21 (6):982-8 (2004).
Weber, et al. "Probenecid pharmacokinetics in cystic fibrosis." Dev Pharmacol Ther., 16(1):7-12 (1991).
Wolf, et al. "Pharmacokinetics and renal effects of cidofovir with a reduced dose of probenecid in HIV-infected patients with cytomegalovirus retinitis", J Clin Pharmacol., 43(1):43-51 (2003).
Wu, et al. "Pharmacokinetic properties and bioequivalence of two compound formulations of 1500 mg ampicillin (1167 mg)/probenecid (333 mg): a randomized-sequence, single-dose, open-label, two-period crossover study in healthy Chinese male volunteers", Clin Then, 32(3):597-606 (2010).
Zacchei & Weidner, "GLC determination of probenecid in biological fluids." J Pharm Sci., 62(12):1972-5 (1973).
Zhang, et al. "Simultaneous Determination of Cefalexin, Cefazolin, Flucloxacillin, and Probenecid by Liquid Chromatography-Tandem Mass Spectrometry for Total and Unbound Concentrations in Human Plasma," Ther Drug Monit. 40(6):682-692 (2018).
Cheng, et al., "Kidney impairment is associated with in-hospital death of COVID-19 patients", MedRxiv, 1-21 (2020).
European Search Report dated Apr. 23, 2021, in European Patent Application No. 20202059.0.

* cited by examiner

SEQUENCE LISTING

<160> NUMBER OF SEQ ID NOS: 4

<210> SEQ ID NO 1
<211> LENGTH: 29903
<212> TYPE: DNA
<213> ORGANISM: Human coronavirus

<400> SEQUENCE: 1
attaaaggtt tataccttcc caggtaacaa accaaccaac tttcgatctc ttgtagatct 60
gttctctaaa cgaactttaa aatctgtgtg gctgtcactc ggctgcatgc ttagtgcact 120
cacgcagtat aattaataac taattactgt cgttgacagg acacgagtaa ctcgtctatc 180
ttctgcaggc tgcttacggt ttcgtccgtg ttgcagccga tcatcagcac atctaggttt 240
cgtccgggtg tgaccgaaag gtaagatgga gagccttgtc cctggtttca acgagaaaac 300
acacgtccaa ctcagtttgc ctgttttaca ggttcgcgac gtgctcgtac gtggctttgg 360
agactccgtg gaggaggtct tatcagaggc acgtcaacat cttaaagatg gcacttgtgg 420
cttagtagaa gttgaaaaag gcgttttgcc tcaacttgaa cagccctatg tgttcatcaa 480
acgttcggat gctcgaactg cacctcatgg tcatgttatg gttgagctgg tagcagaact 540
cgaaggcatt cagtacggtc gtagtggtga gacacttggt gtccttgtcc ctcatgtggg 600
cgaaatacca gtggcttacc gcaaggttct tcttcgtaag aacggtaata aaggagctgg 660

-continued

```
tggccatagt tacggcgccg atctaaagtc atttgactta ggcgacgagc ttggcactga    720
tccttatgaa gattttcaag aaaactggaa cactaaacat agcagtggtg ttacccgtga    780
actcatgcgt gagcttaacg gaggggcata cactcgctat gtcgataaca acttctgtgg    840
ccctgatggc taccctcttg agtgcattaa agaccttcta gcacgtgctg gtaaagcttc    900
atgcactttg tccgaacaac tggactttat tgacactaag aggggtgtat actgctgccg    960
tgaacatgag catgaaattg cttggtacac ggaacgttct gaaaagagct atgaattgca   1020
gacacctttt gaaattaaat tggcaaagaa atttgacacc ttcaatgggg aatgtccaaa   1080
ttttgtattt cccttaaatt ccataatcaa gactattcaa ccaagggttg aaaagaaaaa   1140
gcttgatggc tttatgggta gaattcgatc tgtctatcca gttgcgtcac caaatgaatg   1200
caaccaaatg tgcctttcaa ctctcatgaa gtgtgatcat tgtggtgaaa cttcatggca   1260
gacgggcgat tttgttaaag ccacttgcga attttgtggc actgagaatt tgactaaaga   1320
aggtgccact acttgtggtt acttacccca aaatgctgtt gttaaaattt attgtccagc   1380
atgtcacaat tcagaagtag gacctgagca tagtcttgcc gaataccata atgaatctgg   1440
cttgaaaacc attcttcgta agggtggtcg cactattgcc tttggaggct gtgtgttctc   1500
ttatgttggt tgccataaca agtgtgccta ttgggttcca cgtgctagcg ctaacatagg   1560
ttgtaaccat acaggtgttg ttggagaagg ttccgaaggt cttaatgaca accttcttga   1620
aatactccaa aaagagaaag tcaacatcaa tattgttggt gactttaaac ttaatgaaga   1680
gatcgccatt attttggcat ctttttctgc ttccacaagt gcttttgtgg aaactgtgaa   1740
aggtttggat tataaagcat tcaaacaaat tgttgaatcc tgtggtaatt ttaaagttac   1800
aaaaggaaaa gctaaaaaag gtgcctggaa tattggtgaa cagaaatcaa tactgagtcc   1860
tctttatgca tttgcatcag aggctgctcg tgttgtacga tcaattttct cccgcactct   1920
tgaaactgct caaaattctg tgcgtgtttt acagaaggcc gctataacaa tactagatgg   1980
aatttcacag tattcactga gactcattga tgctatgatg ttcacatctg atttggctac   2040
taacaatcta gttgtaatgg cctacattac aggtggtgtt gttcagttga cttcgcagtg   2100
gctaactaac atctttggca ctgtttatga aaaactcaaa cccgtccttg attggcttga   2160
agagaagttt aaggaaggtg tagagtttct tagagacggt tgggaaattg ttaaatttat   2220
ctcaacctgt gcttgtgaaa ttgtcggtgg acaaattgtc acctgtgcaa aggaaattaa   2280
ggagagtgtt cagacattct ttaagcttgt aaataaattt ttggctttgt gtgctgactc   2340
tatcattatt ggtggagcta aacttaaagc cttgaattta ggtgaaacat ttgtcacgca   2400
ctcaaaggga ttgtacagaa agtgtgttaa atccagagaa gaaactggcc tactcatgcc   2460
tctaaaagcc ccaaaagaaa ttatcttctt agagggagaa acacttccca cagaagtgtt   2520
aacagaggaa gttgtcttga aaactggtga tttacaacca ttagaacaac ctactagtga   2580
agctgttgaa gctccattgg ttggtacacc agtttgtatt aacgggctta tgttgctcga   2640
aatcaaagac acagaaaagt actgtgccct tgcacctaat atgatggtaa caaacaatac   2700
cttcacactc aaaggcggtg caccaacaaa ggttactttt ggtgatgaca ctgtgataga   2760
agtgcaaggt tacaagagtg tgaatatcac ttttgaactt gatgaaagga ttgataaagt   2820
acttaatgag aagtgctctg cctatacagt tgaactcggt acagaagtaa atgagttcgc   2880
ctgtgttgtg gcagatgctg tcataaaaac tttgcaacca gtatctgaat tacttacacc   2940
actgggcatt gatttagatg agtggagtat ggctacatac tacttatttg atgagtctgg   3000
tgagtttaaa ttggcttcac atatgtattg ttctttctac cctccagatg aggatgaaga   3060
```

```
agaaggtgat tgtgaagaag aagagtttga gccatcaact caatatgagt atggtactga   3120
agatgattac caaggtaaac ctttggaatt tggtgccact tctgctgctc ttcaacctga   3180
agaagagcaa gaagaagatt ggttagatga tgatagtcaa caaactgttg gtcaacaaga   3240
cggcagtgag gacaatcaga caactactat tcaaacaatt gttgaggttc aacctcaatt   3300
agagatggaa cttacaccag ttgttcagac tattgaagtg aatagtttta gtggttattt   3360
aaaacttact gacaatgtat acattaaaaa tgcagacatt gtggaagaag ctaaaaaggt   3420
aaaaccaaca gtggttgtta atgcagccaa tgtttacctt aaacatggag gaggtgttgc   3480
aggagcctta aataaggcta ctaacaatgc catgcaagtt gaatctgatg attacatagc   3540
tactaatgga ccacttaaag tgggtggtag ttgtgtttta agcggacaca atcttgctaa   3600
acactgtctt catgttgtcg gcccaaatgt taacaaaggt gaagacattc aacttcttaa   3660
gagtgcttat gaaaatttta atcagcacga agttctactt gcaccattat tatcagctgg   3720
tatttttggt gctgacccta tacattcttt aagagtttgt gtagatactg ttcgcacaaa   3780
tgtctactta gctgtctttg ataaaaatct ctatgacaaa cttgtttcaa gctttttgga   3840
aatgaagagt gaaaagcaag ttgaacaaaa gatcgctgag attcctaaag aggaagttaa   3900
gccatttata actgaaagta aaccttcagt tgaacagaga aaacaagatg ataagaaaat   3960
caaagcttgt gttgaagaag ttacaacaac tctggaagaa actaagttcc tcacagaaaa   4020
cttgttactt tatattgaca ttaatggcaa tcttcatcca gattctgcca ctcttgttag   4080
tgacattgac atcactttct taaagaaaga tgctccatat atagtgggtg atgttgttca   4140
agagggtgtt ttaactgctg tggttatacc tactaaaaag gctggtggca ctactgaaat   4200
gctagcgaaa gctttgagaa aagtgccaac agacaattat ataaccactt acccgggtca   4260
gggtttaaat ggttacactg tagaggaggc aaagacagtg cttaaaaagt gtaaaagtgc   4320
cttttacatt ctaccatcta ttatctctaa tgagaagcaa gaaattcttg gaactgtttc   4380
ttggaatttg cgagaaatgc ttgcacatgc agaagaaaca cgcaaattaa tgcctgtctg   4440
tgtggaaact aaagccatag tttcaactat acagcgtaaa tataagggta ttaaaataca   4500
agagggtgtg gttgattatg gtgctagatt ttacttttac accagtaaaa caactgtagc   4560
gtcacttatc aacacactta acgatctaaa tgaaactctt gttacaatgc cacttggcta   4620
tgtaacacat ggcttaaatt tggaagaagc tgctcggtat atgagatctc tcaaagtgcc   4680
agctacagtt tctgtttctt cacctgatgc tgttacagcg tataatggtt atcttacttc   4740
ttcttctaaa acacctgaag aacattttat tgaaaccatc tcacttgctg gttcctataa   4800
agattggtcc tattctggac aatctacaca actaggtata gaatttctta agagaggtga   4860
taaaagtgta tattacacta gtaatcctac cacattccac ctagatggtg aagttatcac   4920
ctttgacaat cttaagacac ttctttcttt gagagaagtg aggactatta aggtgtttac   4980
aacagtagac aacattaacc tccacacgca agttgtggac atgtcaatga catatggaca   5040
acagtttggt ccaacttatt tggatggagc tgatgttact aaaataaaac ctcataattc   5100
acatgaaggt aaaacatttt atgttttacc taatgatgac actctacgtg ttgaggcttt   5160
tgagtactac cacacaactg atcctagttt tctgggtagg tacatgtcag cattaaatca   5220
cactaaaaag tggaaatacc cacaagttaa tggtttaact tctattaaat gggcagataa   5280
caactgttat cttgccactg cattgttaac actccaacaa atagagttga agtttaatcc   5340
acctgctcta caagatgctt attacagagc aagggctggt gaagctgcta acttttgtgc   5400
```

-continued acttatctta gcctactgta ataagacagt aggtgagtta ggtgatgtta gagaaacaat 5460
gagttacttg tttcaacatg ccaatttaga ttcttgcaaa agagtcttga acgtggtgtg 5520
taaaacttgt ggacaacagc agacaaccct taagggtgta gaagctgtta tgtacatggg 5580
cacactttct tatgaacaat ttaagaaagg tgttcagata ccttgtacgt gtggtaaaca 5640
agctacaaaa tatctagtac aacaggagtc accttttgtt atgatgtcag caccacctgc 5700
tcagtatgaa cttaagcatg gtacatttac ttgtgctagt gagtacactg gtaattacca 5760
gtgtggtcac tataaacata taacttctaa agaaactttg tattgcatag acggtgcttt 5820
acttacaaag tcctcagaat acaaaggtcc tattacggat gttttctaca aagaaaacag 5880
ttacacaaca accataaaac cagttactta taaattggat ggtgttgttt gtacagaaat 5940
tgaccctaag ttggacaatt attataagaa agacaattct tatttcacag agcaaccaat 6000
tgatcttgta ccaaaccaac catatccaaa cgcaagcttc gataatttta agtttgtatg 6060
tgataatatc aaatttgctg atgatttaaa ccagttaact ggttataaga aacctgcttc 6120
aagagagctt aaagttacat ttttccctga cttaaatggt gatgtggtgg ctattgatta 6180
taaacactac acaccctctt ttaagaaagg agctaaattg ttacataaac ctattgtttg 6240
gcatgttaac aatgcaacta ataaagccac gtataaacca aatacctggt gtatacgttg 6300
tctttggagc acaaaaccag ttgaaacatc aaattcgttt gatgtactga agtcagagga 6360
cgcgcaggga atggataatc ttgcctgcga agatctaaaa ccagtctctg aagaagtagt 6420
ggaaaatcct accatacaga aagacgttct tgagtgtaat gtgaaaacta ccgaagttgt 6480
aggagacatt atacttaaac cagcaaataa tagtttaaaa attacagaag aggttggcca 6540
cacagatcta atggctgctt atgtagacaa ttctagtctt actattaaga aacctaatga 6600
attatctaga gtattaggtt tgaaaaccct tgctactcat ggtttagctg ctgttaatag 6660
tgtcccttgg gatactatag ctaattatgc taagcctttt cttaacaaag ttgttagtac 6720
aactactaac atagttacac ggtgtttaaa ccgtgtttgt actaattata tgccttattt 6780
ctttacttta ttgctacaat tgtgtacttt tactagaagt acaaattcta gaattaaagc 6840
atctatgccg actactatag caaagaatac tgttaagagt gtcggtaaat tttgtctaga 6900
ggcttcattt aattatttga agtcacctaa tttttctaaa ctgataaata ttataatttg 6960
gtttttacta ttaagtgttt gcctaggttc tttaatctac tcaaccgctg ctttaggtgt 7020
tttaatgtct aatttaggca tgccttctta ctgtactggt tacagagaag gctatttgaa 7080
ctctactaat gtcactattg caacctactg tactggttct ataccttgta gtgtttgtct 7140
tagtggttta gattctttag acacctatcc ttctttagaa actatacaaa ttaccatttc 7200
atcttttaaa tgggatttaa ctgcttttgg cttagttgca gagtggtttt tggcatatat 7260
tcttttcact aggtttttct atgtacttgg attggctgca atcatgcaat tgtttttcag 7320
ctattttgca gtacatttta ttagtaattc ttggcttatg tggttaataa ttaatcttgt 7380
acaaatggcc ccgatttcag ctatggttag aatgtacatc ttctttgcat cattttatta 7440
tgtatggaaa agttatgtgc atgttgtaga cggttgtaat tcatcaactt gtatgatgtg 7500
ttacaaacgt aatagagcaa caagagtcga atgtacaact attgttaatg gtgttagaag 7560
gtccttttat gtctatgcta atggaggtaa aggcttttgc aaactacaca attggaattg 7620
tgttaattgt gatacattct gtgctggtag tacatttatt agtgatgaag ttgcgagaga 7680
cttgtcacta cagtttaaaa gaccaataaa tcctactgac cagtcttctt acatcgttga 7740
tagtgttaca gtgaagaatg gttccatcca tctttacttt gataaagctg gtcaaaagac 7800

-continued

```
ttatgaaaga cattctctct ctcattttgt taacttagac aacctgagag ctaataacac   7860
taaaggttca ttgcctatta atgttatagt ttttgatggt aaatcaaaat gtgaagaatc   7920
atctgcaaaa tcagcgtctg tttactacag tcagcttatg tgtcaaccta tactgttact   7980
agatcaggca ttagtgtctg atgttggtga tagtgcggaa gttgcagtta aaatgtttga   8040
tgcttacgtt aatacgtttt catcaacttt taacgtacca atggaaaaac tcaaaacact   8100
agttgcaact gcagaagctg aacttgcaaa gaatgtgtcc ttagacaatg tcttatctac   8160
ttttatttca gcagctcggc aagggtttgt tgattcagat gtagaaacta aagatgttgt   8220
tgaatgtctt aaattgtcac atcaatctga catagaagtt actggcgata gttgtaataa   8280
ctatatgctc acctataaca aagttgaaaa catgacaccc cgtgaccttg gtgcttgtat   8340
tgactgtagt gcgcgtcata ttaatgcgca ggtagcaaaa agtcacaaca ttgctttgat   8400
atggaacgtt aaagatttca tgtcattgtc tgaacaacta cgaaaacaaa tacgtagtgc   8460
tgctaaaaag aataacttac cttttaagtt gacatgtgca actactagac aagttgttaa   8520
tgttgtaaca acaaagatag cacttaaggg tggtaaaatt gttaataatt ggttgaagca   8580
gttaattaaa gttacacttg tgttcctttt tgttgctgct attttctatt taataacacc   8640
tgttcatgtc atgtctaaac atactgactt ttcaagtgaa atcataggat acaaggctat   8700
tgatggtggt gtcactcgtg acatagcatc tacagatact tgttttgcta acaaacatgc   8760
tgattttgac acatggttta gccagcgtgg tggtagttat actaatgaca aagcttgccc   8820
attgattgct gcagtcataa caagagaagt gggttttgtc gtgcctggtt tgcctggcac   8880
gatattacgc acaactaatg gtgacttttt gcatttctta cctagagttt ttagtgcagt   8940
tggtaacatc tgttacacac catcaaaact tatagagtac actgactttg caacatcagc   9000
ttgtgttttg gctgctgaat gtacaatttt taaagatgct tctggtaagc cagtaccata   9060
ttgttatgat accaatgtac tagaaggttc tgttgcttat gaaagtttac gccctgacac   9120
acgttatgtg ctcatggatg gctctattat tcaatttcct aacacctacc ttgaaggttc   9180
tgttagagtg gtaacaactt ttgattctga gtactgtagg cacggcactt gtgaaagatc   9240
agaagctggt gtttgtgtat ctactagtgg tagatgggta cttaacaatg attattacag   9300
atctttacca ggagttttct gtggtgtaga tgctgtaaat ttacttacta atatgtttac   9360
accactaatt caacctattg gtgctttgga catatcagca tctatagtag ctggtggtat   9420
tgtagctatc gtagtaacat gccttgccta ctattttatg aggtttagaa gagcttttgg   9480
tgaatacagt catgtagttg cctttaatac tttactattc cttatgtcat tcactgtact   9540
ctgtttaaca ccagtttact cattcttacc tggtgtttat tctgttattt acttgtactt   9600
gacattttat cttactaatg atgtttcttt tttagcacat attcagtgga tggttatgtt   9660
cacaccttta gtacctttct ggataacaat tgcttatatc atttgtattt ccacaaagca   9720
tttctattgg ttctttagta attacctaaa gagacgtgta gtctttaatg gtgtttcctt   9780
tagtactttt gaagaagctg cgctgtgcac ctttttgtta aataaagaaa tgtatctaaa   9840
gttgcgtagt gatgtgctat tacctcttac gcaatataat agatacttag ctctttataa   9900
taagtacaag tattttagtg gagcaatgga tacaactagc tacagagaag ctgcttgttg   9960
tcatctcgca aaggctctca atgacttcag taactcaggt tctgatgttc tttaccaacc  10020
accacaaacc tctatcacct cagctgtttt gcagagtggt tttagaaaaa tggcattccc  10080
atctggtaaa gttgagggtt gtatggtaca agtaacttgt ggtacaacta cacttaacgg  10140
```

tctttggctt gatgacgtag tttactgtcc aagacatgtg atctgcacct ctgaagacat 10200
gcttaaccct aattatgaag atttactcat tcgtaagtct aatcataatt tcttggtaca 10260
ggctggtaat gttcaactca gggttattgg acattctatg caaaattgtg tacttaagct 10320
taaggttgat acagccaatc ctaagacacc taagtataag tttgttcgca ttcaaccagg 10380
acagactttt tcagtgttag cttgttacaa tggttcacca tctggtgttt accaatgtgc 10440
tatgaggccc aatttcacta ttaagggttc attccttaat ggttcatgtg gtagtgttgg 10500
ttttaacata gattatgact gtgtctcttt ttgttacatg caccatatgg aattaccaac 10560
tggagttcat gctggcacag acttagaagg taacttttat ggaccttttg ttgacaggca 10620
aacagcacaa gcagctggta cggacacaac tattacagtt aatgttttag cttggttgta 10680
cgctgctgtt ataaatggag acaggtggtt tctcaatcga tttaccacaa ctcttaatga 10740
ctttaacctt gtggctatga agtacaatta tgaacctcta acacaagacc atgttgacat 10800
actaggacct ctttctgctc aaactggaat tgccgtttta gatatgtgtg cttcattaaa 10860
agaattactg caaaatggta tgaatggacg taccatattg ggtagtgctt tattagaaga 10920
tgaatttaca ccttttgatg ttgttagaca atgctcaggt gttactttcc aaagtgcagt 10980
gaaaagaaca atcaagggta cacaccactg gttgttactc acaattttga cttcactttt 11040
agttttagtc cagagtactc aatggtcttt gttctttttt ttgtatgaaa atgccttttt 11100
accttttgct atgggtatta ttgctatgtc tgcttttgca atgatgtttg tcaaacataa 11160
gcatgcattt ctctgtttgt ttttgttacc ttctcttgcc actgtagctt attttaatat 11220
ggtctatatg cctgctagtt gggtgatgcg tattatgaca tggttggata tggttgatac 11280
tagtttgtct ggttttaagc taaaagactg tgttatgtat gcatcagctg tagtgttact 11340
aatccttatg acagcaagaa ctgtgtatga tgatggtgct aggagagtgt ggacacttat 11400
gaatgtcttg acactcgttt ataaagttta ttatggtaat gctttagatc aagccatttc 11460
catgtgggct cttataatct ctgttacttc taactactca ggtgtagtta caactgtcat 11520
gtttttggcc agaggtattg tttttatgtg tgttgagtat tgccctattt tcttcataac 11580
tggtaataca cttcagtgta taatgctagt ttattgtttc ttaggctatt tttgtacttg 11640
ttactttggc ctcttttgtt tactcaaccg ctactttaga ctgactcttg gtgtttatga 11700
ttacttagtt tctacacagg agtttagata tatgaattca cagggactac tcccacccaa 11760
gaatagcata gatgccttca aactcaacat taaattgttg ggtgttggtg gcaaaccttg 11820
tatcaaagta gccactgtac agtctaaaat gtcagatgta aagtgcacat cagtagtctt 11880
actctcagtt ttgcaacaac tcagagtaga atcatcatct aaattgtggg ctcaatgtgt 11940
ccagttacac aatgacattc tcttagctaa agatactact gaagcctttg aaaaaatggt 12000
ttcactactt tctgttttgc tttccatgca gggtgctgta gacataaaca agctttgtga 12060
agaaatgctg gacaacaggg caaccttaca agctatagcc tcagagttta gttcccttcc 12120
atcatatgca gcttttgcta ctgctcaaga agcttatgag caggctgttg ctaatggtga 12180
ttctgaagtt gttcttaaaa agttgaagaa gtctttgaat gtggctaaat ctgaatttga 12240
ccgtgatgca gccatgcaac gtaagttgga aaagatggct gatcaagcta tgacccaaat 12300
gtataaacag gctagatctg aggacaagag ggcaaaagtt actagtgcta tgcagacaat 12360
gcttttcact atgcttagaa agttggataa tgatgcactc aacaacatta tcaacaatgc 12420
aagagatggt tgtgttccct tgaacataat acctcttaca acagcagcca aactaatggt 12480
tgtcatacca gactataaca catataaaaa tacgtgtgat ggtacaacat ttacttatgc 12540

```
atcagcattg tgggaaatcc aacaggttgt agatgcagat agtaaaattg ttcaacttag  12600
tgaaattagt atggacaatt cacctaattt agcatggcct cttattgtaa cagctttaag  12660
ggccaattct gctgtcaaat tacagaataa tgagcttagt cctgttgcac tacgacagat  12720
gtcttgtgct gccggtacta cacaaactgc ttgcactgat gacaatgcgt tagcttacta  12780
caacacaaca aagggaggta ggtttgtact tgcactgtta tccgatttac aggatttgaa  12840
atgggctaga ttccctaaga gtgatggaac tggtactatc tatacagaac tggaaccacc  12900
ttgtaggttt gttacagaca cacctaaagg tcctaaagtg aagtatttat actttattaa  12960
aggattaaac aacctaaata gaggtatggt acttggtagt ttagctgcca cagtacgtct  13020
acaagctggt aatgcaacag aagtgcctgc caattcaact gtattatctt tctgtgcttt  13080
tgctgtagat gctgctaaag cttacaaaga ttatctagct agtgggggac aaccaatcac  13140
taattgtgtt aagatgttgt gtacacacac tggtactggt caggcaataa cagttacacc  13200
ggaagccaat atggatcaag aatcctttgg tggtgcatcg tgttgtctgt actgccgttg  13260
ccacatagat catccaaatc ctaaaggatt ttgtgactta aaaggtaagt atgtacaaat  13320
acctacaact tgtgctaatg accctgtggg ttttacactt aaaaacacag tctgtaccgt  13380
ctgcggtatg tggaaaggtt atggctgtag ttgtgatcaa ctccgcgaac ccatgcttca  13440
gtcagctgat gcacaatcgt ttttaaacgg gtttgcggtg taagtgcagc ccgtcttaca  13500
ccgtgcggca caggcactag tactgatgtc gtatacaggg cttttgacat ctacaatgat  13560
aaagtagctg gttttgctaa attcctaaaa actaattgtt gtcgcttcca agaaaaggac  13620
gaagatgaca atttaattga ttcttacttt gtagttaaga gacacacttt ctctaactac  13680
caacatgaag aaacaattta taatttactt aaggattgtc cagctgttgc taaacatgac  13740
ttctttaagt ttagaataga cggtgacatg gtaccacata tatcacgtca acgtcttact  13800
aaatacacaa tggcagacct cgtctatgct ttaaggcatt ttgatgaagg taattgtgac  13860
acattaaaag aaatacttgt cacatacaat tgttgtgatg atgattattt caataaaaag  13920
gactggtatg attttgtaga aaacccagat atattacgcg tatacgccaa cttaggtgaa  13980
cgtgtacgcc aagctttgtt aaaaacagta caattctgtg atgccatgcg aaatgctggt  14040
attgttggtg tactgacatt agataatcaa gatctcaatg gtaactggta tgatttcggt  14100
gatttcatac aaaccacgcc aggtagtgga gttcctgttg tagattctta ttattcattg  14160
ttaatgccta tattaacctt gaccagggct ttaactgcag agtcacatgt tgacactgac  14220
ttaacaaagc cttacattaa gtgggatttg ttaaaatatg acttcacgga agagaggtta  14280
aaactctttg accgttattt taaatattgg gatcagacat accacccaaa ttgtgttaac  14340
tgtttggatg acagatgcat tctgcattgt gcaaacttta atgttttatt ctctacagtg  14400
ttcccaccta caagttttgg accactagtg agaaaaatat ttgttgatgg tgttccattt  14460
gtagtttcaa ctggatacca cttcagagag ctaggtgttg tacataatca ggatgtaaac  14520
ttacatagct ctagacttag ttttaaggaa ttacttgtgt atgctgctga ccctgctatg  14580
cacgctgctt ctggtaatct attactagat aaacgcacta cgtgcttttc agtagctgca  14640
cttactaaca atgttgcttt tcaaactgtc aaacccggta attttaacaa agacttctat  14700
gactttgctg tgtctaaggg tttctttaag gaaggaagtt ctgttgaatt aaaacacttc  14760
ttctttgctc aggatggtaa tgctgctatc agcgattatg actactatcg ttataatcta  14820
ccaacaatgt gtgatatcag acaactacta tttgtagttg aagttgttga taagtacttt  14880
```

-continued

```
gattgttacg atggtggctg tattaatgct aaccaagtca tcgtcaacaa cctagacaaa  14940
tcagctggtt ttccatttaa taaatggggt aaggctagac tttattatga ttcaatgagt  15000
tatgaggatc aagatgcact tttcgcatat acaaaacgta atgtcatccc tactataact  15060
caaatgaatc ttaagtatgc cattagtgca aagaatagag ctcgcaccgt agctggtgtc  15120
tctatctgta gtactatgac caatagacag tttcatcaaa aattattgaa atcaatagcc  15180
gccactagag gagctactgt agtaattgga acaagcaaat tctatggtgg ttggcacaac  15240
atgttaaaaa ctgtttatag tgatgtagaa aaccctcacc ttatgggttg ggattatcct  15300
aaatgtgata gagccatgcc taacatgctt agaattatgg cctcacttgt tcttgctcgc  15360
aaacatacaa cgtgttgtag cttgtcacac cgtttctata gattagctaa tgagtgtgct  15420
caagtattga gtgaaatggt catgtgtggc ggttcactat atgttaaacc aggtggaacc  15480
tcatcaggag atgccacaac tgcttatgct aatagtgttt ttaacatttg tcaagctgtc  15540
acggccaatg ttaatgcact tttatctact gatggtaaca aaattgccga taagtatgtc  15600
cgcaatttac aacacagact ttatgagtgt ctctatagaa atagagatgt tgacacagac  15660
tttgtgaatg agttttacgc atatttgcgt aaacatttct caatgatgat actctctgac  15720
gatgctgttg tgtgtttcaa tagcacttat gcatctcaag gtctagtggc tagcataaag  15780
aactttaagt cagttcttta ttatcaaaac aatgttttta tgtctgaagc aaaatgttgg  15840
actgagactg accttactaa aggacctcat gaattttgct ctcaacatac aatgctagtt  15900
aaacagggtg atgattatgt gtaccttcct tacccagatc catcaagaat cctaggggcc  15960
ggctgttttg tagatgatat cgtaaaaaca gatggtacac ttatgattga acggttcgtg  16020
tctttagcta tagatgctta cccacttact aaacatccta atcaggagta tgctgatgtc  16080
tttcatttgt acttacaata cataagaaag ctacatgatg agttaacagg acacatgtta  16140
gacatgtatt ctgttatgct tactaatgat aacacttcaa ggtattggga acctgagttt  16200
tatgaggcta tgtacacacc gcatacagtc ttacaggctg ttggggcttg tgttctttgc  16260
aattcacaga cttcattaag atgtggtgct tgcatacgta gaccattctt atgttgtaaa  16320
tgctgttacg accatgtcat atcaacatca cataaattag tcttgtctgt taatccgtat  16380
gtttgcaatg ctccaggttg tgatgtcaca gatgtgactc aactttactt aggaggtatg  16440
agctattatt gtaaatcaca taaaccaccc attagttttc cattgtgtgc taatggacaa  16500
gtttttggtt tatataaaaa tacatgtgtt ggtagcgata atgttactga ctttaatgca  16560
attgcaacat gtgactggac aaatgctggt gattacattt tagctaacac ctgtactgaa  16620
agactcaagc tttttgcagc agaaacgctc aaagctactg aggagacatt taaactgtct  16680
tatggtattg ctactgtacg tgaagtgctg tctgacagag aattacatct ttcatgggaa  16740
gttggtaaac ctagaccacc acttaaccga aattatgtct ttactggtta tcgtgtaact  16800
aaaaacagta aagtacaaat aggagagtac acctttgaaa aaggtgacta tggtgatgct  16860
gttgtttacc gaggtacaac aacttacaaa ttaaatgttg gtgattattt tgtgctgaca  16920
tcacatacag taatgccatt aagtgcacct acactagtgc cacaagagca ctatgttaga  16980
attactggct tatacccaac actcaatatc tcagatgagt tttctagcaa tgttgcaaat  17040
tatcaaaagg ttggtatgca aaagtattct acactccagg gaccacctgg tactggtaag  17100
agtcattttg ctattggcct agctctctac taccctcctg ctcgcatagt gtatacagct  17160
tgctctcatg ccgctgttga tgcactatgt gagaaggcat taaaatattt gcctatagat  17220
aaatgtagta gaattatacc tgcacgtgct cgtgtagagt gttttgataa attcaaagtg  17280
```

-continued

```
aattcaacat tagaacagta tgtcttttgt actgtaaatg cattgcctga gacgacagca  17340
gatatagttg tctttgatga aatttcaatg gccacaaatt atgatttgag tgttgtcaat  17400
gccagattac gtgctaagca ctatgtgtac attggcgacc ctgctcaatt acctgcacca  17460
cgcacattgc taactaaggg cacactagaa ccagaatatt tcaattcagt gtgtagactt  17520
atgaaaacta taggtccaga catgttcctc ggaacttgtc ggcgttgtcc tgctgaaatt  17580
gttgacactg tgagtgcttt ggtttatgat aataagctta aagcacataa agacaaatca  17640
gctcaatgct ttaaaatgtt ttataagggt gttatcacgc atgatgtttc atctgcaatt  17700
aacaggccac aaataggcgt ggtaagagaa ttccttacac gtaaccctgc ttggagaaaa  17760
gctgtcttta tttcacctta taattcacag aatgctgtag cctcaaagat tttgggacta  17820
ccaactcaaa ctgttgattc atcacagggc tcagaatatg actatgtcat attcactcaa  17880
accactgaaa cagctcactc ttgtaatgta aacagattta atgttgctat taccagagca  17940
aaagtaggca tactttgcat aatgtctgat agagaccttt atgacaagtt gcaatttaca  18000
agtcttgaaa ttccacgtag gaatgtggca actttacaag ctgaaaatgt aacaggactc  18060
tttaaagatt gtagtaaggt aatcactggg ttacatccta cacaggcacc tacacacctc  18120
agtgttgaca ctaaattcaa aactgaaggt ttatgtgttg acatacctgg catacctaag  18180
gacatgacct atagaagact catctctatg atgggtttta aaatgaatta tcaagttaat  18240
ggttacccta acatgtttat cacccgcgaa gaagctataa gacatgtacg tgcatggatt  18300
ggcttcgatg tcgaggggtg tcatgctact agagaagctg ttggtaccaa tttaccttta  18360
cagctaggtt tttctacagg tgttaaccta gttgctgtac ctacaggtta tgttgataca  18420
cctaataata cagatttttc cagagttagt gctaaaccac cgcctggaga tcaatttaaa  18480
cacctcatac cacttatgta caaaggactt ccttggaatg tagtgcgtat aaagattgta  18540
caaatgttaa gtgacacact taaaaatctc tctgacagag tcgtatttgt cttatgggca  18600
catggctttg agttgacatc tatgaagtat tttgtgaaaa taggacctga gcgcacctgt  18660
tgtctatgtg atagacgtgc cacatgcttt tccactgctt cagacactta tgcctgttgg  18720
catcattcta ttggatttga ttacgtctat aatccgttta tgattgatgt tcaacaatgg  18780
ggttttacag gtaacctaca aagcaaccat gatctgtatt gtcaagtcca tggtaatgca  18840
catgtagcta gttgtgatgc aatcatgact aggtgtctag ctgtccacga gtgctttgtt  18900
aagcgtgttg actggactat tgaatatcct ataattggtg atgaactgaa gattaatgcg  18960
gcttgtagaa aggttcaaca catggttgtt aaagctgcat tattagcaga caaattccca  19020
gttcttcacg acattggtaa ccctaaagct attaagtgtg tacctcaagc tgatgtagaa  19080
tggaagttct atgatgcaca gccttgtagt gacaaagctt ataaaataga agaattattc  19140
tattcttatg ccacacattc tgacaaattc acagatggtg tatgcctatt ttggaattgc  19200
aatgtcgata gatatcctgc taattccatt gtttgtagat ttgacactag agtgctatct  19260
aaccttaact tgcctggttg tgatggtggc agtttgtatg taaataaaca tgcattccac  19320
acaccagctt ttgataaaag tgcttttgtt aatttaaaac aattaccatt tttctattac  19380
tctgacagtc catgtgagtc tcatggaaaa caagtagtgt cagatataga ttatgtacca  19440
ctaaagtctg ctacgtgtat aacacgttgc aatttaggtg gtgctgtctg tagacatcat  19500
gctaatgagt acagattgta tctcgatgct tataacatga tgatctcagc tggctttagc  19560
ttgtgggttt acaaacaatt tgatacttat aacctctgga acacttttac aagacttcag  19620
```

-continued

```
agtttagaaa atgtggcttt taatgttgta aataagggac actttgatgg acaacagggt  19680
gaagtaccag tttctatcat taataacact gtttacacaa aagttgatgg tgttgatgta  19740
gaattgtttg aaaataaaac aacattacct gttaatgtag catttgagct ttgggctaag  19800
cgcaacatta aaccagtacc agaggtgaaa atactcaata atttgggtgt ggacattgct  19860
gctaatactg tgatctggga ctacaaaaga gatgctccag cacatatatc tactattggt  19920
gtttgttcta tgactgacat agccaagaaa ccaactgaaa cgatttgtgc accactcact  19980
gtcttttttg atggtagagt tgatggtcaa gtagacttat ttagaaatgc ccgtaatggt  20040
gttcttatta cagaaggtag tgttaaaggt ttacaaccat ctgtaggtcc caaacaagct  20100
agtcttaatg gagtcacatt aattggagaa gccgtaaaaa cacagttcaa ttattataag  20160
aaagttgatg gtgttgtcca acaattacct gaaacttact ttactcagag tagaaattta  20220
caagaattta aacccaggag tcaaatggaa attgatttct tagaattagc tatggatgaa  20280
ttcattgaac ggtataaatt agaaggctat gccttcgaac atatcgttta tggagatttt  20340
agtcatagtc agttaggtgg tttacatcta ctgattggac tagctaaacg ttttaaggaa  20400
tcaccttttg aattagaaga ttttattcct atggacagta cagttaaaaa ctatttcata  20460
acagatgcgc aaacaggttc atctaagtgt gtgtgttctg ttattgattt attacttgat  20520
gattttgttg aaataataaa atcccaagat ttatctgtag tttctaaggt tgtcaaagtg  20580
actattgact atacagaaat ttcatttatg ctttggtgta aagatggcca tgtagaaaca  20640
ttttacccaa aattacaatc tagtcaagcg tggcaaccgg gtgttgctat gcctaatctt  20700
tacaaaatgc aaagaatgct attagaaaag tgtgaccttc aaaattatgg tgatagtgca  20760
acattaccta aaggcataat gatgaatgtc gcaaaatata ctcaactgtg tcaatattta  20820
aacacattaa cattagctgt accctataat atgagagtta tacattttgg tgctggttct  20880
gataaaggag ttgcaccagg tacagctgtt ttaagacagt ggttgcctac gggtacgctg  20940
cttgtcgatt cagatcttaa tgactttgtc tctgatgcag attcaacttt gattggtgat  21000
tgtgcaactg tacatacagc taataaatgg gatctcatta ttagtgatat gtacgaccct  21060
aagactaaaa atgttacaaa agaaaatgac tctaaagagg gtttttcac ttacatttgt  21120
gggtttatac aacaaaagct agctcttgga ggttccgtgg ctataaagat aacagaacat  21180
tcttggaatg ctgatcttta taagctcatg ggacacttcg catggtggac agcctttgtt  21240
actaatgtga atgcgtcatc atctgaagca tttttaattg gatgtaatta tcttggcaaa  21300
ccacgcgaac aaatagatgg ttatgtcatg catgcaaatt acatattttg gaggaataca  21360
aatccaattc agttgtcttc ctattcttta tttgacatga gtaaatttcc ccttaaatta  21420
aggggtactg ctgttatgtc tttaaaagaa ggtcaaatca atgatatgat tttatctctt  21480
cttagtaaag gtagacttat aattagagaa aacaacagag ttgttatttc tagtgatgtt  21540
cttgttaaca actaaacgaa caatgtttgt ttttcttgtt ttattgccac tagtctctag  21600
tcagtgtgtt aatcttacaa ccagaactca attacccct gcatacacta attctttcac  21660
acgtggtgtt tattaccctg acaaagtttt cagatcctca gttttacatt caactcagga  21720
cttgttctta cctttctttt ccaatgttac ttggttccat gctatacatg tctctgggac  21780
caatggtact aagaggtttg ataaccctgt cctaccattt aatgatggtg tttattttgc  21840
ttccactgag aagtctaaca taataagagg ctggattttt ggtactactt tagattcgaa  21900
gacccagtcc ctacttattg ttaataacgc tactaatgtt gttattaaag tctgtgaatt  21960
tcaattttgt aatgatccat ttttgggtgt ttattaccac aaaaacaaca aaagttggat  22020
```

ggaaagtgag ttcagagttt attctagtgc gaataattgc acttttgaat atgtctctca 22080
gccttttctt atggaccttg aaggaaaaca gggtaatttc aaaaatctta gggaatttgt 22140
gtttaagaat attgatggtt attttaaaat atattctaag cacacgccta ttaatttagt 22200
gcgtgatctc cctcagggtt tttcggcttt agaaccattg gtagatttgc caataggtat 22260
taacatcact aggtttcaaa ctttacttgc tttacataga agttatttga ctcctggtga 22320
ttcttcttca ggttggacag ctggtgctgc agcttattat gtgggttatc ttcaacctag 22380
gacttttcta ttaaaatata atgaaaatgg aaccattaca gatgctgtag actgtgcact 22440
tgaccctctc tcagaaacaa agtgtacgtt gaaatccttc actgtagaaa aaggaatcta 22500
tcaaacttct aactttagag tccaaccaac agaatctatt gttagatttc ctaatattac 22560
aaacttgtgc ccttttggtg aagtttttaa cgccaccaga tttgcatctg tttatgcttg 22620
gaacaggaag agaatcagca actgtgttgc tgattattct gtcctatata attccgcatc 22680
attttccact tttaagtgtt atggagtgtc tcctactaaa ttaaatgatc tctgctttac 22740
taatgtctat gcagattcat ttgtaattag aggtgatgaa gtcagacaaa tcgctccagg 22800
gcaaactgga aagattgctg attataatta taaattacca gatgatttta caggctgcgt 22860
tatagcttgg aattctaaca atcttgattc taaggttggt ggtaattata attacctgta 22920
tagattgttt aggaagtcta atctcaaacc ttttgagaga gatatttcaa ctgaaatcta 22980
tcaggccggt agcacacctt gtaatggtgt tgaaggtttt aattgttact ttcctttaca 23040
atcatatggt ttccaaccca ctaatggtgt tggttaccaa ccatacagag tagtagtact 23100
ttcttttgaa cttctacatg caccagcaac tgtttgtgga cctaaaaagt ctactaattt 23160
ggttaaaaac aaatgtgtca atttcaactt caatggttta acaggcacag gtgttcttac 23220
tgagtctaac aaaaagtttc tgcctttcca acaatttggc agagacattg ctgacactac 23280
tgatgctgtc cgtgatccac agacacttga gattcttgac attacaccat gttcttttgg 23340
tggtgtcagt gttataacac caggaacaaa tacttctaac caggttgctg ttctttatca 23400
ggatgttaac tgcacagaag tccctgttgc tattcatgca gatcaactta ctcctacttg 23460
gcgtgtttat tctacaggtt ctaatgtttt tcaaacacgt gcaggctgtt taatagggggc 23520
tgaacatgtc aacaactcat atgagtgtga catacccatt ggtgcaggta tatgcgctag 23580
ttatcagact cagactaatt ctcctcggcg ggcacgtagt gtagctagtc aatccatcat 23640
tgcctacact atgtcacttg gtgcagaaaa ttcagttgct tactctaata actctattgc 23700
catacccaca aattttacta ttagtgttac cacagaaatt ctaccagtgt ctatgaccaa 23760
gacatcagta gattgtacaa tgtacatttg tggtgattca actgaatgca gcaatctttt 23820
gttgcaatat ggcagttttt gtacacaatt aaaccgtgct ttaactggaa tagctgttga 23880
acaagacaaa aacacccaag aagtttttgc acaagtcaaa caaatttaca aaacaccacc 23940
aattaaagat tttggtggtt ttaatttttc acaaatatta ccagatccat caaaaccaag 24000
caagaggtca tttattgaag atctactttt caacaaagtg acacttgcag atgctggctt 24060
catcaaacaa tatggtgatt gccttggtga tattgctgct agagacctca tttgtgcaca 24120
aaagtttaac ggccttactg ttttgccacc tttgctcaca gatgaaatga ttgctcaata 24180
cacttctgca ctgttagcgg gtacaatcac ttctggttgg acctttggtg caggtgctgc 24240
attacaaata ccatttgcta tgcaaatggc ttataggttt aatggtattg gagttacaca 24300
gaatgttctc tatgagaacc aaaaattgat tgccaaccaa tttaatagtg ctattggcaa 24360

-continued aattcaagac tcactttctt ccacagcaag tgcacttgga aaacttcaag atgtggtcaa 24420
ccaaaatgca caagctttaa acacgcttgt taaacaactt agctccaatt ttggtgcaat 24480
ttcaagtgtt ttaaatgata tcctttcacg tcttgacaaa gttgaggctg aagtgcaaat 24540
tgataggttg atcacaggca gacttcaaag tttgcagaca tatgtgactc aacaattaat 24600
tagagctgca gaaatcagag cttctgctaa tcttgctgct actaaaatgt cagagtgtgt 24660
acttggacaa tcaaaaagag ttgatttttg tggaaagggc tatcatctta tgtccttccc 24720
tcagtcagca cctcatggtg tagtcttctt gcatgtgact tatgtccctg cacaagaaaa 24780
gaacttcaca actgctcctg ccatttgtca tgatggaaaa gcacactttc ctcgtgaagg 24840
tgtctttgtt tcaaatggca cacactggtt tgtaacacaa aggaattttt atgaaccaca 24900
aatcattact acagacaaca catttgtgtc tggtaactgt gatgttgtaa taggaattgt 24960
caacaacaca gtttatgatc ctttgcaacc tgaattagac tcattcaagg aggagttaga 25020
taaatatttt aagaatcata catcaccaga tgttgattta ggtgacatct ctggcattaa 25080
tgcttcagtt gtaaacattc aaaaagaaat tgaccgcctc aatgaggttg ccaagaattt 25140
aaatgaatct ctcatcgatc tccaagaact tggaaagtat gagcagtata taaaatggcc 25200
atggtacatt tggctaggtt ttatagctgg cttgattgcc atagtaatgg tgacaattat 25260
gctttgctgt atgaccagtt gctgtagttg tctcaagggc tgttgttctt gtggatcctg 25320
ctgcaaattt gatgaagacg actctgagcc agtgctcaaa ggagtcaaat tacattacac 25380
ataaacgaac ttatggattt gtttatgaga atcttcacaa ttggaactgt aactttgaag 25440
caaggtgaaa tcaaggatgc tactccttca gattttgttc gcgctactgc aacgataccg 25500
atacaagcct cactcccttt cggatggctt attgttggcg ttgcacttct tgctgttttt 25560
cagagcgctt ccaaaatcat aaccctcaaa aagagatggc aactagcact ctccaagggt 25620
gttcactttg tttgcaactt gctgttgttg tttgtaacag tttactcaca ccttttgctc 25680
gttgctgctg gccttgaagc cccttttctc tatctttatg ctttagtcta cttcttgcag 25740
agtataaact ttgtaagaat aataatgagg ctttggcttt gctggaaatg ccgttccaaa 25800
aacccattac tttatgatgc caactatttt ctttgctggc atactaattg ttacgactat 25860
tgtatacctt acaatagtgt aacttcttca attgtcatta cttcaggtga tggcacaaca 25920
agtcctattt ctgaacatga ctaccagatt ggtggttata ctgaaaaatg ggaatctgga 25980
gtaaaagact gtgttgtatt acacagttac ttcacttcag actattacca gctgtactca 26040
actcaattga gtacagacac tggtgttgaa catgttacct tcttcatcta caataaaatt 26100
gttgatgagc ctgaagaaca tgtccaaatt cacacaatcg acggttcatc cggagttgtt 26160
aatccagtaa tggaaccaat ttatgatgaa ccgacgacga ctactagcgt gcctttgtaa 26220
gcacaagctg atgagtacga acttatgtac tcattcgttt cggaagagac aggtacgtta 26280
atagttaata gcgtacttct tttcttgct ttcgtggtat tcttgctagt tacactagcc 26340
atccttactg cgcttcgatt gtgtgcgtac tgctgcaata ttgttaacgt gagtcttgta 26400
aaaccttctt tttacgttta ctctcgtgtt aaaaatctga attcttctag agttcctgat 26460
cttctggtct aaacgaacta aatattatat tagtttttct gtttggaact ttaattttag 26520
ccatggcaga ttccaacggt actattaccg ttgaagagct taaaaagctc cttgaacaat 26580
ggaacctagt aataggtttc ctattcctta catggatttg tcttctacaa tttgcctatg 26640
ccaacaggaa taggtttttg tatataatta agttaatttt cctctggctg ttatggccag 26700
taactttagc ttgttttgtg cttgctgctg tttacagaat aaattggatc accggtggaa 26760
ttgctatcgc aatggcttgt cttgtaggct tgatgtggct cagctacttc attgcttctt 26820
tcagactgtt tgcgcgtacg cgttccatgt ggtcattcaa tccagaaact aacattcttc 26880
tcaacgtgcc actccatggc actattctga ccagaccgct tctagaaagt gaactcgtaa 26940
tcggagctgt gatccttcgt ggacatcttc gtattgctgg acaccatcta ggacgctgtg 27000
acatcaagga cctgcctaaa gaaatcactg ttgctacatc acgaacgctt tcttattaca 27060
aattgggagc ttcgcagcgt gtagcaggtg actcaggttt tgctgcatac agtcgctaca 27120
ggattggcaa ctataaatta aacacagacc attccagtag cagtgacaat attgctttgc 27180
ttgtacagta agtgacaaca gatgtttcat ctcgttgact ttcaggttac tatagcagag 27240
atattactaa ttattatgag gacttttaaa gtttccattt ggaatcttga ttacatcata 27300
aacctcataa ttaaaaattt atctaagtca ctaactgaga ataaatattc tcaattagat 27360
gaagagcaac caatggagat tgattaaacg aacatgaaaa ttattctttt cttggcactg 27420
ataacactcg ctacttgtga gctttatcac taccaagagt gtgttagagg tacaacagta 27480
cttttaaaag aaccttgctc ttctggaaca tacgagggca attcaccatt tcatcctcta 27540
gctgataaca aatttgcact gacttgcttt agcactcaat ttgcttttgc ttgtcctgac 27600
ggcgtaaaac acgtctatca gttacgtgcc agatcagttt cacctaaact gttcatcaga 27660
caagaggaag ttcaagaact ttactctcca atttttctta ttgttgcggc aatagtgttt 27720
ataacacttt gcttcacact caaaagaaag acagaatgat tgaactttca ttaattgact 27780
tctatttgtg ctttttagcc tttctgctat tccttgtttt aattatgctt attatctttt 27840
ggttctcact tgaactgcaa gatcataatg aaacttgtca cgcctaaacg aacatgaaat 27900
ttcttgtttt cttaggaatc atcacaactg tagctgcatt tcaccaagaa tgtagtttac 27960
agtcatgtac tcaacatcaa ccatatgtag ttgatgaccc gtgtcctatt cacttctatt 28020
ctaaatggta tattagagta ggagctagaa aatcagcacc tttaattgaa ttgtgcgtgg 28080
atgaggctgg ttctaaatca cccattcagt acatcgatat cggtaattat acagtttcct 28140
gtttaccttt tacaattaat tgccaggaac ctaaattggg tagtcttgta gtgcgttgtt 28200
cgttctatga agacttttta gagtatcatg acgttcgtgt tgttttagat ttcatctaaa 28260
cgaacaaact aaaatgtctg ataatggacc ccaaaatcag cgaaatgcac cccgcattac 28320
gtttggtgga ccctcagatt caactggcag taaccagaat ggagaacgca gtggggcgcg 28380
atcaaaacaa cgtcggcccc aaggtttacc caataatact gcgtcttggt tcaccgctct 28440
cactcaacat ggcaaggaag accttaaatt ccctcgagga caaggcgttc caattaacac 28500
caatagcagt ccagatgacc aaattggcta ctaccgaaga gctaccagac gaattcgtgg 28560
tggtgacggt aaaatgaaag atctcagtcc aagatggtat ttctactacc taggaactgg 28620
gccagaagct ggacttccct atggtgctaa caaagacggc atcatatggg ttgcaactga 28680
gggagccttg aatacaccaa aagatcacat tggcacccgc aatcctgcta acaatgctgc 28740
aatcgtgcta caacttcctc aaggaacaac attgccaaaa ggcttctacg cagaagggag 28800
cagaggcggc agtcaagcct cttctcgttc ctcatcacgt agtcgcaaca gttcaagaaa 28860
ttcaactcca ggcagcagta ggggaacttc tcctgctaga atggctggca atggcggtga 28920
tgctgctctt gctttgctgc tgcttgacag attgaaccag cttgagagca aaatgtctgg 28980
taaaggccaa caacaacaag gccaaactgt cactaagaaa tctgctgctg aggcttctaa 29040
gaagcctcgg caaaaacgta ctgccactaa agcatacaat gtaacacaag ctttcggcag 29100

-continued

```
acgtggtcca gaacaaaccc aaggaaattt tggggaccag gaactaatca gacaaggaac  29160

tgattacaaa cattggccgc aaattgcaca atttgccccc agcgcttcag cgttcttcgg  29220

aatgtcgcgc attggcatgg aagtcacacc ttcgggaacg tggttgacct acacaggtgc  29280

catcaaattg gatgacaaag atccaaattt caaagatcaa gtcattttgc tgaataagca  29340

tattgacgca tacaaaacat tcccaccaac agagcctaaa aaggacaaaa agaagaaggc  29400

tgatgaaact caagccttac cgcagagaca gaagaaacag caaactgtga ctcttcttcc  29460

tgctgcagat ttggatgatt tctccaaaca attgcaacaa tccatgagca gtgctgactc  29520

aactcaggcc taaactcatg cagaccacac aaggcagatg ggctatataa acgttttcgc  29580

ttttccgttt acgatatata gtctactctt gtgcagaatg aattctcgta actacatagc  29640

acaagtagat gtagttaact ttaatctcac atagcaatct ttaatcagtg tgtaacatta  29700

gggaggactt gaaagagcca ccacattttc accgaggcca cgcggagtac gatcgagtgt  29760

acagtgaaca atgctaggga gagctgccta tatggaagag ccctaatgtg taaaattaat  29820

tttagtagtg ctatccccat gtgattttaa tagcttctta ggagaatgac aaaaaaaaaa  29880

aaaaaaaaaa aaaaaaaaaa aaa                                         29903
```

<210> SEQ ID NO 2
<211> LENGTH: 29882
<212> TYPE: DNA
<213> ORGANISM: Human coronavirus

<400> SEQUENCE: 2

```
attaaaggtt tataccttcc caggtaacaa accaaccaac tttcgatctc ttgtagatct     60

gttctctaaa cgaactttaa aatctgtgtg gctgtcactc ggctgcatgc ttagtgcact    120

cacgcagtat aattaataac taattactgt cgttgacagg acacgagtaa ctcgtctatc    180

ttctgcaggc tgcttacggt ttcgtccgtg ttgcagccga tcatcagcac atctaggttt    240

cgtccgggtg tgaccgaaag gtaagatgga gagccttgtc cctggtttca acgagaaaac    300

acacgtccaa ctcagtttgc ctgttttaca ggttcgcgac gtgctcgtac gtggctttgg    360

agactccgtg gaggaggtct tatcagaggc acgtcaacat cttaaagatg gcacttgtgg    420

cttagtagaa gttgaaaaag gcgttttgcc tcaacttgaa cagccctatg tgttcatcaa    480

acgttcggat gctcgaactg cacctcatgg tcatgttatg gttgagctgg tagcagaact    540

cgaaggcatt cagtacggtc gtagtggtga gacacttggt gtccttgtcc ctcatgtggg    600

cgaaatacca gtggcttacc gcaaggttct tcttcgtaag aacggtaata aaggagctgg    660

tggccatagt tacggcgccg atctaaagtc atttgactta ggcgacgagc ttggcactga    720

tccttatgaa gattttcaag aaaactggaa cactaaacat agcagtggtg ttacccgtga    780

actcatgcgt gagcttaacg gaggggcata cactcgctat gtcgataaca acttctgtgg    840

ccctgatggc taccctcttg agtgcattaa agaccttcta gcacgtgctg gtaaagcttc    900

atgcactttg tccgaacaac tggactttat tgacactaag aggggtgtat actgctgccg    960

tgaacatgag catgaaattg cttggtacac ggaacgttct gaaaagagct atgaattgca   1020

gacacctttt gaaattaaat tggcaaagaa atttgacacc ttcaatgggg aatgtccaaa   1080

ttttgtattt cccttaaatt ccataatcaa gactattcaa ccaagggttg aaaagaaaaa   1140

gcttgatggc tttatgggta gaattcgatc tgtctatcca gttgcgtcac caaatgaatg   1200

caaccaaatg tgcctttcaa ctctcatgaa gtgtgatcat tgtggtgaaa cttcatggca   1260

gacgggcgat tttgttaaag ccacttgcga attttgtggc actgagaatt tgactaaaga   1320
```

aggtgccact acttgtggtt acttacccca aaatgctgtt gttaaaattt attgtccagc 1380
atgtcacaat tcagaagtag gacctgagca tagtcttgcc gaataccata atgaatctgg 1440
cttgaaaacc attcttcgta agggtggtcg cactattgcc tttggaggct gtgtgttctc 1500
ttatgttggt tgccataaca agtgtgccta ttgggttcca cgtgctagcg ctaacatagg 1560
ttgtaaccat acaggtgttg ttggagaagg ttccgaaggt cttaatgaca accttcttga 1620
aatactccaa aaagagaaag tcaacatcaa tattgttggt gactttaaac ttaatgaaga 1680
gatcgccatt attttggcat ctttttctgc ttccacaagt gcttttgtgg aaactgtgaa 1740
aggtttggat tataaagcat tcaaacaaat tgttgaatcc tgtggtaatt ttaaagttac 1800
aaaaggaaaa gctaaaaaag gtgcctggaa tattggtgaa cagaaatcaa tactgagtcc 1860
tctttatgca tttgcatcag aggctgctcg tgttgtacga tcaattttct cccgcactct 1920
tgaaactgct caaaattctg tgcgtgtttt acagaaggcc gctataacaa tactagatgg 1980
aatttcacag tattcactga gactcattga tgctatgatg ttcacatctg atttggctac 2040
taacaatcta gttgtaatgg cctacattac aggtggtgtt gttcagttga cttcgcagtg 2100
gctaactaac atctttggca ctgtttatga aaaactcaaa cccgtccttg attggcttga 2160
agagaagttt aaggaaggtg tagagtttct tagagacggt tgggaaattg ttaaatttat 2220
ctcaacctgt gcttgtgaaa ttgtcggtgg acaaattgtc acctgtgcaa aggaaattaa 2280
ggagagtgtt cagacattct ttaagcttgt aaataaattt ttggctttgt gtgctgactc 2340
tatcattatt ggtggagcta aacttaaagc cttgaattta ggtgaaacat ttgtcacgca 2400
ctcaaaggga ttgtacagaa agtgtgttaa atccagagaa gaaactggcc tactcatgcc 2460
tctaaaagcc ccaaaagaaa ttatcttctt agagggagaa acacttccca cagaagtgtt 2520
aacagaggaa gttgtcttga aaactggtga tttacaacca ttagaacaac ctactagtga 2580
agctgttgaa gctccattgg ttggtacacc agtttgtatt aacgggctta tgttgctcga 2640
aatcaaagac acagaaaagt actgtgccct tgcacctaat atgatggtaa caaacaatac 2700
cttcacactc aaaggcggtg caccaacaaa ggttactttt ggtgatgaca ctgtgataga 2760
agtgcaaggt tacaagagtg tgaatatcac ttttgaactt gatgaaagga ttgataaagt 2820
acttaatgag aagtgctctg cctatacagt tgaactcggt acagaagtaa atgagttcgc 2880
ctgtgttgtg gcagatgctg tcataaaaac tttgcaacca gtatctgaat tacttacacc 2940
actgggcatt gatttagatg agtggagtat ggctacatac tacttatttg atgagtctgg 3000
tgagtttaaa ttggcttcac atatgtattg ttctttctac cctccagatg aggatgaaga 3060
agaaggtgat tgtgaagaag aagagtttga gccatcaact caatatgagt atggtactga 3120
agatgattac caaggtaaac ctttggaatt tggtgccact tctgctgctc ttcaacctga 3180
agaagagcaa gaagaagatt ggttagatga tgatagtcaa caaactgttg gtcaacaaga 3240
cggcagtgag gacaatcaga caactactat tcaaacaatt gttgaggttc aacctcaatt 3300
agagatggaa cttacaccag ttgttcagac tattgaagtg aatagtttta gtggttattt 3360
aaaacttact gacaatgtat acattaaaaa tgcagacatt gtggaagaag ctaaaaaggt 3420
aaaaccaaca gtggttgtta atgcagccaa tgtttacctt aaacatggag gaggtgttgc 3480
aggagcctta aataaggcta ctaacaatgc catgcaagtt gaatctgatg attacatagc 3540
tactaatgga ccacttaaag tgggtggtag ttgtgtttta agcggacaca atcttgctaa 3600
acactgtctt catgttgtcg gcccaaatgt taacaaaggt gaagacattc aacttcttaa 3660

-continued gagtgcttat gaaaatttta atcagcacga agttctactt gcaccattat tatcagctgg 3720
tatttttggt gctgacccta tacattcttt aagagtttgt gtagatactg ttcgcacaaa 3780
tgtctactta gctgtctttg ataaaaatct ctatgacaaa cttgtttcaa gctttttgga 3840
aatgaagagt gaaaagcaag ttgaacaaaa gatcgctgag attcctaaag aggaagttaa 3900
gccatttata actgaaagta aaccttcagt tgaacagaga aaacaagatg ataagaaaat 3960
caaagcttgt gttgaagaag ttacaacaac tctggaagaa actaagttcc tcacagaaaa 4020
cttgttactt tatattgaca ttaatggcaa tcttcatcca gattctgcca ctcttgttag 4080
tgacattgac atcactttct taaagaaaga tgctccatat atagtgggtg atgttgttca 4140
agagggtgtt ttaactgctg tggttatacc tactaaaaag gctggtggca ctactgaaat 4200
gctagcgaaa gctttgagaa aagtgccaac agacaattat ataaccactt acccgggtca 4260
gggtttaaat ggttacactg tagaggaggc aaagacagtg cttaaaaagt gtaaaagtgc 4320
cttttacatt ctaccatcta ttatctctaa tgagaagcaa gaaattcttg gaactgtttc 4380
ttggaatttg cgagaaatgc ttgcacatgc agaagaaaca cgcaaattaa tgcctgtctg 4440
tgtggaaact aaagccatag tttcaactat acagcgtaaa tataagggta ttaaaataca 4500
agagggtgtg gttgattatg gtgctagatt ttacttttac accagtaaaa caactgtagc 4560
gtcacttatc aacacactta acgatctaaa tgaaactctt gttacaatgc cacttggcta 4620
tgtaacacat ggcttaaatt tggaagaagc tgctcggtat atgagatctc tcaaagtgcc 4680
agctacagtt tctgtttctt cacctgatgc tgttacagcg tataatggtt atcttacttc 4740
ttcttctaaa acacctgaag aacattttat tgaaaccatc tcacttgctg gttcctataa 4800
agattggtcc tattctggac aatctacaca actaggtata gaatttctta agagaggtga 4860
taaaagtgta tattacacta gtaatcctac cacattccac ctagatggtg aagttatcac 4920
ctttgacaat cttaagacac ttctttcttt gagagaagtg aggactatta aggtgtttac 4980
aacagtagac aacattaacc tccacacgca agttgtggac atgtcaatga catatggaca 5040
acagtttggt ccaacttatt tggatggagc tgatgttact aaaataaaac ctcataattc 5100
acatgaaggt aaaacatttt atgttttacc taatgatgac actctacgtg ttgaggcttt 5160
tgagtactac cacacaactg atcctagttt tctgggtagg tacatgtcag cattaaatca 5220
cactaaaaag tggaaatacc cacaagttaa tggtttaact tctattaaat gggcagataa 5280
caactgttat cttgccactg cattgttaac actccaacaa atagagttga agtttaatcc 5340
acctgctcta caagatgctt attacagagc aagggctggt gaagctgcta actttttgtgc 5400 acttatctta gcctactgta ataagacagt aggtgagtta ggtgatgtta gagaaacaat 5460
gagttacttg tttcaacatg ccaatttaga ttcttgcaaa agagtcttga acgtggtgtg 5520
taaaacttgt ggacaacagc agacaaccct taagggtgta gaagctgtta tgtacatggg 5580
cacactttct tatgaacaat ttaagaaagg tgttcagata ccttgtacgt gtggtaaaca 5640
agctacaaaa tatctagtac aacaggagtc accttttgtt atgatgtcag caccacctgc 5700
tcagtatgaa cttaagcatg gtacatttac ttgtgctagt gagtacactg gtaattacca 5760
gtgtggtcac tataaacata taacttctaa agaaactttg tattgcatag acggtgcttt 5820
acttacaaag tcctcagaat acaaaggtcc tattacggat gttttctaca aagaaaacag 5880
ttacacaaca accataaaac cagttactta taaattggat ggtgttgttt gtacagaaat 5940
tgaccctaag ttggacaatt attataagaa agacaattct tatttcacag agcaaccaat 6000
tgatcttgta ccaaaccaac catatccaaa cgcaagcttc gataatttta agtttgtatg 6060
tgataatatc aaatttgctg atgatttaaa ccagttaact ggttataaga aacctgcttc 6120
aagagagctt aaagttacat ttttccctga cttaaatggt gatgtggtgg ctattgatta 6180
taaacactac acaccctctt ttaagaaagg agctaaattg ttacataaac ctattgtttg 6240
gcatgttaac aatgcaacta ataaagccac gtataaacca aatacctggt gtatacgttg 6300
tctttggagc acaaaaccag ttgaaacatc aaattcgttt gatgtactga agtcagagga 6360
cgcgcaggga atggataatc ttgcctgcga agatctaaaa ccagtctctg aagaagtagt 6420
ggaaaatcct accatacaga aagacgttct tgagtgtaat gtgaaaacta ccgaagttgt 6480
aggagacatt atacttaaac cagcaaataa tagtttaaaa attacagaag aggttggcca 6540
cacagatcta atggctgctt atgtagacaa ttctagtctt actattaaga aacctaatga 6600
attatctaga gtattaggtt tgaaaaccct tgctactcat ggtttagctg ctgttaatag 6660
tgtcccttgg gatactatag ctaattatgc taagcctttt cttaacaaag ttgttagtac 6720
aactactaac atagttacac ggtgtttaaa ccgtgtttgt actaattata tgccttattt 6780
ctttacttta ttgctacaat tgtgtacttt tactagaagt acaaattcta gaattaaagc 6840
atctatgccg actactatag caaagaatac tgttaagagt gtcggtaaat tttgtctaga 6900
ggcttcattt aattatttga agtcacctaa tttttctaaa ctgataaata ttataatttg 6960
gtttttacta ttaagtgttt gcctaggttc tttaatctac tcaaccgctg ctttaggtgt 7020
tttaatgtct aatttaggca tgccttctta ctgtactggt tacagagaag gctatttgaa 7080
ctctactaat gtcactattg caacctactg tactggttct ataccttgta gtgtttgtct 7140
tagtggttta gattctttag acacctatcc ttctttagaa actatacaaa ttaccatttc 7200
atcttttaaa tgggatttaa ctgcttttgg cttagttgca gagtggtttt tggcatatat 7260
tcttttcact aggtttttct atgtacttgg attggctgca atcatgcaat tgtttttcag 7320
ctattttgca gtacatttta ttagtaattc ttggcttatg tggttaataa ttaatcttgt 7380
acaaatggcc ccgatttcag ctatggttag aatgtacatc ttctttgcat cattttatta 7440
tgtatggaaa agttatgtgc atgttgtaga cggttgtaat tcatcaactt gtatgatgtg 7500
ttacaaacgt aatagagcaa caagagtcga atgtacaact attgttaatg gtgttagaag 7560
gtccttttat gtctatgcta atggaggtaa aggcttttgc aaactacaca attggaattg 7620
tgttaattgt gatacattct gtgctggtag tacatttatt agtgatgaag ttgcgagaga 7680
cttgtcacta cagtttaaaa gaccaataaa tcctactgac cagtcttctt acatcgttga 7740
tagtgttaca gtgaagaatg gttccatcca tctttacttt gataaagctg gtcaaaagac 7800
ttatgaaaga cattctctct ctcattttgt taacttagac aacctgagag ctaataacac 7860
taaaggttca ttgcctatta atgttatagt ttttgatggt aaatcaaaat gtgaagaatc 7920
atctgcaaaa tcagcgtctg tttactacag tcagcttatg tgtcaaccta tactgttact 7980
agatcaggca ttagtgtctg atgttggtga tagtgcggaa gttgcagtta aaatgtttga 8040
tgcttacgtt aatacgtttt catcaacttt taacgtacca atggaaaaac tcaaaacact 8100
agttgcaact gcagaagctg aacttgcaaa gaatgtgtcc ttagacaatg tcttatctac 8160
ttttatttca gcagctcggc aagggtttgt tgattcagat gtagaaacta aagatgttgt 8220
tgaatgtctt aaattgtcac atcaatctga catagaagtt actggcgata gttgtaataa 8280
ctatatgctc acctataaca aagttgaaaa catgacaccc cgtgaccttg gtgcttgtat 8340
tgactgtagt gcgcgtcata ttaatgcgca ggtagcaaaa agtcacaaca ttgctttgat 8400
atggaacgtt aaagatttca tgtcattgtc tgaacaacta cgaaaacaaa tacgtagtgc 8460
tgctaaaaag aataacttac cttttaagtt gacatgtgca actactagac aagttgttaa 8520
tgttgtaaca acaaagatag cacttaaggg tggtaaaatt gttaataatt ggttgaagca 8580
gttaattaaa gttacacttg tgttcctttt tgttgctgct attttctatt taataacacc 8640
tgttcatgtc atgtctaaac atactgactt ttcaagtgaa atcataggat acaaggctat 8700
tgatggtggt gtcactcgtg acatagcatc tacagatact tgttttgcta acaaacatgc 8760
tgattttgac acatggttta gtcagcgtgg tggtagttat actaatgaca aagcttgccc 8820
attgattgct gcagtcataa caagagaagt gggttttgtc gtgcctggtt tgcctggcac 8880
gatattacgc acaactaatg gtgacttttt gcatttctta cctagagttt ttagtgcagt 8940
tggtaacatc tgttacacac catcaaaact tatagagtac actgactttg caacatcagc 9000
ttgtgttttg gctgctgaat gtacaatttt taaagatgct tctggtaagc cagtaccata 9060
ttgttatgat accaatgtac tagaaggttc tgttgcttat gaaagtttac gccctgacac 9120
acgttatgtg ctcatggatg gctctattat tcaatttcct aacacctacc ttgaaggttc 9180
tgttagagtg gtaacaactt ttgattctga gtactgtagg cacggcactt gtgaaagatc 9240
agaagctggt gtttgtgtat ctactagtgg tagatgggta cttaacaatg attattacag 9300
atctttacca ggagttttct gtggtgtaga tgctgtaaat ttacttacta atatgtttac 9360
accactaatt caacctattg gtgctttgga catatcagca tctatagtag ctggtggtat 9420
tgtagctatc gtagtaacat gccttgccta ctattttatg aggtttagaa gagcttttgg 9480
tgaatacagt catgtagttg cctttaatac tttactattc cttatgtcat tcactgtact 9540
ctgtttaaca ccagtttact cattcttacc tggtgtttat tctgttattt acttgtactt 9600
gacattttat cttactaatg atgtttcttt tttagcacat attcagtgga tggttatgtt 9660
cacaccttta gtacctttct ggataacaat tgcttatatc atttgtattt ccacaaagca 9720
tttctattgg ttctttagta attacctaaa gagacgtgta gtctttaatg gtgtttcctt 9780
tagtactttt gaagaagctg cgctgtgcac ctttttgtta aataaagaaa tgtatctaaa 9840
gttgcgtagt gatgtgctat tacctcttac gcaatataat agatacttag ctctttataa 9900
taagtacaag tattttagtg gagcaatgga tacaactagc tacagagaag ctgcttgttg 9960
tcatctcgca aaggctctca atgacttcag taactcaggt tctgatgttc tttaccaacc 10020
accacaaacc tctatcacct cagctgtttt gcagagtggt tttagaaaaa tggcattccc 10080
atctggtaaa gttgagggtt gtatggtaca agtaacttgt ggtacaacta cacttaacgg 10140
tctttggctt gatgacgtag tttactgtcc aagacatgtg atctgcacct ctgaagacat 10200
gcttaaccct aattatgaag atttactcat tcgtaagtct aatcataatt tcttggtaca 10260
ggctggtaat gttcaactca gggttattgg acattctatg caaaattgtg tacttaagct 10320
taaggttgat acagccaatc ctaagacacc taagtataag tttgttcgca ttcaaccagg 10380
acagactttt tcagtgttag cttgttacaa tggttcacca tctggtgttt accaatgtgc 10440
tatgaggccc aatttcacta ttaagggttc attccttaat ggttcatgtg gtagtgttgg 10500
ttttaacata gattatgact gtgtctcttt ttgttacatg caccatatgg aattaccaac 10560
tggagttcat gctggcacag acttagaagg taacttttat ggaccttttg ttgacaggca 10620
aacagcacaa gcagctggta cggacacaac tattacagtt aatgttttag cttggttgta 10680
cgctgctgtt ataaatggag acaggtggtt tctcaatcga tttaccacaa ctcttaatga 10740
ctttaacctt gtggctatga agtacaatta tgaacctcta acacaagacc atgttgacat 10800

-continued

```
actaggacct ctttctgctc aaactggaat tgccgtttta gatatgtgtg cttcattaaa  10860
agaattactg caaaatggta tgaatggacg taccatattg ggtagtgctt tattagaaga  10920
tgaatttaca cctttttgatg ttgttagaca atgctcaggt gttactttcc aaagtgcagt  10980
gaaaagaaca atcaagggta cacaccactg gttgttactc acaattttga cttcactttt  11040
agttttagtc cagagtactc aatggtcttt gttctttttt ttgtatgaaa atgccttttt  11100
acctttttgct atgggtatta ttgctatgtc tgcttttgca atgatgtttg tcaaacataa  11160
gcatgcattt ctctgtttgt ttttgttacc ttctcttgcc actgtagctt attttaatat  11220
ggtctatatg cctgctagtt gggtgatgcg tattatgaca tggttggata tggttgatac  11280
tagtttgtct ggttttaagc taaaagactg tgttatgtat gcatcagctg tagtgttact  11340
aatccttatg acagcaagaa ctgtgtatga tgatggtgct aggagagtgt ggacacttat  11400
gaatgtcttg acactcgttt ataaagttta ttatggtaat gctttagatc aagccatttc  11460
catgtgggct cttataatct ctgttacttc taactactca ggtgtagtta caactgtcat  11520
gtttttggcc agaggtattg tttttatgtg tgttgagtat tgccctattt tcttcataac  11580
tggtaataca cttcagtgta taatgctagt ttattgtttc ttaggctatt tttgtacttg  11640
ttactttggc ctcttttgtt tactcaaccg ctactttaga ctgactcttg gtgtttatga  11700
ttacttagtt tctacacagg agtttagata tatgaattca cagggactac tcccacccaa  11760
gaatagcata gatgccttca aactcaacat taaattgttg ggtgttggtg gcaaaccttg  11820
tatcaaagta gccactgtac agtctaaaat gtcagatgta aagtgcacat cagtagtctt  11880
actctcagtt ttgcaacaac tcagagtaga atcatcatct aaattgtggg ctcaatgtgt  11940
ccagttacac aatgacattc tcttagctaa agatactact gaagcctttg aaaaaatggt  12000
ttcactactt tctgttttgc tttccatgca gggtgctgta gacataaaca agctttgtga  12060
agaaatgctg gacaacaggg caaccttaca agctatagcc tcagagttta gttcccttcc  12120
atcatatgca gcttttgcta ctgctcaaga agcttatgag caggctgttg ctaatggtga  12180
ttctgaagtt gttcttaaaa agttgaagaa gtctttgaat gtggctaaat ctgaatttga  12240
ccgtgatgca gccatgcaac gtaagttgga aaagatggct gatcaagcta tgacccaaat  12300
gtataaacag gctagatctg aggacaagag ggcaaaagtt actagtgcta tgcagacaat  12360
gcttttcact atgcttagaa agttggataa tgatgcactc aacaacatta tcaacaatgc  12420
aagagatggt tgtgttccct tgaacataat acctcttaca acagcagcca aactaatggt  12480
tgtcatacca gactataaca catataaaaa tacgtgtgat ggtacaacat ttacttatgc  12540
atcagcattg tgggaaatcc aacaggttgt agatgcagat agtaaaattg ttcaacttag  12600
tgaaattagt atggacaatt cacctaattt agcatggcct cttattgtaa cagctttaag  12660
ggccaattct gctgtcaaat tacagaataa tgagcttagt cctgttgcac tacgacagat  12720
gtcttgtgct gccggtacta cacaaactgc ttgcactgat gacaatgcgt tagcttacta  12780
caacacaaca aagggaggta ggtttgtact tgcactgtta tccgatttac aggatttgaa  12840
atgggctaga ttccctaaga gtgatggaac tggtactatc tatacagaac tggaaccacc  12900
ttgtaggttt gttacagaca cacctaaagg tcctaaagtg aagtatttat actttattaa  12960
aggattaaac aacctaaata gaggtatggt acttggtagt ttagctgcca cagtacgtct  13020
acaagctggt aatgcaacag aagtgcctgc caattcaact gtattatctt tctgtgcttt  13080
tgctgtagat gctgctaaag cttacaaaga ttatctagct agtgggggac aaccaatcac  13140
```

-continued

```
taattgtgtt aagatgttgt gtacacacac tggtactggt caggcaataa cagttacacc  13200
ggaagccaat atggatcaag aatcctttgg tggtgcatcg tgttgtctgt actgccgttg  13260
ccacatagat catccaaatc ctaaaggatt ttgtgactta aaaggtaagt atgtacaaat  13320
acctacaact tgtgctaatg accctgtggg ttttacactt aaaaacacag tctgtaccgt  13380
ctgcggtatg tggaaaggtt atggctgtag ttgtgatcaa ctccgcgaac ccatgcttca  13440
gtcagctgat gcacaatcgt ttttaaacgg gtttgcggtg taagtgcagc ccgtcttaca  13500
ccgtgcggca caggcactag tactgatgtc gtatacaggg cttttgacat ctacaatgat  13560
aaagtagctg gttttgctaa attcctaaaa actaattgtt gtcgcttcca agaaaaggac  13620
gaagatgaca atttaattga ttcttacttt gtagttaaga gacacacttt ctctaactac  13680
caacatgaag aaacaattta taatttactt aaggattgtc cagctgttgc taaacatgac  13740
ttctttaagt ttagaataga cggtgacatg gtaccacata tatcacgtca acgtcttact  13800
aaatacacaa tggcagacct cgtctatgct ttaaggcatt ttgatgaagg taattgtgac  13860
acattaaaag aaatacttgt cacatacaat tgttgtgatg atgattattt caataaaaag  13920
gactggtatg attttgtaga aaacccagat atattacgcg tatacgccaa cttaggtgaa  13980
cgtgtacgcc aagctttgtt aaaaacagta caattctgtg atgccatgcg aaatgctggt  14040
attgttggtg tactgacatt agataatcaa gatctcaatg gtaactggta tgatttcggt  14100
gatttcatac aaaccacgcc aggtagtgga gttcctgttg tagattctta ttattcattg  14160
ttaatgccta tattaacctt gaccagggct ttaactgcag agtcacatgt tgacactgac  14220
ttaacaaagc cttacattaa gtgggatttg ttaaaatatg acttcacgga agagaggtta  14280
aaactctttg accgttattt taaatattgg gatcagacat accacccaaa ttgtgttaac  14340
tgtttggatg acagatgcat tctgcattgt gcaaacttta atgttttatt ctctacagtg  14400
ttcccaccta caagttttgg accactagtg agaaaaatat ttgttgatgg tgttccattt  14460
gtagtttcaa ctggatacca cttcagagag ctaggtgttg tacataatca ggatgtaaac  14520
ttacatagct ctagacttag ttttaaggaa ttacttgtgt atgctgctga ccctgctatg  14580
cacgctgctt ctggtaatct attactagat aaacgcacta cgtgcttttc agtagctgca  14640
cttactaaca atgttgcttt tcaaactgtc aaacccggta attttaacaa agacttctat  14700
gactttgctg tgtctaaggg tttctttaag gaaggaagtt ctgttgaatt aaaacacttc  14760
ttctttgctc aggatggtaa tgctgctatc agcgattatg actactatcg ttataatcta  14820
ccaacaatgt gtgatatcag acaactacta tttgtagttg aagttgttga taagtacttt  14880
gattgttacg atggtggctg tattaatgct aaccaagtca tcgtcaacaa cctagacaaa  14940
tcagctggtt ttccatttaa taaatggggt aaggctagac tttattatga ttcaatgagt  15000
tatgaggatc aagatgcact tttcgcatat acaaaacgta atgtcatccc tactataact  15060
caaatgaatc ttaagtatgc cattagtgca aagaatagag ctcgcaccgt agctggtgtc  15120
tctatctgta gtactatgac caatagacag tttcatcaaa aattattgaa atcaatagcc  15180
gccactagag gagctactgt agtaattgga acaagcaaat tctatggtgg ttggcacaac  15240
atgttaaaaa ctgtttatag tgatgtagaa aaccctcacc ttatgggttg ggattatcct  15300
aaatgtgata gagccatgcc taacatgctt agaattatgg cctcacttgt tcttgctcgc  15360
aaacatacaa cgtgttgtag cttgtcacac cgtttctata gattagctaa tgagtgtgct  15420
caagtattga gtgaaatggt catgtgtggc ggttcactat atgttaaacc aggtggaacc  15480
tcatcaggag atgccacaac tgcttatgct aatagtgttt ttaacatttg tcaagctgtc  15540
```

-continued

```
acggccaatg ttaatgcact tttatctact gatggtaaca aaattgccga taagtatgtc  15600
cgcaatttac aacacagact ttatgagtgt ctctatagaa atagagatgt tgacacagac  15660
tttgtgaatg agttttacgc atatttgcgt aaacatttct caatgatgat actctctgac  15720
gatgctgttg tgtgtttcaa tagcacttat gcatctcaag gtctagtggc tagcataaag  15780
aactttaagt cagttcttta ttatcaaaac aatgttttta tgtctgaagc aaaatgttgg  15840
actgagactg accttactaa aggacctcat gaattttgct ctcaacatac aatgctagtt  15900
aaacagggtg atgattatgt gtaccttcct tacccagatc catcaagaat cctaggggcc  15960
ggctgttttg tagatgatat cgtaaaaaca gatggtacac ttatgattga acggttcgtg  16020
tctttagcta tagatgctta cccacttact aaacatccta atcaggagta tgctgatgtc  16080
tttcatttgt acttacaata cataagaaag ctacatgatg agttaacagg acacatgtta  16140
gacatgtatt ctgttatgct tactaatgat aacacttcaa ggtattggga acctgagttt  16200
tatgaggcta tgtacacacc gcatacagtc ttacaggctg ttggggcttg tgttctttgc  16260
aattcacaga cttcattaag atgtggtgct tgcatacgta gaccattctt atgttgtaaa  16320
tgctgttacg accatgtcat atcaacatca cataaattag tcttgtctgt taatccgtat  16380
gtttgcaatg ctccaggttg tgatgtcaca gatgtgactc aactttactt aggaggtatg  16440
agctattatt gtaaatcaca taaaccaccc attagttttc cattgtgtgc taatggacaa  16500
gtttttggtt tatataaaaa tacatgtgtt ggtagcgata atgttactga ctttaatgca  16560
attgcaacat gtgactggac aaatgctggt gattacattt tagctaacac ctgtactgaa  16620
agactcaagc tttttgcagc agaaacgctc aaagctactg aggagacatt taaactgtct  16680
tatggtattg ctactgtacg tgaagtgctg tctgacagag aattacatct ttcatgggaa  16740
gttggtaaac ctagaccacc acttaaccga aattatgtct ttactggtta tcgtgtaact  16800
aaaaacagta aagtacaaat aggagagtac acctttgaaa aaggtgacta tggtgatgct  16860
gttgtttacc gaggtacaac aacttacaaa ttaaatgttg gtgattattt tgtgctgaca  16920
tcacatacag taatgccatt aagtgcacct acactagtgc cacaagagca ctatgttaga  16980
attactggct tatacccaac actcaatatc tcagatgagt tttctagcaa tgttgcaaat  17040
tatcaaaagg ttggtatgca aaagtattct acactccagg gaccacctgg tactggtaag  17100
agtcattttg ctattggcct agctctctac tacccttctg ctcgcatagt gtatacagct  17160
tgctctcatg ccgctgttga tgcactatgt gagaaggcat taaaatattt gcctatagat  17220
aaatgtagta gaattatacc tgcacgtgct cgtgtagagt gttttgataa attcaaagtg  17280
aattcaacat tagaacagta tgtcttttgt actgtaaatg cattgcctga gacgacagca  17340
gatatagttg tctttgatga aatttcaatg gccacaaatt atgatttgag tgttgtcaat  17400
gccagattac gtgctaagca ctatgtgtac attggcgacc ctgctcaatt acctgcacca  17460
cgcacattgc taactaaggg cacactagaa ccagaatatt tcaattcagt gtgtagactt  17520
atgaaaacta taggtccaga catgttcctc ggaacttgtc ggcgttgtcc tgctgaaatt  17580
gttgacactg tgagtgcttt ggtttatgat aataagctta aagcacataa agacaaatca  17640
gctcaatgct ttaaaatgtt ttataagggt gttatcacgc atgatgtttc atctgcaatt  17700
aacaggccac aaataggcgt ggtaagagaa ttccttacac gtaaccctgc ttggagaaaa  17760
gctgtcttta tttcacctta taattcacag aatgctgtag cctcaaagat tttgggacta  17820
ccaactcaaa ctgttgattc atcacagggc tcagaatatg actatgtcat attcactcaa  17880
```

accactgaaa cagctcactc ttgtaatgta aacagattta atgttgctat taccagagca 17940
aaagtaggca tactttgcat aatgtctgat agagaccttt atgacaagtt gcaatttaca 18000
agtcttgaaa ttccacgtag gaatgtggca actttacaag ctgaaaatgt aacaggactt 18060
tttaaagatt gtagtaaggt aatcactggg ttacatccta cacaggcacc tacacacctc 18120
agtgttgaca ctaaattcaa aactgaaggt ttatgtgttg acatacctgg catacctaag 18180
gacatgacct atagaagact catctctatg atgggtttta aaatgaatta tcaagttaat 18240
ggttacccta acatgtttat cacccgcgaa gaagctataa gacatgtacg tgcatggatt 18300
ggcttcgatg tcgaggggtg tcatgctact agagaagctg ttggtaccaa tttaccttta 18360
cagctaggtt tttctacagg tgttaaccta gttgctgtac ctacaggtta tgttgataca 18420
cctaataata cagatttttc cagagttagt gctaaaccac cgcctggaga tcaatttaaa 18480
cacctcatac cacttatgta caaaggactt ccttggaatg tagtgcgtat aaagattgta 18540
caaatgttaa gtgacacact taaaaatctc tctgacagag tcgtatttgt cttatgggca 18600
catggctttg agttgacatc tatgaagtat tttgtgaaaa taggacctga gcgcacctgt 18660
tgtctatgtg atagacgtgc cacatgcttt tccactgctt cagacactta tgcctgttgg 18720
catcattcta ttggatttga ttacgtctat aatccgttta tgattgatgt tcaacaatgg 18780
ggttttacag gtaacctaca aagcaaccat gatctgtatt gtcaagtcca tggtaatgca 18840
catgtagcta gttgtgatgc aatcatgact aggtgtctag ctgtccacga gtgctttgtt 18900
aagcgtgttg actggactat tgaatatcct ataattggtg atgaactgaa gattaatgcg 18960
gcttgtagaa aggttcaaca catggttgtt aaagctgcat tattagcaga caaattccca 19020
gttcttcacg acattggtaa ccctaaagct attaagtgtg tacctcaagc tgatgtagaa 19080
tggaagttct atgatgcaca gccttgtagt gacaaagctt ataaaataga agaattattc 19140
tattcttatg ccacacattc tgacaaattc acagatggtg tatgcctatt ttggaattgc 19200
aatgtcgata gatatcctgc taattccatt gtttgtagat ttgacactag agtgctatct 19260
aaccttaact tgcctggttg tgatggtggc agtttgtatg taaataaaca tgcattccac 19320
acaccagctt ttgataaaag tgcttttgtt aatttaaaac aattaccatt tttctattac 19380
tctgacagtc catgtgagtc tcatggaaaa caagtagtgt cagatataga ttatgtacca 19440
ctaaagtctg ctacgtgtat aacacgttgc aatttaggtg gtgctgtctg tagacatcat 19500
gctaatgagt acagattgta tctcgatgct tataacatga tgatctcagc tggctttagc 19560
ttgtgggttt acaaacaatt tgatacttat aacctctgga acacttttac aagacttcag 19620
agtttagaaa atgtggcttt taatgttgta aataagggac actttgatgg acaacagggt 19680
gaagtaccag tttctatcat taataacact gtttacacaa aagttgatgg tgttgatgta 19740
gaattgtttg aaaataaaac aacattacct gttaatgtag catttgagct ttgggctaag 19800
cgcaacatta aaccagtacc agaggtgaaa atactcaata atttgggtgt ggacattgct 19860
gctaatactg tgatctggga ctacaaaaga gatgctccag cacatatatc tactattggt 19920
gtttgttcta tgactgacat agccaagaaa ccaactgaaa cgatttgtgc accactcact 19980
gtcttttttg atggtagagt tgatggtcaa gtagacttat ttagaaatgc ccgtaatggt 20040
gttcttatta cagaaggtag tgttaaaggt ttacaaccat ctgtaggtcc caaacaagct 20100
agtcttaatg gagtcacatt aattggagaa gccgtaaaaa cacagttcaa ttattataag 20160
aaagttgatg gtgttgtcca acaattacct gaaacttact ttactcagag tagaaattta 20220
caagaattta aacccaggag tcaaatggaa attgatttct tagaattagc tatggatgaa 20280

```
ttcattgaac ggtataaatt agaaggctat gccttcgaac atatcgttta tggagatttt  20340
agtcatagtc agttaggtgg tttacatcta ctgattggac tagctaaacg ttttaaggaa  20400
tcaccttttg aattagaaga ttttattcct atggacagta cagttaaaaa ctatttcata  20460
acagatgcgc aaacaggttc atctaagtgt gtgtgttctg ttattgattt attacttgat  20520
gattttgttg aaataataaa atcccaagat ttatctgtag tttctaaggt tgtcaaagtg  20580
actattgact atacagaaat ttcatttatg ctttggtgta aagatggcca tgtagaaaca  20640
ttttacccaa aattacaatc tagtcaagcg tggcaaccgg gtgttgctat gcctaatctt  20700
tacaaaatgc aaagaatgct attagaaaag tgtgaccttc aaaattatgg tgatagtgca  20760
acattaccta aaggcataat gatgaatgtc gcaaaatata ctcaactgtg tcaatattta  20820
aacacattaa cattagctgt accctataat atgagagtta tacattttgg tgctggttct  20880
gataaaggag ttgcaccagg tacagctgtt ttaagacagt ggttgcctac gggtacgctg  20940
cttgtcgatt cagatcttaa tgactttgtc tctgatgcag attcaacttt gattggtgat  21000
tgtgcaactg tacatacagc taataaatgg gatctcatta ttagtgatat gtacgaccct  21060
aagactaaaa atgttacaaa agaaaatgac tctaaagagg gtttttttcac ttacatttgt  21120
gggtttatac aacaaaagct agctcttgga ggttccgtgg ctataaagat aacagaacat  21180
tcttggaatg ctgatcttta taagctcatg ggacacttcg catggtggac agcctttgtt  21240
actaatgtga atgcgtcatc atctgaagca tttttaattg gatgtaatta tcttggcaaa  21300
ccacgcgaac aaatagatgg ttatgtcatg catgcaaatt acatattttg gaggaataca  21360
aatccaattc agttgtcttc ctattcttta tttgacatga gtaaatttcc ccttaaatta  21420
aggggtactg ctgttatgtc tttaaaagaa ggtcaaatca atgatatgat tttatctctt  21480
cttagtaaag gtagacttat aattagagaa aacaacagag ttgttatttc tagtgatgtt  21540
cttgttaaca actaaacgaa caatgtttgt ttttcttgtt ttattgccac tagtctctag  21600
tcagtgtgtt aatcttacaa ccagaactca attacccccct gcatacacta attctttcac  21660
acgtggtgtt tattaccctg acaaagtttt cagatcctca gttttacatt caactcagga  21720
cttgttctta cctttctttt ccaatgttac ttggttccat gctatacatg tctctgggac  21780
caatggtact aagaggtttg ataaccctgt cctaccattt aatgatggtg tttattttgc  21840
ttccactgag aagtctaaca taataagagg ctggattttt ggtactactt tagattcgaa  21900
gacccagtcc ctacttattg ttaataacgc tactaatgtt gttattaaag tctgtgaatt  21960
tcaattttgt aatgatccat ttttgggtgt ttattaccac aaaaacaaca aaagttggat  22020
ggaaagtgag ttcagagttt attctagtgc gaataattgc acttttgaat atgtctctca  22080
gccttttctt atggaccttg aaggaaaaca gggtaatttc aaaaatctta gggaatttgt  22140
gtttaagaat attgatggtt attttaaaat atattctaag cacacgccta ttaatttagt  22200
gcgtgatctc cctcagggtt tttcggcttt agaaccattg gtagatttgc caataggtat  22260
taacatcact aggtttcaaa ctttacttgc tttacataga agttatttga ctcctggtga  22320
ttcttcttca ggttggacag ctggtgctgc agcttattat gtgggttatc ttcaacctag  22380
gacttttcta ttaaaatata atgaaaatgg aaccattaca gatgctgtag actgtgcact  22440
tgaccctctc tcagaaacaa agtgtacgtt gaaatccttc actgtagaaa aaggaatcta  22500
tcaaacttct aactttagag tccaaccaac agaatctatt gttagatttc ctaatattac  22560
aaacttgtgc ccttttggtg aagtttttaa cgccaccaga tttgcatctg tttatgcttg  22620
```

-continued

```
gaacaggaag agaatcagca actgtgttgc tgattattct gtcctatata attccgcatc  22680
attttccact tttaagtgtt atggagtgtc tcctactaaa ttaaatgatc tctgctttac  22740
taatgtctat gcagattcat ttgtaattag aggtgatgaa gtcagacaaa tcgctccagg  22800
gcaaactgga aagattgctg attataatta taaattacca gatgatttta caggctgcgt  22860
tatagcttgg aattctaaca atcttgattc taaggttggt ggtaattata attacctgta  22920
tagattgttt aggaagtcta atctcaaacc ttttgagaga gatatttcaa ctgaaatcta  22980
tcaggccggt agcacacctt gtaatggtgt tgaaggtttt aattgttact ttcctttaca  23040
atcatatggt ttccaaccca ctaatggtgt tggttaccaa ccatacagag tagtagtact  23100
ttcttttgaa cttctacatg caccagcaac tgtttgtgga cctaaaaagt ctactaattt  23160
ggttaaaaac aaatgtgtca atttcaactt caatggttta acaggcacag gtgttcttac  23220
tgagtctaac aaaaagtttc tgcctttcca acaatttggc agagacattg ctgacactac  23280
tgatgctgtc cgtgatccac agacacttga gattcttgac attacaccat gttcttttgg  23340
tggtgtcagt gttataacac caggaacaaa tacttctaac caggttgctg ttctttatca  23400
ggatgttaac tgcacagaag tccctgttgc tattcatgca gatcaactta ctcctacttg  23460
gcgtgtttat tctacaggtt ctaatgtttt tcaaacacgt gcaggctgtt taataggggc  23520
tgaacatgtc aacaactcat atgagtgtga catacccatt ggtgcaggta tatgcgctag  23580
ttatcagact cagactaatt ctcctcggcg ggcacgtagt gtagctagtc aatccatcat  23640
tgcctacact atgtcacttg gtgcagaaaa ttcagttgct tactctaata actctattgc  23700
catacccaca aattttacta ttagtgttac cacagaaatt ctaccagtgt ctatgaccaa  23760
gacatcagta gattgtacaa tgtacatttg tggtgattca actgaatgca gcaatctttt  23820
gttgcaatat ggcagttttt gtacacaatt aaaccgtgct ttaactggaa tagctgttga  23880
acaagacaaa aacacccaag aagtttttgc acaagtcaaa caaatttaca aaacaccacc  23940
aattaaagat tttggtggtt ttaatttttc acaaatatta ccagatccat caaaaccaag  24000
caagaggtca tttattgaag atctactttt caacaaagtg acacttgcag atgctggctt  24060
catcaaacaa tatggtgatt gccttggtga tattgctgct agagacctca tttgtgcaca  24120
aaagtttaac ggccttactg ttttgccacc tttgctcaca gatgaaatga ttgctcaata  24180
cacttctgca ctgttagcgg gtacaatcac ttctggttgg acctttggtg caggtgctgc  24240
attacaaata ccatttgcta tgcaaatggc ttataggttt aatggtattg gagttacaca  24300
gaatgttctc tatgagaacc aaaaattgat tgccaaccaa tttaatagtg ctattggcaa  24360
aattcaagac tcactttctt ccacagcaag tgcacttgga aaacttcaag atgtggtcaa  24420
ccaaaatgca caagctttaa acacgcttgt taaacaactt agctccaatt ttggtgcaat  24480
ttcaagtgtt ttaaatgata tcctttcacg tcttgacaaa gttgaggctg aagtgcaaat  24540
tgataggttg atcacaggca gacttcaaag tttgcagaca tatgtgactc aacaattaat  24600
tagagctgca gaaatcagag cttctgctaa tcttgctgct actaaaatgt cagagtgtgt  24660
acttggacaa tcaaaaagag ttgatttttg tggaaagggc tatcatctta tgtccttccc  24720
tcagtcagca cctcatggtg tagtcttctt gcatgtgact tatgtccctg cacaagaaaa  24780
gaacttcaca actgctcctg ccatttgtca tgatggaaaa gcacactttc ctcgtgaagg  24840
tgtctttgtt tcaaatggca cacactggtt tgtaacacaa aggaattttt atgaaccaca  24900
aatcattact acagacaaca catttgtgtc tggtaactgt gatgttgtaa taggaattgt  24960
caacaacaca gtttatgatc ctttgcaacc tgaattagac tcattcaagg aggagttaga  25020
```

```
taaatatttt aagaatcata catcaccaga tgttgattta ggtgacatct ctggcattaa  25080
tgcttcagtt gtaaacattc aaaaagaaat tgaccgcctc aatgaggttg ccaagaattt  25140
aaatgaatct ctcatcgatc tccaagaact tggaaagtat gagcagtata taaaatggcc  25200
atggtacatt tggctaggtt ttatagctgg cttgattgcc atagtaatgg tgacaattat  25260
gctttgctgt atgaccagtt gctgtagttg tctcaagggc tgttgttctt gtggatcctg  25320
ctgcaaattt gatgaagacg actctgagcc agtgctcaaa ggagtcaaat tacattacac  25380
ataaacgaac ttatggattt gtttatgaga atcttcacaa ttggaactgt aactttgaag  25440
caaggtgaaa tcaaggatgc tactccttca gattttgttc gcgctactgc aacgataccg  25500
atacaagcct cactcccttt cggatggctt attgttggcg ttgcacttct tgctgttttt  25560
cagagcgctt ccaaaatcat aaccctcaaa aagagatggc aactagcact ctccaagggt  25620
gttcactttg tttgcaactt gctgttgttg tttgtaacag tttactcaca ccttttgctc  25680
gttgctgctg gccttgaagc ccctttctc tatctttatg ctttagtcta cttcttgcag  25740
agtataaact ttgtaagaat aataatgagg ctttggcttt gctggaaatg ccgttccaaa  25800
aacccattac tttatgatgc caactatttt ctttgctggc atactaattg ttacgactat  25860
tgtatacctt acaatagtgt aacttcttca attgtcatta cttcaggtga tggcacaaca  25920
agtcctattt ctgaacatga ctaccagatt ggtggttata ctgaaaaatg ggaatctgga  25980
gtaaaagact gtgttgtatt acacagttac ttcacttcag actattacca gctgtactca  26040
actcaattga gtacagacac tggtgttgaa catgttacct tcttcatcta caataaaatt  26100
gttgatgagc ctgaagaaca tgtccaaatt cacacaatcg acggttcatc cggagttgtt  26160
aatccagtaa tggaaccaat ttatgatgaa ccgacgacga ctactagcgt gcctttgtaa  26220
gcacaagctg atgagtacga acttatgtac tcattcgttt cggaagagac aggtacgtta  26280
atagttaata gcgtacttct ttttcttgct ttcgtggtat tcttgctagt tacactagcc  26340
atccttactg cgcttcgatt gtgtgcgtac tgctgcaata ttgttaacgt gagtcttgta  26400
aaaccttctt tttacgttta ctctcgtgtt aaaaatctga attcttctag agttcctgat  26460
cttctggtct aaacgaacta aatattatat tagtttttct gtttggaact ttaattttag  26520
ccatggcaga ttccaacggt actattaccg ttgaagagct taaaaagctc cttgaacaat  26580
ggaacctagt aataggtttc ctattcctta catggatttg tcttctacaa tttgcctatg  26640
ccaacaggaa taggtttttg tatataatta agttaatttt cctctggctg ttatggccag  26700
taactttagc ttgttttgtg cttgctgctg tttacagaat aaattggatc accggtggaa  26760
ttgctatcgc aatggcttgt cttgtaggct tgatgtggct cagctacttc attgcttctt  26820
tcagactgtt tgcgcgtacg cgttccatgt ggtcattcaa tccagaaact aacattcttc  26880
tcaacgtgcc actccatggc actattctga ccagaccgct tctagaaagt gaactcgtaa  26940
tcggagctgt gatccttcgt ggacatcttc gtattgctgg acaccatcta ggacgctgtg  27000
acatcaagga cctgcctaaa gaaatcactg ttgctacatc acgaacgctt tcttattaca  27060
aattgggagc ttcgcagcgt gtagcaggtg actcaggttt tgctgcatac agtcgctaca  27120
ggattggcaa ctataaatta aacacagacc attccagtag cagtgacaat attgctttgc  27180
ttgtacagta agtgacaaca gatgtttcat ctcgttgact ttcaggttac tatagcagag  27240
atattactaa ttattatgag gacttttaaa gtttccattt ggaatcttga ttacatcata  27300
aacctcataa ttaaaaattt atctaagtca ctaactgaga ataaatattc tcaattagat  27360
```

```
gaagagcaac caatggagat tgattaaacg aacatgaaaa ttattctttt cttggcactg  27420
ataacactcg ctacttgtga gctttatcac taccaagagt gtgttagagg tacaacagta  27480
cttttaaaag aaccttgctc ttctggaaca tacgagggca attcaccatt tcatcctcta  27540
gctgataaca aatttgcact gacttgcttt agcactcaat ttgcttttgc ttgtcctgac  27600
ggcgtaaaac acgtctatca gttacgtgcc agatcagttt cacctaaact gttcatcaga  27660
caagaggaag ttcaagaact ttactctcca atttttctta ttgttgcggc aatagtgttt  27720
ataacacttt gcttcacact caaaagaaag acagaatgat tgaactttca ttaattgact  27780
tctatttgtg ctttttagcc tttctgctat tccttgtttt aattatgctt attatctttt  27840
ggttctcact tgaactgcaa gatcataatg aaacttgtca cgcctaaacg aacatgaaat  27900
ttcttgtttt cttaggaatc atcacaactg tagctgcatt tcaccaagaa tgtagtttac  27960
agtcatgtac tcaacatcaa ccatatgtag ttgatgaccc gtgtcctatt cacttctatt  28020
ctaaatggta tattagagta ggagctagaa aatcagcacc tttaattgaa ttgtgcgtgg  28080
atgaggctgg ttctaaatca cccattcagt acatcgatat cggtaattat acagtttcct  28140
gttcaccttt tacaattaat tgccaggaac ctaaattggg tagtcttgta gtgcgttgtt  28200
cgttctatga agacttttta gagtatcatg acgttcgtgt tgttttagat ttcatctaaa  28260
cgaacaaact aaaatgtctg ataatggacc ccaaaatcag cgaaatgcac cccgcattac  28320
gtttggtgga ccctcagatt caactggcag taaccagaat ggagaacgca gtggggcgcg  28380
atcaaaacaa cgtcggcccc aaggtttacc caataatact gcgtcttggt tcaccgctct  28440
cactcaacat ggcaaggaag accttaaatt ccctcgagga caaggcgttc caattaacac  28500
caatagcagt ccagatgacc aaattggcta ctaccgaaga gctaccagac gaattcgtgg  28560
tggtgacggt aaaatgaaag atctcagtcc aagatggtat ttctactacc taggaactgg  28620
gccagaagct ggacttccct atggtgctaa caaagacggc atcatatggg ttgcaactga  28680
gggagccttg aatacaccaa aagatcacat tggcacccgc aatcctgcta acaatgctgc  28740
aatcgtgcta caacttcctc aaggaacaac attgccaaaa ggcttctacg cagaagggag  28800
cagaggcggc agtcaagcct cttctcgttc ctcatcacgt agtcgcaaca gttcaagaaa  28860
ttcaactcca ggcagcagta ggggaacttc tcctgctaga atggctggca atggcggtga  28920
tgctgctctt gctttgctgc tgcttgacag attgaaccag cttgagagca aaatgtctgg  28980
taaaggccaa caacaacaag gccaaactgt cactaagaaa tctgctgctg aggcttctaa  29040
gaagcctcgg caaaaacgta ctgccactaa agcatacaat gtaacacaag ctttcggcag  29100
acgtggtcca gaacaaaccc aaggaaattt tggggaccag gaactaatca gacaaggaac  29160
tgattacaaa cattggccgc aaattgcaca atttgccccc agcgcttcag cgttcttcgg  29220
aatgtcgcgc attggcatgg aagtcacacc ttcgggaacg tggttgacct acacaggtgc  29280
catcaaattg gatgacaaag atccaaattt caaagatcaa gtcattttgc tgaataagca  29340
tattgacgca tacaaaacat tcccaccaac agagcctaaa aaggacaaaa agaagaaggc  29400
tgatgaaact caagccttac cgcagagaca gaagaaacag caaactgtga ctcttcttcc  29460
tgctgcagat ttggatgatt tctccaaaca attgcaacaa tccatgagca gtgctgactc  29520
aactcaggcc taaactcatg cagaccacac aaggcagatg ggctatataa acgttttcgc  29580
ttttccgttt acgatatata gtctactctt gtgcagaatg aattctcgta actacatagc  29640
acaagtagat gtagttaact ttaatctcac atagcaatct ttaatcagtg tgtaacatta  29700
gggaggactt gaaagagcca ccacattttc accgaggcca cgcggagtac gatcgagtgt  29760
```

acagtgaaca atgctaggga gagctgccta tatggaagag ccctaatgtg taaaattaat 29820
tttagtagtg ctatccccat gtgattttaa tagcttctta ggagaatgac aaaaaaaaaa 29880
aa 29882

<210> SEQ ID NO 3
<211> LENGTH: 29751
<212> TYPE: DNA
<213> ORGANISM: Human coronavirus

<400> SEQUENCE: 3
atattaggtt tttacctacc caggaaaagc caaccaacct cgatctcttg tagatctgtt 60
ctctaaacga actttaaaat ctgtgtagct gtcgctcggc tgcatgccta gtgcacctac 120
gcagtataaa caataataaa ttttactgtc gttgacaaga aacgagtaac tcgtccctct 180
tctgcagact gcttacggtt tcgtccgtgt tgcagtcgat catcagcata cctaggtttc 240
gtccgggtgt gaccgaaagg taagatggag agccttgttc ttggtgtcaa cgagaaaaca 300
cacgtccaac tcagtttgcc tgtccttcag gttagagacg tgctagtgcg tggcttcggg 360
gactctgtgg aagaggccct atcggaggca cgtgaacacc tcaaaaatgg cacttgtggt 420
ctagtagagc tggaaaaagg cgtactgccc cagcttgaac agccctatgt gttcattaaa 480
cgttctgatg ccttaagcac caatcacggc cacaaggtcg ttgagctggt tgcagaaatg 540
gacggcattc agtacggtcg tagcggtata acactgggag tactcgtgcc acatgtgggc 600
gaaaccccaa ttgcataccg caatgttctt cttcgtaaga acggtaataa gggagccggt 660
ggtcatagct atggcatcga tctaaagtct tatgacttag gtgacgagct tggcactgat 720
cccattgaag attatgaaca aaactggaac actaagcatg gcagtggtgc actccgtgaa 780
ctcactcgtg agctcaatgg aggtgcagtc actcgctatg tcgacaacaa tttctgtggc 840
ccagatgggt accctcttga ttgcatcaaa gattttctcg cacgcgcggg caagtcaatg 900
tgcactcttt ccgaacaact tgattacatc gagtcgaaga gaggtgtcta ctgctgccgt 960
gaccatgagc atgaaattgc ctggttcact gagcgctctg ataagagcta cgagcaccag 1020
acacccttcg aaattaagag tgccaagaaa tttgacactt tcaaagggga atgcccaaag 1080
tttgtgtttc ctcttaactc aaaagtcaaa gtcattcaac cacgtgttga aaagaaaaag 1140
actgagggtt tcatggggcg tatacgctct gtgtaccctg ttgcatctcc acaggagtgt 1200
aacaatatgc acttgtctac cttgatgaaa tgtaatcatt gcgatgaagt ttcatggcag 1260
acgtgcgact ttctgaaagc cacttgtgaa cattgtggca ctgaaaattt agttattgaa 1320
ggacctacta catgtgggta cctacctact aatgctgtag tgaaaatgcc atgtcctgcc 1380
tgtcaagacc cagagattgg acctgagcat agtgttgcag attatcacaa ccactcaaac 1440
attgaaactc gactccgcaa gggaggtagg actagatgtt ttggaggctg tgtgtttgcc 1500
tatgttggct gctataataa gcgtgcctac tgggttcctc gtgctagtgc tgatattggc 1560
tcaggccata ctggcattac tggtgacaat gtggagacct tgaatgagga tctccttgag 1620
atactgagtc gtgaacgtgt taacattaac attgttggcg attttcattt gaatgaagag 1680
gttgccatca ttttggcatc tttctctgct tctacaagtg cctttattga cactataaag 1740
agtcttgatt acaagtcttt caaaaccatt gttgagtcct gcggtaacta taaagttacc 1800
aagggaaagc ccgtaaaagg tgcttggaac attggacaac agagatcagt tttaacacca 1860
ctgtgtggtt ttccctcaca ggctgctggt gttatcagat caatttttgc gcgcacactt 1920

-continued

```
gatgcagcaa accactcaat tcctgatttg caaagagcag ctgtcaccat acttgatggt   1980
atttctgaac agtcattacg tcttgtcgac gccatggttt atacttcaga cctgctcacc   2040
aacagtgtca ttattatggc atatgtaact ggtggtcttg tacaacagac ttctcagtgg   2100
ttgtctaatc ttttgggcac tactgttgaa aaactcaggc ctatctttga atggattgag   2160
gcgaaactta gtgcaggagt tgaatttctc aaggatgctt gggagattct caaatttctc   2220
attacaggtg tttttgacat cgtcaagggt caaatacagg ttgcttcaga taacatcaag   2280
gattgtgtaa aatgcttcat tgatgttgtt aacaaggcac tcgaaatgtg cattgatcaa   2340
gtcactatcg ctggcgcaaa gttgcgatca ctcaacttag gtgaagtctt catcgctcaa   2400
agcaagggac tttaccgtca gtgtatacgt ggcaaggagc agctgcaact actcatgcct   2460
cttaaggcac caaaagaagt aacctttctt gaaggtgatt cacatgacac agtacttacc   2520
tctgaggagg ttgttctcaa gaacggtgaa ctcgaagcac tcgagacgcc cgttgatagc   2580
ttcacaaatg gagctatcgt tggcacacca gtctgtgtaa atggcctcat gctcttagag   2640
attaaggaca aagaacaata ctgcgcattg tctcctggtt tactggctac aaacaatgtc   2700
tttcgcttaa aagggggtgc accaattaaa ggtgtaacct ttggagaaga tactgtttgg   2760
gaagttcaag gttacaagaa tgtgagaatc acatttgagc ttgatgaacg tgttgacaaa   2820
gtgcttaatg aaaagtgctc tgtctacact gttgaatccg gtaccgaagt tactgagttt   2880
gcatgtgttg tagcagaggc tgttgtgaag actttacaac cagtttctga tctccttacc   2940
aacatgggta ttgatcttga tgagtggagt gtagctacat tctacttatt tgatgatgct   3000
ggtgaagaaa acttttcatc acgtatgtat tgttcctttt accctccaga tgaggaagaa   3060
gaggacgatg cagagtgtga ggaagaagaa attgatgaaa cctgtgaaca tgagtacggt   3120
acagaggatg attatcaagg tctccctctg gaatttggtg cctcagctga aacagttcga   3180
gttgaggaag aagaagagga agactggctg gatgatacta ctgagcaatc agagattgag   3240
ccagaaccag aacctacacc tgaagaacca gttaatcagt ttactggtta tttaaaactt   3300
actgacaatg ttgccattaa atgtgttgac atcgttaagg aggcacaaag tgctaatcct   3360
atggtgattg taaatgctgc taacatacac ctgaaacatg gtggtggtgt agcaggtgca   3420
ctcaacaagg caaccaatgg tgccatgcaa aaggagagtg atgattacat taagctaaat   3480
ggccctctta cagtaggagg gtcttgtttg ctttctggac ataatcttgc taagaagtgt   3540
ctgcatgttg ttggacctaa cctaaatgca ggtgaggaca tccagcttct taaggcagca   3600
tatgaaaatt tcaattcaca ggacatctta cttgcaccat tgttgtcagc aggcatattt   3660
ggtgctaaac cacttcagtc tttacaagtg tgcgtgcaga cggttcgtac acaggtttat   3720
attgcagtca atgacaaagc tctttatgag caggttgtca tggattatct tgataacctg   3780
aagcctagag tggaagcacc taaacaagag gagccaccaa acacagaaga ttccaaaact   3840
gaggagaaat ctgtcgtaca gaagcctgtc gatgtgaagc caaaaattaa ggcctgcatt   3900
gatgaggtta ccacaacact ggaagaaact aagtttctta ccaataagtt actcttgttt   3960
gctgatatca atggtaagct ttaccatgat tctcagaaca tgcttagagg tgaagatatg   4020
tctttccttg agaaggatgc accttacatg gtaggtgatg ttatcactag tggtgatatc   4080
acttgtgttg taataccctc caaaaaggct ggtggcacta ctgagatgct ctcaagagct   4140
ttgaagaaag tgccagttga tgagtatata accacgtacc ctggacaagg atgtgctggt   4200
tatacacttg aggaagctaa gactgctctt aagaaatgca aatctgcatt ttatgtacta   4260
ccttcagaag cacctaatgc taaggaagag attctaggaa ctgtatcctg gaatttgaga   4320
```

-continued

```
gaaatgcttg ctcatgctga agagacaaga aaattaatgc ctatatgcat ggatgttaga   4380
gccataatgg caaccatcca acgtaagtat aaaggaatta aaattcaaga gggcatcgtt   4440
gactatggtg tccgattctt cttttatact agtaaagagc ctgtagcttc tattattacg   4500
aagctgaact ctctaaatga gccgcttgtc acaatgccaa ttggttatgt gacacatggt   4560
tttaatcttg aagaggctgc gcgctgtatg cgttctctta aagctcctgc cgtagtgtca   4620
gtatcatcac cagatgctgt tactacatat aatggatacc tcacttcgtc atcaaagaca   4680
tctgaggagc actttgtaga aacagtttct ttggctggct cttacagaga ttggtcctat   4740
tcaggacagc gtacagagtt aggtgttgaa tttcttaagc gtggtgacaa aattgtgtac   4800
cacactctgg agagccccgt cgagtttcat cttgacggtg aggttctttc acttgacaaa   4860
ctaaagagtc tcttatccct gcgggaggtt aagactataa aagtgttcac aactgtggac   4920
aacactaatc tccacacaca gcttgtggat atgtctatga catatggaca gcagtttggt   4980
ccaacatact tggatggtgc tgatgttaca aaaattaaac ctcatgtaaa tcatgagggt   5040
aagactttct ttgtactacc tagtgatgac acactacgta gtgaagcttt cgagtactac   5100
catactcttg atgagagttt tcttggtagg tacatgtctg ctttaaacca cacaaagaaa   5160
tggaaatttc ctcaagttgg tggtttaact tcaattaaat gggctgataa caattgttat   5220
ttgtctagtg ttttattagc acttcaacag cttgaagtca aattcaatgc accagcactt   5280
caagaggctt attatagagc ccgtgctggt gatgctgcta acttttgtgc actcatactc   5340
gcttacagta ataaaactgt tggcgagctt ggtgatgtca gagaaactat gacccatctt   5400
ctacagcatg ctaatttgga atctgcaaag cgagttctta atgtggtgtg taaacattgt   5460
ggtcagaaaa ctactacctt aacgggtgta gaagctgtga tgtatatggg tactctatct   5520
tatgataatc ttaagacagg tgtttccatt ccatgtgtgt gtggtcgtga tgctacacaa   5580
tatctagtac aacaagagtc ttcttttgtt atgatgtctg caccacctgc tgagtataaa   5640
ttacagcaag gtacattctt atgtgcgaat gagtacactg gtaactatca gtgtggtcat   5700
tacactcata taactgctaa ggagaccctc tatcgtattg acggagctca ccttacaaag   5760
atgtcagagt acaaaggacc agtgactgat gttttctaca aggaaacatc ttacactaca   5820
accatcaagc ctgtgtcgta taaactcgat ggagttactt acacagagat tgaaccaaaa   5880
ttggatgggt attataaaaa ggataatgct tactatacag agcagcctat agaccttgta   5940
ccaactcaac cattaccaaa tgcgagtttt gataatttca aactcacatg ttctaacaca   6000
aaatttgctg atgatttaaa tcaaatgaca ggcttcacaa agccagcttc acgagagcta   6060
tctgtcacat tcttcccaga cttgaatggc gatgtagtgg ctattgacta tagacactat   6120
tcagcgagtt tcaagaaagg tgctaaatta ctgcataagc caattgtttg gcacattaac   6180
caggctacaa ccaagacaac gttcaaacca aacacttggt gtttacgttg tctttggagt   6240
acaaagccag tagatacttc aaattcattt gaagttctgg cagtagaaga cacacaagga   6300
atggacaatc ttgcttgtga aagtcaacaa cccacctctg aagaagtagt ggaaaatcct   6360
accatacaga aggaagtcat agagtgtgac gtgaaaacta ccgaagttgt aggcaatgtc   6420
atacttaaac catcagatga aggtgttaaa gtaacacaag agttaggtca tgaggatctt   6480
atggctgctt atgtggaaaa cacaagcatt accattaaga aacctaatga gctttcacta   6540
gccttaggtt taaaaacaat tgccactcat ggtattgctg caattaatag tgttccttgg   6600
agtaaaattt tggcttatgt caaaccattc ttaggacaag cagcaattac aacatcaaat   6660
```

```
tgcgctaaga gattagcaca acgtgtgttt aacaattata tgccttatgt gtttacatta   6720
ttgttccaat tgtgtacttt tactaaaagt accaattcta gaattagagc ttcactacct   6780
acaactattg ctaaaaatag tgttaagagt gttgctaaat tatgtttgga tgccggcatt   6840
aattatgtga agtcacccaa attttctaaa ttgttcacaa tcgctatgtg gctattgttg   6900
ttaagtattt gcttaggttc tctaatctgt gtaactgctg cttttggtgt actcttatct   6960
aattttggtg ctccttctta ttgtaatggc gttagagaat tgtatcttaa ttcgtctaac   7020
gttactacta tggatttctg tgaaggttct tttccttgca gcatttgttt aagtggatta   7080
gactcccttg attcttatcc agctcttgaa accattcagg tgacgatttc atcgtacaag   7140
ctagacttga caattttagg tctggccgct gagtgggttt tggcatatat gttgttcaca   7200
aaattctttt atttattagg tctttcagct ataatgcagg tgttctttgg ctattttgct   7260
agtcatttca tcagcaattc ttggctcatg tggtttatca ttagtattgt acaaatggca   7320
cccgtttctg caatggttag gatgtacatc ttctttgctt ctttctacta catatggaag   7380
agctatgttc atatcatgga tggttgcacc tcttcgactt gcatgatgtg ctataagcgc   7440
aatcgtgcca cacgcgttga gtgtacaact attgttaatg gcatgaagag atctttctat   7500
gtctatgcaa atggaggccg tggcttctgc aagactcaca attggaattg tctcaattgt   7560
gacacatttt gcactggtag tacattcatt agtgatgaag ttgctcgtga tttgtcactc   7620
cagtttaaaa gaccaatcaa ccctactgac cagtcatcgt atattgttga tagtgttgct   7680
gtgaaaaatg gcgcgcttca cctctacttt gacaaggctg gtcaaaagac ctatgagaga   7740
catccgctct cccattttgt caatttagac aatttgagag ctaacaacac taaaggttca   7800
ctgcctatta atgtcatagt ttttgatggc aagtccaaat gcgacgagtc tgcttctaag   7860
tctgcttctg tgtactacag tcagctgatg tgccaaccta ttctgttgct tgaccaagct   7920
cttgtatcag acgttggaga tagtactgaa gtttccgtta agatgtttga tgcttatgtc   7980
gacacctttt cagcaacttt tagtgttcct atggaaaaac ttaaggcact tgttgctaca   8040
gctcacagcg agttagcaaa gggtgtagct ttagatggtg tcctttctac attcgtgtca   8100
gctgcccgac aaggtgttgt tgataccgat gttgacacaa aggatgttat tgaatgtctc   8160
aaactttcac atcactctga cttagaagtg acaggtgaca gttgtaacaa tttcatgctc   8220
acctataata aggttgaaaa catgacgccc agagatcttg gcgcatgtat tgactgtaat   8280
gcaaggcata tcaatgccca agtagcaaaa agtcacaatg tttcactcat ctggaatgta   8340
aaagactaca tgtctttatc tgaacagctg cgtaaacaaa ttcgtagtgc tgccaagaag   8400
aacaacatac cttttagact aacttgtgct acaactagac aggttgtcaa tgtcataact   8460
actaaaatct cactcaaggg tggtaagatt gttagtactt gttttaaact tatgcttaag   8520
gccacattat tgtgcgttct tgctgcattg gtttgttata tcgttatgcc agtacataca   8580
ttgtcaatcc atgatggtta cacaaatgaa atcattggtt acaaagccat tcaggatggt   8640
gtcactcgtg acatcatttc tactgatgat tgttttgcaa ataaacatgc tggttttgac   8700
gcatggttta gccagcgtgg tggttcatac aaaaatgaca aaagctgccc tgtagtagct   8760
gctatcatta caagagagat tggtttcata gtgcctggct taccgggtac tgtgctgaga   8820
gcaatcaatg gtgacttctt gcattttcta cctcgtgttt ttagtgctgt tggcaacatt   8880
tgctacacac cttccaaact cattgagtat agtgattttg ctacctctgc ttgcgttctt   8940
gctgctgagt gtacaatttt taaggatgct atgggcaaac ctgtgccata ttgttatgac   9000
actaatttgc tagagggttc tatttcttat agtgagcttc gtccagacac tcgttatgtg   9060
```

cttatggatg gttccatcat acagtttcct aacacttacc tggagggttc tgttagagta 9120
gtaacaactt ttgatgctga gtactgtaga catggtacat gcgaaaggtc agaagtaggt 9180
atttgcctat ctaccagtgg tagatgggtt cttaataatg agcattacag agctctatca 9240
ggagttttct gtggtgttga tgcgatgaat ctcatagcta acatctttac tcctcttgtg 9300
caacctgtgg gtgctttaga tgtgtctgct tcagtagtgg ctggtggtat tattgccata 9360
ttggtgactt gtgctgccta ctactttatg aaattcagac gtgtttttgg tgagtacaac 9420
catgttgttg ctgctaatgc acttttgttt ttgatgtctt tcactatact ctgtctggta 9480
ccagcttaca gctttctgcc gggagtctac tcagtctttt acttgtactt gacattctat 9540
ttcaccaatg atgtttcatt cttggctcac cttcaatggt ttgccatgtt ttctcctatt 9600
gtgccttttt ggataacagc aatctatgta ttctgtattt ctctgaagca ctgccattgg 9660
ttctttaaca actatcttag gaaaagagtc atgtttaatg gagttacatt tagtaccttc 9720
gaggaggctg ctttgtgtac ctttttgctc aacaaggaaa tgtacctaaa attgcgtagc 9780
gagacactgt tgccacttac acagtataac aggtatcttg ctctatataa caagtacaag 9840
tatttcagtg gagccttaga tactaccagc tatcgtgaag cagcttgctg ccacttagca 9900
aaggctctaa atgactttag caactcaggt gctgatgttc tctaccaacc accacagaca 9960
tcaatcactt ctgctgttct gcagagtggt tttaggaaaa tggcattccc gtcaggcaaa 10020
gttgaagggt gcatggtaca agtaacctgt ggaactacaa ctcttaatgg attgtggttg 10080
gatgacacag tatactgtcc aagacatgtc atttgcacag cagaagacat gcttaatcct 10140
aactatgaag atctgctcat tcgcaaatcc aaccatagct ttcttgttca ggctggcaat 10200
gttcaacttc gtgttattgg ccattctatg caaaattgtc tgcttaggct taaagttgat 10260
acttctaacc ctaagacacc caagtataaa tttgtccgta tccaacctgg tcaaacattt 10320
tcagttctag catgctacaa tggttcacca tctggtgttt atcagtgtgc catgagacct 10380
aatcatacca ttaaaggttc tttccttaat ggatcatgtg gtagtgttgg ttttaacatt 10440
gattatgatt gcgtgtcttt ctgctatatg catcatatgg agcttccaac aggagtacac 10500
gctggtactg acttagaagg taaattctat ggtccatttg ttgacagaca aactgcacag 10560
gctgcaggta cagacacaac cataacatta aatgttttgg catggctgta tgctgctgtt 10620
atcaatggtg ataggtggtt tcttaataga ttcaccacta ctttgaatga ctttaacctt 10680
gtggcaatga agtacaacta tgaacctttg acacaagatc atgttgacat attgggacct 10740
ctttctgctc aaacaggaat tgccgtctta gatatgtgtg ctgctttgaa agagctgctg 10800
cagaatggta tgaatggtcg tactatcctt ggtagcacta ttttagaaga tgagtttaca 10860
ccatttgatg ttgttagaca atgctctggt gttaccttcc aaggtaagtt caagaaaatt 10920
gttaagggca ctcatcattg gatgctttta actttcttga catcactatt gattcttgtt 10980
caaagtacac agtggtcact gtttttcttt gtttacgaga atgctttctt gccatttact 11040
cttggtatta tggcaattgc tgcatgtgct atgctgcttg ttaagcataa gcacgcattc 11100
ttgtgcttgt ttctgttacc ttctcttgca acagttgctt actttaatat ggtctacatg 11160
cctgctagct gggtgatgcg tatcatgaca tggcttgaat tggctgacac tagcttgtct 11220
ggttataggc ttaaggattg tgttatgtat gcttcagctt tagttttgct tattctcatg 11280
acagctcgca ctgtttatga tgatgctgct agacgtgttt ggacactgat gaatgtcatt 11340
acacttgttt acaaagtcta ctatggtaat gctttagatc aagctatttc catgtgggcc 11400

-continued

```
ttagttattt ctgtaacctc taactattct ggtgtcgtta cgactatcat gtttttagct  11460
agagctatag tgtttgtgtg tgttgagtat tacccattgt tatttattac tggcaacacc  11520
ttacagtgta tcatgcttgt ttattgtttc ttaggctatt gttgctgctg ctactttggc  11580
cttttctgtt tactcaaccg ttacttcagg cttactcttg gtgtttatga ctacttggtc  11640
tctacacaag aatttaggta tatgaactcc caggggcttt tgcctcctaa gagtagtatt  11700
gatgctttca agcttaacat taagttgttg ggtattggag gtaaaccatg tatcaaggtt  11760
gctactgtac agtctaaaat gtctgacgta aagtgcacat ctgtggtact gctctcggtt  11820
cttcaacaac ttagagtaga gtcatcttct aaattgtggg cacaatgtgt acaactccac  11880
aatgatattc ttcttgcaaa agacacaact gaagctttcg agaagatggt ttctcttttg  11940
tctgttttgc tatccatgca gggtgctgta gacattaata ggttgtgcga ggaaatgctc  12000
gataaccgtg ctactcttca ggctattgct tcagaattta gttctttacc atcatatgcc  12060
gcttatgcca ctgcccagga ggcctatgag caggctgtag ctaatggtga ttctgaagtc  12120
gttctcaaaa agttaaagaa atctttgaat gtggctaaat ctgagtttga ccgtgatgct  12180
gccatgcaac gcaagttgga aaagatggca gatcaggcta tgacccaaat gtacaaacag  12240
gcaagatctg aggacaagag ggcaaaagta actagtgcta tgcaaacaat gctcttcact  12300
atgcttagga agcttgataa tgatgcactt aacaacatta tcaacaatgc gcgtgatggt  12360
tgtgttccac tcaacatcat accattgact acagcagcca aactcatggt tgttgtccct  12420
gattatggta cctacaagaa cacttgtgat ggtaacacct ttacatatgc atctgcactc  12480
tgggaaatcc agcaagttgt tgatgcggat agcaagattg ttcaacttag tgaaattaac  12540
atggacaatt caccaaattt ggcttggcct cttattgtta cagctctaag agccaactca  12600
gctgttaaac tacagaataa tgaactgagt ccagtagcac tacgacagat gtcctgtgcg  12660
gctggtacca cacaaacagc ttgtactgat gacaatgcac ttgcctacta taacaattcg  12720
aagggaggta ggtttgtgct ggcattacta tcagaccacc aagatctcaa atgggctaga  12780
ttccctaaga gtgatggtac aggtacaatt tacacagaac tggaaccacc ttgtaggttt  12840
gttacagaca caccaaaagg gcctaaagtg aaatacttgt acttcatcaa aggcttaaac  12900
aacctaaata gaggtatggt gctgggcagt ttagctgcta cagtacgtct tcaggctgga  12960
aatgctacag aagtacctgc caattcaact gtgctttcct tctgtgcttt tgcagtagac  13020
cctgctaaag catataagga ttacctagca agtggaggac aaccaatcac caactgtgtg  13080
aagatgttgt gtacacacac tggtacagga caggcaatta ctgtaacacc agaagctaac  13140
atggaccaag agtcctttgg tggtgcttca tgttgtctgt attgtagatg ccacattgac  13200
catccaaatc ctaaaggatt ctgtgacttg aaaggtaagt acgtccaaat acctaccact  13260
tgtgctaatg acccagtggg ttttacactt agaaacacag tctgtaccgt ctgcggaatg  13320
tggaaaggtt atggctgtag ttgtgaccaa ctccgcgaac ccttgatgca gtctgcggat  13380
gcatcaacgt tttaaacgg gtttgcggtg taagtgcagc ccgtcttaca ccgtgcggca  13440
caggcactag tactgatgtc gtctacaggg cttttgatat ttacaacgaa aaagttgctg  13500
gttttgcaaa gttcctaaaa actaattgct gtcgcttcca ggagaaggat gaggaaggca  13560
atttattaga ctcttacttt gtagttaaga ggcatactat gtctaactac caacatgaag  13620
agactattta taacttggtt aaagattgtc cagcggttgc tgtccatgac tttttcaagt  13680
ttagagtaga tggtgacatg gtaccacata tatcacgtca gcgtctaact aaatacacaa  13740
tggctgattt agtctatgct ctacgtcatt ttgatgaggg taattgtgat acattaaaag  13800
```

aaatactcgt cacatacaat tgctgtgatg atgattattt caataagaag gattggtatg 13860
acttcgtaga gaatcctgac atcttacgcg tatatgctaa cttaggtgag cgtgtacgcc 13920
aatcattatt aaagactgta caattctgcg atgctatgcg tgatgcaggc attgtaggcg 13980
tactgacatt agataatcag gatcttaatg ggaactggta cgatttcggt gatttcgtac 14040
aagtagcacc aggctgcgga gttcctattg tggattcata ttactcattg ctgatgccca 14100
tcctcacttt gactagggca ttggctgctg agtcccatat ggatgctgat ctcgcaaaac 14160
cacttattaa gtgggatttg ctgaaatatg attttacgga agagagactt tgtctcttcg 14220
accgttattt taaatattgg gaccagacat accatcccaa ttgtattaac tgtttggatg 14280
ataggtgtat ccttcattgt gcaaacttta atgtgttatt ttctactgtg tttccaccta 14340
caagttttgg accactagta agaaaaatat ttgtagatgg tgttcctttt gttgtttcaa 14400
ctggatacca ttttcgtgag ttaggagtcg tacataatca ggatgtaaac ttacatagct 14460
cgcgtctcag tttcaaggaa cttttagtgt atgctgctga tccagctatg catgcagctt 14520
ctggcaattt attgctagat aaacgcacta catgcttttc agtagctgca ctaacaaaca 14580
atgttgcttt tcaaactgtc aaacccggta attttaataa agacttttat gactttgctg 14640
tgtctaaagg tttctttaag gaaggaagtt ctgttgaact aaaacacttc ttctttgctc 14700
aggatggcaa cgctgctatc agtgattatg actattatcg ttataatctg ccaacaatgt 14760
gtgatatcag acaactccta ttcgtagttg aagttgttga taaatacttt gattgttacg 14820
atggtggctg tattaatgcc aaccaagtaa tcgttaacaa tctggataaa tcagctggtt 14880
tcccatttaa taaatggggt aaggctagac tttattatga ctcaatgagt tatgaggatc 14940
aagatgcact tttcgcgtat actaagcgta atgtcatccc tactataact caaatgaatc 15000
ttaagtatgc cattagtgca aagaatagag ctcgcaccgt agctggtgtc tctatctgta 15060
gtactatgac aaatagacag tttcatcaga aattattgaa gtcaatagcc gccactagag 15120
gagctactgt ggtaattgga acaagcaagt tttacggtgg ctggcataat atgttaaaaa 15180
ctgtttacag tgatgtagaa actccacacc ttatgggttg ggattatcca aaatgtgaca 15240
gagccatgcc taacatgctt aggataatgg cctctcttgt tcttgctcgc aaacataaca 15300
cttgctgtaa cttatcacac cgtttctaca ggttagctaa cgagtgtgcg caagtattaa 15360
gtgagatggt catgtgtggc ggctcactat atgttaaacc aggtggaaca tcatccggtg 15420
atgctacaac tgcttatgct aatagtgtct ttaacatttg tcaagctgtt acagccaatg 15480
taaatgcact tctttcaact gatggtaata agatagctga caagtatgtc cgcaatctac 15540
aacacaggct ctatgagtgt ctctatagaa atagggatgt tgatcatgaa ttcgtggatg 15600
agttttacgc ttacctgcgt aaacatttct ccatgatgat tctttctgat gatgccgttg 15660
tgtgctataa cagtaactat gcggctcaag gtttagtagc tagcattaag aactttaagg 15720
cagttcttta ttatcaaaat aatgtgttca tgtctgaggc aaaatgttgg actgagactg 15780
accttactaa aggacctcac gaattttgct cacagcatac aatgctagtt aaacaaggag 15840
atgattacgt gtacctgcct tacccagatc catcaagaat attaggcgca ggctgttttg 15900
tcgatgatat tgtcaaaaca gatggtacac ttatgattga aaggttcgtg tcactggcta 15960
ttgatgctta cccacttaca aaacatccta atcaggagta tgctgatgtc tttcacttgt 16020
atttacaata cattagaaag ttacatgatg agcttactgg ccacatgttg gacatgtatt 16080
ccgtaatgct aactaatgat aacacctcac ggtactggga acctgagttt tatgaggcta 16140

-continued

```
tgtacacacc acatacagtc ttgcaggctg taggtgcttg tgtattgtgc aattcacaga  16200
cttcacttcg ttgcggtgcc tgtattagga gaccattcct atgttgcaag tgctgctatg  16260
accatgtcat ttcaacatca cacaaattag tgttgtctgt taatccctat gtttgcaatg  16320
ccccaggttg tgatgtcact gatgtgacac aactgtatct aggaggtatg agctattatt  16380
gcaagtcaca taagcctccc attagttttc cattatgtgc taatggtcag gtttttggtt  16440
tatacaaaaa cacatgtgta ggcagtgaca atgtcactga cttcaatgcg atagcaacat  16500
gtgattggac taatgctggc gattacatac ttgccaacac ttgtactgag agactcaagc  16560
ttttcgcagc agaaacgctc aaagccactg aggaaacatt taagctgtca tatggtattg  16620
ccactgtacg cgaagtactc tctgacagag aattgcatct ttcatgggag gttggaaaac  16680
ctagaccacc attgaacaga aactatgtct ttactggtta ccgtgtaact aaaaatagta  16740
aagtacagat tggagagtac acctttgaaa aaggtgacta tggtgatgct gttgtgtaca  16800
gaggtactac gacatacaag ttgaatgttg gtgattactt tgtgttgaca tctcacactg  16860
taatgccact tagtgcacct actctagtgc cacaagagca ctatgtgaga attactggct  16920
tgtacccaac actcaacatc tcagatgagt tttctagcaa tgttgcaaat tatcaaaagg  16980
tcggcatgca aaagtactct acactccaag gaccacctgg tactggtaag agtcattttg  17040
ccatcggact tgctctctat tacccatctg ctcgcatagt gtatacggca tgctctcatg  17100
cagctgttga tgccctatgt gaaaaggcat taaaatattt gcccatagat aaatgtagta  17160
gaatcatacc tgcgcgtgcg cgcgtagagt gttttgataa attcaaagtg aattcaacac  17220
tagaacagta tgttttctgc actgtaaatg cattgccaga aacaactgct gacattgtag  17280
tctttgatga aatctctatg gctactaatt atgacttgag tgttgtcaat gctagacttc  17340
gtgcaaaaca ctacgtctat attggcgatc ctgctcaatt accagccccc cgcacattgc  17400
tgactaaagg cacactagaa ccagaatatt ttaattcagt gtgcagactt atgaaaacaa  17460
taggtccaga catgttcctt ggaacttgtc gccgttgtcc tgctgaaatt gttgacactg  17520
tgagtgcttt agtttatgac aataagctaa aagcacacaa ggataagtca gctcaatgct  17580
tcaaaatgtt ctacaaaggt gttattacac atgatgtttc atctgcaatc aacagacctc  17640
aaataggcgt tgtaagagaa tttcttacac gcaatcctgc ttggagaaaa gctgttttta  17700
tctcacctta taattcacag aacgctgtag cttcaaaaat cttaggattg cctacgcaga  17760
ctgttgattc atcacagggt tctgaatatg actatgtcat attcacacaa actactgaaa  17820
cagcacactc ttgtaatgtc aaccgcttca atgtggctat cacaagggca aaaattggca  17880
ttttgtgcat aatgtctgat agagatcttt atgacaaact gcaatttaca agtctagaaa  17940
taccacgtcg caatgtggct acattacaag cagaaaatgt aactggactt tttaaggact  18000
gtagtaagat cattactggt cttcatccta cacaggcacc tacacacctc agcgttgata  18060
taaagttcaa gactgaagga ttatgtgttg acataccagg cataccaaag gacatgacct  18120
accgtagact catctctatg atgggtttca aaatgaatta ccaagtcaat ggttacccta  18180
atatgtttat cacccgcgaa gaagctattc gtcacgttcg tgcgtggatt ggctttgatg  18240
tagagggctg tcatgcaact agagatgctg tgggtactaa cctacctctc cagctaggat  18300
tttctacagg tgttaactta gtagctgtac cgactggtta tgttgacact gaaaataaca  18360
cagaattcac cagagttaat gcaaaacctc caccaggtga ccagtttaaa catcttatac  18420
cactcatgta taaaggcttg ccctggaatg tagtgcgtat taagatagta caaatgctca  18480
gtgatacact gaaaggattg tcagacagag tcgtgttcgt cctttgggcg catggctttg  18540
```

agcttacatc aatgaagtac tttgtcaaga ttggacctga aagaacgtgt tgtctgtgtg 18600
acaaacgtgc aacttgcttt tctacttcat cagatactta tgcctgctgg aatcattctg 18660
tgggttttga ctatgtctat aacccattta tgattgatgt tcagcagtgg ggctttacgg 18720
gtaaccttca gagtaaccat gaccaacatt gccaggtaca tggaaatgca catgtggcta 18780
gttgtgatgc tatcatgact agatgtttag cagtccatga gtgctttgtt aagcgcgttg 18840
attggtctgt tgaataccct attataggag atgaactgag ggttaattct gcttgcagaa 18900
aagtacaaca catggttgtg aagtctgcat tgcttgctga taagtttcca gttcttcatg 18960
acattggaaa tccaaaggct atcaagtgtg tgcctcaggc tgaagtagaa tggaagttct 19020
acgatgctca gccatgtagt gacaaagctt acaaaataga ggaactcttc tattcttatg 19080
ctacacatca cgataaattc actgatggtg tttgtttgtt ttggaattgt aacgttgatc 19140
gttacccagc caatgcaatt gtgtgtaggt ttgacacaag agtcttgtca aacttgaact 19200
taccaggctg tgatggtggt agtttgtatg tgaataagca tgcattccac actccagctt 19260
tcgataaaag tgcatttact aatttaaagc aattgccttt cttttactat tctgatagtc 19320
cttgtgagtc tcatggcaaa caagtagtgt cggatattga ttatgttcca ctcaaatctg 19380
ctacgtgtat tacacgatgc aatttaggtg gtgctgtttg cagacaccat gcaaatgagt 19440
accgacagta cttggatgca tataatatga tgatttctgc tggatttagc ctatggattt 19500
acaaacaatt tgatacttat aacctgtgga atacatttac caggttacag agtttagaaa 19560
atgtggctta taatgttgtt aataaaggac actttgatgg acacgccggc gaagcacctg 19620
tttccatcat taataatgct gtttacacaa aggtagatgg tattgatgtg gagatctttg 19680
aaaataagac aacacttcct gttaatgttg catttgagct ttgggctaag cgtaacatta 19740
aaccagtgcc agagattaag atactcaata atttgggtgt tgatatcgct gctaatactg 19800
taatctggga ctacaaaaga gaagccccag cacatgtatc tacaataggt gtctgcacaa 19860
tgactgacat tgccaagaaa cctactgaga gtgcttgttc ttcacttact gtcttgtttg 19920
atggtagagt ggaaggacag gtagaccttt ttagaaacgc ccgtaatggt gttttaataa 19980
cagaaggttc agtcaaaggt ctaacacctt caaagggacc agcacaagct agcgtcaatg 20040
gagtcacatt aattggagaa tcagtaaaaa cacagtttaa ctactttaag aaagtagacg 20100
gcattattca acagttgcct gaaacctact ttactcagag cagagactta gaggatttta 20160
agcccagatc acaaatggaa actgactttc tcgagctcgc tatggatgaa ttcatacagc 20220
gatataagct cgagggctat gccttcgaac acatcgttta tggagatttc agtcatggac 20280
aacttggcgg tcttcattta atgataggct tagccaagcg ctcacaagat tcaccactta 20340
aattagagga ttttatccct atggacagca cagtgaaaaa ttacttcata acagatgcgc 20400
aaacaggttc atcaaaatgt gtgtgttctg tgattgatct tttacttgat gactttgtcg 20460
agataataaa gtcacaagat ttgtcagtga tttcaaaagt ggtcaaggtt acaattgact 20520
atgctgaaat ttcattcatg ctttggtgta aggatggaca tgttgaaacc ttctacccaa 20580
aactacaagc aagtcaagcg tggcaaccag gtgttgcgat gcctaacttg tacaagatgc 20640
aaagaatgct tcttgaaaag tgtgaccttc agaattatgg tgaaaatgct gttataccaa 20700
aaggaataat gatgaatgtc gcaaagtata ctcaactgtg tcaatactta aatacactta 20760
ctttagctgt accctacaac atgagagtta ttcactttgg tgctggctct gataaaggag 20820
ttgcaccagg tacagctgtg ctcagacaat ggttgccaac tggcacacta cttgtcgatt 20880

-continued

```
cagatcttaa tgacttcgtc tccgacgcag attctacttt aattggagac tgtgcaacag  20940
tacatacggc taataaatgg gaccttatta ttagcgatat gtatgaccct aggaccaaac  21000
atgtgacaaa agagaatgac tctaaagaag ggtttttcac ttatctgtgt ggatttataa  21060
agcaaaaact agccctgggt ggttctatag ctgtaaagat aacagagcat tcttggaatg  21120
ctgaccttta caagcttatg ggccatttct catggtggac agcttttgtt acaaatgtaa  21180
atgcatcatc atcggaagca tttttaattg ggctaacta tcttggcaag ccgaaggaac  21240
aaattgatgg ctataccatg catgctaact acattttctg gaggaacaca aatcctatcc  21300
agttgtcttc ctattcactc tttgacatga gcaaatttcc tcttaaatta agaggaactg  21360
ctgtaatgtc tcttaaggag aatcaaatca atgatatgat ttattctctt ctggaaaaag  21420
gtaggcttat cattagagaa aacaacagag ttgtggtttc aagtgatatt cttgttaaca  21480
actaaacgaa catgtttatt ttcttattat ttcttactct cactagtggt agtgaccttg  21540
accggtgcac cacttttgat gatgttcaag ctcctaatta cactcaacat acttcatcta  21600
tgaggggggt ttactatcct gatgaaattt ttagatcaga cactctttat ttaactcagg  21660
atttatttct tccattttat tctaatgtta cagggtttca tactattaat catacgtttg  21720
gcaaccctgt catacctttt aaggatggta tttattttgc tgccacagag aaatcaaatg  21780
ttgtccgtgg ttgggttttt ggttctacca tgaacaacaa gtcacagtcg gtgattatta  21840
ttaacaattc tactaatgtt gttatacgag catgtaactt tgaattgtgt gacaaccctt  21900
tctttgctgt ttctaaaccc atgggtacac agacacatac tatgatattc gataatgcat  21960
ttaattgcac tttcgagtac atatctgatg ccttttcgct tgatgtttca gaaaagtcag  22020
gtaattttaa acacttacga gagtttgtgt ttaaaaataa agatgggttt ctctatgttt  22080
ataagggcta tcaacctata gatgtagttc gtgatctacc ttctggtttt aacactttga  22140
aacctatttt taagttgcct cttggtatta acattacaaa ttttagagcc attcttacag  22200
ccttttcacc tgctcaagac atttggggca cgtcagctgc agcctatttt gttggctatt  22260
taaagccaac tacatttatg ctcaagtatg atgaaaatgg tacaatcaca gatgctgttg  22320
attgttctca aaatccactt gctgaactca aatgctctgt taagagcttt gagattgaca  22380
aaggaattta ccagacctct aatttcaggg ttgttccctc aggagatgtt gtgagattcc  22440
ctaatattac aaacttgtgt ccttttggag aggtttttaa tgctactaaa ttcccttctg  22500
tctatgcatg ggagagaaaa aaaatttcta attgtgttgc tgattactct gtgctctaca  22560
actcaacatt tttttcaacc tttaagtgct atggcgtttc tgccactaag ttgaatgatc  22620
tttgcttctc caatgtctat gcagattctt ttgtagtcaa gggagatgat gtaagacaaa  22680
tagcgccagg acaaactggt gttattgctg attataatta taaattgcca gatgatttca  22740
tgggttgtgt ccttgcttgg aatactagga acattgatgc tacttcaact ggtaattata  22800
attataaata taggtatctt agacatggca agcttaggcc ctttgagaga gacatatcta  22860
atgtgccttt ctcccctgat ggcaaacctt gcaccccacc tgctcttaat tgttattggc  22920
cattaaatga ttatggtttt tacaccacta ctggcattgg ctaccaacct tacagagttg  22980
tagtactttc ttttgaactt ttaaatgcac cggccacggt ttgtggacca aaattatcca  23040
ctgaccttat taagaaccag tgtgtcaatt ttaattttaa tggactcact ggtactggtg  23100
tgttaactcc ttcttcaaag agatttcaac catttcaaca atttggccgt gatgtttctg  23160
atttcactga ttccgttcga gatcctaaaa catctgaaat attagacatt tcaccttgcg  23220
cttttggggg tgtaagtgta attacacctg gaacaaatgc ttcatctgaa gttgctgttc  23280
```

-continued tatatcaaga tgttaactgc actgatgttt ctacagcaat tcatgcagat caactcacac 23340
cagcttggcg catatattct actggaaaca atgtattcca gactcaagca ggctgtctta 23400
taggagctga gcatgtcgac acttcttatg agtgcgacat tcctattgga gctggcattt 23460
gtgctagtta ccatacagtt tctttattac gtagtactag ccaaaaatct attgtggctt 23520
atactatgtc tttaggtgct gatagttcaa ttgcttactc taataacacc attgctatac 23580
ctactaactt ttcaattagc attactacag aagtaatgcc tgtttctatg gctaaaacct 23640
ccgtagattg taatatgtac atctgcggag attctactga atgtgctaat ttgcttctcc 23700
aatatggtag cttttgcaca caactaaatc gtgcactctc aggtattgct gctgaacagg 23760
atcgcaacac acgtgaagtg ttcgctcaag tcaaacaaat gtacaaaacc ccaactttga 23820
aatattttgg tggttttaat ttttcacaaa tattacctga ccctctaaag ccaactaaga 23880
ggtcttttat tgaggacttg ctctttaata aggtgacact cgctgatgct ggcttcatga 23940
agcaatatgg cgaatgccta ggtgatatta atgctagaga tctcatttgt gcgcagaagt 24000
tcaatggact tacagtgttg ccacctctgc tcactgatga tatgattgct gcctacactg 24060
ctgctctagt tagtggtact gccactgctg gatggacatt tggtgctggc gctgctcttc 24120
aaataccttt tgctatgcaa atggcatata ggttcaatgg cattggagtt acccaaaatg 24180
ttctctatga gaaccaaaaa caaatcgcca accaatttaa caaggcgatt agtcaaattc 24240
aagaatcact tacaacaaca tcaactgcat tgggcaagct gcaagacgtt gttaaccaga 24300
atgctcaagc attaaacaca cttgttaaac aacttagctc taattttggt gcaatttcaa 24360
gtgtgctaaa tgatatcctt tcgcgacttg ataaagtcga ggcggaggta caaattgaca 24420
ggttaattac aggcagactt caaagccttc aaacctatgt aacacaacaa ctaatcaggg 24480
ctgctgaaat cagggcttct gctaatcttg ctgctactaa aatgtctgag tgtgttcttg 24540
gacaatcaaa aagagttgac ttttgtggaa agggctacca ccttatgtcc ttcccacaag 24600
cagccccgca tggtgttgtc ttcctacatg tcacgtatgt gccatcccag gagaggaact 24660
tcaccacagc gccagcaatt tgtcatgaag gcaaagcata cttccctcgt gaaggtgttt 24720
ttgtgtttaa tggcacttct tggtttatta cacagaggaa cttcttttct ccacaaataa 24780
ttactacaga caatacattt gtctcaggaa attgtgatgt cgttattggc atcattaaca 24840
acacagttta tgatcctctg caacctgagc ttgactcatt caaagaagag ctggacaagt 24900
acttcaaaaa tcatacatca ccagatgttg atcttggcga catttcaggc attaacgctt 24960
ctgtcgtcaa cattcaaaaa gaaattgacc gcctcaatga ggtcgctaaa aatttaaatg 25020
aatcactcat tgaccttcaa gaattgggaa aatatgagca atatattaaa tggccttggt 25080
atgtttggct cggcttcatt gctggactaa ttgccatcgt catggttaca atcttgcttt 25140
gttgcatgac tagttgttgc agttgcctca agggtgcatg ctcttgtggt tcttgctgca 25200
agtttgatga ggatgactct gagccagttc tcaagggtgt caaattacat tacacataaa 25260
cgaacttatg gatttgttta tgagattttt tactcttaga tcaattactg cacagccagt 25320
aaaaattgac aatgcttctc ctgcaagtac tgttcatgct acagcaacga taccgctaca 25380
agcctcactc cctttcggat ggcttgttat tggcgttgca tttcttgctg tttttcagag 25440
cgctaccaaa ataattgcgc tcaataaaag atggcagcta gccctttata agggcttcca 25500
gttcatttgc aatttactgc tgctatttgt taccatctat tcacatcttt tgcttgtcgc 25560
tgcaggtatg gaggcgcaat tttgtacct ctatgccttg atatattttc tacaatgcat 25620

-continued caacgcatgt agaattatta tgagatgttg gctttgttgg aagtgcaaat ccaagaaccc 25680
attactttat gatgccaact actttgtttg ctggcacaca cataactatg actactgtat 25740
accatataac agtgtcacag atacaattgt cgttactgaa ggtgacggca tttcaacacc 25800
aaaactcaaa gaagactacc aaattggtgg ttattctgag gataggcact caggtgttaa 25860
agactatgtc gttgtacatg gctatttcac cgaagtttac taccagcttg agtctacaca 25920
aattactaca gacactggta ttgaaaatgc tacattcttc atctttaaca agcttgttaa 25980
agacccaccg aatgtgcaaa tacacacaat cgacggctct tcaggagttg ctaatccagc 26040
aatggatcca atttatgatg agccgacgac gactactagc gtgcctttgt aagcacaaga 26100
aagtgagtac gaacttatgt actcattcgt ttcggaagaa acaggtacgt taatagttaa 26160
tagcgtactt ctttttcttg ctttcgtggt attcttgcta gtcacactag ccatccttac 26220
tgcgcttcga ttgtgtgcgt actgctgcaa tattgttaac gtgagtttag taaaaccaac 26280
ggtttacgtc tactcgcgtg ttaaaaatct gaactcttct gaaggagttc ctgatcttct 26340
ggtctaaacg aactaactat tattattatt ctgtttggaa ctttaacatt gcttatcatg 26400
gcagacaacg gtactattac cgttgaggag cttaaacaac tcctggaaca atggaaccta 26460
gtaataggtt tcctattcct agcctggatt atgttactac aatttgccta ttctaatcgg 26520
aacaggtttt tgtacataat aaagcttgtt ttcctctggc tcttgtggcc agtaacactt 26580
gcttgttttg tgcttgctgc tgtctacaga attaattggg tgactggcgg gattgcgatt 26640
gcaatggctt gtattgtagg cttgatgtgg cttagctact tcgttgcttc cttcaggctg 26700
tttgctcgta cccgctcaat gtggtcattc aacccagaaa caaacattct tctcaatgtg 26760
cctctccggg ggacaattgt gaccagaccg ctcatggaaa gtgaacttgt cattggtgct 26820
gtgatcattc gtggtcactt gcgaatggcc ggacactccc tagggcgctg tgacattaag 26880
gacctgccaa aagagatcac tgtggctaca tcacgaacgc tttcttatta caaattagga 26940
gcgtcgcagc gtgtaggcac tgattcaggt tttgctgcat acaaccgcta ccgtattgga 27000
aactataaat taaatacaga ccacgccggt agcaacgaca atattgcttt gctagtacag 27060
taagtgacaa cagatgtttc atcttgttga cttccaggtt acaatagcag agatattgat 27120
tatcattatg aggactttca ggattgctat ttggaatctt gacgttataa taagttcaat 27180
agtgagacaa ttatttaagc ctctaactaa gaagaattat tcggagttag atgatgaaga 27240
acctatggag ttagattatc cataaaacga acatgaaaat tattctcttc ctgacattga 27300
ttgtatttac atcttgcgag ctatatcact atcaggagtg tgttagaggt acgactgtac 27360
tactaaaaga accttgccca tcaggaacat acgagggcaa ttcaccattt caccctcttg 27420
ctgacaataa atttgcacta acttgcacta gcacacactt tgcttttgct tgtgctgacg 27480
gtactcgaca tacctatcag ctgcgtgcaa gatcagtttc accaaaactt ttcatcagac 27540
aagaggaggt tcaacaagag ctctactcgc cactttttct cattgttgct gctctagtat 27600
ttttaatact ttgcttcacc attaagagaa agacagaatg aatgagctca ctttaattga 27660
cttctatttg tgctttttag cctttctgct attccttgtt ttaataatgc ttattatatt 27720
ttggttttca ctcgaaatcc aggatctaga agaaccttgt accaaagtct aaacgaacat 27780
gaaacttctc attgttttga cttgtatttc tctatgcagt tgcatatgca ctgtagtaca 27840
gcgctgtgca tctaataaac ctcatgtgct tgaagatcct tgtaaggtac aacactaggg 27900
gtaatactta tagcactgct tggctttgtg ctctaggaaa ggttttacct tttcatagat 27960
ggcacactat ggttcaaaca tgcacaccta atgttactat caactgtcaa gatccagctg 28020

-continued

```
gtggtgcgct tatagctagg tgttggtacc ttcatgaagg tcaccaaact gctgcattta  28080
gagacgtact tgttgtttta aataaacgaa caaattaaaa tgtctgataa tggaccccaa  28140
tcaaaccaac gtagtgcccc ccgcattaca tttggtggac ccacagattc aactgacaat  28200
aaccagaatg gaggacgcaa tggggcaagg ccaaaacagc gccgacccca aggtttaccc  28260
aataatactg cgtcttggtt cacagctctc actcagcatg gcaaggagga acttagattc  28320
cctcgaggcc agggcgttcc aatcaacacc aatagtggtc cagatgacca aattggctac  28380
taccgaagag ctacccgacg agttcgtggt ggtgacggca aaatgaaaga gctcagcccc  28440
agatggtact tctattacct aggaactggc ccagaagctt cacttcccta cggcgctaac  28500
aaagaaggca tcgtatgggt tgcaactgag ggagccttga atacacccaa agaccacatt  28560
ggcacccgca atcctaataa caatgctgcc accgtgctac aacttcctca aggaacaaca  28620
ttgccaaaag gcttctacgc agagggaagc agaggcggca gtcaagcctc ttctcgctcc  28680
tcatcacgta gtcgcggtaa ttcaagaaat tcaactcctg gcagcagtag gggaaattct  28740
cctgctcgaa tggctagcgg aggtggtgaa actgccctcg cgctattgct gctagacaga  28800
ttgaaccagc ttgagagcaa agtttctggt aaaggccaac aacaacaagg ccaaactgtc  28860
actaagaaat ctgctgctga ggcatctaaa aagcctcgcc aaaaacgtac tgccacaaaa  28920
cagtacaacg tcactcaagc atttgggaga cgtggtccag aacaaaccca aggaaatttc  28980
ggggaccaag acctaatcag acaaggaact gattacaaac attggccgca aattgcacaa  29040
tttgctccaa gtgcctctgc attctttgga atgtcacgca ttggcatgga agtcacacct  29100
tcgggaacat ggctgactta tcatggagcc attaaattgg atgacaaaga tccacaattc  29160
aaagacaacg tcatactgct gaacaagcac attgacgcat acaaaacatt cccaccaaca  29220
gagcctaaaa aggacaaaaa gaaaaagact gatgaagctc agcctttgcc gcagagacaa  29280
aagaagcagc ccactgtgac tcttcttcct gcggctgaca tggatgattt ctccagacaa  29340
cttcaaaatt ccatgagtgg agcttctgct gattcaactc aggcataaac actcatgatg  29400
accacacaag gcagatgggc tatgtaaacg ttttcgcaat tccgtttacg atacatagtc  29460
tactcttgtg cagaatgaat tctcgtaact aaacagcaca agtaggttta gttaacttta  29520
atctcacata gcaatcttta atcaatgtgt aacattaggg aggacttgaa agagccacca  29580
cattttcatc gaggccacgc ggagtacgat cgagggtaca gtgaataatg ctagggagag  29640
ctgcctatat ggaagagccc taatgtgtaa aattaatttt agtagtgcta tccccatgtg  29700
attttaatag cttcttagga gaatgacaaa aaaaaaaaaa aaaaaaaaaa a           29751
```

<210> SEQ ID NO 4
<211> LENGTH: 30119
<212> TYPE: DNA
<213> ORGANISM: Human coronavirus

<400> SEQUENCE: 4

```
gatttaagtg aatagcttgg ctatctcact tcccctcgtt ctcttgcaga actttgattt     60
taacgaactt aaataaaagc cctgttgttt agcgtatcgt tgcacttgtc tggtgggatt    120
gtggcattaa tttgcctgct catctaggca gtggacatat gctcaacact gggtataatt    180
ctaattgaat actatttttc agttagagcg tcgtgtctct tgtacgtctc ggtcacaata    240
cacggtttcg tccggtgcgt ggcaattcgg ggcacatcat gtctttcgtg gctggtgtga    300
ccgcgcaagg tgcgcgcggt acgtatcgag cagcgctcaa ctctgaaaaa catcaagacc    360
```

-continued

```
atgtgtctct aactgtgcca ctctgtggtt caggaaacct ggttgaaaaa ctttcaccat    420
ggttcatgga tggcgaaaat gcctatgaag tggtgaaggc catgttactt aaaaaggagc    480
cacttctcta tgtgcccatc cggctggctg gacacactag acacctccca ggtcctcgtg    540
tgtacctggt tgagaggctc attgcttgtg aaaatccatt catggttaac caattggctt    600
atagctctag tgcaaatggc agcctggttg gcacaacttt gcagggcaag cctattggta    660
tgttcttccc ttatgacatc gaacttgtca caggaaagca aaatattctc ctgcgcaagt    720
atggccgtgg tggttatcac tacaccccat tccactatga gcgagacaac acctcttgcc    780
ctgagtggat ggacgatttt gaggcggatc ctaaaggcaa atatgcccag aatctgctta    840
agaagttgat tggcggtgat gtcactccag ttgaccaata catgtgtggc gttgatggaa    900
aacccattag tgcctacgca tttttaatgg ccaaggatgg aataaccaaa ctggctgatg    960
ttgaagcgga cgtcgcagca cgtgctgatg acgaaggctt catcacatta aagaacaatc   1020
tatatagatt ggtttggcat gttgagcgta aagacgttcc atatcctaag caatctattt   1080
ttactattaa tagtgtggtc caaaaggatg gtgttgaaaa cactcctcct cactatttta   1140
ctcttggatg caaaatttta acgctcaccc cacgcaacaa gtggagtggc gtttctgact   1200
tgtccctcaa acaaaaactc ctttacacct tctatggtaa ggagtcactt gagaacccaa   1260
cctacattta ccactccgca ttcattgagt gtggaagttg tggtaatgat tcctggctta   1320
cagggaatgc tatccaaggg tttgcctgtg gatgtggggc atcatataca gctaatgatg   1380
tcgaagtcca atcatctggc atgattaagc caaatgctct tctttgtgct acttgcccct   1440
ttgctaaggg tgatagctgt tcttctaatt gcaaacattc agttgctcag ttggttagtt   1500
acctttctga acgctgtaat gttattgctg attctaagtc cttcacactt atctttggtg   1560
gcgtagctta cgcctacttt ggatgtgagg aaggtactat gtactttgtg cctagagcta   1620
agtctgttgt ctcaaggatt ggagactcca tctttacagg ctgtactggc tcttggaaca   1680
aggtcactca aattgctaac atgttcttgg aacagactca gcattccctt aactttgtgg   1740
gagagttcgt tgtcaacgat gttgtcctcg caattctctc tggaaccaca actaatgttg   1800
acaaaatacg ccagcttctc aaaggtgtca cccttgacaa gttgcgtgat tatttagctg   1860
actatgacgt agcagtcact gccggcccat tcatggataa tgctattaat gttggtggta   1920
caggattaca gtatgccgcc attactgcac cttatgtagt tctcactggc ttaggtgagt   1980
cctttaagaa agttgcaacc ataccgtata aggtttgcaa ctctgttaag gatactctgg   2040
cttattatgc tcacagcgtg ttgtacagag tttttcctta tgacatggat tctggtgtgt   2100
catcctttag tgaactactt tttgattgcg ttgatctttc agtagcttct acctattttt   2160
tagtccgcat cttgcaagat aagactggcg actttatgtc tacaattatt acttcctgcc   2220
aaactgctgt tagtaagctt ctagatacat gttttgaagc tacagaagca acatttaact   2280
tcttgttaga tttggcagga ttgttcagaa tctttctccg caatgcctat gtgtacactt   2340
cacaagggtt tgtggtggtc aatggcaaag tttctacact tgtcaaacaa gtgttagact   2400
tgcttaataa gggtatgcaa cttttgcata caaaggtctc ctgggctggt tctaaaatca   2460
ttgctgttat ctacagcggc agggagtctc taatattccc atcgggaacc tattactgtg   2520
tcaccactaa ggctaagtcc gttcaacaag atcttgacgt tattttgcct ggtgagtttt   2580
ccaagaagca gttaggactg ctccaaccta ctgacaattc tacaactgtt agtgttactg   2640
tatccagtaa catggttgaa actgttgtgg gtcaacttga gcaaactaat atgcatagtc   2700
ctgatgttat agtaggtgac tatgtcatta ttagtgaaaa attgtttgtg cgtagtaagg   2760
```

-continued

```
aagaagacgg atttgccttc taccctgctt gcactaatgg tcatgctgta ccgactctct   2820
ttagacttaa gggaggtgca cctgtaaaaa aagtagcctt tggcggtgat caagtacatg   2880
aggttgctgc tgtaagaagt gttactgtcg agtacaacat tcatgctgta ttagacacac   2940
tacttgcttc ttctagtctt agaacctttg ttgtagataa gtctttgtca attgaggagt   3000
ttgctgacgt agtaaaggaa caagtctcag acttgcttgt taaattactg cgtggaatgc   3060
cgattccaga ttttgattta gacgatttta ttgacgcacc atgctattgc tttaacgctg   3120
agggtgatgc atcctggtct tctactatga tcttctctct tcaccccgtc gagtgtgacg   3180
aggagtgttc tgaagtagag gcttcagatt tagaagaagg tgaatcagag tgcatttctg   3240
agacttcaac tgaacaagtt gacgtttctc atgagacttc tgacgacgag tgggctgctg   3300
cagttgatga agcgttccct ctcgatgaag cagaagatgt tactgaatct gtgcaagaag   3360
aagcacaacc agtagaagta cctgttgaag atattgcgca ggttgtcata gctgacacct   3420
tacaggaaac tcctgttgtg cctgatactg ttgaagtccc accgcaagtg gtgaaacttc   3480
cgtctgcacc tcagactatc cagcccgagg taaaagaagt tgcacctgtc tatgaggctg   3540
ataccgaaca gacacagaat gttactgtta aacctaagag gttacgcaaa aagcgtaatg   3600
ttgacccttt gtccaatttt gaacataagg ttattacaga gtgcgttacc atagttttag   3660
gtgacgcaat tcaagtagcc aagtgctatg gggagtctgt gttagttaat gctgctaaca   3720
cacatcttaa gcatggcggt ggtatcgctg gtgctattaa tgcggcttca aaaggggctg   3780
tccaaaaaga gtcagatgag tatattctgg ctaaagggcc gttacaagta ggagattcag   3840
ttctcttgca aggccattct ctagctaaga atatcctgca tgtcgtaggc ccagatgccc   3900
gcgctaaaca ggatgtttct ctccttagta agtgctataa ggctatgaat gcatatcctc   3960
ttgtagtcac tcctcttgtt tcagcaggca tatttggtgt aaaaccagct gtgtcttttg   4020
attatcttat tagggaggct aagactagag ttttagtcgt cgttaattcc caagatgtct   4080
ataagagtct taccatagtt gacattccac agagtttgac tttttcatat gatgggttac   4140
gtggcgcaat acgtaaagct aaagattatg gttttactgt ttttgtgtgc acagacaact   4200
ctgctaacac taaagttctt aggaacaagg gtgttgatta tactaagaag tttcttacag   4260
ttgacggtgt gcaatattat tgctacacgt ctaaggacac tttagatgat atcttacaac   4320
aggctaataa gtctgttggt attatatcta tgcctttggg atatgtgtct catggtttag   4380
acttaatgca agcagggagt gtcgtgcgta gagttaacgt gccctacgtg tgtctcctag   4440
ctaataaaga gcaagaagct attttgatgt ctgaagacgt taagttaaac ccttcagaag   4500
attttataaa gcacgtccgc actaatggtg gttacaattc ttggcattta gtcgagggtg   4560
aactattggt gcaagactta cgcttaaata agctcctgca ttggtctgat caaaccatat   4620
gctacaagga tagtgtgttt tatgttgtaa agaatagtac agcttttcca tttgaaacac   4680
tttcagcatg tcgtgcgtat ttggattcac gcacgacaca gcagttaaca atcgaagtct   4740
tagtgactgt cgatggtgta aattttagaa cagtcgttct aaataataag aacacttata   4800
gatcacagct tggatgcgtt ttctttaatg gtgctgatat ttctgacacc attcctgatg   4860
agaaacagaa tggtcacagt ttatatctag cagacaattt gactgctgat gaaacaaagg   4920
cgcttaaaga gttatatggc cccgttgatc ctactttctt acacagattc tattcactta   4980
aggctgcagt ccatgggtgg aagatggttg tgtgtgataa ggtacgttct ctcaaattga   5040
gtgataataa ttgttatctt aatgcagtta ttatgacact tgatttattg aaggacatta   5100
```

-continued

```
aatttgttat acctgctcta cagcatgcat ttatgaaaca taagggcggt gattcaactg   5160
acttcatagc cctcattatg gcttatggca attgcacatt tggtgctcca gatgatgcct   5220
ctcggttact tcataccgtg cttgcaaagg ctgagttatg ctgttctgca cgcatggttt   5280
ggagagagtg gtgcaatgtc tgtggcataa aagatgttgt tctacaaggc ttaaaagctt   5340
gttgttacgt gggtgtgcaa actgttgaag atctgcgtgc tcgcatgaca tatgtatgcc   5400
agtgtggtgg tgaacgtcat cggcaattag tcgaacacac cacccoctgg ttgctgctct   5460
caggcacacc aaatgaaaaa ttggtgacaa cctccacggc gcctgatttt gtagcattta   5520
atgtctttca gggcattgaa acggctgttg gccattatgt tcatgctcgc ctgaagggtg   5580
gtcttatttt aaagtttgac tctggcaccg ttagcaagac ttcagactgg aagtgcaagg   5640
tgacagatgt acttttcccc ggccaaaaat acagtagcga ttgtaatgtc gtacggtatt   5700
ctttggacgg taatttcaga acagaggttg atcccgacct atctgctttc tatgttaagg   5760
atggtaaata ctttacaagt gaaccacccg taacatattc accagctaca attttagctg   5820
gtagtgtcta cactaatagc tgccttgtat cgtctgatgg acaacctggc ggtgatgcta   5880
ttagtttgag ttttaataac cttttagggt ttgattctag taaaccagtc actaagaaat   5940
acacttactc cttcttgcct aaagaagacg gcgatgtgtt gttggctgag tttgacactt   6000
atgaccctat ttataagaat ggtgccatgt ataaaggcaa accaattctt tgggtcaata   6060
aagcatctta tgatactaat cttaataagt tcaatagagc tagtttgcgt caaatttttg   6120
acgtagcccc cattgaactc gaaaataaat tcacaccttt gagtgtggag tctacaccag   6180
ttgaacctcc aactgtagat gtggtagcac ttcaacagga aatgacaatt gtcaaatgta   6240
agggtttaaa taaacctttc gtgaaggaca atgtcagttt cgttgctgat gattcaggta   6300
ctcccgttgt tgagtatctg tctaaagaag acctacatac attgtatgta gaccctaagt   6360
atcaagtcat tgtcttaaaa gacaatgtac tttcttctat gcttagattg cacaccgttg   6420
agtcaggtga tattaacgtt gttgcagctt ccggatcttt gacacgtaaa gtgaagttac   6480
tatttagggc ttcattttat ttcaaagaat ttgctacccg cactttcact gctaccactg   6540
ctgtaggtag ttgtataaag agtgtagtgc ggcatctagg tgttactaaa ggcatattga   6600
caggctgttt tagttttgcc aagatgttat ttatgcttcc actagcttac tttagtgatt   6660
caaaactcgg caccacagag gttaaagtga gtgctttgaa aacagccggc gttgtgacag   6720
gtaatgttgt aaaacagtgt tgcactgctg ctgttgattt aagtatggat aagttgcgcc   6780
gtgtggattg gaaatcaacc ctacggttgt tacttatgtt atgcacaact atggtattgt   6840
tgtcttctgt gtatcacttg tatgtcttca atcaggtctt atcaagtgat gttatgtttg   6900
aagatgccca aggtttgaaa aagttctaca aagaagttag agcttaccta ggaatctctt   6960
ctgcttgtga cggtcttgct tcagcttata gggcgaattc ctttgatgta cctacattct   7020
gcgcaaaccg ttctgcaatg tgtaattggt gcttgattag ccaagattcc ataactcact   7080
acccagctct taagatggtt caaacacatc ttagccacta tgttcttaac atagattggt   7140
tgtggtttgc atttgagact ggtttggcat acatgctcta tacctcggcc ttcaactggt   7200
tgttgttggc aggtacattg cattatttct ttgcacagac ttccatattt gtagactggc   7260
ggtcatacaa ttatgctgtg tctagtgcct tctggttatt cacccacatt ccaatggcgg   7320
gtttggtacg aatgtataat ttgttagcat gcctttggct tttacgcaag ttttatcagc   7380
atgtaatcaa tggttgcaaa gatacggcat gcttgctctg ctataagagg aaccgactta   7440
ctagagttga agcttctacc gttgtctgtg gtggaaaacg tacgttttat atcacagcaa   7500
```

```
atggcggtat ttcattctgt cgtaggcata attggaattg tgtggattgt gacactgcag   7560
gtgtggggaa taccttcatc tgtgaagaag tcgcaaatga cctcactacc gccctacgca   7620
ggcctattaa cgctacggat agatcacatt attatgtgga ttccgttaca gttaaagaga   7680
ctgttgttca gtttaattat cgtagagacg gtcaaccatt ctacgagcgg tttcccctct   7740
gcgcttttac aaatctagat aagttgaagt tcaaagaggt ctgtaaaact actactggta   7800
tacctgaata caactttatc atctacgact catcagatcg tggccaggaa agtttagcta   7860
ggtctgcatg tgtttattat tctcaagtct tgtgtaaatc aattcttttg gttgactcaa   7920
gtttggttac ttctgttggt gattctagtg aaatcgccac taaaatgttt gattcctttg   7980
ttaatagttt cgtctcgctg tataatgtca cacgcgataa gttggaaaaa cttatctcta   8040
ctgctcgtga tggcgtaagg cgaggcgata acttccatag tgtcttaaca acattcattg   8100
acgcagcacg aggccccgca ggtgtggagt ctgatgttga gaccaatgaa attgttgact   8160
ctgtgcagta tgctcataaa catgacatac aaattactaa tgagagctac aataattatg   8220
taccctcata tgttaaacct gatagtgtgt ctaccagcga tttaggtagt ctcattgatt   8280
gtaatgcggc ttcagttaac caaattgtct tgcgtaattc taatggtgct tgcatttgga   8340
acgctgctgc atatatgaaa ctctcggatg cacttaaacg acagattcgc attgcatgcc   8400
gtaagtgtaa tttagctttc cggttaacca cctcaaagct acgcgctaat gataatatct   8460
tatcagttag attcactgct aacaaaattg ttggtggtgc tcctacatgg tttaatgcgt   8520
tgcgtgactt tacgttaaag ggttatgttc ttgctaccat tattgtgttt ctgtgtgctg   8580
tactgatgta tttgtgttta cctacatttt ctatggcacc tgttgaattt tatgaagacc   8640
gcatcttgga ctttaaagtt cttgataatg gtatcattag ggatgtaaat cctgatgata   8700
agtgctttgc taataagcac cggtccttca cacaatggta tcatgagcat gttggtggtg   8760
tctatgacaa ctctatcaca tgcccattga cagttgcagt aattgctgga gttgctggtg   8820
ctcgcattcc agacgtacct actacattgg cttgggtgaa caatcagata attttctttg   8880
tttctcgagt ctttgctaat acaggcagtg tttgctacac tcctatagat gagataccct   8940
ataagagttt ctctgatagt ggttgcattc ttccatctga gtgcactatg tttagggatg   9000
cagagggccg tatgacacca tactgccatg atcctactgt tttgcctggg gcttttgcgt   9060
acagtcagat gaggcctcat gttcgttacg acttgtatga tggtaacatg tttattaaat   9120
ttcctgaagt agtatttgaa agtacactta ggattactag aactctgtca actcagtact   9180
gccggttcgg tagttgtgag tatgcacaag agggtgtttg tattaccaca aatggctcgt   9240
gggccatttt taatgaccac catcttaata gacctggtgt ctattgtggc tctgatttta   9300
ttgacattgt caggcggtta gcagtatcac tgttccagcc tattacttat ttccaattga   9360
ctacctcatt ggtcttgggt ataggtttgt gtgcgttcct gactttgctc ttctattata   9420
ttaataaagt aaaacgtgct tttgcagatt acacccagtg tgctgtaatt gctgttgttg   9480
ctgctgttct taatagcttg tgcatctgct ttgttacctc tataccattg tgtatagtac   9540
cttacactgc attgtactat tatgctacat tctattttac taatgagcct gcatttatta   9600
tgcatgtttc ttggtacatt atgttcgggc ctatcgttcc catatggatg acctgcgtct   9660
atacagttgc aatgtgcttt agacacttct tctgggtttt agcttatttt agtaagaaac   9720
atgtagaagt ttttactgat ggtaagctta attgtagttt ccaggacgct gcctctaata   9780
tctttgttat taacaaggac acttatgcag ctcttagaaa ctctttaact aatgatgcct   9840
```

-continued

```
attcacgatt tttggggttg tttaacaagt ataagtactt ctctggtgct atggaaacag   9900
ccgcttatcg tgaagctgca gcatgtcatc ttgctaaagc cttacaaaca tacagcgaga   9960
ctggtagtga tcttctttac caaccaccca actgtagcat aacctctggc gtgttgcaaa  10020
gcggtttggt gaaaatgtca catcccagtg gagatgttga ggcttgtatg gttcaggtta  10080
cctgcggtag catgactctt aatggtcttt ggcttgacaa cacagtctgg tgcccacgac  10140
acgtaatgtg cccggctgac cagttgtctg atcctaatta tgatgccttg ttgatttcta  10200
tgactaatca tagtttcagt gtgcaaaaac acattggcgc tccagcaaac ttgcgtgttg  10260
ttggtcatgc catgcaaggc actcttttga agttgactgt cgatgttgct aaccctagca  10320
ctccagccta cacttttaca acagtgaaac ctggcgcagc atttagtgtg ttagcatgct  10380
ataatggtcg tccgactggt acattcactg ttgtaatgcg ccctaactac acaattaagg  10440
gttcctttct gtgtggttct tgtggtagtg ttggttacac caaggagggt agtgtgatca  10500
atttctgtta catgcatcaa atggaacttg ctaatggtac acataccggt tcagcatttg  10560
atggtactat gtatggtgcc tttatggata aacaagtgca ccaagttcag ttaacagaca  10620
aatactgcag tgttaatgta gtagcttggc tttacgcagc aatacttaat ggttgcgctt  10680
ggtttgtaaa acctaatcgc actagtgttg tttcttttaa tgaatgggct cttgccaacc  10740
aattcactga atttgttggc actcaatccg ttgacatgtt agctgtcaaa acaggcgttg  10800
ctattgaaca gctgctttat gcgatccaac aactgtatac tgggttccag ggaaagcaaa  10860
tccttggcag taccatgttg gaagatgaat tcacacctga ggatgttaat atgcagatta  10920
tgggtgtggt tatgcagagt ggtgtgagaa aagttacata tggtactgcg cattggttgt  10980
ttgcgaccct tgtctcaacc tatgtgataa tcttacaagc cactaaattt actttgtgga  11040
actacttgtt tgagactatt cccacacagt tgttcccact cttatttgtg actatggcct  11100
tcgttatgtt gttggttaaa cacaaacaca cctttttgac acttttcttg ttgcctgtgg  11160
ctatttgttt gacttatgca aacatagtct acgagcccac tactcccatt tcgtcagcgc  11220
tgattgcagt tgcaaattgg cttgccccca ctaatgctta tatgcgcact acacatactg  11280
atattggtgt ctacattagt atgtcacttg tattagtcat tgtagtgaag agattgtaca  11340
acccatcact ttctaacttt gcgttagcat tgtgcagtgg tgtaatgtgg ttgtacactt  11400
atagcattgg agaagcctca agccccattg cctatctggt tttgtcact acactcacta  11460
gtgattatac gattacagtc tttgttactg tcaaccttgc aaaagtttgc acttatgcca  11520
tctttgctta ctcaccacag cttacacttg tgtttccgga agtgaagatg atacttttat  11580
tatacacatg tttaggtttc atgtgtactt gctattttgg tgtcttctct cttttgaacc  11640
ttaagcttag agcacctatg ggtgtctatg actttaaggt ctcaacacaa gagttcagat  11700
tcatgactgc taacaatcta actgcaccta gaaattcttg ggaggctatg gctctgaact  11760
ttaagttaat aggtattggc ggtacacctt gtataaaggt tgctgctatg cagtctaaac  11820
ttacagatct taaatgcaca tctgtggttc tcctctctgt gctccaacag ttacacttag  11880
aggctaatag tagggcctgg gctttctgtg ttaaatgcca taatgatata ttggcagcaa  11940
cagaccccag tgaggctttc gagaaattcg taagtctctt tgctacttta atgacttttt  12000
ctggtaatgt agatcttgat gcgttagcta gtgatatttt tgacactcct agcgtacttc  12060
aagctactct ttctgagttt tcacacttag ctacctttgc tgagttggaa gctgcgcaga  12120
aagcctatca ggaagctatg gactctggtg acacctcacc acaagttctt aaggctttgc  12180
agaaggctgt taatatagct aaaaacgcct atgagaagga taaggcagtg gcccgtaagt  12240
```

-continued

```
tagaacgtat ggctgatcag gctatgactt ctatgtataa gcaagcacgt gctgaagaca  12300
agaaagcaaa aattgtcagt gctatgcaaa ctatgttgtt tggtatgatt aagaagctcg  12360
acaacgatgt tcttaatggt atcatttcta acgctaggaa tggttgtata cctcttagtg  12420
tcatcccact gtgtgcttca aataaacttc gcgttgtaat tcctgacttc accgtctgga  12480
atcaggtagt cacatatccc tcgcttaact acgctggggc tttgtgggac attacagtta  12540
taaacaatgt ggacaatgaa attgttaagt cttcagatgt tgtagacagc aatgaaaatt  12600
taacatggcc acttgtttta gaatgcacta gggcatccac ttctgccgtt aagttgcaaa  12660
ataatgagat caaaccttca ggtctaaaaa ccatggttgt gtctgcgggt caagagcaaa  12720
ctaactgtaa tactagttcc ttagcttatt acgaacctgt gcagggtcgt aaaatgctga  12780
tggctcttct ttctgataat gcctatctca aatgggcgcg tgttgaaggt aaggacggat  12840
ttgtcagtgt agagctacaa cctccttgca aattcttgat tgcgggacca aaaggacctg  12900
aaatccgata tctctatttt gttaaaaatc ttaacaacct tcatcgcggg caagtgttag  12960
ggcacattgc tgcgactgtt agattgcaag ctggttctaa caccgagttt gcctctaatt  13020
cctcggtgtt gtcacttgtt aacttcaccg ttgatcctca aaaagcttat ctcgatttcg  13080
tcaatgcggg aggtgcccca ttgacaaatt gtgttaagat gcttactcct aaaactggta  13140
caggtatagc tatatctgtt aaaccagaga gtacagctga tcaagagact tatggtggag  13200
cttcagtgtg tctctattgc cgtgcgcata tagaacatcc tgatgtctct ggtgtttgta  13260
aatataaggg taagtttgtc caaatccctg ctcagtgtgt ccgtgaccct gtgggatttt  13320
gtttgtcaaa tacccccctgt aatgtctgtc aatattggat tggatatggg tgcaattgtg  13380
actcgcttag gcaagcagca ctgccccaat ctaaagattc caatttttta aacgagtccg  13440
gggttctatt gtaaatgccc gaatagaacc ctgttcaagt ggtttgtcca ctgatgtcgt  13500
ctttagggca tttgacatct gcaactataa ggctaaggtt gctggtattg gaaaatacta  13560
caagactaat acttgtaggt ttgtagaatt agatgaccaa gggcatcatt tagactccta  13620
ttttgtcgtt aagaggcata ctatggagaa ttatgaacta gagaagcact gttacgactt  13680
gttacgtgac tgtgatgctg tagctcccca tgatttcttc atctttgatg tagacaaagt  13740
taaaacacct catattgtac gtcagcgttt aactgagtac actatgatgg atcttgtata  13800
tgccctgagg cactttgatc aaaatagcga agtgcttaag gctatcttag tgaagtatgg  13860
ttgctgtgat gttacctact ttgaaaataa actctggttt gattttgttg aaaatcccag  13920
tgttattggt gtttatcata aacttggaga acgtgtacgc caagctatct taaacactgt  13980
taaattttgt gaccacatgg tcaaggctgg tttagtcggt gtgctcacac tagacaacca  14040
ggaccttaat ggcaagtggt atgattttgg tgacttcgta atcactcaac ctggttcagg  14100
agtagctata gttgatagct actattctta tttgatgcct gtgctctcaa tgaccgattg  14160
tctggccgct gagacacata gggattgtga ttttaataaa ccactcattg agtggccact  14220
tactgagtat gattttactg attataaggt acaactcttt gagaagtact ttaaatattg  14280
ggatcagacg tatcacgcaa attgcgttaa ttgtactgat gaccgttgtg tgttacattg  14340
tgctaatttc aatgtattgt ttgctatgac catgcctaag acttgtttcg gacccatagt  14400
ccgaaagatc tttgttgatg gcgtgccatt tgtagtatct tgtggttatc actacaaaga  14460
attaggttta gtcatgaata tggatgttag tctccataga cataggctct ctcttaagga  14520
gttgatgatg tatgccgctg atccagccat gcacattgcc tcctctaacg cttttcttga  14580
```

```
tttgaggaca tcatgtttta gtgtcgctgc acttacaact ggtttgactt ttcaaactgt  14640
gcggcctggc aattttaacc aagacttcta tgatttcgtg gtatctaaag gtttctttaa  14700
ggagggctct tcagtgacgc tcaaacattt tttctttgct caagatggta atgctgctat  14760
tacagattat aattactatt cttataatct gcctactatg tgtgacatca aacaaatgtt  14820
gttctgcatg gaagttgtaa acaagtactt cgaaatctat gacggtggtt gtcttaatgc  14880
ttctgaagtg gttgttaata atttagacaa gagtgctggc catccttta ataagtttgg  14940
caaagctcgt gtctattatg agagcatgtc ttaccaggag caagatgaac tttttgccat  15000
gacaaagcgt aacgtcattc ctaccatgac tcaaatgaat ctaaaatatg ctattagtgc  15060
taagaataga gctcgcactg ttgcaggcgt gtccatactt agcacaatga ctaatcgcca  15120
gtaccatcag aaaatgctta agtccatggc tgcaactcgt ggagcgactt gcgtcattgg  15180
tactacaaag ttctacggtg gctgggattt catgcttaaa acattgtaca aagatgttga  15240
taatccgcat cttatgggtt gggattaccc taagtgtgat agagctatgc ctaatatgtg  15300
tagaatcttc gcttcactca tattagctcg taaacatggc acttgttgta ctacaaggga  15360
cagattttat cgcttggcaa atgagtgtgc tcaggtgcta agcgaatatg ttctatgtgg  15420
tggtggttac tacgtcaaac ctggaggtac cagtagcgga gatgccacca ctgcatatgc  15480
caatagtgtc tttaacattt tgcaggcgac aactgctaat gtcagtgcac ttatgggtgc  15540
taatggcaac aagattgttg acaaagaagt taaagacatg cagtttgatt tgtatgtcaa  15600
tgtttacagg agcactagcc cagaccccaa atttgttgat aaatactatg cttttcttaa  15660
taagcacttt tctatgatga tactgtctga tgacggtgtc gtttgctata atagtgatta  15720
tgcagctaag ggttacattg ctggaataca gaattttaag gaaacgctgt attatcagaa  15780
caatgtcttt atgtctgaag ctaaatgctg ggtggaaacc gatctgaaga aagggccaca  15840
tgaattctgt tcacagcata cgctttatat taaggatggc gacgatggtt acttccttcc  15900
ttatccagac ccttcaagaa ttttgtctgc cggttgcttt gtagatgata tcgttaagac  15960
tgacggtaca ctcatggtag agcggtttgt gtctttggct atagatgctt accctctcac  16020
aaagcatgaa gatatagaat accagaatgt attctgggtc tacttacagt atatagaaaa  16080
actgtataaa gaccttacag gacacatgct tgacagttat tctgtcatgc tatgtggtga  16140
taattctgct aagttttggg aagaggcatt ctatagagat ctctatagtt cgcctaccac  16200
tttgcaggct gtcggttcat gcgttgtatg ccattcacag acttccctac gctgtgggac  16260
atgcatccgt agaccatttc tctgctgtaa atgctgctat gatcatgtta tagcaactcc  16320
acataagatg gttttgtctg tttctcctta cgtttgtaat gcccctggtt gtggcgtttc  16380
agacgttact aagctatatt taggtggtat gagctacttt tgtgtagatc atagacctgt  16440
gtgtagtttt ccactttgcg ctaatggtct tgtattcggc ttatacaaga atatgtgcac  16500
aggtagtcct tctatagttg aatttaatag gttggctacc tgtgactgga ctgaaagtgg  16560
tgattacacc cttgccaata ctacaacaga accactcaaa ctttttgctg ctgagacttt  16620
acgtgccact gaagaggcgt ctaagcagtc ttatgctatt gccaccatca aagaaattgt  16680
tggtgagcgc caactattac ttgtgtggga ggctggcaag tccaaaccac cactcaatcg  16740
taattatgtt tttactggtt atcatataac caaaaatagt aaagtgcagc tcggtgagta  16800
cattttcgag cgcattgatt atagtgatgc tgtatcctac aagtctagta caacgtataa  16860
actgactgta ggtgacatct tcgtacttac ctctcactct gtggctacct tgacggcgcc  16920
cacaattgtg aatcaagaga ggtatgttaa aattactggg ttgtacccaa ccattacggt  16980
```

-continued

```
acctgaagag ttcgcaagtc atgttgccaa cttccaaaaa tcaggttata gtaaatatgt  17040
cactgttcag ggaccacctg gcactggcaa aagtcatttt gctatagggt tagcgattta  17100
ctaccctaca gcacgtgttg tttatacagc atgttcacac gcagctgttg atgctttgtg  17160
tgaaaaagct tttaaatatt tgaacattgc taaatgttcc cgtatcattc ctgcaaaggc  17220
acgtgttgag tgctatgaca ggtttaaagt taatgagaca aattctcaat atttgtttag  17280
tactattaat gctctaccag aaacttctgc cgatattctg gtggttgatg aggttagtat  17340
gtgcactaat tatgatcttt caattattaa tgcacgtatt aaagctaagc acattgtcta  17400
tgtaggagat ccagcacagt tgccagctcc taggactttg ttgactagag gcacattgga  17460
accagaaaat ttcaatagtg tcactagatt gatgtgtaac ttaggtcctg acatattttt  17520
aagtatgtgc tacaggtgtc ctaaggaaat agtaagcact gtgagcgctc ttgtctacaa  17580
taataaattg ttagccaaga aggagctttc aggccagtgc tttaaaatac tctataaggg  17640
caatgtgacg catgatgcta gctctgccat taatagacca caactcacat ttgtgaagaa  17700
ttttattact gccaatccgg catggagtaa ggcagtcttt atttcgcctt acaattcaca  17760
gaatgctgtg tctcgttcaa tgctgggtct taccactcag actgttgatt cctcacaggg  17820
ttcagaatac cagtacgtta tcttctgtca aacagcagat acggcacatg ctaacaacat  17880
taacagattt aatgttgcaa tcactcgtgc ccaaaaaggt attctttgtg ttatgacatc  17940
tcaggcactc tttgagtcct tagagtttac tgaattgtct tttactaatt acaagctcca  18000
gtctcagatt gtaactggcc tttttaaaga ttgctctaga gaaacttctg gcctctcacc  18060
tgcttatgca ccaacatatg ttagtgttga tgacaagtat aagacgagtg atgagctttg  18120
cgtgaatctt aatttacccg caaatgtccc atactctcgt gttatttcca ggatgggctt  18180
taaactcgat gcaacagttc ctggatatcc taagcttttc attactcgtg aagaggctgt  18240
aaggcaagtt cgaagctgga taggcttcga tgttgagggt gctcatgctt cccgtaatgc  18300
atgtggcacc aatgtgcctc tacaattagg attttcaact ggtgtgaact ttgttgttca  18360
gccagttggt gttgtagaca ctgagtgggg taacatgtta acgggcattg ctgcacgtcc  18420
tccaccaggt gaacagttta agcacctcgt gcctcttatg cataaggggg ctgcgtggcc  18480
tattgttaga cgacgtatag tgcaaatgtt gtcagacact ttagacaaat tgtctgatta  18540
ctgtacgttt gtttgttggg ctcatggctt tgaattaacg tctgcatcat acttttgcaa  18600
gataggtaag gaacagaagt gttgcatgtg caatagacgc gctgcagcgt actcttcacc  18660
tctgcaatct tatgcctgct ggactcattc ctgcggttat gattatgtct acaacccttt  18720
ctttgtcgat gttcaacagt ggggttatgt aggcaatctt gctactaatc acgatcgtta  18780
ttgctctgtc catcaaggag ctcatgtggc ttctaatgat gcaataatga ctcgttgttt  18840
agctattcat tcttgtttta tagaacgtgt ggattgggat atagagtatc cttatatctc  18900
acatgaaaag aaattgaatt cctgttgtag aatcgttgag cgcaacgtcg tacgtgctgc  18960
tcttcttgcc ggttcatttg acaaagtcta tgatattggc aatcctaaag gaattcctat  19020
tgttgatgac cctgtggttg attggcatta ttttgatgca cagcccttga ccaggaaggt  19080
acaacagctt ttctatacag aggacatggc ctcaagattt gctgatgggc tctgcttatt  19140
ttggaactgt aatgtaccaa aatatcctaa taatgcaatt gtatgcaggt ttgacacacg  19200
tgtgcattct gagttcaatt tgccaggttg tgatggcggt agtttgtatg ttaacaagca  19260
cgcttttcat acaccagcat atgatgtgag tgcattccgt gatctgaaac ctttaccatt  19320
```

-continued

```
cttttattat tctactacac catgtgaagt gcatggtaat ggtagtatga tagaggatat  19380
tgattatgta cccctaaaat ctgcagtctg tattacagct tgtaatttag ggggcgctgt  19440
ttgtaggaag catgctacag agtacagaga gtatatggaa gcatataatc ttgtctctgc  19500
atcaggtttc cgcctttggt gttataagac ctttgatatt tataatctct ggtctacttt  19560
tacaaaagtt caaggtttgg aaaacattgc ttttaatgtt gttaaacaag gccattttat  19620
tggtgttgag ggtgaactac ctgtagctgt agtcaatgat aagatcttca ccaagagtgg  19680
cgttaatgac atttgtatgt ttgagaataa aaccactttg cctactaata tagcttttga  19740
actctatgct aagcgtgctg tacgctcgca tcccgatttc aaattgctac acaatttaca  19800
agcagacatt tgctacaagt tcgtcctttg ggattatgaa cgtagcaata tttatggtac  19860
tgctactatt ggtgtatgta agtacactga tattgatgtt aattcagctt tgaatatatg  19920
ttttgacata cgcgataatt gttcattgga gaagttcatg tctactccca atgccatctt  19980
tatttctgat agaaaaatca agaaataccc ttgtatggta ggtcctgatt atgcttactt  20040
caatggtgct atcatccgtg atagtgatgt tgttaaacaa ccagtgaagt tctacttgta  20100
taagaaagtc aataatgagt ttattgatcc tactgagtgt atttacactc agagtcgctc  20160
ttgtagtgac ttcctacccc tttctgacat ggagaaagac tttctatctt ttgatagtga  20220
tgttttcatt aagaagtatg gcttggaaaa ctatgctttt gagcacgtag tctatggaga  20280
cttctctcat actacgttag gcggtcttca cttgcttatt ggtttataca agaagcaaca  20340
ggaaggtcat attattatgg aagaaatgct aaaaggtagc tcaactattc ataactattt  20400
tattactgag actaacacag cggcttttaa ggcggtgtgt tctgttatag atttaaagct  20460
tgacgacttt gttatgattt taaagagtca agaccttggc gtagtatcca aggttgtcaa  20520
ggttcctatt gacttaacaa tgattgagtt tatgttatgg tgtaaggatg gacaggttca  20580
aaccttctac cctcgactcc aggcttctgc agattggaaa cctggtcatg caatgccatc  20640
cctctttaaa gttcaaaatg taaaccttga acgttgtgag cttgctaatt acaagcaatc  20700
tattcctatg cctcgcggtg tgcacatgaa catcgctaaa tatatgcaat tgtgccagta  20760
tttaaatact tgcacattag ccgtgcctgc caatatgcgt gttatacatt ttggcgctgg  20820
ttctgataaa ggtatcgctc ctggtacctc agttttacga cagtggcttc ctacagatgc  20880
cattattata gataatgatt taaatgagtt cgtgtcagat gctgacataa ctttatttgg  20940
agattgtgta actgtacgtg tcggccaaca agtggatctt gttatttccg acatgtatga  21000
tcctactact aagaatgtaa caggtagtaa tgagtcaaag gctttattct ttacttacct  21060
gtgtaacctc attaataata atcttgctct tggtgggtct gttgctatta aaataacaga  21120
acactcttgg agcgttgaac tttatgaact tatgggaaaa tttgcttggt ggactgtttt  21180
ctgcaccaat gcaaatgcat cctcatctga aggattcctc ttaggtatta attacttggg  21240
tactattaaa gaaaatatag atggtggtgc tatgcacgcc aactatatat tttggagaaa  21300
ttccactcct atgaatctga gtacttactc actttttgat ttatccaagt ttcaattaaa  21360
attaaaagga acaccagttc ttcaattaaa ggagagtcaa attaacgaac tcgtaatatc  21420
tctcctgtcg cagggtaagt tacttatccg tgacaatgat acactcagtg tttctactga  21480
tgttcttgtt aacacctaca gaaagttacg ttgatgtagg gccagattct gttaagtctg  21540
cttgtattga ggttgatata caacagactt tctttgataa aacttggcct aggccaattg  21600
atgtttctaa ggctgacggt attatatacc ctcaaggccg tacatattct aacataacta  21660
tcacttatca aggtcttttt ccctatcagg gagaccatgg tgatatgtat gtttactctg  21720
```

caggacatgc tacaggcaca actccacaaa agttgtttgt agctaactat tctcaggacg 21780
tcaaacagtt tgctaatggg tttgtcgtcc gtataggagc agctgccaat tccactggca 21840
ctgttattat tagcccatct accagcgcta ctatacgaaa aatttaccct gcttttatgc 21900
tgggttcttc agttggtaat ttctcagatg gtaaaatggg ccgcttcttc aatcatactc 21960
tagttctttt gcccgatgga tgtggcactt tacttagagc tttttattgt attctagagc 22020
ctcgctctgg aaatcattgt cctgctggca attcctatac ttcttttgcc acttatcaca 22080
ctcctgcaac agattgttct gatggcaatt acaatcgtaa tgccagtctg aactctttta 22140
aggagtattt taatttacgt aactgcacct ttatgtacac ttataacatt accgaagatg 22200
agattttaga gtggtttggc attacacaaa ctgctcaagg tgttcacctc ttctcatctc 22260
ggtatgttga tttgtacggc ggcaatatgt ttcaatttgc caccttgcct gtttatgata 22320
ctattaagta ttattctatc attcctcaca gtattcgttc tatccaaagt gatagaaaag 22380
cttgggctgc cttctacgta tataaacttc aaccgttaac tttcctgttg gatttttctg 22440
ttgatggtta tatacgcaga gctatagact gtggttttaa tgatttgtca caactccact 22500
gctcatatga atccttcgat gttgaatctg gagtttattc agtttcgtct ttcgaagcaa 22560
aaccttctgg ctcagttgtg gaacaggctg aaggtgttga atgtgatttt tcacctcttc 22620
tgtctggcac acctcctcag gtttataatt tcaagcgttt ggtttttacc aattgcaatt 22680
ataatcttac caaattgctt tcactttttt ctgtgaatga ttttacttgt agtcaaatat 22740
ctccagcagc aattgctagc aactgttatt cttcactgat tttggattac ttttcatacc 22800
cacttagtat gaaatccgat ctcagtgtta gttctgctgg tccaatatcc cagtttaatt 22860
ataaacagtc cttttctaat cccacatgtt tgattttagc gactgttcct cataacctta 22920
ctactattac taagcctctt aagtacagct atattaacaa gtgctctcgt cttctttctg 22980
atgatcgtac tgaagtacct cagttagtga acgctaatca atactcaccc tgtgtatcca 23040
ttgtcccatc cactgtgtgg gaagacggtg attattatag gaaacaacta tctccacttg 23100
aaggtggtgg ctggcttgtt gctagtggct caactgttgc catgactgag caattacaga 23160
tgggctttgg tattacagtt caatatggta cagacaccaa tagtgtttgc cccaagcttg 23220
aatttgctaa tgacacaaaa attgcctctc aattaggcaa ttgcgtggaa tattccctct 23280
atggtgtttc gggccgtggt gtttttcaga attgcacagc tgtaggtgtt cgacagcagc 23340
gctttgttta tgatgcgtac cagaatttag ttggctatta ttctgatgat ggcaactact 23400
actgtttgcg tgcttgtgtt agtgttcctg tttctgtcat ctatgataaa gaaactaaaa 23460
cccacgctac tctatttggt agtgttgcat gtgaacacat ttcttctacc atgtctcaat 23520
actcccgttc tacgcgatca atgcttaaac ggcgagattc tacatatggc ccccttcaga 23580
cacctgttgg ttgtgtccta ggacttgtta attcctcttt gttcgtagag gactgcaagt 23640
tgcctcttgg tcaatctctc tgtgctcttc ctgacacacc tagtactctc acacctcgca 23700
gtgtgcgctc tgttccaggt gaaatgcgct tggcatccat tgcttttaat catcctattc 23760
aggttgatca acttaatagt agttatttta aattaagtat acccactaat tttttccttttg 23820
gtgtgactca ggagtacatt cagacaacca ttcagaaagt tactgttgat tgtaaacagt 23880
acgtttgcaa tggtttccag aagtgtgagc aattactgcg cgagtatggc cagttttgtt 23940
ccaaaataaa ccaggctctc catggtgcca atttacgcca ggatgattct gtacgtaatt 24000
tgtttgcgag cgtgaaaagc tctcaatcat ctcctatcat accaggtttt ggaggtgact 24060

-continued

```
ttaatttgac acttctagaa cctgtttcta tatctactgg cagtcgtagt gcacgtagtg  24120
ctattgagga tttgctattt gacaaagtca ctatagctga tcctggttat atgcaaggtt  24180
acgatgattg catgcagcaa ggtccagcat cagctcgtga tcttatttgt gctcaatatg  24240
tggctggtta caaagtatta cctcctctta tggatgttaa tatggaagcc gcgtatactt  24300
catctttgct tggcagcata gcaggtgttg gctggactgc tggcttatcc tcctttgctg  24360
ctattccatt tgcacagagt atcttttata ggttaaacgg tgttggcatt actcaacagg  24420
ttctttcaga gaaccaaaag cttattgcca ataagtttaa tcaggctctg ggagctatgc  24480
aaacaggctt cactacaact aatgaagctt ttcagaaggt tcaggatgct gtgaacaaca  24540
atgcacaggc tctatccaaa ttagctagcg agctatctaa tacttttggt gctatttccg  24600
cctctattgg agacatcata caacgtcttg atgttctcga acaggacgcc caaatagaca  24660
gacttattaa tggccgtttg acaacactaa atgcttttgt tgcacagcag cttgttcgtt  24720
ccgaatcagc tgctctttcc gctcaattgg ctaaagataa agtcaatgag tgtgtcaagg  24780
cacaatccaa gcgttctgga ttttgcggtc aaggcacaca tatagtgtcc tttgttgtaa  24840
atgcccctaa tggcctttac ttcatgcatg ttggttatta ccctagcaac cacattgagg  24900
ttgtttctgc ttatggtctt tgcgatgcag ctaaccctac taattgtata gcccctgtta  24960
atggctactt tattaaaact aataacacta ggattgttga tgagtggtca tatactggct  25020
cgtccttcta tgcacctgag cccattacct cccttaatac taagtatgtt gcaccacagg  25080
tgacatacca aaacatttct actaacctcc ctcctcctct tctcggcaat tccaccggga  25140
ttgacttcca agatgagttg gatgagtttt tcaaaaatgt tagcaccagt atacctaatt  25200
ttggttccct aacacagatt aatactacat tactcgatct tacctacgag atgttgtctc  25260
ttcaacaagt tgttaaagcc cttaatgagt cttacataga ccttaaagag cttggcaatt  25320
atacttatta caacaaatgg ccgtggtaca tttggcttgg tttcattgct gggcttgttg  25380
ccttagctct atgcgtcttc ttcatactgt gctgcactgg ttgtggcaca aactgtatgg  25440
gaaaacttaa gtgtaatcgt tgttgtgata gatacgagga atacgacctc gagccgcata  25500
aggttcatgt tcactaatta acgaactatt aatgagagtt caaagaccac ccactctctt  25560
gttagtgttt tcactctctc ttttggtcac tgcatcctca aaacctctct atgtacctga  25620
gcattgtcag aattattctg gttgcatgct tagggcttgt attaaaactg cccaagctga  25680
tacagctggt ctttatacaa attttcgaat tgacgtccca tctgcagaat caactggtac  25740
tcaatcagtt tctgtcgatc ttgagtcaac ttcaactcat gatggtccta ccgaacatgt  25800
tactagtgtg aatctttttg acgttggtta ctcagttaat taacgaactc tatggattac  25860
gtgtctctgc ttaatcaaat ttggcagaag taccttaact caccgtatac tacttgtttg  25920
tacatcccta aacccacagc taagtataca cctttagttg gcacttcatt gcaccctgtg  25980
ctgtggaact gtcagctatc ctttgctggt tatactgaat ctgctgttaa ttctacaaaa  26040
gctttggcca aacaggacgc agctcagcga atcgcttggt tgctacataa ggatggagga  26100
atccctgatg gatgttccct ctacctccgg cactcaagtt tattcgcgca aagcgaggaa  26160
gaggagccat tctccaacta agaaactgcg ctacgttaag cgtagatttt ctcttctgcg  26220
ccatgaagac cttagtgtta ttgtccaacc aacacactat gtcagggtta cattttcaga  26280
ccccaacatg tggtatctac gttcgggtca tcatttacac tcagttcaca attggcttaa  26340
accttatggc ggccaacctg tttctgagta ccatattact ctagctttgc taaatctcac  26400
tgatgaagat ttagctagag atttttcacc cattgcgctc tttttgcgca atgtcagatt  26460
```

-continued

```
tgagctacat gagttcgcct tgctgcgcaa aactcttgtt cttaatgcat cagagatcta  26520
ctgtgctaac atacatagat ttaagcctgt gtatagagtt aacacggcaa tccctactat  26580
taaggattgg cttctcgttc agggatttc cctttaccat agtggcctcc ctttacatat  26640
gtcaatctct aaattgcatg cactggatga tgttactcgc aattacatca ttacaatgcc  26700
atgctttaga acttaccctc aacaaatgtt tgttactcct ttggccgtag atgttgtctc  26760
catacggtct tccaatcagg gtaataaaca aattgttcat tcttatccca ttttacatca  26820
tccaggattt taacgaacta tggctttctc ggcgtcttta tttaaacccg tccagctagt  26880
cccagtttct cctgcatttc atcgcattga gtctactgac tctattgttt tcacatacat  26940
tcctgctagc ggctatgtag ctgctttagc tgtcaatgtg tgtctcattc ccctattatt  27000
actgctacgt caagatactt gtcgtcgcag cattatcaga actatggttc tctatttcct  27060
tgttctgtat aactttttat tagccattgt actagtcaat ggtgtacatt atccaactgg  27120
aagttgcctg atagccttct tagttatcct cataatactt tggtttgtag atagaattcg  27180
tttctgtctc atgctgaatt cctacattcc actgtttgac atgcgttccc actttattcg  27240
tgttagtaca gtttcttctc atggtatggt ccctgtaata cacaccaaac cattatttat  27300
tagaaacttc gatcagcgtt gcagctgttc tcgttgtttt tatttgcact cttccactta  27360
tatagagtgc acttatatta gccgttttag taagattagc ctagtttctg taactgactt  27420
ctccttaaac ggcaatgttt ccactgtttt cgtgcctgca acgcgcgatt cagttcctct  27480
tcacataatc gccccgagct cgcttatcgt ttaagcagct ctgcgctact atgggtcccg  27540
tgtagaggct aatccattag tctctctttg gacatatgga aaacgaacta tgttaccctt  27600
tgtccaagaa cgaatagggt tgttcatagt aaactttttc atttttaccg tagtatgtgc  27660
tataacactc ttggtgtgta tggctttcct tacggctact agattatgtg tgcaatgtat  27720
gacaggcttc aataccctgt tagttcagcc cgcattatac ttgtataata ctggacgttc  27780
agtctatgta aaattccagg atagtaaacc ccctctacca cctgacgagt gggtttaacg  27840
aactccttca taatgtctaa tatgacgcaa ctcactgagg cgcagattat tgccattatt  27900
aaagactgga actttgcatg gtccctgatc tttctcttaa ttactatcgt actacagtat  27960
ggatacccat cccgtagtat gactgtctat gtctttaaaa tgtttgtttt atggctccta  28020
tggccatctt ccatggcgct atcaatattt agcgccgttt atccaattga tctagcttcc  28080
cagataatct ctggcattgt agcagctgtt tcagctatga tgtggatttc ctactttgtg  28140
cagagtatcc ggctgtttat gagaactgga tcatggtggt cattcaatcc tgagactaat  28200
tgccttttga acgttccatt tggtggtaca actgtcgtac gtccactcgt agaggactct  28260
accagtgtaa ctgctgttgt aaccaatggc cacctcaaaa tggctggcat gcatttcggt  28320
gcttgtgact acgacagact tcctaatgaa gtcaccgtgg ccaaacccaa tgtgctgatt  28380
gctttaaaaa tggtgaagcg gcaaagctac ggaactaatt ccggcgttgc catttaccat  28440
agatataagg caggtaatta caggagtccg cctattacgg cggatattga acttgcattg  28500
cttcgagctt aggctcttta gtaagagtat cttaattgat tttaacgaat ctcaatttca  28560
ttgttatggc atcccctgct gcacctcgtg ctgtttcctt tgccgataac aatgatataa  28620
caaatacaaa cctatctcga ggtagaggac gtaatccaaa accacgagct gcaccaaata  28680
acactgtctc ttggtacact gggcttaccc aacacgggaa agtccctctt acctttccac  28740
ctgggcaggg tgtacctctt aatgccaatt ctacccctgc gcaaaatgct gggtattggc  28800
```

-continued

```
ggagacagga cagaaaaatt aataccggga atggaattaa gcaactggct cccaggtggt  28860

acttctacta cactggaact ggacccgaag cagcactccc attccgggct gttaaggatg  28920

gcatcgtttg ggtccatgaa gatggcgcca ctgatgctcc ttcaactttt gggacgcgga  28980

accctaacaa tgattcagct attgttacac aattcgcgcc cggtactaag cttcctaaaa  29040

acttccacat tgaggggact ggaggcaata gtcaatcatc ttcaagagcc tctagcttaa  29100

gcagaaactc ttccagatct agttcacaag gttcaagatc aggaaactct acccgcggca  29160

cttctccagg tccatctgga atcggagcag taggaggtga tctactttac cttgatcttc  29220

tgaacagact acaagccctt gagtctggca aagtaaagca atcgcagcca aaagtaatca  29280

ctaagaaaga tgctgctgct gctaaaaata agatgcgcca caagcgcact tccaccaaaa  29340

gtttcaacat ggtgcaagct tttggtcttc gcggaccagg agacctccag ggaaactttg  29400

gtgatcttca attgaataaa ctcggcactg aggacccacg ttggccccaa attgctgagc  29460

ttgctcctac agccagtgct tttatgggta tgtcgcaatt taaacttacc catcagaaca  29520

atgatgatca tggcaaccct gtgtacttcc ttcggtacag tggagccatt aaacttgacc  29580

caaagaatcc caactacaat aagtggttgg agcttcttga gcaaaatatt gatgcctaca  29640

aaaccttccc taagaaggaa aagaaacaaa aggcaccaaa agaagaatca acagaccaaa  29700

tgtctgaacc tccaaaggag cagcgtgtgc aaggtagcat cactcagcgc actcgcaccc  29760

gtccaagtgt tcagcctggt ccaatgattg atgttaacac tgattagtgt cactcaaagt  29820

aacaagatcg cggcaatcgt ttgtgtttgg caaccccatc tcaccatcgc ttgtccactc  29880

ttgcacagaa tggaatcatg ttgtaattac agtgcaataa ggtaattata acccatttaa  29940

ttgatagcta tgctttatta aagtgtgtag ctgtagagag aatgttaaag actgtcacct  30000

ctgcttgatt gcaagtgaac agtgcccccc gggaagagct ctacagtgtg aaatgtaaat  30060

aaaaaatagc tattattcaa ttagattagg ctaattagat gatttgcaaa aaaaaaaaa   30119
```

METHODS OF USING PROBENECID FOR TREATMENT OF CORONAVIRUS INFECTIONS

CROSS REFERENCE TO RELATED APPLICATIONS

This application claims benefit of U.S. Provisional Application No. 63/008,624, filed Apr. 10, 2020, and U.S. Provisional Application No. 63/023,021, filed May 11, 2020, each of which is specifically incorporated by reference herein in its entirety.

REFERENCE TO SEQUENCE LISTING

The Sequence Listing submitted as a text file named "UGA_2020_148_03_2.txt" created on Jun. 5, 2020, and having a size of 156,414 bytes is hereby incorporated by reference pursuant to 37 C.F.R. § 1.52(e)(5).

FIELD OF THE INVENTION

The field of the invention generally related to compositions and methods for the treatment of coronavirus-related illnesses.

BACKGROUND OF THE INVENTION

A seventh human coronavirus was recently identified in Wuhan, China (Coronaviridae Study Group of the International Committee on Taxonomy of Viruses, *Nat Microbiol* 2020. DOI: 10.1038/s41564-020-0695-z, WHO "Pneumonia of unknown cause—China;" World Health Organization: Online, 2020). Initially described as COVID-19 after its discovery in December 2019, this virus has now been classified as a betacoronavirus within the same species as the Severe acute respiratory syndrome coronavirus (SARS-CoV), which was responsible for a pandemic in 2002-2003 (Coronaviridae Study Group of the International Committee on Taxonomy of Viruses, *Nat Microbiol* 2020. DOI: 10.1038/s41564-020-0695-z, Ratia, et al., *Proc Natl Acad Sci USA* 2008, 105 (42), 16119-24. DOI: 10.1073/pnas.0805240105). Hence, COVID-19 has now been classified as SARS-CoV-2. Although SARS-CoV-2 does not appear to be lethal as SARS-CoV, it has rapidly spread worldwide according to a World Health Organization situation report. The rapid spread of SARS-CoV-2 and its ability to cause death particular in older individuals, or individuals with underlying conditions, has created an urgency for the need of antiviral therapeutics and vaccines for use against the virus ("CDC People at Risk for Serious Illness from COVID-19," CDC website).

Thus, it is an object of the invention to provide compositions and methods of treating infections caused by coronaviruses, particularly coronaviruses that cause severe acute respiratory syndrome, including, but limited to SARS-CoV-2.

SUMMARY OF THE INVENTION

Compositions and methods of treating a subject for a coronavirus infection are provided. The methods typically include administering the subject an effective amount of probenecid, a metabolite or analog thereof, or a pharmaceutically acceptable salt thereof. The amount of probenecid, metabolite or analog thereof, or a pharmaceutically acceptable salt thereof can be effective to, for example, reduce viral replication, reduce one or more symptoms of a disease, disorder, or illness associated with virus, or a combination thereof. Symptoms include, but are not limited to, fever, congestion in the nasal sinuses and/or lungs, runny or stuffy nose, cough, sneezing, sore throat, body aches, fatigue, shortness of breath, chest tightness, wheezing when exhaling, chills, muscle aches, headache, diarrhea, tiredness, nausea, vomiting, and combinations thereof. The subject can be, for example, a mammal or a bird. In preferred embodiments, the subject is a human.

The subject can be symptomatic or asymptomatic. In some embodiments, the subject has been, or will be, exposed to the virus. In some embodiments, treatment begins 1, 2, 3, 4, 5, or more hours, days, or weeks prior to or after exposure to the virus. In some embodiments, the subject has not been exposed to the virus. In some embodiments, the subject anticipates being exposed to the virus. Thus, preventative and prophylactic methods are also provided.

The virus can be a Severe acute respiratory syndrome-related coronavirus, a Bat Hp-betacoronavirus Zhejiang2013, a *Rousettus* bat coronavirus GCCDC1, a *Rousettus* bat coronavirus HKU9, Eidolon bat coronavirus C704, a *Pipistrellus* bat coronavirus HKU5, a *Tylonycteris* bar coronavirus HKU4, a Middle East respiratory syndrome-related coronavirus, a Hedgehog coronavirus, a murine coronavirus, a Human coronavirus HKU1, a *China Rattus* coronavirus HKU24, a Betacoronavirus 1, a *Myodes* coronavirus 2JL14, a Human coronavirus NL63, a Human coronavirus 229E, or a Human coronavirus OC43.

In preferred embodiments, the virus is a Severe acute respiratory syndrome-related coronavirus, such as SARS-CoV-2, SARS-CoV, SARSr-CoV RaTG13, SARS-CoV PC4-227, or SARSr-CoV BtKY72.

In some embodiments, the virus is a SARS-CoV-2 having a genome encoded by a nucleic acid sequence having at least 85%, 86%, 87%, 88%, 89%, 90%, 91%, 92%, 93%, 94%, 95%, 96%, 97%, 98%, 99%, or 100% sequence identity SEQ ID NO:1 or 2.

In some embodiments, the Severe acute respiratory syndrome-related coronavirus is SARS-CoV, for example, a SAR-CoV having a genome encoded by a nucleic acid sequence having at least 85%, 86%, 87%, 88%, 89%, 90%, 91%, 92%, 93%, 94%, 95%, 96%, 97%, 98%, 99%, or 100% sequence identity SEQ ID NO:3.

In some embodiments, the virus is a Middle East respiratory syndrome-related coronavirus, for example, a MERS-CoV having a genome encoded by a nucleic acid sequence having at least 85%, 86%, 87%, 88%, 89%, 90%, 91%, 92%, 93%, 94%, 95%, 96%, 97%, 98%, 99%, or 100% sequence identity SEQ ID NO:4.

In some embodiments, the subject has a disease or disorder associated with the virus. For example, in embodiments, a subject exposed or infected with SARS-CoV-2 has COVID-19.

The probenecid, metabolite or analog thereof, or pharmaceutically acceptable salt thereof is typically administered in a pharmaceutical composition including a pharmaceutically acceptable carrier and/or excipient. Thus, pharmaceutical compositions are also provided. Dosage forms are also provided and include, but not limited to 500 mg tablets of probenecid, a metabolite or analog thereof, or pharmaceutically acceptable salt thereof. In some embodiments, the subject is administered a 10 mg-1,000 mg or, 50 mg-500 mg dose of probenecid, metabolite or analog thereof, or pharmaceutically acceptable salt thereof 1, 2, 3, 4, or 5 times per day. In some embodiments, the dosage regimen is a pulse dosage regimen that include 1, 2, 3, or more large bolus doses in close proximity (e.g., minutes or hours apart). In some embodiments, the bolus doses are followed by a drug administration holiday, optionally until the drug level in the subject's serum drops to zero or near zero.

The probenecid, a metabolite or analog thereof, or a pharmaceutically acceptable salt thereof can be administered systemically or locally. Exemplary routes of administration include, but are not limited to, oral, parenteral, topical or mucosal. In some embodiments, the composition is administered to lungs (e.g., pulmonary administration) by oral inhalation or intranasal administration. In some embodiments, the composition is administered intranasally to the nasal mucosa.

DETAILED DESCRIPTION OF THE INVENTION

I. Definitions

Figure 1:
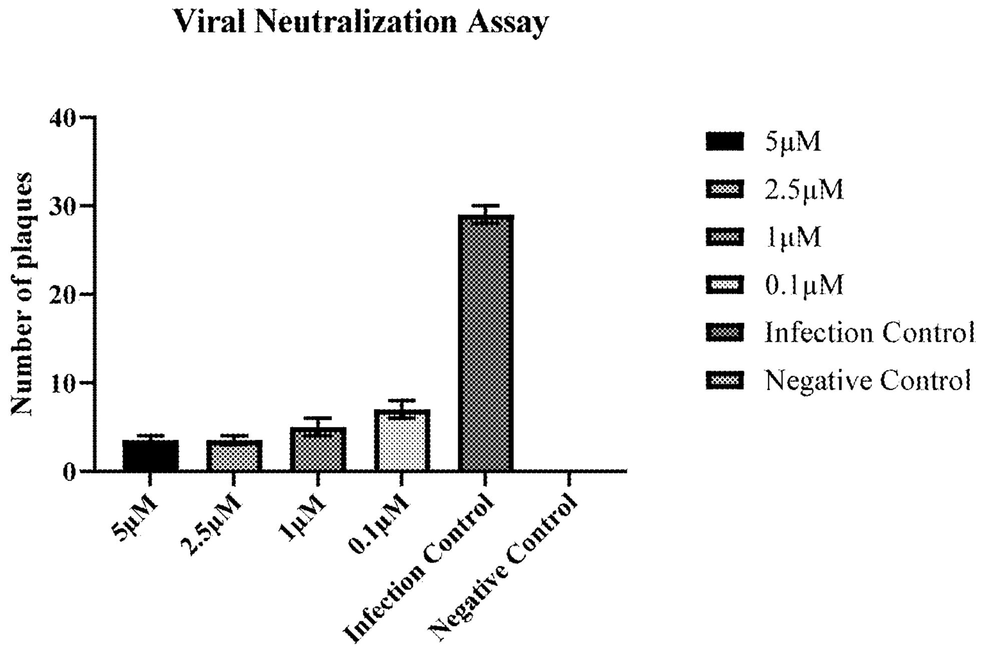
FIG. 1 is a bar graph showing (left-to-right) the effect of probenecid (5 μM, 2.5 μM, 1 μM, or 0.1 μM) compared to controls (DMSO (infected), DMSO (only)) on viral replication using a plaque reduction assay.

As used herein, the terms "individual", "host", "subject", and "patient" are used interchangeably herein, and refer animals, particularly birds and mammals, including, but not limited to, primates such as humans, bats, rodents, such as mice and rats, and other laboratory animals.

As used herein the term "effective amount" or "therapeutically effective amount" means a dosage sufficient to treat, inhibit, or alleviate one or more symptoms of a disease state being treated or to otherwise provide a desired pharmacologic and/or physiologic effect. The precise dosage will vary according to a variety of factors such as subject-dependent variables (e.g., age, immune system health, etc.), the disease, and the treatment being administered.

As used herein, the term "carrier" or "excipient" refers to an organic or inorganic ingredient, natural or synthetic inactive ingredient in a formulation, with which one or more active ingredients are combined.

As used herein, the term "pharmaceutically acceptable" means a non-toxic material that does not interfere with the effectiveness of the biological activity of the active ingredients.

As used herein, the term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. +/−10%; in other forms the values may range in value either above or below the stated value in a range of approx. +/−5%; in other forms the values may range in value either above or below the stated value in a range of approx. +/−2%; in other forms the values may range in value either above or below the stated value in a range of approx. +/−1%. The preceding ranges are intended to be made clear by context, and no further limitation is implied.

II. Compositions

A. Probenecid, Metabolites, Analogs, and Pharmaceutically Acceptable Salts Thereof The disclosed methods include administering a subject in need thereof an effective amount of probenecid, a metabolite or analog thereof, or a pharmaceutically acceptable salt thereof, including, but not limited to a sodium salt thereof.

Probenecid (4-[(dipropylamino) sulfonyl]benzoic acid (CAS No. 57-66-9)) has the structure:

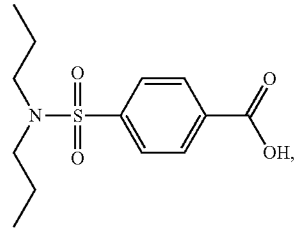 [SMILES: CCCN(CCC)S(=O)(=O)c1ccc(C(=O)O)cc1]

and has been sold under the brand names BENEMID and PROBALAN.

Probenecid is a highly lipid soluble benzoic acid derivative with an excellent safety profile that was developed in the 1950's to decrease the renal tubular excretion of penicillin. Probenecid, USP is a white or nearly white, fine, crystalline powder. Probenecid is soluble in dilute alkali, in alcohol, in chloroform, and in acetone; it is practically insoluble in water and in dilute acids. It has a half life of 6-12 hours. See also Drugbank Accession Number DB01032 (APRD00167).

Metabolites and analogs of probenecid are known, see, for example, Guarino, et al., "Mass spectral identification of probenecid metabolites in rat bile," *Eur. J. Pharmacol.,* 8, 244-252 (1969), Perel, et al., "Identification and renal excretion of probenecid metabolites in man," *Life Sciences,* 9, 23, 1337-1343 (1970), Perel, et al., "Studies of the renal excretion of probenecid acyl glucuronide in man," *Eur. J. Clin. Pharmacol,* 3, 106-112 (1971), Dayton and Perel, "The metabolism of probenecid in man,". *N. Y. Acad. Sci.,* 179, 399-402 (1971), Dayton, et al., "The effect of probenecid, phenylbutazone and their analogues on the excretion of L-ascorbic acid in rats," *J. Med. Chem.* 9, 941-944 (1966), and Israili, et al., "Metabolites of probenecid. Chemical, physical, and pharmacological studies," *J. Med. Chem.*, 15, 7, 709-713 (1972), each of which is specifically incorporated by reference in its entirety.

In some embodiments, the metabolite is a glucuronide derivative of probenecid such as acyl glucuronide or a β-ether glucuronide.

Exemplary probenecid metabolites and analogs include, but are not limited to, dl-p-(N-Propy-N-2-hydroxypropylsulfamoyl)benzoic Acid,
Propylaminopropyl Acetate,
Piopylaminopropan-3-ol,
p-(N-Propyl-N-3-hydroxypropylsulfamoyl)benzoic Acid,
Propylaminopropionitrile,
p-(N-Propyl-N-3-propionitrilosulfamoyl)benzoic Acid,
p-(N-Propyl-N-2-carboxyethylsulfamoyl)benzoic Acid,
p-(N-Propylsulfamoyl)benzoic Acid,
p-(N,N-Pentamethylenesulfamoyl)benzoic Acid (Piperidyl Analog),
p-(N-Propyl-N-2-propenylsulfamoyl)benzoic Acid, and
p-(N-Propyl-N-2-oxopropylsulfamoyl)benzoic Acid.

Typically the metabolite or analog can on its own, or upon further metabolism thereof by a subject, treat a coronavirus when administered in an effective amount as discussed herein. For example, in some embodiments, the metabolite or analog can on its own, or upon further metabolism thereof by a subject, reduce viral replication.

B. Formulations

Probenecid, metabolites and analogs thereof, and pharmaceutically acceptable salts thereof can be formulated in a pharmaceutical composition. Pharmaceutical compositions can be for administration by parenteral (intramuscular, intraperitoneal, intravenous (IV) or subcutaneous injection), enteral, transdermal (either passively or using iontophoresis or electroporation), or transmucosal (nasal, pulmonary, vaginal, rectal, or sublingual) routes of administration or using bioerodible inserts and can be formulated in dosage forms appropriate for each route of administration.

The compositions can be administered systemically.

The compositions can be formulated for immediate release, extended release, or modified release. A delayed release dosage form is one that releases a drug (or drugs) at a time other than promptly after administration. An extended release dosage form is one that allows at least a twofold reduction in dosing frequency as compared to that drug presented as a conventional dosage form (e.g. as a solution or prompt drug-releasing, conventional solid dosage form). A modified release dosage form is one for which the drug release characteristics of time course and/or location are chosen to accomplish therapeutic or convenience objectives not offered by conventional dosage forms such as solutions, ointments, or promptly dissolving dosage forms. Delayed release and extended release dosage forms and their combinations are types of modified release dosage forms.

Formulations are prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes, but is not limited to, diluents, binders, lubricants, desintegrators, fillers, and coating compositions.

"Carrier" also includes all components of the coating composition which may include plasticizers, pigments, colorants, stabilizing agents, and glidants. The delayed release dosage formulations may be prepared as described in references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", $6^{th}$ Edition, Ansel et. al., (Media, Pa.: Williams and Wilkins, 1995) which provides information on carriers, materials, equipment and process for preparing tablets and capsules and delayed release dosage forms of tablets, capsules, and granules.

The compound can be administered to a subject with or without the aid of a delivery vehicle. Appropriate delivery vehicles for the compounds are known in the art and can be selected to suit the particular active agent. For example, in some embodiments, the active agent(s) is incorporated into or encapsulated by, or bound to, a nanoparticle, microparticle, micelle, synthetic lipoprotein particle, or carbon nanotube. For example, the compositions can be incorporated into a vehicle such as polymeric microparticles which provide controlled release of the active agent(s). In some embodiments, release of the drug(s) is controlled by diffusion of the active agent(s) out of the microparticles and/or degradation of the polymeric particles by hydrolysis and/or enzymatic degradation.

Suitable polymers include ethylcellulose and other natural or synthetic cellulose derivatives. Polymers which are slowly soluble and form a gel in an aqueous environment, such as hydroxypropyl methylcellulose or polyethylene oxide, may also be suitable as materials for drug containing microparticles or particles. Other polymers include, but are not limited to, polyanhydrides, poly (ester anhydrides), polyhydroxy acids, such as polylactide (PLA), polyglycolide (PGA), poly(lactide-co-glycolide) (PLGA), poly-3-hydroxybut rate (PHB) and copolymers thereof, poly-4-hydroxybutyrate (P4HB) and copolymers thereof, polycaprolactone and copolymers thereof, and combinations thereof. In some embodiments, both agents are incorporated into the same particles and are formulated for release at different times and/or over different time periods. For example, in some embodiments, one of the agents is released entirely from the particles before release of the second agent begins. In other embodiments, release of the first agent begins followed by release of the second agent before the all of the first agent is released. In still other embodiments, both agents are released at the same time over the same period of time or over different periods of time.

1. Oral Immediate Release Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), Zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powder sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydorxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, POLOXAMER® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads granules or particles may also contain minor amount of nontoxic auxiliary substances such as wetting or emulsifying agents, dyes, pH buffering agents, and preservatives.

2. Extended Release Dosage Forms

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, reservoir and matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but not limited to, methyl acrylate-methyl methacrylate, polyvinyl chloride, and polyethylene. Hydrophilic polymers include, but are not limited to, methylcellulose, hydroxypropylcellulose, hydroxypropylmethylcellulose, sodium carboxymethylcellulose, and carbopol 934, polyethylene oxides. Fatty compounds include, but are not limited to, various waxes such as carnauba wax and glyceryl tristearate.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above could be combined in a final dosage form comprising single or multiple units. Examples of multiple units include multilayer tablets, capsules containing tablets, beads, granules, etc.

An immediate release portion can be added to the extended release system by means of either applying an immediate release layer on top of the extended release core using coating or compression process or in a multiple unit system such as a capsule containing extended and immediate release beads.

Extended release tablets containing hydrophilic polymers are prepared by techniques commonly known in the art such as direct compression, wet granulation, or dry granulation processes. Their formulations usually incorporate polymers, diluents, binders, and lubricants as well as the active pharmaceutical ingredient. The usual diluents include inert powdered substances such as any of many different kinds of starch, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidine can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In a congealing method, the drug is mixed with a wax material and either spray-congealed or congealed and screened and processed.

3. Delayed Release Dosage Forms

Delayed release formulations are created by coating a solid dosage form with a film of a polymer which is insoluble in the acid environment of the stomach, and soluble in the neutral environment of small intestines.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename EUDRAGIT®. (Rohm Pharma; Westerstadt, Germany), including EUDRAGIT®. L30D-55 and L100-55 (soluble at pH 5.5 and above), EUDRAGIT®. L-100 (soluble at pH 6.0 and above), EUDRAGIT®. S (soluble at pH 7.0 and above, as a result of a higher degree of esterification), and EUDRAGITS®. NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

Methods of Manufacturing

As will be appreciated by those skilled in the art and as described in the pertinent texts and literature, a number of methods are available for preparing drug-containing tablets, beads, granules or particles that provide a variety of drug release profiles. Such methods include, but are not limited to, the following: coating a drug or drug-containing composition with an appropriate coating material, typically although not necessarily incorporating a polymeric material, increasing drug particle size, placing the drug within a matrix, and forming complexes of the drug with a suitable complexing agent.

The delayed release dosage units may be coated with the delayed release polymer coating using conventional techniques, e.g., using a conventional coating pan, an airless spray technique, fluidized bed coating equipment (with or without a Wurster insert). For detailed information concerning materials, equipment and processes for preparing tablets and delayed release dosage forms, see Pharmaceutical Dosage Forms: Tablets, eds. Lieberman et al. (New York: Marcel Dekker, Inc., 1989), and Ansel et al., Pharmaceutical Dosage Forms and Drug Delivery Systems, 6.sup.th Ed. (Media, Pa.: Williams & Wilkins, 1995).

A preferred method for preparing extended release tablets is by compressing a drug-containing blend, e.g., blend of granules, prepared using a direct blend, wet-granulation, or dry-granulation process. Extended release tablets may also be molded rather than compressed, starting with a moist material containing a suitable water-soluble lubricant. However, tablets are preferably manufactured using compression rather than molding. A preferred method for forming extended release drug-containing blend is to mix drug particles directly with one or more excipients such as diluents (or fillers), binders, disintegrants, lubricants, glidants, and colorants. As an alternative to direct blending, a drug-containing blend may be prepared by using wet-granulation or dry-granulation processes. Beads containing the active agent may also be prepared by any one of a number of conventional techniques, typically starting from a fluid dispersion. For example, a typical method for preparing drug-containing beads involves dispersing or dissolving the active agent in a coating suspension or solution containing pharmaceutical excipients such as polyvinylpyrrolidone, methylcellulose, talc, metallic stearates, silicone dioxide, plasticizers or the like. The admixture is used to coat a bead core such as a sugar sphere (or so-called "non-pareil") having a size of approximately 60 to 20 mesh.

An alternative procedure for preparing drug beads is by blending drug with one or more pharmaceutically acceptable excipients, such as microcrystalline cellulose, lactose, cellulose, polyvinyl pyrrolidone, talc, magnesium stearate, a disintegrant, etc., extruding the blend, spheronizing the extrudate, drying and optionally coating to form the immediate release beads.

4. Formulations for Mucosal and Pulmonary Administration

The probenecid, metabolites and analogs thereof, and pharmaceutical compositions thereof can be formulated for pulmonary or mucosal administration. The administration can include delivery of the composition to the lungs, nasal, oral (sublingual, buccal), vaginal, or rectal mucosa. In a particular embodiment, the composition is formulated for and delivered to the subject sublingually.

In some embodiments, the compound is formulated for pulmonary delivery, such as intranasal administration or oral inhalation. The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorption occurs. The alveoli are covered by a thin epithelium without cilia or a mucus blanket and secrete surfactant phospholipids. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchiole, which then lead to the ultimate respiratory zone, the alveoli, or deep lung. The deep lung, or alveoli, is the primary target of inhaled therapeutic aerosols for systemic drug delivery.

Pulmonary administration of therapeutic compositions comprised of low molecular weight drugs has been observed, for example, beta-androgenic antagonists to treat asthma. Other therapeutic agents that are active in the lungs have been administered systemically and targeted via pulmonary absorption.

Nasal delivery is considered to be a promising technique for administration of therapeutics for the following reasons: the nose has a large surface area available for drug absorption due to the coverage of the epithelial surface by numerous microvilli, the subepithelial layer is highly vascularized, the venous blood from the nose passes directly into the systemic circulation and therefore avoids the loss of drug by first-pass metabolism in the liver, it offers lower doses, more rapid attainment of therapeutic blood levels, quicker onset of pharmacological activity, fewer side effects, high total blood flow per $cm^3$, porous endothelial basement membrane, and it is easily accessible.

The term aerosol as used herein refers to any preparation of a fine mist of particles, which can be in solution or a suspension, whether or not it is produced using a propellant. Aerosols can be produced using standard techniques, such as ultrasonication or high-pressure treatment.

Carriers for pulmonary formulations can be divided into those for dry powder formulations and for administration as solutions. Aerosols for the delivery of therapeutic agents to the respiratory tract are known in the art. For administration via the upper respiratory tract, the formulation can be formulated into a solution, e.g., water or isotonic saline, buffered or un-buffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

Preferably, the aqueous solution is water, physiologically acceptable aqueous solutions containing salts and/or buffers, such as phosphate buffered saline (PBS), or any other aqueous solution acceptable for administration to an animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In another embodiment, solvents that are low toxicity organic (i.e. nonaqueous) class 3 residual solvents, such as ethanol, acetone, ethyl acetate, tetrahydrofuran, ethyl ether, and propanol may be used for the formulations. The solvent is selected based on its ability to readily aerosolize the formulation. The solvent should not detrimentally react with the compounds. An appropriate solvent should be used that dissolves the compounds or forms a suspension of the compounds. The solvent should be sufficiently volatile to enable formation of an aerosol of the solution or suspension. Additional solvents or aerosolizing agents, such as freons, can be added as desired to increase the volatility of the solution or suspension.

In one embodiment, compositions may contain minor amounts of polymers, surfactants, or other excipients well known to those of the art. In this context, "minor amounts" means no excipients are present that might affect or mediate uptake of the compounds in the lungs and that the excipients that are present are present in amount that do not adversely affect uptake of compounds in the lungs.

Dry lipid powders can be directly dispersed in ethanol because of their hydrophobic character. For lipids stored in organic solvents such as chloroform, the desired quantity of solution is placed in a vial, and the chloroform is evaporated under a stream of nitrogen to form a dry thin film on the surface of a glass vial. The film swells easily when reconstituted with ethanol. To fully disperse the lipid molecules in the organic solvent, the suspension is sonicated. Nonaqueous suspensions of lipids can also be prepared in absolute ethanol using a reusable PARI LC Jet+ nebulizer (PARI Respiratory Equipment, Monterey, Calif.).

Dry powder formulations ("DPFs") with large particle size have improved flowability characteristics, such as less aggregation, easier aerosolization, and potentially less phagocytosis. Dry powder aerosols for inhalation therapy are generally produced with mean diameters primarily in the range of less than 5 microns, although a preferred range is between one and ten microns in aerodynamic diameter. Large "carrier" particles (containing no drug) have been co-delivered with therapeutic aerosols to aid in achieving efficient aerosolization among other possible benefits.

Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art. The preferred methods of manufacture are by spray drying and freeze drying, which entails using a solution containing the surfactant, spraying to form droplets of the desired size, and removing the solvent.

The particles may be fabricated with the appropriate material, surface roughness, diameter, and tap density for localized delivery to selected regions of the respiratory tract such as the deep lung or upper airways. For example, higher density or larger particles may be used for upper airway delivery. Similarly, a mixture of different sized particles, provided with the same or different active agents may be administered to target different regions of the lung in one administration.

Compositions and methods of preparing inhalation-type pharmaceutical compositions including probenecid are described in U.S. Published Application No. 2015/0272870.

Thus, formulations and methods of administering the disclosed compositions to the nasal mucosa and/or the lungs by intranasal delivery, and to the lung by oral inhalation are provided. With respect to intranasal delivery, the formulation and delivery device can be selected and prepared to drive absorption through the nasal mucosa or the lungs. The nasal mucosa is—compared to other mucous membranes—easily accessible and provides a practical entrance portal for small and large molecules (Bitter, et al., "Nasal Drug Delivery in Humans," in Surber, et al., (eds): *Topical Applications and the Mucosa. Curr Probl Dermatol.* Basel, Karger, 2011, vol 40, pp 20-35, Pires, et al., *J Pharm Pharmaceut Sci.,* 12(3) 288-311, 2009, and Djupesland, *Drug Deliv.* and Transl. Res., 3:42-62 (2013) DOI 10.1007/s13346-012-0108-9). Intranasal administration offers a rapid onset of therapeutic effects, reduced first-pass effect, reduced gastrointestinal degradation and lung toxicity, noninvasiveness, essentially painless application, and easy and ready use by patients—particularly suited for children—or by physicians in emergency settings. Flu Mist®, for example, is an an exemplary effective nasal influenza vaccine spray.

Numerous delivery devices are available for intranasal administration. Devices vary in accuracy of delivery, dose reproducibility, cost and ease of use. Metered-dose systems provide dose accuracy and reproducibility. Differences also exist in force of delivery, spray patterns and emitted droplet size. The latter being important for drug deposition within the nasal cavity. Parameters can be can be modulated to enhance deposition while limiting the fraction of small particles able to bypass the nose and enter the lungs, or reduce deposition while increasing the fraction of small particles able to bypass the nose and enter the lungs.

The following aspects of nasal anatomy can influence drug delivery. During exhalation the soft palate closes automatically, separating the nasal and oral cavities. Thus, it becomes possible to use smaller particles in a nasal spray and still avoid lung deposition. Additionally, during closure of the soft palate there is a communication pathway between the two nostrils, located behind the walls separating the two passages. Under these circumstances, it is possible for airflow to enter via one nostril and leave by the other. This bidirectional delivery concept combines the two anatomical facts into one fully functional device. The device is inserted into one nostril by a sealing nozzle, and the patient blows into the mouthpiece. The combination of closed soft palate and sealed nozzle creates an airflow which enters one nostril, turns 180° through the communication pathway and exits through the other nostril (bidirectional flow). Since delivery occurs during exhalation, small particles cannot enter the lungs.

Particle size, flow rate and direction can be tuned for efficient delivery to the nasal mucosa. By adding an exit resistor to give additional control of the input pressure, it is possible to improve distribution to the sinuses and the middle ear. Manipulation of the flow pattern enables delivery to the olfactory region, thereby possibly achieving direct 'nose-to-brain' delivery. The 180-degree turn behind the septum will trap particles still airborne, allowing targeted delivery of cargo to the adenoid.

Strategies for enhancing drug absorption via nasal and pulmonary routes are also know in the art and can be utilized in the disclosed formulations and methods of delivery. Such strategies include, for example, use of absorption enhancers such as surfactants, cyclodextrins, protease inhibitors, and tight junction modulators, as well as application of carriers such as liposomes and nanoparticles. See, e.g., Ghadiri, et al., *Pharmaceutics,* 11(3): 113 (2019), which is specifically incorporated by reference herein in its entirety.

5. Formulations for Parenteral Administration

Probenecid, metabolites and analogs thereof, and pharmaceutical compositions thereof can be administered in an aqueous solution, by parenteral injection or infusion. The formulation may also be in the form of a suspension or emulsion. In general, pharmaceutical compositions are provided including effective amounts of the active agent(s) and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as POLYSORBATE® 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

III. Methods of Treatment

Methods of treating a viral infection in subject in need thereof are provided. In some embodiments, the virus can be one that causes a respiratory disease or illness. Thus, methods of treating a respiratory disease or illness, particularly in subject infected with a virus are also provided.

The methods can include administering to a subject an effective amount of probenecid, a metabolite or analog thereof, or a pharmaceutically acceptable salt thereof to reduce viral replication, infection, or a combination thereof.

In some embodiments, the subject has been, or will be, exposed to the virus. In some embodiments, the subject has been exposed to the virus or is experiencing an active viral infection.

The compositions can also be administered prophylactically to, for example, reduce or prevent the effects of future exposure to virus and the infection that may associated therewith. Thus, in some embodiments, the subject has not been exposed to the virus and/or is not yet experiencing an active viral infection. In some embodiments, the subject is a healthy subject.

In some embodiments, the subject will be exposed to the virus. In some embodiments, treatment begins 1, 2, 3, 4, 5, or more hours, days, or weeks prior to or after exposure to the virus.

In some embodiments, the probenecid, a metabolite or analog thereof, or a pharmaceutically acceptable salt thereof is administered in an effective amount to reduce or prevent one or more symptoms of a viral infection. Symptoms include those of an acute respiratory illness, for example, fever, congestion in the nasal sinuses and/or lungs, runny or stuffy nose, cough, sneezing, sore throat, body aches, fatigue, shortness of breath, chest tightness, and wheezing when exhaling. Exemplary viruses and particular symptoms associated with infection thereby are discussed in more detail below. Most typically, the virus is a coronavirus.

In some embodiments, the subject does not have gout, need prolonged penicillin (or other antibiotic) serum levels, pelvic inflammatory disease, or gonorrhea.

In some embodiments, the subject has an influenza infection. See, e.g., Perwitasari, et al., *Antimicrob Agents Chemother,* 57(1):475-83 (2013). doi: 10.1128/AAC.01532-12.)). For example, in some embodiments, the subject has an influenza (e.g., influenza A, influenza B, influenza C, and/or influenza D) infection and an infection from another virus, such as a coronavirus. In some embodiments, the subject does not have an influenza viral infection.

A. Exemplary Dosages and Regimens

Probenecid, metabolites and analogs thereof and pharmaceutically acceptable salt thereof can be administered to a subject in a pharmaceutical composition, such as those discussed above, and can be administered by parenteral (intramuscular, intraperitoneal, intravenous (IV) or subcutaneous injection), enteral, transdermal (either passively or using iontophoresis or electroporation), or transmucosal (nasal, pulmonary, vaginal, rectal, or sublingual) routes, as discussed in more detail above.

The precise dosage will vary according to a variety of factors such as subject-dependent variables (e.g., age, immune system health, clinical symptoms, route of delivery, etc.).

For treating gout, probenecid has been administered at 250 mg Per os/oral (PO) twice daily for 1 week; increasing to 500 mg PO twice daily to 2 g/day maximum with dosage increases of 500 mg.

For treating prolong penicillin serum levels, probenecid has been administered at 500 mg PO four times daily.

For pelvic inflammatory disease probenecid has been administered at 1 g PO with 2 g cefoxitin intramuscular (IM) as single dose.

For gonorrhea, probenecid has been administered at 1 g PO with 2 g cefoxitin IM as single dose.

A typically pediatric (e.g., age: 2 to 14 years and weight less than 50 kg) administration as an adjuvant to antibiotic therapy is Initial: 25 mg/kg (or 0.7 g/m2) orally once; Maintenance: 40 mg/kg (or 1.2 g/m2) per day orally administered in 4 equally divided doses 4 times a day.

Thus, in general, by way of example only, dosage forms useful in the disclosed methods may include doses in the range of 0.1 mg to 3,000 mg; 25 mg to 2,000 mg; 25 mg to 1,000 mg; 50 mg to 1,000 mg; 100 mg to 1,000 mg; or 250 mg to 1,000 mg, with doses of 10 mg, 25 mg, 45 mg, 50 mg, 100 mg, 150 mg, 200 mg, 250 mg, 300 mg, 350 mg, 400 mg, 450 mg, 500 mg, 550 mg, 600 mg, 750 mg, and 1,000 mg being exemplary doses, which can be administered, for example, 1, 2, 3, 4, or 5 times daily, weekly, bi-week, etc., for 1, 2, 3, 4, or more weeks, and for example until symptoms improve or disappear. In some embodiments, a single treatment can be repeated 1, 2, 3, 4, 5, 6, 7, or more days, weeks, or months apart.

In some embodiments, the treatment regimen is similar to those describe above for, e.g., gout, prolonging penicillin serum levels, pelvic inflammatory disease, gonorrhea, etc.

In a particular embodiments, the probenecid or a metabolite or analog thereof or pharmaceutically acceptable salt thereof is administered as 250 mg twice per day.

As introduced above, recitation of ranges of values herein including the dosage ranges above and elsewhere herein, are merely intended to serve as a shorthand method of referring individually to each separate value falling within the range and each separate value is incorporated into the specification as if it were individually recited herein.

Dosing regimens may be, for example, intermittent dosing or continuous (e.g., constant infusion). The dosing regimens can include administrations of the same or different doses. Thus, the dosing regimen can include dose escalation, dose reduction, or a combination thereof.

In some embodiments, the composition is administered in a pulsed dosage regimen. Pulse dosing refers to dosing approach that produces escalating drug levels early in the dosing interval followed by a prolonged dose-free period. For example, in some embodiments, drug administration is frontloaded by means of, for example, 1, 2, 3, 4, or 5 sequential bolus administrations, after which drug levels are allowed to diminish until the next dose. In some embodiments, the serum drug level is allowed to diminish to about 0.

This type of drug delivery technology could offer therapeutic advantages such as reduced dose frequency and greater patient compliance. In comparison to intermittent dosing, pulse dosing front loads the drug, allowing an extended dose-free period during which drug concentration falls close to zero. However, unlike a single, large bolus dose (e.g., given once daily), short bursts of drug are separated by short dose-free periods, allowing the serum concentration to fluctuate (Ibrahim, et al., *Antimicrobial Agents and Chemotherapy,* 48(11):4195-4199 (2004)). In particular embodiments, pulse dosing is carried out by oral administration or intravenous administration. For example, in some embodiments, the therapy includes discontinuous/intermittent intravenous infusion of very high doses of probenecid, a metabolite or analog thereof, or a pharmaceutically acceptable salt thereof over a short period.

In some embodiments, a large bolus dose of probenecid, a metabolite or analog thereof, or pharmaceutically acceptable salt thereof is between about 1,000 mg and 5,000 mg inclusive, or any subrange or specific dosage there between.

The maximum recommended dosage for probenecid is 2 grams/day PO for adults, adolescents, and children of more than 50 kg, and 40 mg/kg/day (1.2 grams/m2/day) PO (not to exceed 2 grams/day PO) for adolescents and children of 50 kg or less. Thus, in some embodiments, administration does not exceed 5 g, 4 g, 3 g, or 2 g per day. In some embodiments, administration does not exceed 40 mg/kg/day. See also "probenecid—Drug Summary", the Prescribers' Digital Reference.

In some embodiments, a tablet for oral administration contains e.g., 500 mg of probenecid and optionally, one or more of the following inactive ingredients: microcrystalline cellulose, sodium lauryl sulfate, sodium starch glycolate, starch (corn), povidone, colloidal silicon dioxide, magnesium stearate, polyvinyl alcohol, titanium dioxide, polyethylene glycol, talc, D&C Yellow #10 Aluminum Lake, FD&C Yellow #6 Aluminum Lake, and FD&C Blue #2 Aluminum Lake.

B. Combination Therapies

In some embodiments, probenecid, a metabolite or analog thereof, or a pharmaceutically acceptable salt thereof is administered in combination with one or more additional active agents. The combination therapies can include administration of the active agents together in the same admixture, or in separate admixtures. Therefore, in some embodiments, the pharmaceutical composition includes two, three, or more active agents. Such formulations typically include an effective amount of probenecid, a metabolite or analog thereof, or a pharmaceutically acceptable salt thereof. In some embodiments, the second active agent is an antiviral (i.e., a second antiviral), a fever reducer, an antinflammatory, an analgesic, or a combination thereof. In a particular embodiment, the antiviral is oseltamivir phosphate (TAMIFLU®). Tamiflu is a prescription medicine used to treat the flu (influenza) in people 2 weeks of age and older who have had flu symptoms. Probenecid or metabolites or analogs or pharmaceutical salts thereof may enhance the efficacy of antivirals like oseltamivir phosphate as it helps retain excretion of the drug during treatment.

C. Exemplary Viruses and Symptoms

Exemplary viruses and symptoms of illness stemming from infection by the viruses that are treatable by the disclosed methods are also provided. The virus is typically a coronavirus. The current classification of coronaviruses recognizes 39 species in 27 subgenera, five genera and two subfamilies that belong to the family Coronaviridae, suborder Cornidovirineae, order Nidovirales and realm Riboviria (Coronaviridae Study Group of the International Committee on Taxonomy of Viruses, *Nat Microbiol* 2020. DOI: 10.1038/s41564-020-0695-z). They are enveloped viruses with a positive-sense single-stranded RNA genome and a nucleocapsid of helical symmetry. The genome size of coronaviruses ranges from approximately 26 to 32 kilobases, one of the largest among RNA viruses.

Coronaviruses cause diseases in mammals and birds.

In preferred embodiments, the subject is a human. In humans, coronaviruses can cause respiratory tract infections that can range from mild to lethal. Mild illnesses include some cases of the common cold, while more lethal varieties can cause SARS, MERS, and COVID-19 (i.e., caused by SARS-CoV-2).

The subject may have one or more symptoms characteristic of SARS, MERS, or COVID-19.

SARS (i.e., SAR-CoV) usually begins with flu-like signs and symptoms such as fever, chills, muscle aches, headache and occasionally diarrhea. After about a week, signs and symptoms include fever of 100.5 F (38 C) or higher, dry cough, and shortness of breath.

Reported illnesses from COVID-19 (i.e., caused by SARS-CoV-2) have ranged from mild symptoms to severe illness and death for confirmed cases. The most common symptoms are fever, tiredness, dry cough, and shortness of breath. Runny nose, vomiting and diarrhea have also been reported. These symptoms may appear 2-14 days after exposure.

Most people confirmed to have MERS-CoV infection have had severe respiratory illness with symptoms of fever, cough, and/or shortness of breath. Some people also had diarrhea and nausea/vomiting. For many people with MERS, more severe complications followed, such as pneumonia and kidney failure. Some infected people had mild symptoms (such as cold-like symptoms) or no symptoms at all.

In some embodiments, the subject has an underlying condition such as asthma, heart disease, diabetes, cancer, chronic lung disease, chronic heart disease, chronic kidney disease, or a combination thereof.

In other embodiments, the subject is a non-human mammal or a bird. Symptoms caused by coronavirus infection in non-human species vary: in chickens, they cause an upper respiratory tract disease, while in cows and pigs they cause diarrhea.

Coronavirus species and representative viruses thereof include [representative virus (of species)]: SARSr-CoV BtKY72 (Severe acute respiratory syndrome-related coronavirus), SARS-CoV-2 (Severe acute respiratory syndrome-related coronavirus), SARSr-CoV RaTG13 (Severe acute respiratory syndrome-related coronavirus), SARS-CoV PC4-227 (Severe acute respiratory syndrome-related coronavirus), SARS-CoV (Severe acute respiratory syndrome-related coronavirus), Bat-Hp-BetaCovC (Bat Hp-betacoronavirus Zhejiang2013), Ro-BatCoV GCCDC1 (*Rousettus* bat coronavirus GCCDC1), Ro-BatCoV HKU9 (*Rousettus* bat coronavirus HKU9), Ei-BatCoV C704 (Eidolon bat coronavirus C704), Pi-BatCoV HKU5 (*Pipistrellus* bat coronavirus HKU5), Ty-BatCoV HKU4 (*Tylonycteris* bar coronavirus HKU4), MERS-CoV (Middle East respiratory syndrome-related coronavirus), EriCoV (Hedgehog coronavirus), MHV (murine coronavirus), HCoV HKU1 (Human coronavirus HKU1), ChRCoV HKU24 (China *Rattus* coronavirus HKU24), ChRCovC HKU24 (Betacoronavirus 1), MrufCoV 2JL14 (*Myodes* coronavirus 2JL14), HCoV NL63 (Human coronavirus NL63), HCoV 229E (Human coronavirus 229E), and HCoV OC43 (Human coronavirus OC43). See, e.g., Coronaviridae Study Group of the International Committee on Taxonomy of Viruses, *Nat Microbiol* 2020. DOI: 10.1038/s41564-020-0695-z), which is specifically incorporated by reference in its entirety. In some embodiments, the coronavirus is a common cold coronavirus such as 229E, NL63, OC43, and HKU1.

In particularly preferred embodiments, the virus is a Severe acute respiratory syndrome-related virus, such as, SARSr-CoV BtKY72, SARS-CoV-2, SARSr-CoV RaTG13, SARS-CoV PC4-227, or SARS-CoV, preferably one that infects humans such as SARS-CoV or SARS-CoV-2.

In some embodiments, the virus is a Middle East respiratory syndrome-related virus such as MERS-CoV.

Various strains of the foregoing viruses are known and include the representative genomic sequences provided as, for example, SEQ ID NOS:1-4, the accession numbers provided herein, and those sequences and accession numbers provided in, e.g., Coronaviridae Study Group of the International Committee on Taxonomy of Viruses, *Nat Microbiol* 2020. DOI: 10.1038/s41564-020-0695-z). These, however, are non-limiting examples, and the disclosed compositions and methods can also be used to treat other strains of coronavirus, particularly SARS and MERS coronaviruses. In some embodiments, the (DNA sequence) of the viral genome has a sequence at least 80%, preferably at 85%, more preferably at least 86%, 87%, 88%, 89%, 90%, 91%, 92%, 93%, 94%, 95%, 96%, 97%, 98%, 99%, or 100% sequence identity to one or more of SEQ ID NOS:1, 2, 3, or 4, or another viral accession number provided herein, or a sequence or accession number provided in Coronaviridae Study Group of the International Committee on Taxonomy of Viruses, *Nat Microbiol* 2020. DOI: 10.1038/s41564-020-

0695-z, all of which are specifically incorporated by reference herein in their entireties. It will be appreciated that the sequences are provided as DNA sequences, but the viral genome itself will typically have the corresponding RNA sequences. Thus, the corresponding RNA sequences are also expressly provided herein.

GenBank Accession No. MN908947.3, which is specifically incorporated by reference herein in its entirety, provides the following (DNA) genomic sequence for SARS-CoV-2 (Severe acute respiratory syndrome coronavirus 2 isolate Wuhan-Hu-1, complete genome):

```
                                                    (SEQ ID NO: 1)
   1 attaaaggtt tataccttcc caggtaacaa accaaccaac tttcgatctc ttgtagatct

  61 gttctctaaa cgaactttaa aatctgtgtg gctgtcactc ggctgcatgc ttagtgcact

 121 cacgcagtat aattaataac taattactgt cgttgacagg acacgagtaa ctcgtctatc

 181 ttctgcaggc tgcttacggt ttcgtccgtg ttgcagccga tcatcagcac atctaggttt

 241 cgtccgggtg tgaccgaaag gtaagatgga gagccttgtc cctggtttca acgagaaaac

 301 acacgtccaa ctcagtttgc ctgttttaca ggttcgcgac gtgctcgtac gtggctttgg

 361 agactccgtg gaggaggtct tatcagaggc acgtcaacat cttaaagatg gcacttgtgg

 421 cttagtagaa gttgaaaaag gcgttttgcc tcaacttgaa cagccctatg tgttcatcaa

 481 acgttcggat gctcgaactg cacctcatgg tcatgttatg gttgagctgg tagcagaact

 541 cgaaggcatt cagtacggtc gtagtggtga gacacttggt gtccttgtcc ctcatgtggg

 601 cgaaatacca gtggcttacc gcaaggttct tcttcgtaag aacggtaata aaggagctgg

 661 tggccatagt tacggcgccg atctaaagtc atttgactta ggcgacgagc ttggcactga

 721 tccttatgaa gattttcaag aaaactggaa cactaaacat agcagtggtg ttacccgtga

 781 actcatgcgt gagcttaacg gaggggcata cactcgctat gtcgataaca acttctgtgg

 841 ccctgatggc taccctcttg agtgcattaa agaccttcta gcacgtgctg gtaaagcttc

 901 atgcactttg tccgaacaac tggactttat tgacactaag aggggtgtat actgctgccg

 961 tgaacatgag catgaaattg cttggtacac ggaacgttct gaaaagagct atgaattgca

1021 gacacctttt gaaattaaat tggcaaagaa atttgacacc ttcaatgggg aatgtccaaa

1081 ttttgtattt cccttaaatt ccataatcaa gactattcaa ccaagggttg aaaagaaaaa

1141 gcttgatggc tttatgggta gaattcgatc tgtctatcca gttgcgtcac caaatgaatg

1201 caaccaaatg tgcctttcaa ctctcatgaa gtgtgatcat tgtggtgaaa cttcatggca

1261 gacgggcgat tttgttaaag ccacttgcga attttgtggc actgagaatt tgactaaaga

1321 aggtgccact acttgtggtt acttacccca aaatgctgtt gttaaaattt attgtccagc

1381 atgtcacaat tcagaagtag gacctgagca tagtcttgcc gaataccata atgaatctgg

1441 cttgaaaacc attcttcgta agggtggtcg cactattgcc tttggaggct gtgtgttctc

1501 ttatgttggt tgccataaca agtgtgccta ttgggttcca cgtgctagcg ctaacatagg

1561 ttgtaaccat acaggtgttg ttggagaagg ttccgaaggt cttaatgaca accttcttga

1621 aatactccaa aaagagaaag tcaacatcaa tattgttggt gactttaaac ttaatgaaga

1681 gatcgccatt attttggcat ctttttctgc ttccacaagt gcttttgtgg aaactgtgaa

1741 aggtttggat tataaagcat tcaaacaaat tgttgaatcc tgtggtaatt ttaaagttac

1801 aaaaggaaaa gctaaaaaag gtgcctggaa tattggtgaa cagaaatcaa tactgagtcc

1861 tctttatgca tttgcatcag aggctgctcg tgttgtacga tcaattttct cccgcactct

1921 tgaaactgct caaaattctg tgcgtgtttt acagaaggcc gctataacaa tactagatgg

1981 aatttcacag tattcactga gactcattga tgctatgatg ttcacatctg atttggctac

2041 taacaatcta gttgtaatgg cctacattac aggtggtgtt gttcagttga cttcgcagtg

2101 gctaactaac atctttggca ctgtttatga aaaactcaaa cccgtccttg attggcttga
```

-continued

```
2161 agagaagttt aaggaaggtg tagagtttct tagagacggt tgggaaattg ttaaatttat
2221 ctcaacctgt gcttgtgaaa ttgtcggtgg acaaattgtc acctgtgcaa aggaaattaa
2281 ggagagtgtt cagacattct ttaagcttgt aaataaattt ttggctttgt gtgctgactc
2341 tatcattatt ggtggagcta aacttaaagc cttgaattta ggtgaaacat ttgtcacgca
2401 ctcaaaggga ttgtacagaa agtgtgttaa atccagagaa gaaactggcc tactcatgcc
2461 tctaaaagcc ccaaaagaaa ttatcttctt agagggagaa acacttccca cagaagtgtt
2521 aacagaggaa gttgtcttga aaactggtga tttacaacca ttagaacaac ctactagtga
2581 agctgttgaa gctccattgg ttggtacacc agtttgtatt aacgggctta tgttgctcga
2641 aatcaaagac acagaaaagt actgtgccct tgcacctaat atgatggtaa caaacaatac
2701 cttcacactc aaaggcggtg caccaacaaa ggttactttt ggtgatgaca ctgtgataga
2761 agtgcaaggt tacaagagtg tgaatatcac ttttgaactt gatgaaagga ttgataaagt
2821 acttaatgag aagtgctctg cctatacagt tgaactcggt acagaagtaa atgagttcgc
2881 ctgtgttgtg gcagatgctg tcataaaaac tttgcaacca gtatctgaat tacttacacc
2941 actgggcatt gatttagatg agtggagtat ggctacatac tacttatttg atgagtctgg
3001 tgagtttaaa ttggcttcac atatgtattg ttctttctac cctccagatg aggatgaaga
3061 agaaggtgat tgtgaagaag aagagtttga gccatcaact caatatgagt atggtactga
3121 agatgattac caaggtaaac ctttggaatt tggtgccact tctgctgctc ttcaacctga
3181 agaagagcaa gaagaagatt ggttagatga tgatagtcaa caaactgttg gtcaacaaga
3241 cggcagtgag gacaatcaga caactactat tcaaacaatt gttgaggttc aacctcaatt
3301 agagatggaa cttacaccag ttgttcagac tattgaagtg aatagtttta gtggttattt
3361 aaaacttact gacaatgtat acattaaaaa tgcagacatt gtggaagaag ctaaaaaggt
3421 aaaaccaaca gtggttgtta atgcagccaa tgtttacctt aaacatggag gaggtgttgc
3481 aggagcctta aataaggcta ctaacaatgc catgcaagtt gaatctgatg attacatagc
3541 tactaatgga ccacttaaag tgggtggtag ttgtgtttta agcggacaca atcttgctaa
3601 acactgtctt catgttgtcg gcccaaatgt taacaaaggt gaagacattc aacttcttaa
3661 gagtgcttat gaaaatttta atcagcacga agttctactt gcaccattat tatcagctgg
3721 tatttttggt gctgacccta tacattcttt aagagtttgt gtagatactg ttcgcacaaa
3781 tgtctactta gctgtctttg ataaaaatct ctatgacaaa cttgtttcaa gctttttgga
3841 aatgaagagt gaaaagcaag ttgaacaaaa gatcgctgag attcctaaag aggaagttaa
3901 gccatttata actgaaagta aaccttcagt tgaacagaga aaacaagatg ataagaaaat
3961 caaagcttgt gttgaagaag ttacaacaac tctggaagaa actaagttcc tcacagaaaa
4021 cttgttactt tatattgaca ttaatggcaa tcttcatcca gattctgcca ctcttgttag
4081 tgacattgac atcactttct taaagaaaga tgctccatat atagtgggtg atgttgttca
4141 agagggtgtt ttaactgctg tggttatacc tactaaaaag gctggtggca ctactgaaat
4201 gctagcgaaa gctttgagaa aagtgccaac agacaattat ataaccactt acccgggtca
4261 gggtttaaat ggttacactg tagaggaggc aaagacagtg cttaaaaagt gtaaaagtgc
4321 cttttacatt ctaccatcta ttatctctaa tgagaagcaa gaaattcttg gaactgtttc
4381 ttggaatttg cgagaaatgc ttgcacatgc agaagaaaca cgcaaattaa tgcctgtctg
4441 tgtggaaact aaagccatag tttcaactat acagcgtaaa tataagggta ttaaaataca
4501 agagggtgtg gttgattatg gtgctagatt ttacttttac accagtaaaa caactgtagc
4561 gtcacttatc aacacactta acgatctaaa tgaaactctt gttacaatgc cacttggcta
```

-continued 4621 tgtaacacat ggcttaaatt tggaagaagc tgctcggtat atgagatctc tcaaagtgcc
4681 agctacagtt tctgtttctt cacctgatgc tgttacagcg tataatggtt atcttacttc
4741 ttcttctaaa acacctgaag aacattttat tgaaaccatc tcacttgctg gttcctataa
4801 agattggtcc tattctggac aatctacaca actaggtata gaatttctta agagaggtga
4861 taaaagtgta tattacacta gtaatcctac cacattccac ctagatggtg aagttatcac
4921 ctttgacaat cttaagacac ttctttcttt gagagaagtg aggactatta aggtgtttac
4981 aacagtagac aacattaacc tccacacgca agttgtggac atgtcaatga catatggaca
5041 acagtttggt ccaacttatt tggatggagc tgatgttact aaaataaaac ctcataattc
5101 acatgaaggt aaaacatttt atgttttacc taatgatgac actctacgtg ttgaggcttt
5161 tgagtactac cacacaactg atcctagttt tctgggtagg tacatgtcag cattaaatca
5221 cactaaaaag tggaaatacc cacaagttaa tggtttaact tctattaaat gggcagataa
5281 caactgttat cttgccactg cattgttaac actccaacaa atagagttga agtttaatcc
5341 acctgctcta caagatgctt attacagagc aagggctggt gaagctgcta acttttgtgc
5401 acttatctta gcctactgta ataagacagt aggtgagtta ggtgatgtta gagaaacaat
5461 gagttacttg tttcaacatg ccaatttaga ttcttgcaaa agagtcttga acgtggtgtg
5521 taaaacttgt ggacaacagc agacaaccct taagggtgta gaagctgtta tgtacatggg
5581 cacactttct tatgaacaat ttaagaaagg tgttcagata ccttgtacgt gtggtaaaca
5641 agctacaaaa tatctagtac aacaggagtc accttttgtt atgatgtcag caccacctgc
5701 tcagtatgaa cttaagcatg gtacatttac ttgtgctagt gagtacactg gtaattacca
5761 gtgtggtcac tataaacata taacttctaa agaaactttg tattgcatag acggtgcttt
5821 acttacaaag tcctcagaat acaaaggtcc tattacggat gttttctaca aagaaaacag
5881 ttacacaaca accataaaac cagttactta taaattggat ggtgttgttt gtacagaaat
5941 tgaccctaag ttggacaatt attataagaa agacaattct tatttcacag agcaaccaat
6001 tgatcttgta ccaaaccaac catatccaaa cgcaagcttc gataatttta agtttgtatg
6061 tgataatatc aaatttgctg atgatttaaa ccagttaact ggttataaga aacctgcttc
6121 aagagagctt aaagttacat ttttccctga cttaaatggt gatgtggtgg ctattgatta
6181 taaacactac acaccctctt ttaagaaagg agctaaattg ttacataaac ctattgtttg
6241 gcatgttaac aatgcaacta ataaagccac gtataaacca aatacctggt gtatacgttg
6301 tctttggagc acaaaaccag ttgaaacatc aaattcgttt gatgtactga agtcagagga
6361 cgcgcaggga atggataatc ttgcctgcga agatctaaaa ccagtctctg aagaagtagt
6421 ggaaaatcct accatacaga aagacgttct tgagtgtaat gtgaaaacta ccgaagttgt
6481 aggagacatt atacttaaac cagcaaataa tagtttaaaa attacagaag aggttggcca
6541 cacagatcta atggctgctt atgtagacaa ttctagtctt actattaaga aacctaatga
6601 attatctaga gtattaggtt tgaaaaccct tgctactcat ggtttagctg ctgttaatag
6661 tgtcccttgg gatactatag ctaattatgc taagcctttt cttaacaaag ttgttagtac
6721 aactactaac atagttacac ggtgtttaaa ccgtgtttgt actaattata tgccttattt
6781 ctttacttta ttgctacaat tgtgtacttt tactagaagt acaaattcta gaattaaagc
6841 atctatgccg actactatag caaagaatac tgttaagagt gtcggtaaat tttgtctaga
6901 ggcttcattt aattatttga agtcacctaa tttttctaaa ctgataaata ttataatttg
6961 gtttttacta ttaagtgttt gcctaggttc tttaatctac tcaaccgctg ctttaggtgt -continued 7021 tttaatgtct aatttaggca tgccttctta ctgtactggt tacagagaag gctatttgaa 7081 ctctactaat gtcactattg caacctactg tactggttct ataccttgta gtgtttgtct 7141 tagtggttta gattctttag acacctatcc ttctttagaa actatacaaa ttaccatttc 7201 atcttttaaa tgggatttaa ctgcttttgg cttagttgca gagtggtttt tggcatatat 7261 tcttttcact aggtttttct atgtacttgg attggctgca atcatgcaat tgtttttcag 7321 ctattttgca gtacatttta ttagtaattc ttggcttatg tggttaataa ttaatcttgt 7381 acaaatggcc ccgatttcag ctatggttag aatgtacatc ttctttgcat cattttatta 7441 tgtatggaaa agttatgtgc atgttgtaga cggttgtaat tcatcaactt gtatgatgtg 7501 ttacaaacgt aatagagcaa caagagtcga atgtacaact attgttaatg gtgttagaag 7561 gtccttttat gtctatgcta atggaggtaa aggcttttgc aaactacaca attggaattg 7621 tgttaattgt gatacattct gtgctggtag tacatttatt agtgatgaag ttgcgagaga 7681 cttgtcacta cagtttaaaa gaccaataaa tcctactgac cagtcttctt acatcgttga 7741 tagtgttaca gtgaagaatg gttccatcca tctttacttt gataaagctg gtcaaaagac 7801 ttatgaaaga cattctctct ctcattttgt taacttagac aacctgagag ctaataacac 7861 taaaggttca ttgcctatta atgttatagt ttttgatggt aaatcaaaat gtgaagaatc 7921 atctgcaaaa tcagcgtctg tttactacag tcagcttatg tgtcaaccta tactgttact 7981 agatcaggca ttagtgtctg atgttggtga tagtgcggaa gttgcagtta aaatgtttga 8041 tgcttacgtt aatacgtttt catcaacttt taacgtacca atggaaaaac tcaaaacact 8101 agttgcaact gcagaagctg aacttgcaaa gaatgtgtcc ttagacaatg tcttatctac 8161 ttttatttca gcagctcggc aagggtttgt tgattcagat gtagaaacta aagatgttgt 8221 tgaatgtctt aaattgtcac atcaatctga catagaagtt actggcgata gttgtaataa 8281 ctatatgctc acctataaca aagttgaaaa catgacaccc cgtgaccttg gtgcttgtat 8341 tgactgtagt gcgcgtcata ttaatgcgca ggtagcaaaa agtcacaaca ttgctttgat 8401 atggaacgtt aaagatttca tgtcattgtc tgaacaacta cgaaaacaaa tacgtagtgc 8461 tgctaaaaag aataacttac cttttaagtt gacatgtgca actactagac aagttgttaa 8521 tgttgtaaca acaaagatag cacttaaggg tggtaaaatt gttaataatt ggttgaagca 8581 gttaattaaa gttacacttg tgttcctttt tgttgctgct attttctatt taataacacc 8641 tgttcatgtc atgtctaaac atactgactt ttcaagtgaa atcataggat acaaggctat 8701 tgatggtggt gtcactcgtg acatagcatc tacagatact tgttttgcta acaaacatgc 8761 tgattttgac acatggttta gccagcgtgg tggtagttat actaatgaca aagcttgccc 8821 attgattgct gcagtcataa caagagaagt gggttttgtc gtgcctggtt tgcctggcac 8881 gatattacgc acaactaatg gtgacttttt gcatttctta cctagagttt ttagtgcagt 8941 tggtaacatc tgttacacac catcaaaact tatagagtac actgactttg caacatcagc 9001 ttgtgttttg gctgctgaat gtacaatttt taaagatgct tctggtaagc cagtaccata 9061 ttgttatgat accaatgtac tagaaggttc tgttgcttat gaaagtttac gccctgacac 9121 acgttatgtg ctcatggatg gctctattat tcaatttcct aacacctacc ttgaaggttc 9181 tgttagagtg gtaacaactt ttgattctga gtactgtagg cacggcactt gtgaaagatc 9241 agaagctggt gtttgtgtat ctactagtgg tagatgggta cttaacaatg attattacag 9301 atctttacca ggagttttct gtggtgtaga tgctgtaaat ttacttacta atatgtttac 9361 accactaatt caacctattg gtgctttgga catatcagca tctatagtag ctggtggtat 9421 tgtagctatc gtagtaacat gccttgccta ctattttatg aggtttagaa gagcttttgg -continued 9481 tgaatacagt catgtagttg cctttaatac tttactattc cttatgtcat tcactgtact
9541 ctgtttaaca ccagtttact cattcttacc tggtgtttat tctgttattt acttgtactt
9601 gacattttat cttactaatg atgtttcttt tttagcacat attcagtgga tggttatgtt
9661 cacaccttta gtacctttct ggataacaat tgcttatatc atttgtattt ccacaaagca
9721 tttctattgg ttctttagta attacctaaa gagacgtgta gtctttaatg gtgtttcctt
9781 tagtactttt gaagaagctg cgctgtgcac ctttttgtta aataaagaaa tgtatctaaa
9841 gttgcgtagt gatgtgctat tacctcttac gcaatataat agatacttag ctctttataa
9901 taagtacaag tattttagtg gagcaatgga tacaactagc tacagagaag ctgcttgttg
9961 tcatctcgca aaggctctca atgacttcag taactcaggt tctgatgttc tttaccaacc
10021 accacaaacc tctatcacct cagctgtttt gcagagtggt tttagaaaaa tggcattccc
10081 atctggtaaa gttgagggtt gtatggtaca agtaacttgt ggtacaacta cacttaacgg
10141 tctttggctt gatgacgtag tttactgtcc aagacatgtg atctgcacct ctgaagacat
10201 gcttaaccct aattatgaag atttactcat tcgtaagtct aatcataatt tcttggtaca
10261 ggctggtaat gttcaactca gggttattgg acattctatg caaaattgtg tacttaagct
10321 taaggttgat acagccaatc ctaagacacc taagtataag tttgttcgca ttcaaccagg
10381 acagactttt tcagtgttag cttgttacaa tggttcacca tctggtgttt accaatgtgc
10441 tatgaggccc aatttcacta ttaagggttc attccttaat ggttcatgtg gtagtgttgg
10501 ttttaacata gattatgact gtgtctcttt ttgttacatg caccatatgg aattaccaac
10561 tggagttcat gctggcacag acttagaagg taacttttat ggacctttttg ttgacaggca
10621 aacagcacaa gcagctggta cggacacaac tattacagtt aatgttttag cttggttgta
10681 cgctgctgtt ataaatggag acaggtggtt tctcaatcga tttaccacaa ctcttaatga
10741 ctttaacctt gtggctatga agtacaatta tgaacctcta acacaagacc atgttgacat
10801 actaggacct ctttctgctc aaactggaat tgccgtttta gatatgtgtg cttcattaaa
10861 agaattactg caaaatggta tgaatggacg taccatattg ggtagtgctt tattagaaga
10921 tgaatttaca ccttttgatg ttgttagaca atgctcaggt gttactttcc aaagtgcagt
10981 gaaaagaaca atcaagggta cacaccactg gttgttactc acaattttga cttcactttt
11041 agttttagtc cagagtactc aatggtcttt gttctttttt ttgtatgaaa atgccttttt
11101 accttttgct atgggtatta ttgctatgtc tgcttttgca atgatgtttg tcaaacataa
11161 gcatgcattt ctctgtttgt ttttgttacc ttctcttgcc actgtagctt attttaatat
11221 ggtctatatg cctgctagtt gggtgatgcg tattatgaca tggttggata tggttgatac
11281 tagtttgtct ggttttaagc taaaagactg tgttatgtat gcatcagctg tagtgttact
11341 aatccttatg acagcaagaa ctgtgtatga tgatggtgct aggagagtgt ggacacttat
11401 gaatgtcttg acactcgttt ataaagttta ttatggtaat gctttagatc aagccatttc
11461 catgtgggct cttataatct ctgttacttc taactactca ggtgtagtta caactgtcat
11521 gtttttggcc agaggtattg tttttatgtg tgttgagtat tgccctattt tcttcataac
11581 tggtaataca cttcagtgta taatgctagt ttattgtttc ttaggctatt tttgtacttg
11641 ttactttggc ctcttttgtt tactcaaccg ctactttaga ctgactcttg gtgtttatga
11701 ttacttagtt tctacacagg agtttagata tatgaattca cagggactac tcccacccaa
11761 gaatagcata gatgccttca aactcaacat taaattgttg ggtgttggtg gcaaaccttg
11821 tatcaaagta gccactgtac agtctaaaat gtcagatgta aagtgcacat cagtagtctt -continued 11881 actctcagtt ttgcaacaac tcagagtaga atcatcatct aaattgtggg ctcaatgtgt 11941 ccagttacac aatgacattc tcttagctaa agatactact gaagcctttg aaaaaatggt 12001 ttcactactt tctgttttgc tttccatgca gggtgctgta gacataaaca agctttgtga 12061 agaaatgctg gacaacaggg caaccttaca agctatagcc tcagagttta gttcccttcc 12121 atcatatgca gcttttgcta ctgctcaaga agcttatgag caggctgttg ctaatggtga 12181 ttctgaagtt gttcttaaaa agttgaagaa gtctttgaat gtggctaaat ctgaatttga 12241 ccgtgatgca gccatgcaac gtaagttgga aaagatggct gatcaagcta tgacccaaat 12301 gtataaacag gctagatctg aggacaagag ggcaaaagtt actagtgcta tgcagacaat 12361 gcttttcact atgcttagaa agttggataa tgatgcactc aacaacatta tcaacaatgc 12421 aagagatggt tgtgttccct tgaacataat acctcttaca acagcagcca aactaatggt 12481 tgtcatacca gactataaca catataaaaa tacgtgtgat ggtacaacat ttacttatgc 12541 atcagcattg tgggaaatcc aacaggttgt agatgcagat agtaaaattg ttcaacttag 12601 tgaaattagt atggacaatt cacctaattt agcatggcct cttattgtaa cagctttaag 12661 ggccaattct gctgtcaaat tacagaataa tgagcttagt cctgttgcac tacgacagat 12721 gtcttgtgct gccggtacta cacaaactgc ttgcactgat gacaatgcgt tagcttacta 12781 caacacaaca aagggaggta ggtttgtact tgcactgtta tccgatttac aggatttgaa 12841 atgggctaga ttccctaaga gtgatggaac tggtactatc tatacagaac tggaaccacc 12901 ttgtaggttt gttacagaca cacctaaagg tcctaaagtg aagtatttat actttattaa 12961 aggattaaac aacctaaata gaggtatggt acttggtagt ttagctgcca cagtacgtct 13021 acaagctggt aatgcaacag aagtgcctgc caattcaact gtattatctt tctgtgcttt 13081 tgctgtagat gctgctaaag cttacaaaga ttatctagct agtgggggac aaccaatcac 13141 taattgtgtt aagatgttgt gtacacacac tggtactggt caggcaataa cagttacacc 13201 ggaagccaat atggatcaag aatcctttgg tggtgcatcg tgttgtctgt actgccgttg 13261 ccacatagat catccaaatc ctaaaggatt ttgtgactta aaaggtaagt atgtacaaat 13321 acctacaact tgtgctaatg accctgtggg ttttacactt aaaaacacag tctgtaccgt 13381 ctgcggtatg tggaaaggtt atggctgtag ttgtgatcaa ctccgcgaac ccatgcttca 13441 gtcagctgat gcacaatcgt ttttaaacgg gtttgcggtg taagtgcagc ccgtcttaca 13501 ccgtgcggca caggcactag tactgatgtc gtatacaggg cttttgacat ctacaatgat 13561 aaagtagctg gttttgctaa attcctaaaa actaattgtt gtcgcttcca agaaaaggac 13621 gaagatgaca atttaattga ttcttacttt gtagttaaga gacacacttt ctctaactac 13681 caacatgaag aaacaattta taatttactt aaggattgtc cagctgttgc taaacatgac 13741 ttctttaagt ttagaataga cggtgacatg gtaccacata tatcacgtca acgtcttact 13801 aaatacacaa tggcagacct cgtctatgct ttaaggcatt ttgatgaagg taattgtgac 13861 acattaaaag aaatacttgt cacatacaat tgttgtgatg atgattattt caataaaaag 13921 gactggtatg attttgtaga aaacccagat atattacgcg tatacgccaa cttaggtgaa 13981 cgtgtacgcc aagctttgtt aaaaacagta caattctgtg atgccatgcg aaatgctggt 14041 attgttggtg tactgacatt agataatcaa gatctcaatg gtaactggta tgatttcggt 14101 gatttcatac aaaccacgcc aggtagtgga gttcctgttg tagattctta ttattcattg 14161 ttaatgccta tattaacctt gaccagggct ttaactgcag agtcacatgt tgacactgac 14221 ttaacaaagc cttacattaa gtgggatttg ttaaaatatg acttcacgga agagaggtta 14281 aaactctttg accgttattt taaatattgg gatcagacat accacccaaa ttgtgttaac -continued 14341 tgtttggatg acagatgcat tctgcattgt gcaaacttta atgttttatt ctctacagtg 14401 ttcccaccta caagttttgg accactagtg agaaaaatat ttgttgatgg tgttccattt 14461 gtagtttcaa ctggatacca cttcagagag ctaggtgttg tacataatca ggatgtaaac 14521 ttacatagct ctagacttag ttttaaggaa ttacttgtgt atgctgctga ccctgctatg 14581 cacgctgctt ctggtaatct attactagat aaacgcacta cgtgcttttc agtagctgca 14641 cttactaaca atgttgcttt tcaaactgtc aaacccggta attttaacaa agacttctat 14701 gactttgctg tgtctaaggg tttctttaag gaaggaagtt ctgttgaatt aaaacacttc 14761 ttctttgctc aggatggtaa tgctgctatc agcgattatg actactatcg ttataatcta 14821 ccaacaatgt gtgatatcag acaactacta tttgtagttg aagttgttga taagtacttt 14881 gattgttacg atggtggctg tattaatgct aaccaagtca tcgtcaacaa cctagacaaa 14941 tcagctggtt ttccatttaa taaatggggt aaggctagac tttattatga ttcaatgagt 15001 tatgaggatc aagatgcact tttcgcatat acaaaacgta atgtcatccc tactataact 15061 caaatgaatc ttaagtatgc cattagtgca aagaatagag ctcgcaccgt agctggtgtc 15121 tctatctgta gtactatgac caatagacag tttcatcaaa aattattgaa atcaatagcc 15181 gccactagag gagctactgt agtaattgga acaagcaaat tctatggtgg ttggcacaac 15241 atgttaaaaa ctgtttatag tgatgtagaa aaccctcacc ttatgggttg ggattatcct 15301 aaatgtgata gagccatgcc taacatgctt agaattatgg cctcacttgt tcttgctcgc 15361 aaacatacaa cgtgttgtag cttgtcacac cgtttctata gattagctaa tgagtgtgct 15421 caagtattga gtgaaatggt catgtgtggc ggttcactat atgttaaacc aggtggaacc 15481 tcatcaggag atgccacaac tgcttatgct aatagtgttt ttaacatttg tcaagctgtc 15541 acggccaatg ttaatgcact tttatctact gatggtaaca aaattgccga taagtatgtc 15601 cgcaatttac aacacagact ttatgagtgt ctctatagaa atagagatgt tgacacagac 15661 tttgtgaatg agttttacgc atatttgcgt aaacatttct caatgatgat actctctgac 15721 gatgctgttg tgtgtttcaa tagcacttat gcatctcaag gtctagtggc tagcataaag 15781 aactttaagt cagttcttta ttatcaaaac aatgttttta tgtctgaagc aaaatgttgg 15841 actgagactg accttactaa aggacctcat gaattttgct ctcaacatac aatgctagtt 15901 aaacagggtg atgattatgt gtaccttcct tacccagatc catcaagaat cctaggggcc 15961 ggctgttttg tagatgatat cgtaaaaaca gatggtacac ttatgattga acggttcgtg 16021 tctttagcta tagatgctta cccacttact aaacatccta atcaggagta tgctgatgtc 16081 tttcatttgt acttacaata cataagaaag ctacatgatg agttaacagg acacatgtta 16141 gacatgtatt ctgttatgct tactaatgat aacacttcaa ggtattggga acctgagttt 16201 tatgaggcta tgtacacacc gcatacagtc ttacaggctg ttggggcttg tgttctttgc 16261 aattcacaga cttcattaag atgtggtgct tgcatacgta gaccattctt atgttgtaaa 16321 tgctgttacg accatgtcat atcaacatca cataaattag tcttgtctgt taatccgtat 16381 gtttgcaatg ctccaggttg tgatgtcaca gatgtgactc aactttactt aggaggtatg 16441 agctattatt gtaaatcaca taaaccaccc attagttttc cattgtgtgc taatggacaa 16501 gtttttggtt tatataaaaa tacatgtgtt ggtagcgata atgttactga ctttaatgca 16561 attgcaacat gtgactggac aaatgctggt gattacattt tagctaacac ctgtactgaa 16621 agactcaagc tttttgcagc agaaacgctc aaagctactg aggagacatt taaactgtct 16681 tatggtattg ctactgtacg tgaagtgctg tctgacagag aattacatct ttcatgggaa -continued 16741 gttggtaaac ctagaccacc acttaaccga aattatgtct ttactggtta tcgtgtaact
16801 aaaaacagta aagtacaaat aggagagtac acctttgaaa aaggtgacta tggtgatgct
16861 gttgtttacc gaggtacaac aacttacaaa ttaaatgttg gtgattattt tgtgctgaca
16921 tcacatacag taatgccatt aagtgcacct acactagtgc cacaagagca ctatgttaga
16981 attactggct tatacccaac actcaatatc tcagatgagt tttctagcaa tgttgcaaat
17041 tatcaaaagg ttggtatgca aaagtattct acactccagg gaccacctgg tactggtaag
17101 agtcattttg ctattggcct agctctctac tacccttctg ctcgcatagt gtatacagct
17161 tgctctcatg ccgctgttga tgcactatgt gagaaggcat taaaatattt gcctatagat
17221 aaatgtagta gaattatacc tgcacgtgct cgtgtagagt gttttgataa attcaaagtg
17281 aattcaacat tagaacagta tgtcttttgt actgtaaatg cattgcctga gacgacagca
17341 gatatagttg tctttgatga aatttcaatg gccacaaatt atgatttgag tgttgtcaat
17401 gccagattac gtgctaagca ctatgtgtac attggcgacc ctgctcaatt acctgcacca
17461 cgcacattgc taactaaggg cacactagaa ccagaatatt tcaattcagt gtgtagactt
17521 atgaaaacta taggtccaga catgttcctc ggaacttgtc ggcgttgtcc tgctgaaatt
17581 gttgacactg tgagtgcttt ggtttatgat aataagctta aagcacataa agacaaatca
17641 gctcaatgct ttaaaatgtt ttataagggt gttatcacgc atgatgtttc atctgcaatt
17701 aacaggccac aaataggcgt ggtaagagaa ttccttacac gtaaccctgc ttggagaaaa
17761 gctgtcttta tttcacctta taattcacag aatgctgtag cctcaaagat tttgggacta
17821 ccaactcaaa ctgttgattc atcacagggc tcagaatatg actatgtcat attcactcaa
17881 accactgaaa cagctcactc ttgtaatgta aacagattta atgttgctat taccagagca
17941 aaagtaggca tactttgcat aatgtctgat agagaccttt atgacaagtt gcaatttaca
18001 agtcttgaaa ttccacgtag gaatgtggca actttacaag ctgaaaatgt aacaggactc
18061 tttaaagatt gtagtaaggt aatcactggg ttacatccta cacaggcacc tacacacctc
18121 agtgttgaca ctaaattcaa aactgaaggt ttatgtgttg acatacctgg catacctaag
18181 gacatgacct atagaagact catctctatg atgggtttta aaatgaatta tcaagttaat
18241 ggttacccta acatgtttat cacccgcgaa gaagctataa gacatgtacg tgcatggatt
18301 ggcttcgatg tcgaggggtg tcatgctact agagaagctg ttggtaccaa tttaccttta
18361 cagctaggtt tttctacagg tgttaaccta gttgctgtac ctacaggtta tgttgataca
18421 cctaataata cagatttttc cagagttagt gctaaaccac cgcctggaga tcaatttaaa
18481 cacctcatac cacttatgta caaaggactt ccttggaatg tagtgcgtat aaagattgta
18541 caaatgttaa gtgacacact taaaaatctc tctgacagag tcgtatttgt cttatgggca
18601 catggctttg agttgacatc tatgaagtat tttgtgaaaa taggacctga gcgcacctgt
18661 tgtctatgtg atagacgtgc cacatgcttt tccactgctt cagacactta tgcctgttgg
18721 catcattcta ttggatttga ttacgtctat aatccgttta tgattgatgt tcaacaatgg
18781 ggttttacag gtaacctaca aagcaaccat gatctgtatt gtcaagtcca tggtaatgca
18841 catgtagcta gttgtgatgc aatcatgact aggtgtctag ctgtccacga gtgctttgtt
18901 aagcgtgttg actggactat tgaatatcct ataattggtg atgaactgaa gattaatgcg
18961 gcttgtagaa aggttcaaca catggttgtt aaagctgcat tattagcaga caaattccca
19021 gttcttcacg acattggtaa ccctaaagct attaagtgtg tacctcaagc tgatgtagaa
19081 tggaagttct atgatgcaca gccttgtagt gacaaagctt ataaaataga agaattattc
19141 tattcttatg ccacacattc tgacaaattc acagatggtg tatgcctatt ttggaattgc -continued 19201 aatgtcgata gatatcctgc taattccatt gtttgtagat ttgacactag agtgctatct
19261 aaccttaact tgcctggttg tgatggtggc agtttgtatg taaataaaca tgcattccac
19321 acaccagctt ttgataaaag tgcttttgtt aatttaaaac aattaccatt tttctattac
19381 tctgacagtc catgtgagtc tcatggaaaa caagtagtgt cagatataga ttatgtacca
19441 ctaaagtctg ctacgtgtat aacacgttgc aatttaggtg gtgctgtctg tagacatcat
19501 gctaatgagt acagattgta tctcgatgct tataacatga tgatctcagc tggctttagc
19561 ttgtgggttt acaaacaatt tgatacttat aacctctgga acacttttac aagacttcag
19621 agtttagaaa atgtggcttt taatgttgta aataagggac actttgatgg acaacagggt
19681 gaagtaccag tttctatcat taataacact gtttacacaa aagttgatgg tgttgatgta
19741 gaattgtttg aaaataaaac aacattacct gttaatgtag catttgagct ttgggctaag
19801 cgcaacatta aaccagtacc agaggtgaaa atactcaata atttgggtgt ggacattgct
19861 gctaatactg tgatctggga ctacaaaaga gatgctccag cacatatatc tactattggt
19921 gtttgttcta tgactgacat agccaagaaa ccaactgaaa cgatttgtgc accactcact
19981 gtcttttttg atggtagagt tgatggtcaa gtagacttat ttagaaatgc ccgtaatggt
20041 gttcttatta cagaaggtag tgttaaaggt ttacaaccat ctgtaggtcc caaacaagct
20101 agtcttaatg gagtcacatt aattggagaa gccgtaaaaa cacagttcaa ttattataag
20161 aaagttgatg gtgttgtcca acaattacct gaaacttact ttactcagag tagaaattta
20221 caagaattta aacccaggag tcaaatggaa attgatttct tagaattagc tatggatgaa
20281 ttcattgaac ggtataaatt agaaggctat gccttcgaac atatcgttta tggagatttt
20341 agtcatagtc agttaggtgg tttacatcta ctgattggac tagctaaacg ttttaaggaa
20401 tcacctttg aattagaaga ttttattcct atggacagta cagttaaaaa ctatttcata
20461 acagatgcgc aaacaggttc atctaagtgt gtgtgttctg ttattgattt attacttgat
20521 gattttgttg aaataataaa atcccaagat ttatctgtag tttctaaggt tgtcaaagtg
20581 actattgact atacagaaat ttcatttatg ctttggtgta aagatggcca tgtagaaaca
20641 ttttacccaa aattacaatc tagtcaagcg tggcaaccgg gtgttgctat gcctaatctt
20701 tacaaaatgc aaagaatgct attagaaaag tgtgaccttc aaaattatgg tgatagtgca
20761 acattaccta aaggcataat gatgaatgtc gcaaaatata ctcaactgtg tcaatattta
20821 aacacattaa cattagctgt accctataat atgagagtta tacattttgg tgctggttct
20881 gataaaggag ttgcaccagg tacagctgtt ttaagacagt ggttgcctac gggtacgctg
20941 cttgtcgatt cagatcttaa tgactttgtc tctgatgcag attcaacttt gattggtgat
21001 tgtgcaactg tacatacagc taataaatgg gatctcatta ttagtgatat gtacgaccct
21061 aagactaaaa atgttacaaa agaaaatgac tctaaagagg gtttttcac ttacatttgt
21121 gggtttatac aacaaaagct agctcttgga ggttccgtgg ctataaagat aacagaacat
21181 tcttggaatg ctgatcttta taagctcatg ggacacttcg catggtggac agcctttgtt
21241 actaatgtga atgcgtcatc atctgaagca tttttaattg gatgtaatta tcttggcaaa
21301 ccacgcgaac aaatagatgg ttatgtcatg catgcaaatt acatatttg gaggaataca
21361 aatccaattc agttgtcttc ctattcttta tttgacatga gtaaatttcc ccttaaatta
21421 aggggtactg ctgttatgtc tttaaaagaa ggtcaaatca atgatatgat tttatctctt
21481 cttagtaaag gtagacttat aattagagaa aacaacagag ttgttatttc tagtgatgtt
21541 cttgttaaca actaaacgaa caatgtttgt ttttcttgtt ttattgccac tagtctctag -continued 21601 tcagtgtgtt aatcttacaa ccagaactca attacccccct gcatacacta attctttcac 21661 acgtggtgtt tattaccctg acaaagtttt cagatcctca gttttacatt caactcagga 21721 cttgttctta cctttctttt ccaatgttac ttggttccat gctatacatg tctctgggac 21781 caatggtact aagaggtttg ataaccctgt cctaccattt aatgatggtg tttattttgc 21841 ttccactgag aagtctaaca taataagagg ctggattttt ggtactactt tagattcgaa 21901 gacccagtcc ctacttattg ttaataacgc tactaatgtt gttattaaag tctgtgaatt 21961 tcaattttgt aatgatccat ttttgggtgt ttattaccac aaaaacaaca aaagttggat 22021 ggaaagtgag ttcagagttt attctagtgc gaataattgc acttttgaat atgtctctca 22081 gccttttctt atggaccttg aaggaaaaca gggtaatttc aaaaatctta gggaatttgt 22141 gtttaagaat attgatggtt attttaaaat atattctaag cacacgccta ttaatttagt 22201 gcgtgatctc cctcagggtt tttcggcttt agaaccattg gtagatttgc caataggtat 22261 taacatcact aggtttcaaa ctttacttgc tttacataga agttatttga ctcctggtga 22321 ttcttcttca ggttggacag ctggtgctgc agcttattat gtgggttatc ttcaacctag 22381 gacttttcta ttaaaatata atgaaaatgg aaccattaca gatgctgtag actgtgcact 22441 tgaccctctc tcagaaacaa agtgtacgtt gaaatccttc actgtagaaa aaggaatcta 22501 tcaaacttct aactttagag tccaaccaac agaatctatt gttagatttc ctaatattac 22561 aaacttgtgc ccttttggtg aagtttttaa cgccaccaga tttgcatctg tttatgcttg 22621 gaacaggaag agaatcagca actgtgttgc tgattattct gtcctatata attccgcatc 22681 attttccact tttaagtgtt atggagtgtc tcctactaaa ttaaatgatc tctgctttac 22741 taatgtctat gcagattcat ttgtaattag aggtgatgaa gtcagacaaa tcgctccagg 22801 gcaaactgga aagattgctg attataatta taaattacca gatgatttta caggctgcgt 22861 tatagcttgg aattctaaca atcttgattc taaggttggt ggtaattata attacctgta 22921 tagattgttt aggaagtcta atctcaaacc ttttgagaga gatatttcaa ctgaaatcta 22981 tcaggccggt agcacacctt gtaatggtgt tgaaggtttt aattgttact ttcctttaca 23041 atcatatggt ttccaaccca ctaatggtgt tggttaccaa ccatacagag tagtagtact 23101 ttcttttgaa cttctacatg caccagcaac tgtttgtgga cctaaaaagt ctactaattt 23161 ggttaaaaac aaatgtgtca atttcaactt caatggttta acaggcacag gtgttcttac 23221 tgagtctaac aaaaagtttc tgcctttcca acaatttggc agagacattg ctgacactac 23281 tgatgctgtc cgtgatccac agacacttga gattcttgac attacaccat gttcttttgg 23341 tggtgtcagt gttataacac caggaacaaa tacttctaac caggttgctg ttctttatca 23401 ggatgttaac tgcacagaag tccctgttgc tattcatgca gatcaactta ctcctacttg 23461 gcgtgtttat tctacaggtt ctaatgtttt tcaaacacgt gcaggctgtt taatagggggc 23521 tgaacatgtc aacaactcat atgagtgtga catacccatt ggtgcaggta tatgcgctag 23581 ttatcagact cagactaatt ctcctcggcg ggcacgtagt gtagctagtc aatccatcat 23641 tgcctacact atgtcacttg gtgcagaaaa ttcagttgct tactctaata actctattgc 23701 catacccaca aattttacta ttagtgttac cacagaaatt ctaccagtgt ctatgaccaa 23761 gacatcagta gattgtacaa tgtacatttg tggtgattca actgaatgca gcaatctttt 23821 gttgcaatat ggcagttttt gtacacaatt aaaccgtgct ttaactggaa tagctgttga 23881 acaagacaaa aacacccaag aagtttttgc acaagtcaaa caaatttaca aaacaccacc 23941 aattaaagat tttggtggtt ttaatttttc acaaatatta ccagatccat caaaaccaag 24001 caagaggtca tttattgaag atctactttt caacaaagtg acacttgcag atgctggctt -continued

```
24061 catcaaacaa tatggtgatt gccttggtga tattgctgct agagacctca tttgtgcaca
24121 aaagtttaac ggccttactg ttttgccacc tttgctcaca gatgaaatga ttgctcaata
24181 cacttctgca ctgttagcgg gtacaatcac ttctggttgg acctttggtg caggtgctgc
24241 attacaaata ccatttgcta tgcaaatggc ttataggttt aatggtattg gagttacaca
24301 gaatgttctc tatgagaacc aaaaattgat tgccaaccaa tttaatagtg ctattggcaa
24361 aattcaagac tcactttctt ccacagcaag tgcacttgga aaacttcaag atgtggtcaa
24421 ccaaaatgca caagctttaa acacgcttgt taaacaactt agctccaatt ttggtgcaat
24481 ttcaagtgtt ttaaatgata tcctttcacg tcttgacaaa gttgaggctg aagtgcaaat
24541 tgataggttg atcacaggca gacttcaaag tttgcagaca tatgtgactc aacaattaat
24601 tagagctgca gaaatcagag cttctgctaa tcttgctgct actaaaatgt cagagtgtgt
24661 acttggacaa tcaaaaagag ttgatttttg tggaaagggc tatcatctta tgtccttccc
24721 tcagtcagca cctcatggtg tagtcttctt gcatgtgact tatgtccctg cacaagaaaa
24781 gaacttcaca actgctcctg ccatttgtca tgatggaaaa gcacactttc ctcgtgaagg
24841 tgtctttgtt tcaaatggca cacactggtt tgtaacacaa aggaattttt atgaaccaca
24901 aatcattact acagacaaca catttgtgtc tggtaactgt gatgttgtaa taggaattgt
24961 caacaacaca gtttatgatc ctttgcaacc tgaattagac tcattcaagg aggagttaga
25021 taaatatttt aagaatcata catcaccaga tgttgattta ggtgacatct ctggcattaa
25081 tgcttcagtt gtaaacattc aaaaagaaat tgaccgcctc aatgaggttg ccaagaattt
25141 aaatgaatct ctcatcgatc tccaagaact tggaaagtat gagcagtata taaaatggcc
25201 atggtacatt tggctaggtt ttatagctgg cttgattgcc atagtaatgg tgacaattat
25261 gctttgctgt atgaccagtt gctgtagttg tctcaagggc tgttgttctt gtggatcctg
25321 ctgcaaattt gatgaagacg actctgagcc agtgctcaaa ggagtcaaat tacattacac
25381 ataaacgaac ttatggattt gtttatgaga atcttcacaa ttggaactgt aactttgaag
25441 caaggtgaaa tcaaggatgc tactccttca gattttgttc gcgctactgc aacgataccg
25501 atacaagcct cactcccttt cggatggctt attgttggcg ttgcacttct tgctgttttt
25561 cagagcgctt ccaaaatcat aaccctcaaa aagagatggc aactagcact ctccaagggt
25621 gttcactttg tttgcaactt gctgttgttg tttgtaacag tttactcaca ccttttgctc
25681 gttgctgctg gccttgaagc cccttttctc tatctttatg ctttagtcta cttcttgcag
25741 agtataaact tgtaagaat aataatgagg ctttggcttt gctggaaatg ccgttccaaa
25801 aacccattac tttatgatgc caactatttt ctttgctggc atactaattg ttacgactat
25861 tgtataccct acaatagtgt aacttcttca attgtcatta cttcaggtga tggcacaaca
25921 agtcctattt ctgaacatga ctaccagatt ggtggttata ctgaaaaatg ggaatctgga
25981 gtaaaagact gtgttgtatt acacagttac ttcacttcag actattacca gctgtactca
26041 actcaattga gtacagacac tggtgttgaa catgttacct tcttcatcta caataaaatt
26101 gttgatgagc ctgaagaaca tgtccaaatt cacacaatcg acggttcatc cggagttgtt
26161 aatccagtaa tggaaccaat ttatgatgaa ccgacgacga ctactagcgt gcctttgtaa
26221 gcacaagctg atgagtacga acttatgtac tcattcgttt cggaagagac aggtacgtta
26281 atagttaata gcgtacttct ttttcttgct ttcgtggtat tcttgctagt tacactagcc
26341 atccttactg cgcttcgatt gtgtgcgtac tgctgcaata ttgttaacgt gagtcttgta
26401 aaaccttctt tttacgttta ctctcgtgtt aaaaatctga attcttctag agttcctgat
```

-continued 26461 cttctggtct aaacgaacta aatattatat tagtttttct gtttggaact ttaattttag 26521 ccatggcaga ttccaacggt actattaccg ttgaagagct taaaaagctc cttgaacaat 26581 ggaacctagt aataggtttc ctattcctta catggatttg tcttctacaa tttgcctatg 26641 ccaacaggaa taggtttttg tatataatta agttaatttt cctctggctg ttatggccag 26701 taactttagc ttgttttgtg cttgctgctg tttacagaat aaattggatc accggtggaa 26761 ttgctatcgc aatggcttgt cttgtaggct tgatgtggct cagctacttc attgcttctt 26821 tcagactgtt tgcgcgtacg cgttccatgt ggtcattcaa tccagaaact aacattcttc 26881 tcaacgtgcc actccatggc actattctga ccagaccgct tctagaaagt gaactcgtaa 26941 tcggagctgt gatccttcgt ggacatcttc gtattgctgg acaccatcta ggacgctgtg 27001 acatcaagga cctgcctaaa gaaatcactg ttgctacatc acgaacgctt tcttattaca 27061 aattgggagc ttcgcagcgt gtagcaggtg actcaggttt tgctgcatac agtcgctaca 27121 ggattggcaa ctataaatta aacacagacc attccagtag cagtgacaat attgctttgc 27181 ttgtacagta agtgacaaca gatgtttcat ctcgttgact ttcaggttac tatagcagag 27241 atattactaa ttattatgag gacttttaaa gtttccattt ggaatcttga ttacatcata 27301 aacctcataa ttaaaaattt atctaagtca ctaactgaga ataaatattc tcaattagat 27361 gaagagcaac caatggagat tgattaaacg aacatgaaaa ttattctttt cttggcactg 27421 ataacactcg ctacttgtga gctttatcac taccaagagt gtgttagagg tacaacagta 27481 cttttaaaag aaccttgctc ttctggaaca tacgagggca attcaccatt tcatcctcta 27541 gctgataaca aatttgcact gacttgcttt agcactcaat ttgcttttgc ttgtcctgac 27601 ggcgtaaaac acgtctatca gttacgtgcc agatcagttt cacctaaact gttcatcaga 27661 caagaggaag ttcaagaact ttactctcca atttttctta ttgttgcggc aatagtgttt 27721 ataacacttt gcttcacact caaaagaaag acagaatgat tgaactttca ttaattgact 27781 tctatttgtg ctttttagcc tttctgctat tccttgtttt aattatgctt attatctttt 27841 ggttctcact tgaactgcaa gatcataatg aaacttgtca cgcctaaacg aacatgaaat 27901 ttcttgtttt cttaggaatc atcacaactg tagctgcatt tcaccaagaa tgtagtttac 27961 agtcatgtac tcaacatcaa ccatatgtag ttgatgaccc gtgtcctatt cacttctatt 28021 ctaaatggta tattagagta ggagctagaa aatcagcacc tttaattgaa ttgtgcgtgg 28081 atgaggctgg ttctaaatca cccattcagt acatcgatat cggtaattat acagtttcct 28141 gtttaccttt tacaattaat tgccaggaac ctaaattggg tagtcttgta gtgcgttgtt 28201 cgttctatga agacttttta gagtatcatg acgttcgtgt tgttttagat ttcatctaaa 28261 cgaacaaact aaaatgtctg ataatggacc ccaaaatcag cgaaatgcac cccgcattac 28321 gtttggtgga ccctcagatt caactggcag taaccagaat ggagaacgca gtggggcgcg 28381 atcaaaacaa cgtcggcccc aaggtttacc caataatact gcgtcttggt tcaccgctct 28441 cactcaacat ggcaaggaag accttaaatt ccctcgagga caaggcgttc caattaacac 28501 caatagcagt ccagatgacc aaattggcta ctaccgaaga gctaccagac gaattcgtgg 28561 tggtgacggt aaaatgaaag atctcagtcc aagatggtat ttctactacc taggaactgg 28621 gccagaagct ggacttccct atggtgctaa caaagacggc atcatatggg ttgcaactga 28681 gggagccttg aatacaccaa aagatcacat tggcacccgc aatcctgcta acaatgctgc 28741 aatcgtgcta caacttcctc aaggaacaac attgccaaaa ggcttctacg cagaagggag 28801 cagaggcggc agtcaagcct cttctcgttc ctcatcacgt agtcgcaaca gttcaagaaa 28861 ttcaactcca ggcagcagta ggggaacttc tcctgctaga atggctggca atggcggtga -continued

```
28921 tgctgctctt gctttgctgc tgcttgacag attgaaccag cttgagagca aaatgtctgg
28981 taaaggccaa caacaacaag gccaaactgt cactaagaaa tctgctgctg aggcttctaa
29041 gaagcctcgg caaaaacgta ctgccactaa agcatacaat gtaacacaag ctttcggcag
29101 acgtggtcca gaacaaaccc aaggaaattt tggggaccag gaactaatca gacaaggaac
29161 tgattacaaa cattggccgc aaattgcaca atttgccccc agcgcttcag cgttcttcgg
29221 aatgtcgcgc attggcatgg aagtcacacc ttcgggaacg tggttgacct acacaggtgc
29281 catcaaattg gatgacaaag atccaaattt caaagatcaa gtcattttgc tgaataagca
29341 tattgacgca tacaaaacat tcccaccaac agagcctaaa aaggacaaaa agaagaaggc
29401 tgatgaaact caagccttac cgcagagaca gaagaaacag caaactgtga ctcttcttcc
29461 tgctgcagat ttggatgatt tctccaaaca attgcaacaa tccatgagca gtgctgactc
29521 aactcaggcc taaactcatg cagaccacac aaggcagatg ggctatataa acgttttcgc
29581 ttttccgttt acgatatata gtctactctt gtgcagaatg aattctcgta actacatagc
29641 acaagtagat gtagttaact ttaatctcac atagcaatct ttaatcagtg tgtaacatta
29701 gggaggactt gaaagagcca ccacattttc accgaggcca cgcggagtac gatcgagtgt
29761 acagtgaaca atgctaggga gagctgccta tatggaagag ccctaatgtg taaaattaat
29821 tttagtagtg ctatccccat gtgattttaa tagcttctta ggagaatgac aaaaaaaaaa
29881 aaaaaaaaaa aaaaaaaaaa aaa.
```

GenBank Accession No. MN985325.1, which is specifically incorporated by reference herein in its entirety, provides the following (DNA) genomic sequence for SARS-CoV-2 (Severe acute respiratory syndrome coronavirus 2 isolate 2019-nCoV/USA-WA1/2020, complete genome):

```
                                                         (SEQ ID NO: 2)
   1 attaaaggtt tataccttcc caggtaacaa accaaccaac tttcgatctc ttgtagatct
  61 gttctctaaa cgaactttaa aatctgtgtg gctgtcactc ggctgcatgc ttagtgcact
 121 cacgcagtat aattaataac taattactgt cgttgacagg acacgagtaa ctcgtctatc
 181 ttctgcaggc tgcttacggt ttcgtccgtg ttgcagccga tcatcagcac atctaggttt
 241 cgtccgggtg tgaccgaaag gtaagatgga gagccttgtc cctggtttca acgagaaaac
 301 acacgtccaa ctcagtttgc ctgttttaca ggttcgcgac gtgctcgtac gtggctttgg
 361 agactccgtg gaggaggtct tatcagaggc acgtcaacat cttaaagatg gcacttgtgg
 421 cttagtagaa gttgaaaaag gcgttttgcc tcaacttgaa cagccctatg tgttcatcaa
 481 acgttcggat gctcgaactg cacctcatgg tcatgttatg gttgagctgg tagcagaact
 541 cgaaggcatt cagtacggtc gtagtggtga gacacttggt gtccttgtcc ctcatgtggg
 601 cgaaatacca gtggcttacc gcaaggttct tcttcgtaag aacggtaata aaggagctgg
 661 tggccatagt tacggcgccg atctaaagtc atttgactta ggcgacgagc ttggcactga
 721 tccttatgaa gattttcaag aaaactggaa cactaaacat agcagtggtg ttacccgtga
 781 actcatgcgt gagcttaacg gaggggcata cactcgctat gtcgataaca acttctgtgg
 841 ccctgatggc taccctcttg agtgcattaa agaccttcta gcacgtgctg gtaaagcttc
 901 atgcactttg tccgaacaac tggactttat tgacactaag aggggtgtat actgctgccg
 961 tgaacatgag catgaaattg cttggtacac ggaacgttct gaaaagagct atgaattgca
1021 gacacctttt gaaattaaat tggcaaagaa atttgacacc ttcaatgggg aatgtccaaa
```

-continued 1081 ttttgtattt cccttaaatt ccataatcaa gactattcaa ccaagggttg aaaagaaaaa 1141 gcttgatggc tttatgggta gaattcgatc tgtctatcca gttgcgtcac caaatgaatg 1201 caaccaaatg tgcctttcaa ctctcatgaa gtgtgatcat tgtggtgaaa cttcatggca 1261 gacgggcgat tttgttaaag ccacttgcga attttgtggc actgagaatt tgactaaaga 1321 aggtgccact acttgtggtt acttacccca aaatgctgtt gttaaaattt attgtccagc 1381 atgtcacaat tcagaagtag gacctgagca tagtcttgcc gaataccata atgaatctgg 1441 cttgaaaacc attcttcgta agggtggtcg cactattgcc tttggaggct gtgtgttctc 1501 ttatgttggt tgccataaca agtgtgccta ttgggttcca cgtgctagcg ctaacatagg 1561 ttgtaaccat acaggtgttg ttggagaagg ttccgaaggt cttaatgaca accttcttga 1621 aatactccaa aaagagaaag tcaacatcaa tattgttggt gactttaaac ttaatgaaga 1681 gatcgccatt attttggcat ctttttctgc ttccacaagt gcttttgtgg aaactgtgaa 1741 aggtttggat tataaagcat tcaaacaaat tgttgaatcc tgtggtaatt ttaaagttac 1801 aaaaggaaaa gctaaaaaag gtgcctggaa tattggtgaa cagaaatcaa tactgagtcc 1861 tctttatgca tttgcatcag aggctgctcg tgttgtacga tcaattttct cccgcactct 1921 tgaaactgct caaaattctg tgcgtgtttt acagaaggcc gctataacaa tactagatgg 1981 aatttcacag tattcactga gactcattga tgctatgatg ttcacatctg atttggctac 2041 taacaatcta gttgtaatgg cctacattac aggtggtgtt gttcagttga cttcgcagtg 2101 gctaactaac atctttggca ctgtttatga aaaactcaaa cccgtccttg attggcttga 2161 agagaagttt aaggaaggtg tagagtttct tagagacggt tgggaaattg ttaaatttat 2221 ctcaacctgt gcttgtgaaa ttgtcggtgg acaaattgtc acctgtgcaa aggaaattaa 2281 ggagagtgtt cagacattct ttaagcttgt aaataaattt ttggctttgt gtgctgactc 2341 tatcattatt ggtggagcta aacttaaagc cttgaattta ggtgaaacat ttgtcacgca 2401 ctcaaaggga ttgtacagaa agtgtgttaa atccagagaa gaaactggcc tactcatgcc 2461 tctaaaagcc ccaaaagaaa ttatcttctt agagggagaa acacttccca cagaagtgtt 2521 aacagaggaa gttgtcttga aaactggtga tttacaacca ttagaacaac ctactagtga 2581 agctgttgaa gctccattgg ttggtacacc agtttgtatt aacgggctta tgttgctcga 2641 aatcaaagac acagaaaagt actgtgccct tgcacctaat atgatggtaa caaacaatac 2701 cttcacactc aaaggcggtg caccaacaaa ggttactttt ggtgatgaca ctgtgataga 2761 agtgcaaggt tacaagagtg tgaatatcac ttttgaactt gatgaaagga ttgataaagt 2821 acttaatgag aagtgctctg cctatacagt tgaactcggt acagaagtaa atgagttcgc 2881 ctgtgttgtg gcagatgctg tcataaaaac tttgcaacca gtatctgaat tacttacacc 2941 actgggcatt gatttagatg agtggagtat ggctacatac tacttatttg atgagtctgg 3001 tgagtttaaa ttggcttcac atatgtattg ttctttctac cctccagatg aggatgaaga 3061 agaaggtgat tgtgaagaag aagagtttga gccatcaact caatatgagt atggtactga 3121 agatgattac caaggtaaac ctttggaatt tggtgccact tctgctgctc ttcaacctga 3181 agaagagcaa gaagaagatt ggttagatga tgatagtcaa caaactgttg gtcaacaaga 3241 cggcagtgag gacaatcaga caactactat tcaaacaatt gttgaggttc aacctcaatt 3301 agagatggaa cttacaccag ttgttcagac tattgaagtg aatagtttta gtggttattt 3361 aaaacttact gacaatgtat acattaaaaa tgcagacatt gtggaagaag ctaaaaaggt 3421 aaaaccaaca gtggttgtta atgcagccaa tgtttacctt aaacatggag gaggtgttgc 3481 aggagcctta aataaggcta ctaacaatgc catgcaagtt gaatctgatg attacatagc -continued 3541 tactaatgga ccacttaaag tgggtggtag ttgtgtttta agcggacaca atcttgctaa
3601 acactgtctt catgttgtcg gcccaaatgt taacaaaggt gaagacattc aacttcttaa
3661 gagtgcttat gaaaatttta atcagcacga agttctactt gcaccattat tatcagctgg
3721 tatttttggt gctgacccta tacattcttt aagagtttgt gtagatactg ttcgcacaaa
3781 tgtctactta gctgtctttg ataaaaatct ctatgacaaa cttgtttcaa gctttttgga
3841 aatgaagagt gaaaagcaag ttgaacaaaa gatcgctgag attcctaaag aggaagttaa
3901 gccatttata actgaaagta aaccttcagt tgaacagaga aaacaagatg ataagaaaat
3961 caaagcttgt gttgaagaag ttacaacaac tctggaagaa actaagttcc tcacagaaaa
4021 cttgttactt tatattgaca ttaatggcaa tcttcatcca gattctgcca ctcttgttag
4081 tgacattgac atcactttct taaagaaaga tgctccatat atagtgggtg atgttgttca
4141 agagggtgtt ttaactgctg tggttatacc tactaaaaag gctggtggca ctactgaaat
4201 gctagcgaaa gctttgagaa aagtgccaac agacaattat ataaccactt acccgggtca
4261 gggtttaaat ggttacactg tagaggaggc aaagacagtg cttaaaaagt gtaaaagtgc
4321 cttttacatt ctaccatcta ttatctctaa tgagaagcaa gaaattcttg gaactgtttc
4381 ttggaatttg cgagaaatgc ttgcacatgc agaagaaaca cgcaaattaa tgcctgtctg
4441 tgtggaaact aaagccatag tttcaactat acagcgtaaa tataagggta ttaaaataca
4501 agagggtgtg gttgattatg gtgctagatt ttacttttac accagtaaaa caactgtagc
4561 gtcacttatc aacacactta acgatctaaa tgaaactctt gttacaatgc cacttggcta
4621 tgtaacacat ggcttaaatt tggaagaagc tgctcggtat atgagatctc tcaaagtgcc
4681 agctacagtt tctgtttctt cacctgatgc tgttacagcg tataatggtt atcttacttc
4741 ttcttctaaa acacctgaag aacattttat tgaaaccatc tcacttgctg gttcctataa
4801 agattggtcc tattctggac aatctacaca actaggtata gaatttctta agagaggtga
4861 taaaagtgta tattacacta gtaatcctac cacattccac ctagatggtg aagttatcac
4921 ctttgacaat cttaagacac ttctttcttt gagagaagtg aggactatta aggtgtttac
4981 aacagtagac aacattaacc tccacacgca agttgtggac atgtcaatga catatggaca
5041 acagtttggt ccaacttatt tggatggagc tgatgttact aaaataaaac ctcataattc
5101 acatgaaggt aaaacatttt atgttttacc taatgatgac actctacgtg ttgaggcttt
5161 tgagtactac cacacaactg atcctagttt tctgggtagg tacatgtcag cattaaatca
5221 cactaaaaag tggaaatacc cacaagttaa tggtttaact tctattaaat gggcagataa
5281 caactgttat cttgccactg cattgttaac actccaacaa atagagttga agtttaatcc
5341 acctgctcta caagatgctt attacagagc aagggctggt gaagctgcta acttttgtgc
5401 acttatctta gcctactgta ataagacagt aggtgagtta ggtgatgtta gagaaacaat
5461 gagttacttg tttcaacatg ccaatttaga ttcttgcaaa agagtcttga acgtggtgtg
5521 taaaacttgt ggacaacagc agacaaccct taagggtgta gaagctgtta tgtacatggg
5581 cacactttct tatgaacaat ttaagaaagg tgttcagata ccttgtacgt gtggtaaaca
5641 agctacaaaa tatctagtac aacaggagtc accttttgtt atgatgtcag caccacctgc
5701 tcagtatgaa cttaagcatg gtacatttac ttgtgctagt gagtacactg gtaattacca
5761 gtgtggtcac tataaacata taacttctaa agaaactttg tattgcatag acggtgcttt
5821 acttacaaag tcctcagaat acaaaggtcc tattacggat gttttctaca aagaaaacag
5881 ttacacaaca accataaaac cagttactta taaattggat ggtgttgttt gtacagaaat -continued
5941 tgaccctaag ttggacaatt attataagaa agacaattct tatttcacag agcaaccaat
6001 tgatcttgta ccaaaccaac catatccaaa cgcaagcttc gataatttta agtttgtatg
6061 tgataatatc aaatttgctg atgatttaaa ccagttaact ggttataaga aacctgcttc
6121 aagagagctt aaagttacat ttttccctga cttaaatggt gatgtggtgg ctattgatta
6181 taaacactac acaccctctt ttaagaaagg agctaaattg ttacataaac ctattgtttg
6241 gcatgttaac aatgcaacta ataaagccac gtataaacca aatacctggt gtatacgttg
6301 tctttggagc acaaaaccag ttgaaacatc aaattcgttt gatgtactga agtcagagga
6361 cgcgcaggga atggataatc ttgcctgcga agatctaaaa ccagtctctg aagaagtagt
6421 ggaaaatcct accatacaga aagacgttct tgagtgtaat gtgaaaacta ccgaagttgt
6481 aggagacatt atacttaaac cagcaaataa tagtttaaaa attacagaag aggttggcca
6541 cacagatcta atggctgctt atgtagacaa ttctagtctt actattaaga aacctaatga
6601 attatctaga gtattaggtt tgaaaaccct tgctactcat ggtttagctg ctgttaatag
6661 tgtcccttgg gatactatag ctaattatgc taagcctttt cttaacaaag ttgttagtac
6721 aactactaac atagttacac ggtgtttaaa ccgtgtttgt actaattata tgccttattt
6781 ctttacttta ttgctacaat tgtgtacttt tactagaagt acaaattcta gaattaaagc
6841 atctatgccg actactatag caaagaatac tgttaagagt gtcggtaaat tttgtctaga
6901 ggcttcattt aattatttga agtcacctaa tttttctaaa ctgataaata ttataatttg
6961 gtttttacta ttaagtgttt gcctaggttc tttaatctac tcaaccgctg ctttaggtgt
7021 tttaatgtct aatttaggca tgccttctta ctgtactggt tacagagaag gctatttgaa
7081 ctctactaat gtcactattg caacctactg tactggttct ataccttgta gtgtttgtct
7141 tagtggttta gattctttag acacctatcc ttctttagaa actatacaaa ttaccatttc
7201 atcttttaaa tgggatttaa ctgcttttgg cttagttgca gagtggtttt tggcatatat
7261 tcttttcact aggtttttct atgtacttgg attggctgca atcatgcaat tgtttttcag
7321 ctattttgca gtacatttta ttagtaattc ttggcttatg tggttaataa ttaatcttgt
7381 acaaatggcc ccgatttcag ctatggttag aatgtacatc ttctttgcat cattttatta
7441 tgtatggaaa agttatgtgc atgttgtaga cggttgtaat tcatcaactt gtatgatgtg
7501 ttacaaacgt aatagagcaa caagagtcga atgtacaact attgttaatg gtgttagaag
7561 gtccttttat gtctatgcta atggaggtaa aggcttttgc aaactacaca attggaattg
7621 tgttaattgt gatacattct gtgctggtag tacatttatt agtgatgaag ttgcgagaga
7681 cttgtcacta cagtttaaaa gaccaataaa tcctactgac cagtcttctt acatcgttga
7741 tagtgttaca gtgaagaatg gttccatcca tctttacttt gataaagctg gtcaaaagac
7801 ttatgaaaga cattctctct ctcattttgt taacttagac aacctgagag ctaataacac
7861 taaaggttca ttgcctatta atgttatagt ttttgatggt aaatcaaaat gtgaagaatc
7921 atctgcaaaa tcagcgtctg tttactacag tcagcttatg tgtcaaccta tactgttact
7981 agatcaggca ttagtgtctg atgttggtga tagtgcggaa gttgcagtta aaatgtttga
8041 tgcttacgtt aatacgtttt catcaacttt taacgtacca atggaaaaac tcaaaacact
8101 agttgcaact gcagaagctg aacttgcaaa gaatgtgtcc ttagacaatg tcttatctac
8161 ttttatttca gcagctcggc aagggtttgt tgattcagat gtagaaacta aagatgttgt
8221 tgaatgtctt aaattgtcac atcaatctga catagaagtt actggcgata gttgtaataa
8281 ctatatgctc acctataaca aagttgaaaa catgacaccc cgtgaccttg gtgcttgtat
8341 tgactgtagt gcgcgtcata ttaatgcgca ggtagcaaaa agtcacaaca ttgctttgat -continued 8401 atggaacgtt aaagatttca tgtcattgtc tgaacaacta cgaaaacaaa tacgtagtgc
8461 tgctaaaaag aataacttac cttttaagtt gacatgtgca actactagac aagttgttaa
8521 tgttgtaaca acaaagatag cacttaaggg tggtaaaatt gttaataatt ggttgaagca
8581 gttaattaaa gttacacttg tgttcctttt tgttgctgct attttctatt taataacacc
8641 tgttcatgtc atgtctaaac atactgactt ttcaagtgaa atcataggat acaaggctat
8701 tgatggtggt gtcactcgtg acatagcatc tacagatact tgttttgcta acaaacatgc
8761 tgattttgac acatggttta gtcagcgtgg tggtagttat actaatgaca aagcttgccc
8821 attgattgct gcagtcataa caagagaagt gggttttgtc gtgcctggtt tgcctggcac
8881 gatattacgc acaactaatg gtgacttttt gcatttctta cctagagttt ttagtgcagt
8941 tggtaacatc tgttacacac catcaaaact tatagagtac actgactttg caacatcagc
9001 ttgtgttttg gctgctgaat gtacaatttt taaagatgct tctggtaagc cagtaccata
9061 ttgttatgat accaatgtac tagaaggttc tgttgcttat gaaagtttac gccctgacac
9121 acgttatgtg ctcatggatg gctctattat tcaatttcct aacacctacc ttgaaggttc
9181 tgttagagtg gtaacaactt ttgattctga gtactgtagg cacggcactt gtgaaagatc
9241 agaagctggt gtttgtgtat ctactagtgg tagatgggta cttaacaatg attattacag
9301 atctttacca ggagttttct gtggtgtaga tgctgtaaat ttacttacta atatgtttac
9361 accactaatt caacctattg gtgctttgga catatcagca tctatagtag ctggtggtat
9421 tgtagctatc gtagtaacat gccttgccta ctattttatg aggtttagaa gagcttttgg
9481 tgaatacagt catgtagttg cctttaatac tttactattc cttatgtcat tcactgtact
9541 ctgtttaaca ccagtttact cattcttacc tggtgtttat tctgttattt acttgtactt
9601 gacattttat cttactaatg atgtttcttt tttagcacat attcagtgga tggttatgtt
9661 cacacccttta gtacctttct ggataacaat tgcttatatc atttgtattt ccacaaagca
9721 tttctattgg ttctttagta attacctaaa gagacgtgta gtctttaatg gtgtttcctt
9781 tagtactttt gaagaagctg cgctgtgcac ctttttgtta aataaagaaa tgtatctaaa
9841 gttgcgtagt gatgtgctat tacctcttac gcaatataat agatacttag ctctttataa
9901 taagtacaag tattttagtg gagcaatgga tacaactagc tacagagaag ctgcttgttg
9961 tcatctcgca aaggctctca atgacttcag taactcaggt tctgatgttc tttaccaacc
10021 accacaaacc tctatcacct cagctgtttt gcagagtggt tttagaaaaa tggcattccc
10081 atctggtaaa gttgagggtt gtatggtaca agtaacttgt ggtacaacta cacttaacgg
10141 tctttggctt gatgacgtag tttactgtcc aagacatgtg atctgcacct ctgaagacat
10201 gcttaaccct aattatgaag atttactcat tcgtaagtct aatcataatt tcttggtaca
10261 ggctggtaat gttcaactca gggttattgg acattctatg caaaattgtg tacttaagct
10321 taaggttgat acagccaatc ctaagacacc taagtataag tttgttcgca ttcaaccagg
10381 acagactttt tcagtgttag cttgttacaa tggttcacca tctggtgttt accaatgtgc
10441 tatgaggccc aatttcacta ttaagggttc attccttaat ggttcatgtg gtagtgttgg
10501 ttttaacata gattatgact gtgtctcttt ttgttacatg caccatatgg aattaccaac
10561 tggagttcat gctggcacag acttagaagg taacttttat ggaccttttg ttgacaggca
10621 aacagcacaa gcagctggta cggacacaac tattacagtt aatgttttag cttggttgta
10681 cgctgctgtt ataaatggag acaggtggtt tctcaatcga tttaccacaa ctcttaatga
10741 ctttaacctt gtggctatga agtacaatta tgaacctcta acacaagacc atgttgacat -continued 10801 actaggacct ctttctgctc aaactggaat tgccgtttta gatatgtgtg cttcattaaa 10861 agaattactg caaaatggta tgaatggacg taccatattg ggtagtgctt tattagaaga 10921 tgaatttaca ccttttgatg ttgttagaca atgctcaggt gttactttcc aaagtgcagt 10981 gaaaagaaca atcaagggta cacaccactg gttgttactc acaattttga cttcactttt 11041 agttttagtc cagagtactc aatggtcttt gttctttttt ttgtatgaaa atgccttttt 11101 accttttgct atgggtatta ttgctatgtc tgcttttgca atgatgtttg tcaaacataa 11161 gcatgcattt ctctgtttgt tttgttacc ttctcttgcc actgtagctt attttaatat 11221 ggtctatatg cctgctagtt gggtgatgcg tattatgaca tggttggata tggttgatac 11281 tagtttgtct ggttttaagc taaaagactg tgttatgtat gcatcagctg tagtgttact 11341 aatccttatg acagcaagaa ctgtgtatga tgatggtgct aggagagtgt ggacacttat 11401 gaatgtcttg acactcgttt ataaagttta ttatggtaat gctttagatc aagccatttc 11461 catgtgggct cttataatct ctgttacttc taactactca ggtgtagtta caactgtcat 11521 gtttttggcc agaggtattg tttttatgtg tgttgagtat tgccctattt tcttcataac 11581 tggtaataca cttcagtgta taatgctagt ttattgtttc ttaggctatt tttgtacttg 11641 ttactttggc ctcttttgtt tactcaaccg ctactttaga ctgactcttg gtgtttatga 11701 ttacttagtt tctacacagg agtttagata tatgaattca cagggactac tcccacccaa 11761 gaatagcata gatgccttca aactcaacat taaattgttg ggtgttggtg gcaaaccttg 11821 tatcaaagta gccactgtac agtctaaaat gtcagatgta aagtgcacat cagtagtctt 11881 actctcagtt ttgcaacaac tcagagtaga atcatcatct aaattgtggg ctcaatgtgt 11941 ccagttacac aatgacattc tcttagctaa agatactact gaagcctttg aaaaaatggt 12001 ttcactactt tctgttttgc tttccatgca gggtgctgta gacataaaca agctttgtga 12061 agaaatgctg gacaacaggg caaccttaca agctatagcc tcagagttta gttcccttcc 12121 atcatatgca gcttttgcta ctgctcaaga agcttatgag caggctgttg ctaatggtga 12181 ttctgaagtt gttcttaaaa agttgaagaa gtctttgaat gtggctaaat ctgaatttga 12241 ccgtgatgca gccatgcaac gtaagttgga aaagatggct gatcaagcta tgacccaaat 12301 gtataaacag gctagatctg aggacaagag ggcaaaagtt actagtgcta tgcagacaat 12361 gcttttcact atgcttagaa agttggataa tgatgcactc aacaacatta tcaacaatgc 12421 aagagatggt tgtgttccct tgaacataat acctcttaca acagcagcca aactaatggt 12481 tgtcatacca gactataaca catataaaaa tacgtgtgat ggtacaacat ttacttatgc 12541 atcagcattg tgggaaatcc aacaggttgt agatgcagat agtaaaattg ttcaacttag 12601 tgaaattagt atggacaatt cacctaattt agcatggcct cttattgtaa cagctttaag 12661 ggccaattct gctgtcaaat tacagaataa tgagcttagt cctgttgcac tacgacagat 12721 gtcttgtgct gccggtacta cacaaactgc ttgcactgat gacaatgcgt tagcttacta 12781 caacacaaca aagggaggta ggtttgtact tgcactgtta tccgatttac aggatttgaa 12841 atgggctaga ttccctaaga gtgatggaac tggtactatc tatacagaac tggaaccacc 12901 ttgtaggttt gttacagaca cacctaaagg tcctaaagtg aagtatttat actttattaa 12961 aggattaaac aacctaaata gaggtatggt acttggtagt ttagctgcca cagtacgtct 13021 acaagctggt aatgcaacag aagtgcctgc caattcaact gtattatctt tctgtgcttt 13081 tgctgtagat gctgctaaag cttacaaaga ttatctagct agtgggggac aaccaatcac 13141 taattgtgtt aagatgttgt gtacacacac tggtactggt caggcaataa cagttacacc 13201 ggaagccaat atggatcaag aatcctttgg tggtgcatcg tgttgtctgt actgccgttg -continued

```
13261 ccacatagat catccaaatc ctaaaggatt ttgtgactta aaaggtaagt atgtacaaat
13321 acctacaact tgtgctaatg accctgtggg ttttacactt aaaaacacag tctgtaccgt
13381 ctgcggtatg tggaaaggtt atggctgtag ttgtgatcaa ctccgcgaac ccatgcttca
13441 gtcagctgat gcacaatcgt ttttaaacgg gtttgcggtg taagtgcagc ccgtcttaca
13501 ccgtgcggca caggcactag tactgatgtc gtatacaggg cttttgacat ctacaatgat
13561 aaagtagctg gttttgctaa attcctaaaa actaattgtt gtcgcttcca agaaaaggac
13621 gaagatgaca atttaattga ttcttacttt gtagttaaga gacacacttt ctctaactac
13681 caacatgaag aaacaattta taatttactt aaggattgtc cagctgttgc taaacatgac
13741 ttctttaagt ttagaataga cggtgacatg gtaccacata tatcacgtca acgtcttact
13801 aaatacacaa tggcagacct cgtctatgct ttaaggcatt ttgatgaagg taattgtgac
13861 acattaaaag aaatacttgt cacatacaat tgttgtgatg atgattattt caataaaaag
13921 gactggtatg attttgtaga aaacccagat atattacgcg tatacgccaa cttaggtgaa
13981 cgtgtacgcc aagctttgtt aaaaacagta caattctgtg atgccatgcg aaatgctggt
14041 attgttggtg tactgacatt agataatcaa gatctcaatg gtaactggta tgatttcggt
14101 gatttcatac aaaccacgcc aggtagtgga gttcctgttg tagattctta ttattcattg
14161 ttaatgccta tattaacctt gaccagggct ttaactgcag agtcacatgt tgacactgac
14221 ttaacaaagc cttacattaa gtgggatttg ttaaaatatg acttcacgga agagaggtta
14281 aaactctttg accgttattt taaatattgg gatcagacat accacccaaa ttgtgttaac
14341 tgtttggatg acagatgcat tctgcattgt gcaaacttta atgttttatt ctctacagtg
14401 ttcccaccta caagttttgg accactagtg agaaaaatat ttgttgatgg tgttccattt
14461 gtagtttcaa ctggatacca cttcagagag ctaggtgttg tacataatca ggatgtaaac
14521 ttacatagct ctagacttag ttttaaggaa ttacttgtgt atgctgctga ccctgctatg
14581 cacgctgctt ctggtaatct attactagat aaacgcacta cgtgcttttc agtagctgca
14641 cttactaaca atgttgcttt tcaaactgtc aaacccggta attttaacaa agacttctat
14701 gactttgctg tgtctaaggg tttctttaag gaaggaagtt ctgttgaatt aaaacacttc
14761 ttctttgctc aggatggtaa tgctgctatc agcgattatg actactatcg ttataatcta
14821 ccaacaatgt gtgatatcag acaactacta tttgtagttg aagttgttga taagtacttt
14881 gattgttacg atggtggctg tattaatgct aaccaagtca tcgtcaacaa cctagacaaa
14941 tcagctggtt ttccatttaa taaatggggt aaggctagac tttattatga ttcaatgagt
15001 tatgaggatc aagatgcact tttcgcatat acaaaacgta atgtcatccc tactataact
15061 caaatgaatc ttaagtatgc cattagtgca aagaatagag ctcgcaccgt agctggtgtc
15121 tctatctgta gtactatgac caatagacag tttcatcaaa aattattgaa atcaatagcc
15181 gccactagag gagctactgt agtaattgga acaagcaaat tctatggtgg ttggcacaac
15241 atgttaaaaa ctgtttatag tgatgtagaa aaccctcacc ttatgggttg ggattatcct
15301 aaatgtgata gagccatgcc taacatgctt agaattatgg cctcacttgt tcttgctcgc
15361 aaacatacaa cgtgttgtag cttgtcacac cgtttctata gattagctaa tgagtgtgct
15421 caagtattga gtgaaatggt catgtgtggc ggttcactat atgttaaacc aggtggaacc
15481 tcatcaggag atgccacaac tgcttatgct aatagtgttt ttaacatttg tcaagctgtc
15541 acggccaatg ttaatgcact tttatctact gatggtaaca aaattgccga taagtatgtc
15601 cgcaatttac aacacagact ttatgagtgt ctctatagaa atagagatgt tgacacagac
```

-continued

```
15661 tttgtgaatg agttttacgc atatttgcgt aaacatttct caatgatgat actctctgac
15721 gatgctgttg tgtgtttcaa tagcacttat gcatctcaag gtctagtggc tagcataaag
15781 aactttaagt cagttcttta ttatcaaaac aatgttttta tgtctgaagc aaaatgttgg
15841 actgagactg accttactaa aggacctcat gaattttgct ctcaacatac aatgctagtt
15901 aaacagggtg atgattatgt gtaccttcct tacccagatc catcaagaat cctaggggcc
15961 ggctgttttg tagatgatat cgtaaaaaca gatggtacac ttatgattga acggttcgtg
16021 tctttagcta tagatgctta cccacttact aaacatccta atcaggagta tgctgatgtc
16081 tttcatttgt acttacaata cataagaaag ctacatgatg agttaacagg acacatgtta
16141 gacatgtatt ctgttatgct tactaatgat aacacttcaa ggtattggga acctgagttt
16201 tatgaggcta tgtacacacc gcatacagtc ttacaggctg ttggggcttg tgttctttgc
16261 aattcacaga cttcattaag atgtggtgct tgcatacgta gaccattctt atgttgtaaa
16321 tgctgttacg accatgtcat atcaacatca cataaattag tcttgtctgt taatccgtat
16381 gtttgcaatg ctccaggttg tgatgtcaca gatgtgactc aactttactt aggaggtatg
16441 agctattatt gtaaatcaca taaaccaccc attagttttc cattgtgtgc taatggacaa
16501 gtttttggtt tatataaaaa tacatgtgtt ggtagcgata atgttactga ctttaatgca
16561 attgcaacat gtgactggac aaatgctggt gattacattt tagctaacac ctgtactgaa
16621 agactcaagc tttttgcagc agaaacgctc aaagctactg aggagacatt taaactgtct
16681 tatggtattg ctactgtacg tgaagtgctg tctgacagag aattacatct ttcatgggaa
16741 gttggtaaac ctagaccacc acttaaccga aattatgtct ttactggtta tcgtgtaact
16801 aaaaacagta aagtacaaat aggagagtac acctttgaaa aaggtgacta tggtgatgct
16861 gttgtttacc gaggtacaac aacttacaaa ttaaatgttg gtgattattt tgtgctgaca
16921 tcacatacag taatgccatt aagtgcacct acactagtgc cacaagagca ctatgttaga
16981 attactggct tatacccaac actcaatatc tcagatgagt tttctagcaa tgttgcaaat
17041 tatcaaaagg ttggtatgca aaagtattct acactccagg gaccacctgg tactggtaag
17101 agtcattttg ctattggcct agctctctac taccctictg ctcgcatagt gtatacagct
17161 tgctctcatg ccgctgttga tgcactatgt gagaaggcat taaaatattt gcctatagat
17221 aaatgtagta gaattatacc tgcacgtgct cgtgtagagt gttttgataa attcaaagtg
17281 aattcaacat tagaacagta tgtcttttgt actgtaaatg cattgcctga gacgacagca
17341 gatatagttg tctttgatga aatttcaatg gccacaaatt atgatttgag tgttgtcaat
17401 gccagattac gtgctaagca ctatgtgtac attggcgacc ctgctcaatt acctgcacca
17461 cgcacattgc taactaaggg cacactagaa ccagaatatt tcaattcagt gtgtagactt
17521 atgaaaacta taggtccaga catgttcctc ggaacttgtc ggcgttgtcc tgctgaaatt
17581 gttgacactg tgagtgcttt ggtttatgat aataagctta aagcacataa agacaaatca
17641 gctcaatgct ttaaaatgtt ttataagggt gttatcacgc atgatgtttc atctgcaatt
17701 aacaggccac aaataggcgt ggtaagagaa ttccttacac gtaaccctgc ttggagaaaa
17761 gctgtcttta tttcacctta taattcacag aatgctgtag cctcaaagat tttgggacta
17821 ccaactcaaa ctgttgattc atcacagggc tcagaatatg actatgtcat attcactcaa
17881 accactgaaa cagctcactc ttgtaatgta aacagattta atgttgctat taccagagca
17941 aaagtaggca tactttgcat aatgtctgat agagaccttt atgacaagtt gcaatttaca
18001 agtcttgaaa ttccacgtag gaatgtggca actttacaag ctgaaaatgt aacaggactt
18061 tttaaagatt gtagtaaggt aatcactggg ttacatccta cacaggcacc tacacacctc
```

-continued 18121 agtgttgaca ctaaattcaa aactgaaggt ttatgtgttg acatacctgg catacctaag 18181 gacatgacct atagaagact catctctatg atgggtttta aaatgaatta tcaagttaat 18241 ggttacccta acatgtttat cacccgcgaa gaagctataa gacatgtacg tgcatggatt 18301 ggcttcgatg tcgaggggtg tcatgctact agagaagctg ttggtaccaa tttaccttta 18361 cagctaggtt tttctacagg tgttaaccta gttgctgtac ctacaggtta tgttgataca 18421 cctaataata cagatttttc cagagttagt gctaaaccac cgcctggaga tcaatttaaa 18481 cacctcatac cacttatgta caaaggactt ccttggaatg tagtgcgtat aaagattgta 18541 caaatgttaa gtgacacact taaaaatctc tctgacagag tcgtatttgt cttatgggca 18601 catggctttg agttgacatc tatgaagtat tttgtgaaaa taggacctga gcgcacctgt 18661 tgtctatgtg atagacgtgc cacatgcttt tccactgctt cagacactta tgcctgttgg 18721 catcattcta ttggatttga ttacgtctat aatccgttta tgattgatgt tcaacaatgg 18781 ggttttacag gtaacctaca aagcaaccat gatctgtatt gtcaagtcca tggtaatgca 18841 catgtagcta gttgtgatgc aatcatgact aggtgtctag ctgtccacga gtgctttgtt 18901 aagcgtgttg actggactat tgaatatcct ataattggtg atgaactgaa gattaatgcg 18961 gcttgtagaa aggttcaaca catggttgtt aaagctgcat tattagcaga caaattccca 19021 gttcttcacg acattggtaa ccctaaagct attaagtgtg tacctcaagc tgatgtagaa 19081 tggaagttct atgatgcaca gccttgtagt gacaaagctt ataaaataga agaattattc 19141 tattcttatg ccacacattc tgacaaattc acagatggtg tatgcctatt ttggaattgc 19201 aatgtcgata gatatcctgc taattccatt gtttgtagat ttgacactag agtgctatct 19261 aaccttaact tgcctggttg tgatggtggc agtttgtatg taaataaaca tgcattccac 19321 acaccagctt ttgataaaag tgcttttgtt aatttaaaac aattaccatt tttctattac 19381 tctgacagtc catgtgagtc tcatggaaaa caagtagtgt cagatataga ttatgtacca 19441 ctaaagtctg ctacgtgtat aacacgttgc aatttaggtg gtgctgtctg tagacatcat 19501 gctaatgagt acagattgta tctcgatgct tataacatga tgatctcagc tggctttagc 19561 ttgtgggttt acaaacaatt tgatacttat aacctctgga acacttttac aagacttcag 19621 agtttagaaa atgtggcttt taatgttgta aataagggac actttgatgg acaacagggt 19681 gaagtaccag tttctatcat taataacact gtttacacaa aagttgatgg tgttgatgta 19741 gaattgtttg aaaataaaac aacattacct gttaatgtag catttgagct ttgggctaag 19801 cgcaacatta aaccagtacc agaggtgaaa atactcaata atttgggtgt ggacattgct 19861 gctaatactg tgatctggga ctacaaaaga gatgctccag cacatatatc tactattggt 19921 gtttgttcta tgactgacat agccaagaaa ccaactgaaa cgatttgtgc accactcact 19981 gtcttttttg atggtagagt tgatggtcaa gtagacttat ttagaaatgc ccgtaatggt 20041 gttcttatta cagaaggtag tgttaaaggt ttacaaccat ctgtaggtcc caaacaagct 20101 agtcttaatg gagtcacatt aattggagaa gccgtaaaaa cacagttcaa ttattataag 20161 aaagttgatg gtgttgtcca acaattacct gaaacttact ttactcagag tagaaattta 20221 caagaattta aacccaggag tcaaatggaa attgatttct tagaattagc tatggatgaa 20281 ttcattgaac ggtataaatt agaaggctat gccttcgaac atatcgttta tggagatttt 20341 agtcatagtc agttaggtgg tttacatcta ctgattggac tagctaaacg ttttaaggaa 20401 tcacctttg aattagaaga ttttattcct atggacagta cagttaaaaa ctatttcata 20461 acagatgcgc aaacaggttc atctaagtgt gtgtgttctg ttattgattt attacttgat -continued 20521 gattttgttg aaataataaa atcccaagat ttatctgtag tttctaaggt tgtcaaagtg 20581 actattgact atacagaaat ttcatttatg ctttggtgta aagatggcca tgtagaaaca 20641 ttttacccaa aattacaatc tagtcaagcg tggcaaccgg gtgttgctat gcctaatctt 20701 tacaaaatgc aaagaatgct attagaaaag tgtgaccttc aaaattatgg tgatagtgca 20761 acattaccta aaggcataat gatgaatgtc gcaaaatata ctcaactgtg tcaatattta 20821 aacacattaa cattagctgt accctataat atgagagtta tacattttgg tgctggttct 20881 gataaaggag ttgcaccagg tacagctgtt ttaagacagt ggttgcctac gggtacgctg 20941 cttgtcgatt cagatcttaa tgactttgtc tctgatgcag attcaacttt gattggtgat 21001 tgtgcaactg tacatacagc taataaatgg gatctcatta ttagtgatat gtacgaccct 21061 aagactaaaa atgttacaaa agaaaatgac tctaaagagg gtttttcac ttacatttgt 21121 gggtttatac aacaaaagct agctcttgga ggttccgtgg ctataaagat aacagaacat 21181 tcttggaatg ctgatcttta taagctcatg ggacacttcg catggtggac agcctttgtt 21241 actaatgtga atgcgtcatc atctgaagca tttttaattg gatgtaatta tcttggcaaa 21301 ccacgcgaac aaatagatgg ttatgtcatg catgcaaatt acatattttg gaggaataca 21361 aatccaattc agttgtcttc ctattcttta tttgacatga gtaaatttcc ccttaaatta 21421 aggggtactg ctgttatgtc tttaaaagaa ggtcaaatca atgatatgat tttatctctt 21481 cttagtaaag gtagacttat aattagagaa aacaacagag ttgttatttc tagtgatgtt 21541 cttgttaaca actaaacgaa caatgtttgt ttttcttgtt ttattgccac tagtctctag 21601 tcagtgtgtt aatcttacaa ccagaactca attacccct gcatacacta attctttcac 21661 acgtggtgtt tattaccctg acaaagtttt cagatcctca gttttacatt caactcagga 21721 cttgttctta cctttctttt ccaatgttac ttggttccat gctatacatg tctctgggac 21781 caatggtact aagaggtttg ataaccctgt cctaccattt aatgatggtg tttattttgc 21841 ttccactgag aagtctaaca taataagagg ctggattttt ggtactactt tagattcgaa 21901 gacccagtcc ctacttattg ttaataacgc tactaatgtt gttattaaag tctgtgaatt 21961 tcaattttgt aatgatccat ttttgggtgt ttattaccac aaaaacaaca aaagttggat 22021 ggaaagtgag ttcagagttt attctagtgc gaataattgc acttttgaat atgtctctca 22081 gccttttctt atggaccttg aaggaaaaca gggtaatttc aaaaatctta gggaatttgt 22141 gtttaagaat attgatggtt attttaaaat atattctaag cacacgccta ttaatttagt 22201 gcgtgatctc cctcagggtt tttcggcttt agaaccattg gtagatttgc caataggtat 22261 taacatcact aggtttcaaa ctttacttgc tttacataga agttatttga ctcctggtga 22321 ttcttcttca ggttggacag ctggtgctgc agcttattat gtgggttatc ttcaacctag 22381 gacttttcta ttaaaatata atgaaaatgg aaccattaca gatgctgtag actgtgcact 22441 tgaccctctc tcagaaacaa agtgtacgtt gaaatccttc actgtagaaa aaggaatcta 22501 tcaaacttct aactttagag tccaaccaac agaatctatt gttagatttc ctaatattac 22561 aaacttgtgc ccttttggtg aagtttttaa cgccaccaga tttgcatctg tttatgcttg 22621 gaacaggaag agaatcagca actgtgttgc tgattattct gtcctatata attccgcatc 22681 attttccact tttaagtgtt atggagtgtc tcctactaaa ttaaatgatc tctgctttac 22741 taatgtctat gcagattcat ttgtaattag aggtgatgaa gtcagacaaa tcgctccagg 22801 gcaaactgga aagattgctg attataatta taaattacca gatgatttta caggctgcgt 22861 tatagcttgg aattctaaca atcttgattc taaggttggt ggtaattata attacctgta 22921 tagattgttt aggaagtcta atctcaaacc ttttgagaga gatatttcaa ctgaaatcta -continued

```
22981 tcaggccggt agcacacctt gtaatggtgt tgaaggtttt aattgttact ttcctttaca
23041 atcatatggt ttccaaccca ctaatggtgt tggttaccaa ccatacagag tagtagtact
23101 ttcttttgaa cttctacatg caccagcaac tgtttgtgga cctaaaaagt ctactaattt
23161 ggttaaaaac aaatgtgtca atttcaactt caatggttta acaggcacag gtgttcttac
23221 tgagtctaac aaaaagtttc tgcctttcca acaatttggc agagacattg ctgacactac
23281 tgatgctgtc cgtgatccac agacacttga gattcttgac attacaccat gttcttttgg
23341 tggtgtcagt gttataacac caggaacaaa tacttctaac caggttgctg ttctttatca
23401 ggatgttaac tgcacagaag tccctgttgc tattcatgca gatcaactta ctcctacttg
23461 gcgtgtttat tctacaggtt ctaatgtttt tcaaacacgt gcaggctgtt taataggggc
23521 tgaacatgtc aacaactcat atgagtgtga catacccatt ggtgcaggta tatgcgctag
23581 ttatcagact cagactaatt ctcctcggcg ggcacgtagt gtagctagtc aatccatcat
23641 tgcctacact atgtcacttg gtgcagaaaa ttcagttgct tactctaata actctattgc
23701 catacccaca aattttacta ttagtgttac cacagaaatt ctaccagtgt ctatgaccaa
23761 gacatcagta gattgtacaa tgtacatttg tggtgattca actgaatgca gcaatctttt
23821 gttgcaatat ggcagttttt gtacacaatt aaaccgtgct ttaactggaa tagctgttga
23881 acaagacaaa aacacccaag aagtttttgc acaagtcaaa caaatttaca aaacaccacc
23941 aattaaagat tttggtggtt ttaatttttc acaaatatta ccagatccat caaaaccaag
24001 caagaggtca tttattgaag atctactttt caacaaagtg acacttgcag atgctggctt
24061 catcaaacaa tatggtgatt gccttggtga tattgctgct agagacctca tttgtgcaca
24121 aaagtttaac ggccttactg ttttgccacc tttgctcaca gatgaaatga ttgctcaata
24181 cacttctgca ctgttagcgg gtacaatcac ttctggttgg acctttggtg caggtgctgc
24241 attacaaata ccatttgcta tgcaaatggc ttataggttt aatggtattg gagttacaca
24301 gaatgttctc tatgagaacc aaaaattgat tgccaaccaa tttaatagtg ctattggcaa
24361 aattcaagac tcactttctt ccacagcaag tgcacttgga aaacttcaag atgtggtcaa
24421 ccaaaatgca caagctttaa acacgcttgt taaacaactt agctccaatt ttggtgcaat
24481 ttcaagtgtt ttaaatgata tcctttcacg tcttgacaaa gttgaggctg aagtgcaaat
24541 tgataggttg atcacaggca gacttcaaag tttgcagaca tatgtgactc aacaattaat
24601 tagagctgca gaaatcagag cttctgctaa tcttgctgct actaaaatgt cagagtgtgt
24661 acttggacaa tcaaaaagag ttgatttttg tggaaagggc tatcatctta tgtccttccc
24721 tcagtcagca cctcatggtg tagtcttctt gcatgtgact tatgtccctg cacaagaaaa
24781 gaacttcaca actgctcctg ccatttgtca tgatggaaaa gcacactttc ctcgtgaagg
24841 tgtctttgtt tcaaatggca cacactggtt tgtaacacaa aggaattttt atgaaccaca
24901 aatcattact acagacaaca catttgtgtc tggtaactgt gatgttgtaa taggaattgt
24961 caacaacaca gtttatgatc ctttgcaacc tgaattagac tcattcaagg aggagttaga
25021 taaatatttt aagaatcata catcaccaga tgttgattta ggtgacatct ctggcattaa
25081 tgcttcagtt gtaaacattc aaaaagaaat tgaccgcctc aatgaggttg ccaagaattt
25141 aaatgaatct ctcatcgatc tccaagaact tggaaagtat gagcagtata taaaatggcc
25201 atggtacatt tggctaggtt ttatagctgg cttgattgcc atagtaatgg tgacaattat
25261 gctttgctgt atgaccagtt gctgtagttg tctcaagggc tgttgttctt gtggatcctg
25321 ctgcaaattt gatgaagacg actctgagcc agtgctcaaa ggagtcaaat tacattacac
```

-continued 25381 ataaacgaac ttatggattt gtttatgaga atcttcacaa ttggaactgt aactttgaag 25441 caaggtgaaa tcaaggatgc tactccttca gattttgttc gcgctactgc aacgataccg 25501 atacaagcct cactcccttt cggatggctt attgttggcg ttgcacttct tgctgttttt 25561 cagagcgctt ccaaaatcat aaccctcaaa aagagatggc aactagcact ctccaagggt 25621 gttcactttg tttgcaactt gctgttgttg tttgtaacag tttactcaca ccttttgctc 25681 gttgctgctg gccttgaagc ccccttttctc tatctttatg ctttagtcta cttcttgcag 25741 agtataaact ttgtaagaat aataatgagg ctttggcttt gctggaaatg ccgttccaaa 25801 aacccattac tttatgatgc caactatttt ctttgctggc atactaattg ttacgactat 25861 tgtatacctt acaatagtgt aacttcttca attgtcatta cttcaggtga tggcacaaca 25921 agtcctattt ctgaacatga ctaccagatt ggtggttata ctgaaaaatg ggaatctgga 25981 gtaaaagact gtgttgtatt acacagttac ttcacttcag actattacca gctgtactca 26041 actcaattga gtacagacac tggtgttgaa catgttacct tcttcatcta caataaaatt 26101 gttgatgagc ctgaagaaca tgtccaaatt cacacaatcg acggttcatc cggagttgtt 26161 aatccagtaa tggaaccaat ttatgatgaa ccgacgacga ctactagcgt gcctttgtaa 26221 gcacaagctg atgagtacga acttatgtac tcattcgttt cggaagagac aggtacgtta 26281 atagttaata gcgtacttct ttttcttgct ttcgtggtat tcttgctagt tacactagcc 26341 atccttactg cgcttcgatt gtgtgcgtac tgctgcaata ttgttaacgt gagtcttgta 26401 aaaccttctt tttacgttta ctctcgtgtt aaaaatctga attcttctag agttcctgat 26461 cttctggtct aaacgaacta aatattatat tagtttttct gtttggaact ttaattttag 26521 ccatggcaga ttccaacggt actattaccg ttgaagagct taaaaagctc cttgaacaat 26581 ggaacctagt aataggtttc ctattcctta catggatttg tcttctacaa tttgcctatg 26641 ccaacaggaa taggtttttg tatataatta agttaatttt cctctggctg ttatggccag 26701 taactttagc ttgttttgtg cttgctgctg tttacagaat aaattggatc accggtggaa 26761 ttgctatcgc aatggcttgt cttgtaggct tgatgtggct cagctacttc attgcttctt 26821 tcagactgtt tgcgcgtacg cgttccatgt ggtcattcaa tccagaaact aacattcttc 26881 tcaacgtgcc actccatggc actattctga ccagaccgct tctagaaagt gaactcgtaa 26941 tcggagctgt gatccttcgt ggacatcttc gtattgctgg acaccatcta ggacgctgtg 27001 acatcaagga cctgcctaaa gaaatcactg ttgctacatc acgaacgctt tcttattaca 27061 aattgggagc ttcgcagcgt gtagcaggtg actcaggttt tgctgcatac agtcgctaca 27121 ggattggcaa ctataaatta aacacagacc attccagtag cagtgacaat attgctttgc 27181 ttgtacagta agtgacaaca gatgtttcat ctcgttgact ttcaggttac tatagcagag 27241 atattactaa ttattatgag gacttttaaa gtttccattt ggaatcttga ttacatcata 27301 aacctcataa ttaaaaattt atctaagtca ctaactgaga ataaatattc tcaattagat 27361 gaagagcaac caatggagat tgattaaacg aacatgaaaa ttattctttt cttggcactg 27421 ataacactcg ctacttgtga gctttatcac taccaagagt gtgttagagg tacaacagta 27481 cttttaaaag aaccttgctc ttctggaaca tacgagggca attcaccatt tcatcctcta 27541 gctgataaca aatttgcact gacttgcttt agcactcaat ttgcttttgc ttgtcctgac 27601 ggcgtaaaac acgtctatca gttacgtgcc agatcagttt cacctaaact gttcatcaga 27661 caagaggaag ttcaagaact ttactctcca atttttctta ttgttgcggc aatagtgttt 27721 ataacacttt gcttcacact caaaagaaag acagaatgat tgaactttca ttaattgact 27781 tctatttgtg ctttttagcc tttctgctat tccttgtttt aattatgctt attatctttt -continued 27841 ggttctcact tgaactgcaa gatcataatg aaacttgtca cgcctaaacg aacatgaaat 27901 ttcttgtttt cttaggaatc atcacaactg tagctgcatt tcaccaagaa tgtagtttac 27961 agtcatgtac tcaacatcaa ccatatgtag ttgatgaccc gtgtcctatt cacttctatt 28021 ctaaatggta tattagagta ggagctagaa aatcagcacc tttaattgaa ttgtgcgtgg 28081 atgaggctgg ttctaaatca cccattcagt acatcgatat cggtaattat acagtttcct 28141 gttcaccttt tacaattaat tgccaggaac ctaaattggg tagtcttgta gtgcgttgtt 28201 cgttctatga agactttttta gagtatcatg acgttcgtgt tgttttagat ttcatctaaa 28261 cgaacaaact aaaatgtctg ataatggacc ccaaaatcag cgaaatgcac cccgcattac 28321 gtttggtgga ccctcagatt caactggcag taaccagaat ggagaacgca gtggggcgcg 28381 atcaaaacaa cgtcggcccc aaggtttacc caataatact gcgtcttggt tcaccgctct 28441 cactcaacat ggcaaggaag accttaaatt ccctcgagga caaggcgttc caattaacac 28501 caatagcagt ccagatgacc aaattggcta ctaccgaaga gctaccagac gaattcgtgg 28561 tggtgacggt aaaatgaaag atctcagtcc aagatggtat ttctactacc taggaactgg 28621 gccagaagct ggacttccct atggtgctaa caaagacggc atcatatggg ttgcaactga 28681 gggagccttg aatacaccaa aagatcacat tggcacccgc aatcctgcta acaatgctgc 28741 aatcgtgcta caacttcctc aaggaacaac attgccaaaa ggcttctacg cagaagggag 28801 cagaggcggc agtcaagcct cttctcgttc ctcatcacgt agtcgcaaca gttcaagaaa 28861 ttcaactcca ggcagcagta ggggaacttc tcctgctaga atggctggca atggcggtga 28921 tgctgctctt gctttgctgc tgcttgacag attgaaccag cttgagagca aaatgtctgg 28981 taaaggccaa caacaacaag gccaaactgt cactaagaaa tctgctgctg aggcttctaa 29041 gaagcctcgg caaaaacgta ctgccactaa agcatacaat gtaacacaag ctttcggcag 29101 acgtggtcca gaacaaaccc aaggaaattt tggggaccag gaactaatca gacaaggaac 29161 tgattacaaa cattggccgc aaattgcaca atttgccccc agcgcttcag cgttcttcgg 29221 aatgtcgcgc attggcatgg aagtcacacc ttcgggaacg tggttgacct acacaggtgc 29281 catcaaattg gatgacaaag atccaaattt caaagatcaa gtcattttgc tgaataagca 29341 tattgacgca tacaaaacat tcccaccaac agagcctaaa aaggacaaaa agaagaaggc 29401 tgatgaaact caagccttac cgcagagaca gaagaaacag caaactgtga ctcttcttcc 29461 tgctgcagat ttggatgatt tctccaaaca attgcaacaa tccatgagca gtgctgactc 29521 aactcaggcc taaactcatg cagaccacac aaggcagatg ggctatataa acgttttcgc 29581 ttttccgttt acgatatata gtctactctt gtgcagaatg aattctcgta actacatagc 29641 acaagtagat gtagttaact ttaatctcac atagcaatct ttaatcagtg tgtaacatta 29701 gggaggactt gaaagagcca ccacattttc accgaggcca cgcggagtac gatcgagtgt 29761 acagtgaaca atgctaggga gagctgccta tatggaagag ccctaatgtg taaaattaat 29821 tttagtagtg ctatccccat gtgattttaa tagcttctta ggagaatgac aaaaaaaaaa 29881 aa GenBank Accession No. GenBank: AY274119.3, which is specifically incorporated by reference herein in its entirety, provides the following (DNA) genomic sequence for SARS-CoV (Severe acute respiratory syndrome-related coronavirus isolate Tor2, complete genome):

(SEQ ID NO: 3)

```
   1 atattaggtt tttacctacc caggaaaagc caaccaacct cgatctcttg tagatctgtt
  61 ctctaaacga actttaaaat ctgtgtagct gtcgctcggc tgcatgccta gtgcacctac
 121 gcagtataaa caataataaa ttttactgtc gttgacaaga aacgagtaac tcgtccctct
 181 tctgcagact gcttacggtt tcgtccgtgt tgcagtcgat catcagcata cctaggtttc
 241 gtccgggtgt gaccgaaagg taagatggag agccttgttc ttggtgtcaa cgagaaaaca
 301 cacgtccaac tcagtttgcc tgtccttcag gttagagacg tgctagtgcg tggcttcggg
 361 gactctgtgg aagaggccct atcggaggca cgtgaacacc tcaaaaatgg cacttgtggt
 421 ctagtagagc tggaaaaagg cgtactgccc cagcttgaac agccctatgt gttcattaaa
 481 cgttctgatg ccttaagcac caatcacggc cacaaggtcg ttgagctggt tgcagaaatg
 541 gacggcattc agtacggtcg tagcggtata acactgggag tactcgtgcc acatgtgggc
 601 gaaaccccaa ttgcataccg caatgttctt cttcgtaaga acggtaataa gggagccggt
 661 ggtcatagct atggcatcga tctaaagtct tatgacttag gtgacgagct tggcactgat
 721 cccattgaag attatgaaca aaactggaac actaagcatg gcagtggtgc actccgtgaa
 781 ctcactcgtg agctcaatgg aggtgcagtc actcgctatg tcgacaacaa tttctgtggc
 841 ccagatgggt accctcttga ttgcatcaaa gattttctcg cacgcgcggg caagtcaatg
 901 tgcactcttt ccgaacaact tgattacatc gagtcgaaga gaggtgtcta ctgctgccgt
 961 gaccatgagc atgaaattgc ctggttcact gagcgctctg ataagagcta cgagcaccag
1021 acacccttcg aaattaagag tgccaagaaa tttgacactt tcaaagggga atgcccaaag
1081 tttgtgtttc ctcttaactc aaaagtcaaa gtcattcaac cacgtgttga aaagaaaaag
1141 actgagggtt tcatggggcg tatacgctct gtgtaccctg ttgcatctcc acaggagtgt
1201 aacaatatgc acttgtctac cttgatgaaa tgtaatcatt gcgatgaagt ttcatggcag
1261 acgtgcgact ttctgaaagc cacttgtgaa cattgtggca ctgaaaattt agttattgaa
1321 ggacctacta catgtgggta cctacctact aatgctgtag tgaaaatgcc atgtcctgcc
1381 tgtcaagacc cagagattgg acctgagcat agtgttgcag attatcacaa ccactcaaac
1441 attgaaactc gactccgcaa gggaggtagg actagatgtt ttggaggctg tgtgtttgcc
1501 tatgttggct gctataataa gcgtgcctac tgggttcctc gtgctagtgc tgatattggc
1561 tcaggccata ctggcattac tggtgacaat gtggagacct tgaatgagga tctccttgag
1621 atactgagtc gtgaacgtgt taacattaac attgttggcg attttcattt gaatgaagag
1681 gttgccatca ttttggcatc tttctctgct tctacaagtg cctttattga cactataaag
1741 agtcttgatt acaagtcttt caaaaccatt gttgagtcct gcggtaacta taaagttacc
1801 aagggaaagc ccgtaaaagg tgcttggaac attggacaac agagatcagt tttaacacca
1861 ctgtgtggtt ttccctcaca ggctgctggt gttatcagat caatttttgc gcgcacactt
1921 gatgcagcaa accactcaat tcctgatttg caaagagcag ctgtcaccat acttgatggt
1981 atttctgaac agtcattacg tcttgtcgac gccatggttt atacttcaga cctgctcacc
2041 aacagtgtca ttattatggc atatgtaact ggtggtcttg tacaacagac ttctcagtgg
2101 ttgtctaatc ttttgggcac tactgttgaa aaactcaggc ctatctttga atggattgag
2161 gcgaaactta gtgcaggagt tgaatttctc aaggatgctt gggagattct caaatttctc
```

-continued 2221 attacaggtg tttttgacat cgtcaagggt caaatacagg ttgcttcaga taacatcaag 2281 gattgtgtaa aatgcttcat tgatgttgtt aacaaggcac tcgaaatgtg cattgatcaa 2341 gtcactatcg ctggcgcaaa gttgcgatca ctcaacttag gtgaagtctt catcgctcaa 2401 agcaagggac tttaccgtca gtgtatacgt ggcaaggagc agctgcaact actcatgcct 2461 cttaaggcac caaaagaagt aacctttctt gaaggtgatt cacatgacac agtacttacc 2521 tctgaggagg ttgttctcaa gaacggtgaa ctcgaagcac tcgagacgcc cgttgatagc 2581 ttcacaaatg gagctatcgt tggcacacca gtctgtgtaa atggcctcat gctcttagag 2641 attaaggaca aagaacaata ctgcgcattg tctcctggtt tactggctac aaacaatgtc 2701 tttcgcttaa aagggggtgc accaattaaa ggtgtaacct ttggagaaga tactgtttgg 2761 gaagttcaag gttacaagaa tgtgagaatc acatttgagc ttgatgaacg tgttgacaaa 2821 gtgcttaatg aaaagtgctc tgtctacact gttgaatccg gtaccgaagt tactgagttt 2881 gcatgtgttg tagcagaggc tgttgtgaag actttacaac cagtttctga tctccttacc 2941 aacatgggta ttgatcttga tgagtggagt gtagctacat tctacttatt tgatgatgct 3001 ggtgaagaaa acttttcatc acgtatgtat tgttcctttt accctccaga tgaggaagaa 3061 gaggacgatg cagagtgtga ggaagaagaa attgatgaaa cctgtgaaca tgagtacggt 3121 acagaggatg attatcaagg tctccctctg gaatttggtg cctcagctga aacagttcga 3181 gttgaggaag aagaagagga agactggctg gatgatacta ctgagcaatc agagattgag 3241 ccagaaccag aacctacacc tgaagaacca gttaatcagt ttactggtta tttaaaactt 3301 actgacaatg ttgccattaa atgtgttgac atcgttaagg aggcacaaag tgctaatcct 3361 atggtgattg taaatgctgc taacatacac ctgaaacatg gtggtggtgt agcaggtgca 3421 ctcaacaagg caaccaatgg tgccatgcaa aaggagagtg atgattacat taagctaaat 3481 ggccctctta cagtaggagg gtcttgtttg ctttctggac ataatcttgc taagaagtgt 3541 ctgcatgttg ttggacctaa cctaaatgca ggtgaggaca tccagcttct taaggcagca 3601 tatgaaaatt tcaattcaca ggacatctta cttgcaccat tgttgtcagc aggcatattt 3661 ggtgctaaac cacttcagtc tttacaagtg tgcgtgcaga cggttcgtac acaggtttat 3721 attgcagtca atgacaaagc tctttatgag caggttgtca tggattatct tgataacctg 3781 aagcctagag tggaagcacc taaacaagag gagccaccaa acacagaaga ttccaaaact 3841 gaggagaaat ctgtcgtaca gaagcctgtc gatgtgaagc caaaaattaa ggcctgcatt 3901 gatgaggtta ccacaacact ggaagaaact aagtttctta ccaataagtt actcttgttt 3961 gctgatatca atggtaagct ttaccatgat tctcagaaca tgcttagagg tgaagatatg 4021 tctttccttg agaaggatgc accttacatg gtaggtgatg ttatcactag tggtgatatc 4081 acttgtgttg taataccctc caaaaaggct ggtggcacta ctgagatgct ctcaagagct 4141 ttgaagaaag tgccagttga tgagtatata accacgtacc ctggacaagg atgtgctggt 4201 tatacacttg aggaagctaa gactgctctt aagaaatgca aatctgcatt ttatgtacta 4261 ccttcagaag cacctaatgc taaggaagag attctaggaa ctgtatcctg gaatttgaga 4321 gaaatgcttg ctcatgctga agagacaaga aaattaatgc ctatatgcat ggatgttaga 4381 gccataatgg caaccatcca acgtaagtat aaaggaatta aaattcaaga gggcatcgtt 4441 gactatggtg tccgattctt cttttatact agtaaagagc ctgtagcttc tattattacg 4501 aagctgaact ctctaaatga gccgcttgtc acaatgccaa ttggttatgt gacacatggt 4561 tttaatcttg aagaggctgc gcgctgtatg cgttctctta aagctcctgc cgtagtgtca -continued

```
4621 gtatcatcac cagatgctgt tactacatat aatggatacc tcacttcgtc atcaaagaca
4681 tctgaggagc actttgtaga aacagtttct ttggctggct cttacagaga ttggtcctat
4741 tcaggacagc gtacagagtt aggtgttgaa tttcttaagc gtggtgacaa aattgtgtac
4801 cacactctgg agagccccgt cgagtttcat cttgacggtg aggttctttc acttgacaaa
4861 ctaaagagtc tcttatccct gcgggaggtt aagactataa aagtgttcac aactgtggac
4921 aacactaatc tccacacaca gcttgtggat atgtctatga catatggaca gcagtttggt
4981 ccaacatact tggatggtgc tgatgttaca aaaattaaac ctcatgtaaa tcatgagggt
5041 aagactttct ttgtactacc tagtgatgac acactacgta gtgaagcttt cgagtactac
5101 catactcttg atgagagttt tcttggtagg tacatgtctg ctttaaacca cacaaagaaa
5161 tggaaatttc ctcaagttgg tggtttaact tcaattaaat gggctgataa caattgttat
5221 ttgtctagtg ttttattagc acttcaacag cttgaagtca aattcaatgc accagcactt
5281 caagaggctt attatagagc ccgtgctggt gatgctgcta acttttgtgc actcatactc
5341 gcttacagta ataaaactgt tggcgagctt ggtgatgtca gagaaactat gacccatctt
5401 ctacagcatg ctaatttgga atctgcaaag cgagttctta atgtggtgtg taaacattgt
5461 ggtcagaaaa ctactacctt aacgggtgta gaagctgtga tgtatatggg tactctatct
5521 tatgataatc ttaagacagg tgtttccatt ccatgtgtgt gtggtcgtga tgctacacaa
5581 tatctagtac aacaagagtc ttcttttgtt atgatgtctg caccacctgc tgagtataaa
5641 ttacagcaag gtacattctt atgtgcgaat gagtacactg gtaactatca gtgtggtcat
5701 tacactcata taactgctaa ggagaccctc tatcgtattg acggagctca ccttacaaag
5761 atgtcagagt acaaaggacc agtgactgat gttttctaca aggaaacatc ttacactaca
5821 accatcaagc ctgtgtcgta taaactcgat ggagttactt acacagagat tgaaccaaaa
5881 ttggatgggt attataaaaa ggataatgct tactatacag agcagcctat agaccttgta
5941 ccaactcaac cattaccaaa tgcgagtttt gataatttca aactcacatg ttctaacaca
6001 aaatttgctg atgatttaaa tcaaatgaca ggcttcacaa agccagcttc acgagagcta
6061 tctgtcacat tcttcccaga cttgaatggc gatgtagtgg ctattgacta tagacactat
6121 tcagcgagtt tcaagaaagg tgctaaatta ctgcataagc caattgtttg gcacattaac
6181 caggctacaa ccaagacaac gttcaaacca aacacttggt gtttacgttg tctttggagt
6241 acaaagccag tagatacttc aaattcattt gaagttctgg cagtagaaga cacacaagga
6301 atggacaatc ttgcttgtga aagtcaacaa cccacctctg aagaagtagt ggaaaatcct
6361 accatacaga aggaagtcat agagtgtgac gtgaaaacta ccgaagttgt aggcaatgtc
6421 atacttaaac catcagatga aggtgttaaa gtaacacaag agttaggtca tgaggatctt
6481 atggctgctt atgtggaaaa cacaagcatt accattaaga aacctaatga gctttcacta
6541 gccttaggtt taaaaacaat tgccactcat ggtattgctg caattaatag tgttccttgg
6601 agtaaaattt tggcttatgt caaaccattc ttaggacaag cagcaattac aacatcaaat
6661 tgcgctaaga gattagcaca acgtgtgttt aacaattata tgccttatgt gtttacatta
6721 ttgttccaat tgtgtacttt tactaaaagt accaattcta gaattagagc ttcactacct
6781 acaactattg ctaaaaatag tgttaagagt gttgctaaat tatgtttgga tgccggcatt
6841 aattatgtga agtcacccaa attttctaaa ttgttcacaa tcgctatgtg gctattgttg
6901 ttaagtattt gcttaggttc tctaatctgt gtaactgctg cttttggtgt actcttatct
6961 aattttggtg ctccttctta ttgtaatggc gttagagaat tgtatcttaa ttcgtctaac
7021 gttactacta tggatttctg tgaaggttct tttccttgca gcatttgttt aagtggatta
```

-continued 7081 gactcccttg attcttatcc agctcttgaa accattcagg tgacgatttc atcgtacaag
7141 ctagacttga caattttagg tctggccgct gagtgggttt tggcatatat gttgttcaca
7201 aaattctttt atttattagg tctttcagct ataatgcagg tgttctttgg ctattttgct
7261 agtcatttca tcagcaattc ttggctcatg tggtttatca ttagtattgt acaaatggca
7321 cccgtttctg caatggttag gatgtacatc ttctttgctt ctttctacta catatggaag
7381 agctatgttc atatcatgga tggttgcacc tcttcgactt gcatgatgtg ctataagcgc
7441 aatcgtgcca cacgcgttga gtgtacaact attgttaatg gcatgaagag atctttctat
7501 gtctatgcaa atggaggccg tggcttctgc aagactcaca attggaattg tctcaattgt
7561 gacacatttt gcactggtag tacattcatt agtgatgaag ttgctcgtga tttgtcactc
7621 cagtttaaaa gaccaatcaa ccctactgac cagtcatcgt atattgttga tagtgttgct
7681 gtgaaaaatg gcgcgcttca cctctacttt gacaaggctg gtcaaaagac ctatgagaga
7741 catccgctct cccattttgt caatttagac aatttgagag ctaacaacac taaaggttca
7801 ctgcctatta atgtcatagt ttttgatggc aagtccaaat gcgacgagtc tgcttctaag
7861 tctgcttctg tgtactacag tcagctgatg tgccaaccta ttctgttgct tgaccaagct
7921 cttgtatcag acgttggaga tagtactgaa gtttccgtta agatgtttga tgcttatgtc
7981 gacacctttt cagcaacttt tagtgttcct atggaaaaac ttaaggcact tgttgctaca
8041 gctcacagcg agttagcaaa gggtgtagct ttagatggtg tcctttctac attcgtgtca
8101 gctgcccgac aaggtgttgt tgataccgat gttgacacaa aggatgttat tgaatgtctc
8161 aaactttcac atcactctga cttagaagtg acaggtgaca gttgtaacaa tttcatgctc
8221 acctataata aggttgaaaa catgacgccc agagatcttg gcgcatgtat tgactgtaat
8281 gcaaggcata tcaatgccca agtagcaaaa agtcacaatg tttcactcat ctggaatgta
8341 aaagactaca tgtctttatc tgaacagctg cgtaaacaaa ttcgtagtgc tgccaagaag
8401 aacaacatac cttttagact aacttgtgct acaactagac aggttgtcaa tgtcataact
8461 actaaaatct cactcaaggg tggtaagatt gttagtactt gttttaaact tatgcttaag
8521 gccacattat tgtgcgttct tgctgcattg gtttgttata tcgttatgcc agtacataca
8581 ttgtcaatcc atgatggtta cacaaatgaa atcattggtt acaaagccat tcaggatggt
8641 gtcactcgtg acatcatttc tactgatgat tgttttgcaa ataaacatgc tggttttgac
8701 gcatggttta gccagcgtgg tggttcatac aaaaatgaca aaagctgccc tgtagtagct
8761 gctatcatta caagagagat tggtttcata gtgcctggct taccgggtac tgtgctgaga
8821 gcaatcaatg gtgacttctt gcattttcta cctcgtgttt ttagtgctgt tggcaacatt
8881 tgctacacac cttccaaact cattgagtat agtgattttg ctacctctgc ttgcgttctt
8941 gctgctgagt gtacaatttt taaggatgct atgggcaaac ctgtgccata ttgttatgac
9001 actaatttgc tagagggttc tatttcttat agtgagcttc gtccagacac tcgttatgtg
9061 cttatggatg gttccatcat acagtttcct aacacttacc tggagggttc tgttagagta
9121 gtaacaactt ttgatgctga gtactgtaga catggtacat gcgaaaggtc agaagtaggt
9181 atttgcctat ctaccagtgg tagatgggtt cttaataatg agcattacag agctctatca
9241 ggagttttct gtggtgttga tgcgatgaat ctcatagcta acatctttac tcctcttgtg
9301 caacctgtgg gtgctttaga tgtgtctgct tcagtagtgg ctggtggtat tattgccata
9361 ttggtgactt gtgctgccta ctactttatg aaattcagac gtgtttttgg tgagtacaac
9421 catgttgttg ctgctaatgc acttttgttt ttgatgtctt tcactatact ctgtctggta -continued

```
 9481 ccagcttaca gctttctgcc gggagtctac tcagtctttt acttgtactt gacattctat
 9541 ttcaccaatg atgtttcatt cttggctcac cttcaatggt ttgccatgtt ttctcctatt
 9601 gtgccttttt ggataacagc aatctatgta ttctgtattt ctctgaagca ctgccattgg
 9661 ttctttaaca actatcttag gaaaagagtc atgtttaatg gagttacatt tagtaccttc
 9721 gaggaggctg ctttgtgtac ctttttgctc aacaaggaaa tgtacctaaa attgcgtagc
 9781 gagacactgt tgccacttac acagtataac aggtatcttg ctctatataa caagtacaag
 9841 tatttcagtg gagccttaga tactaccagc tatcgtgaag cagcttgctg ccacttagca
 9901 aaggctctaa atgactttag caactcaggt gctgatgttc tctaccaacc accacagaca
 9961 tcaatcactt ctgctgttct gcagagtggt tttaggaaaa tggcattccc gtcaggcaaa
10021 gttgaagggt gcatggtaca agtaacctgt ggaactacaa ctcttaatgg attgtggttg
10081 gatgacacag tatactgtcc aagacatgtc atttgcacag cagaagacat gcttaatcct
10141 aactatgaag atctgctcat tcgcaaatcc aaccatagct ttcttgttca ggctggcaat
10201 gttcaacttc gtgttattgg ccattctatg caaaattgtc tgcttaggct taaagttgat
10261 acttctaacc ctaagacacc caagtataaa tttgtccgta tccaacctgg tcaaacattt
10321 tcagttctag catgctacaa tggttcacca tctggtgttt atcagtgtgc catgagacct
10381 aatcatacca ttaaaggttc tttccttaat ggatcatgtg gtagtgttgg ttttaacatt
10441 gattatgatt gcgtgtcttt ctgctatatg catcatatgg agcttccaac aggagtacac
10501 gctggtactg acttagaagg taaattctat ggtccatttg ttgacagaca aactgcacag
10561 gctgcaggta cagacacaac cataacatta aatgttttgg catggctgta tgctgctgtt
10621 atcaatggtg ataggtggtt tcttaataga ttcaccacta ctttgaatga ctttaacctt
10681 gtggcaatga agtacaacta tgaacctttg acacaagatc atgttgacat attgggacct
10741 ctttctgctc aaacaggaat tgccgtctta gatatgtgtg ctgctttgaa agagctgctg
10801 cagaatggta tgaatggtcg tactatcctt ggtagcacta ttttagaaga tgagtttaca
10861 ccatttgatg ttgttagaca atgctctggt gttaccttcc aaggtaagtt caagaaaatt
10921 gttaagggca ctcatcattg gatgctttta actttcttga catcactatt gattcttgtt
10981 caaagtacac agtggtcact gtttttcttt gtttacgaga atgctttctt gccatttact
11041 cttggtatta tggcaattgc tgcatgtgct atgctgcttg ttaagcataa gcacgcattc
11101 ttgtgcttgt ttctgttacc ttctcttgca acagttgctt actttaatat ggtctacatg
11161 cctgctagct gggtgatgcg tatcatgaca tggcttgaat tggctgacac tagcttgtct
11221 ggttataggc ttaaggattg tgttatgtat gcttcagctt tagttttgct tattctcatg
11281 acagctcgca ctgtttatga tgatgctgct agacgtgttt ggacactgat gaatgtcatt
11341 acacttgttt acaaagtcta ctatggtaat gctttagatc aagctatttc catgtgggcc
11401 ttagttattt ctgtaacctc taactattct ggtgtcgtta cgactatcat gtttttagct
11461 agagctatag tgtttgtgtg tgttgagtat tacccattgt tatttattac tggcaacacc
11521 ttacagtgta tcatgcttgt ttattgtttc ttaggctatt gttgctgctg ctactttggc
11581 cttttctgtt tactcaaccg ttacttcagg cttactcttg gtgtttatga ctacttggtc
11641 tctacacaag aatttaggta tatgaactcc caggggcttt tgcctcctaa gagtagtatt
11701 gatgctttca agcttaacat taagttgttg ggtattggag gtaaaccatg tatcaaggtt
11761 gctactgtac agtctaaaat gtctgacgta aagtgcacat ctgtggtact gctctcggtt
11821 cttcaacaac ttagagtaga gtcatcttct aaattgtggg cacaatgtgt acaactccac
11881 aatgatattc ttcttgcaaa agacacaact gaagctttcg agaagatggt ttctcttttg
```

-continued 11941 tctgttttgc tatccatgca gggtgctgta gacattaata ggttgtgcga ggaaatgctc 12001 gataaccgtg ctactcttca ggctattgct tcagaattta gttctttacc atcatatgcc 12061 gcttatgcca ctgcccagga ggcctatgag caggctgtag ctaatggtga ttctgaagtc 12121 gttctcaaaa agttaaagaa atctttgaat gtggctaaat ctgagtttga ccgtgatgct 12181 gccatgcaac gcaagttgga aaagatggca gatcaggcta tgacccaaat gtacaaacag 12241 gcaagatctg aggacaagag ggcaaaagta actagtgcta tgcaaacaat gctcttcact 12301 atgcttagga agcttgataa tgatgcactt aacaacatta tcaacaatgc gcgtgatggt 12361 tgtgttccac tcaacatcat accattgact acagcagcca aactcatggt tgttgtccct 12421 gattatggta cctacaagaa cacttgtgat ggtaacacct ttacatatgc atctgcactc 12481 tgggaaatcc agcaagttgt tgatgcggat agcaagattg ttcaacttag tgaaattaac 12541 atggacaatt caccaaattt ggcttggcct cttattgtta cagctctaag agccaactca 12601 gctgttaaac tacagaataa tgaactgagt ccagtagcac tacgacagat gtcctgtgcg 12661 gctggtacca cacaaacagc ttgtactgat gacaatgcac ttgcctacta taacaattcg 12721 aagggaggta ggtttgtgct ggcattacta tcagaccacc aagatctcaa atgggctaga 12781 ttccctaaga gtgatggtac aggtacaatt tacacagaac tggaaccacc ttgtaggttt 12841 gttacagaca caccaaaagg gcctaaagtg aaatacttgt acttcatcaa aggcttaaac 12901 aacctaaata gaggtatggt gctgggcagt ttagctgcta cagtacgtct tcaggctgga 12961 aatgctacag aagtacctgc caattcaact gtgctttcct tctgtgcttt tgcagtagac 13021 cctgctaaag catataagga ttacctagca agtggaggac aaccaatcac caactgtgtg 13081 aagatgttgt gtacacacac tggtacagga caggcaatta ctgtaacacc agaagctaac 13141 atggaccaag agtcctttgg tggtgcttca tgttgtctgt attgtagatg ccacattgac 13201 catccaaatc ctaaaggatt ctgtgacttg aaaggtaagt acgtccaaat acctaccact 13261 tgtgctaatg acccagtggg ttttacactt agaaacacag tctgtaccgt ctgcggaatg 13321 tggaaaggtt atggctgtag ttgtgaccaa ctccgcgaac ccttgatgca gtctgcggat 13381 gcatcaacgt ttttaaacgg gtttgcggtg taagtgcagc ccgtcttaca ccgtgcggca 13441 caggcactag tactgatgtc gtctacaggg cttttgatat ttacaacgaa aaagttgctg 13501 gttttgcaaa gttcctaaaa actaattgct gtcgcttcca ggagaaggat gaggaaggca 13561 atttattaga ctcttacttt gtagttaaga ggcatactat gtctaactac caacatgaag 13621 agactattta taacttggtt aaagattgtc cagcggttgc tgtccatgac tttttcaagt 13681 ttagagtaga tggtgacatg gtaccacata tatcacgtca gcgtctaact aaatacacaa 13741 tggctgattt agtctatgct ctacgtcatt ttgatgaggg taattgtgat acattaaaag 13801 aaatactcgt cacatacaat tgctgtgatg atgattattt caataagaag gattggtatg 13861 acttcgtaga gaatcctgac atcttacgcg tatatgctaa cttaggtgag cgtgtacgcc 13921 aatcattatt aaagactgta caattctgcg atgctatgcg tgatgcaggc attgtaggcg 13981 tactgacatt agataatcag gatcttaatg ggaactggta cgatttcggt gatttcgtac 14041 aagtagcacc aggctgcgga gttcctattg tggattcata ttactcattg ctgatgccca 14101 tcctcacttt gactagggca ttggctgctg agtcccatat ggatgctgat ctcgcaaaac 14161 cacttattaa gtgggatttg ctgaaatatg attttacgga agagagactt tgtctcttcg 14221 accgttattt taaatattgg gaccagacat accatcccaa ttgtattaac tgtttggatg 14281 ataggtgtat ccttcattgt gcaaacttta atgtgttatt ttctactgtg tttccaccta -continued 14341 caagttttgg accactagta agaaaaatat ttgtagatgg tgttcctttt gttgtttcaa 14401 ctggatacca ttttcgtgag ttaggagtcg tacataatca ggatgtaaac ttacatagct 14461 cgcgtctcag tttcaaggaa cttttagtgt atgctgctga tccagctatg catgcagctt 14521 ctggcaattt attgctagat aaacgcacta catgcttttc agtagctgca ctaacaaaca 14581 atgttgcttt tcaaactgtc aaacccggta attttaataa agacttttat gactttgctg 14641 tgtctaaagg tttctttaag gaaggaagtt ctgttgaact aaaacacttc ttctttgctc 14701 aggatggcaa cgctgctatc agtgattatg actattatcg ttataatctg ccaacaatgt 14761 gtgatatcag acaactccta ttcgtagttg aagttgttga taaatacttt gattgttacg 14821 atggtggctg tattaatgcc aaccaagtaa tcgttaacaa tctggataaa tcagctggtt 14881 tcccatttaa taaatggggt aaggctagac tttattatga ctcaatgagt tatgaggatc 14941 aagatgcact tttcgcgtat actaagcgta atgtcatccc tactataact caaatgaatc 15001 ttaagtatgc cattagtgca aagaatagag ctcgcaccgt agctggtgtc tctatctgta 15061 gtactatgac aaatagacag tttcatcaga aattattgaa gtcaatagcc gccactagag 15121 gagctactgt ggtaattgga acaagcaagt tttacggtgg ctggcataat atgttaaaaa 15181 ctgtttacag tgatgtagaa actccacacc ttatgggttg ggattatcca aaatgtgaca 15241 gagccatgcc taacatgctt aggataatgg cctctcttgt tcttgctcgc aaacataaca 15301 cttgctgtaa cttatcacac cgtttctaca ggttagctaa cgagtgtgcg caagtattaa 15361 gtgagatggt catgtgtggc ggctcactat atgttaaacc aggtggaaca tcatccggtg 15421 atgctacaac tgcttatgct aatagtgtct ttaacatttg tcaagctgtt acagccaatg 15481 taaatgcact tctttcaact gatggtaata agatagctga caagtatgtc cgcaatctac 15541 aacacaggct ctatgagtgt ctctatagaa atagggatgt tgatcatgaa ttcgtggatg 15601 agttttacgc ttacctgcgt aaacatttct ccatgatgat tctttctgat gatgccgttg 15661 tgtgctataa cagtaactat gcggctcaag gtttagtagc tagcattaag aactttaagg 15721 cagttcttta ttatcaaaat aatgtgttca tgtctgaggc aaaatgttgg actgagactg 15781 accttactaa aggacctcac gaattttgct cacagcatac aatgctagtt aaacaaggag 15841 atgattacgt gtacctgcct tacccagatc catcaagaat attaggcgca ggctgttttg 15901 tcgatgatat tgtcaaaaca gatggtacac ttatgattga aaggttcgtg tcactggcta 15961 ttgatgctta cccacttaca aaacatccta atcaggagta tgctgatgtc tttcacttgt 16021 atttacaata cattagaaag ttacatgatg agcttactgg ccacatgttg gacatgtatt 16081 ccgtaatgct aactaatgat aacacctcac ggtactggga acctgagttt tatgaggcta 16141 tgtacacacc acatacagtc ttgcaggctg taggtgcttg tgtattgtgc aattcacaga 16201 cttcacttcg ttgcggtgcc tgtattagga gaccattcct atgttgcaag tgctgctatg 16261 accatgtcat ttcaacatca cacaaattag tgttgtctgt taatccctat gtttgcaatg 16321 ccccaggttg tgatgtcact gatgtgacac aactgtatct aggaggtatg agctattatt 16381 gcaagtcaca taagcctccc attagttttc cattatgtgc taatggtcag gtttttggtt 16441 tatacaaaaa cacatgtgta ggcagtgaca atgtcactga cttcaatgcg atagcaacat 16501 gtgattggac taatgctggc gattacatac ttgccaacac ttgtactgag agactcaagc 16561 ttttcgcagc agaaacgctc aaagccactg aggaaacatt taagctgtca tatggtattg 16621 ccactgtacg cgaagtactc tctgacagag aattgcatct ttcatgggag gttggaaaac 16681 ctagaccacc attgaacaga aactatgtct ttactggtta ccgtgtaact aaaaatagta 16741 aagtacagat tggagagtac acctttgaaa aaggtgacta tggtgatgct gttgtgtaca -continued 16801 gaggtactac gacatacaag ttgaatgttg gtgattactt tgtgttgaca tctcacactg
16861 taatgccact tagtgcacct actctagtgc cacaagagca ctatgtgaga attactggct
16921 tgtacccaac actcaacatc tcagatgagt tttctagcaa tgttgcaaat tatcaaaagg
16981 tcggcatgca aaagtactct acactccaag gaccacctgg tactggtaag agtcattttg
17041 ccatcggact tgctctctat tacccatctg ctcgcatagt gtatacggca tgctctcatg
17101 cagctgttga tgccctatgt gaaaaggcat taaaatattt gcccatagat aaatgtagta
17161 gaatcatacc tgcgcgtgcg cgcgtagagt gttttgataa attcaaagtg aattcaacac
17221 tagaacagta tgtttttctgc actgtaaatg cattgccaga aacaactgct gacattgtag
17281 tctttgatga aatctctatg gctactaatt atgacttgag tgttgtcaat gctagacttc
17341 gtgcaaaaca ctacgtctat attggcgatc ctgctcaatt accagccccc cgcacattgc
17401 tgactaaagg cacactagaa ccagaatatt ttaattcagt gtgcagactt atgaaaacaa
17461 taggtccaga catgttcctt ggaacttgtc gccgttgtcc tgctgaaatt gttgacactg
17521 tgagtgcttt agtttatgac aataagctaa aagcacacaa ggataagtca gctcaatgct
17581 tcaaaatgtt ctacaaaggt gttattacac atgatgtttc atctgcaatc aacagacctc
17641 aaataggcgt tgtaagagaa tttcttacac gcaatcctgc ttggagaaaa gctgttttta
17701 tctcacctta taattcacag aacgctgtag cttcaaaaat cttaggattg cctacgcaga
17761 ctgttgattc atcacagggt tctgaatatg actatgtcat attcacacaa actactgaaa
17821 cagcacactc ttgtaatgtc aaccgcttca atgtggctat cacaagggca aaaattggca
17881 ttttgtgcat aatgtctgat agagatcttt atgacaaact gcaatttaca agtctagaaa
17941 taccacgtcg caatgtggct acattacaag cagaaaatgt aactggactt tttaaggact
18001 gtagtaagat cattactggt cttcatccta cacaggcacc tacacacctc agcgttgata
18061 taaagttcaa gactgaagga ttatgtgttg acataccagg cataccaaag gacatgacct
18121 accgtagact catctctatg atgggtttca aaatgaatta ccaagtcaat ggttacccta
18181 atatgtttat cacccgcgaa gaagctattc gtcacgttcg tgcgtggatt ggctttgatg
18241 tagagggctg tcatgcaact agagatgctg tgggtactaa cctacctctc cagctaggat
18301 tttctacagg tgttaactta gtagctgtac cgactggtta tgttgacact gaaaataaca
18361 cagaattcac cagagttaat gcaaaacctc caccaggtga ccagtttaaa catcttatac
18421 cactcatgta taaaggcttg ccctggaatg tagtgcgtat taagatagta caaatgctca
18481 gtgatacact gaaaggattg tcagacagag tcgtgttcgt cctttgggcg catggctttg
18541 agcttacatc aatgaagtac tttgtcaaga ttggacctga aagaacgtgt tgtctgtgtg
18601 acaaacgtgc aacttgcttt tctacttcat cagatactta tgcctgctgg aatcattctg
18661 tgggttttga ctatgtctat aacccattta tgattgatgt tcagcagtgg ggctttacgg
18721 gtaaccttca gagtaaccat gaccaacatt gccaggtaca tggaaatgca catgtggcta
18781 gttgtgatgc tatcatgact agatgtttag cagtccatga gtgctttgtt aagcgcgttg
18841 attggtctgt tgaataccct attataggag atgaactgag ggttaattct gcttgcagaa
18901 aagtacaaca catggttgtg aagtctgcat tgcttgctga taagtttcca gttcttcatg
18961 acattggaaa tccaaaggct atcaagtgtg tgcctcaggc tgaagtagaa tggaagttct
19021 acgatgctca gccatgtagt gacaaagctt acaaaataga ggaactcttc tattcttatg
19081 ctacacatca cgataaattc actgatggtg tttgtttgtt ttggaattgt aacgttgatc
19141 gttacccagc caatgcaatt gtgtgtaggt ttgacacaag agtcttgtca aacttgaact -continued 19201 taccaggctg tgatggtggt agtttgtatg tgaataagca tgcattccac actccagctt
19261 tcgataaaag tgcatttact aatttaaagc aattgccttt cttttactat tctgatagtc
19321 cttgtgagtc tcatggcaaa caagtagtgt cggatattga ttatgttcca ctcaaatctg
19381 ctacgtgtat tacacgatgc aatttaggtg gtgctgtttg cagacaccat gcaaatgagt
19441 accgacagta cttggatgca tataatatga tgatttctgc tggatttagc ctatggattt
19501 acaaacaatt tgatacttat aacctgtgga atacatttac caggttacag agtttagaaa
19561 atgtggctta taatgttgtt aataaaggac actttgatgg acacgccggc gaagcacctg
19621 tttccatcat taataatgct gtttacacaa aggtagatgg tattgatgtg gagatctttg
19681 aaaataagac aacacttcct gttaatgttg catttgagct ttgggctaag cgtaacatta
19741 aaccagtgcc agagattaag atactcaata atttgggtgt tgatatcgct gctaatactg
19801 taatctggga ctacaaaaga gaagccccag cacatgtatc tacaataggt gtctgcacaa
19861 tgactgacat tgccaagaaa cctactgaga gtgcttgttc ttcacttact gtcttgtttg
19921 atggtagagt ggaaggacag gtagaccttt ttagaaacgc ccgtaatggt gttttaataa
19981 cagaaggttc agtcaaaggt ctaacacctt caaagggacc agcacaagct agcgtcaatg
20041 gagtcacatt aattggagaa tcagtaaaaa cacagtttaa ctactttaag aaagtagacg
20101 gcattattca acagttgcct gaaacctact ttactcagag cagagactta gaggatttta
20161 agcccagatc acaaatggaa actgactttc tcgagctcgc tatggatgaa ttcatacagc
20221 gatataagct cgagggctat gccttcgaac acatcgttta tggagatttc agtcatggac
20281 aacttggcgg tcttcattta atgataggct tagccaagcg ctcacaagat tcaccactta
20341 aattagagga ttttatccct atggacagca cagtgaaaaa ttacttcata acagatgcgc
20401 aaacaggttc atcaaaatgt gtgtgttctg tgattgatct tttacttgat gactttgtcg
20461 agataataaa gtcacaagat ttgtcagtga tttcaaaagt ggtcaaggtt acaattgact
20521 atgctgaaat ttcattcatg ctttggtgta aggatggaca tgttgaaacc ttctacccaa
20581 aactacaagc aagtcaagcg tggcaaccag gtgttgcgat gcctaacttg tacaagatgc
20641 aaagaatgct tcttgaaaag tgtgaccttc agaattatgg tgaaaatgct gttataccaa
20701 aaggaataat gatgaatgtc gcaaagtata ctcaactgtg tcaatactta aatacactta
20761 ctttagctgt accctacaac atgagagtta ttcactttgg tgctggctct gataaaggag
20821 ttgcaccagg tacagctgtg ctcagacaat ggttgccaac tggcacacta cttgtcgatt
20881 cagatcttaa tgacttcgtc tccgacgcag attctacttt aattggagac tgtgcaacag
20941 tacatacggc taataaatgg gaccttatta ttagcgatat gtatgaccct aggaccaaac
21001 atgtgacaaa agagaatgac tctaaagaag ggttttcac ttatctgtgt ggatttataa
21061 agcaaaaact agccctgggt ggttctatag ctgtaaagat aacagagcat tcttggaatg
21121 ctgaccttta caagcttatg ggccatttct catggtggac agcttttgtt acaaatgtaa
21181 atgcatcatc atcggaagca tttttaattg ggctaacta tcttggcaag ccgaaggaac
21241 aaattgatgg ctataccatg catgctaact acattttctg gaggaacaca aatcctatcc
21301 agttgtcttc ctattcactc tttgacatga gcaaatttcc tcttaaatta agaggaactg
21361 ctgtaatgtc tcttaaggag aatcaaatca atgatatgat ttattctctt ctggaaaaag
21421 gtaggcttat cattagagaa aacaacagag ttgtggtttc aagtgatatt cttgttaaca
21481 actaaacgaa catgtttatt ttcttattat ttcttactct cactagtggt agtgaccttg
21541 accggtgcac cacttttgat gatgttcaag ctcctaatta cactcaacat acttcatcta
21601 tgaggggggt ttactatcct gatgaaattt ttagatcaga cactctttat ttaactcagg -continued

```
21661 atttatttct tccattttat tctaatgtta cagggtttca tactattaat catacgtttg
21721 gcaaccctgt catacctttt aaggatggta tttattttgc tgccacagag aaatcaaatg
21781 ttgtccgtgg ttgggttttt ggttctacca tgaacaacaa gtcacagtcg gtgattatta
21841 ttaacaattc tactaatgtt gttatacgag catgtaactt tgaattgtgt gacaaccctt
21901 tctttgctgt ttctaaaccc atgggtacac agacacatac tatgatattc gataatgcat
21961 ttaattgcac tttcgagtac atatctgatg ccttttcgct tgatgtttca gaaaagtcag
22021 gtaattttaa acacttacga gagtttgtgt ttaaaaataa agatgggttt ctctatgttt
22081 ataagggcta tcaacctata gatgtagttc gtgatctacc ttctggtttt aacactttga
22141 aacctatttt taagttgcct cttggtatta acattacaaa ttttagagcc attcttacag
22201 ccttttcacc tgctcaagac atttggggca cgtcagctgc agcctatttt gttggctatt
22261 taaagccaac tacatttatg ctcaagtatg atgaaaatgg tacaatcaca gatgctgttg
22321 attgttctca aaatccactt gctgaactca aatgctctgt taagagcttt gagattgaca
22381 aaggaattta ccagacctct aatttcaggg ttgttccctc aggagatgtt gtgagattcc
22441 ctaatattac aaacttgtgt ccttttggag aggtttttaa tgctactaaa ttcccttctg
22501 tctatgcatg ggagagaaaa aaaatttcta attgtgttgc tgattactct gtgctctaca
22561 actcaacatt tttttcaacc tttaagtgct atggcgtttc tgccactaag ttgaatgatc
22621 tttgcttctc caatgtctat gcagattctt ttgtagtcaa gggagatgat gtaagacaaa
22681 tagcgccagg acaaactggt gttattgctg attataatta taaattgcca gatgatttca
22741 tgggttgtgt ccttgcttgg aatactagga acattgatgc tacttcaact ggtaattata
22801 attataaata taggtatctt agacatggca agcttaggcc ctttgagaga gacatatcta
22861 atgtgccttt ctcccctgat ggcaaacctt gcaccccacc tgctcttaat tgttattggc
22921 cattaaatga ttatggtttt tacaccacta ctggcattgg ctaccaacct tacagagttg
22981 tagtactttc ttttgaactt ttaaatgcac cggccacggt ttgtggacca aaattatcca
23041 ctgaccttat taagaaccag tgtgtcaatt ttaattttaa tggactcact ggtactggtg
23101 tgttaactcc ttcttcaaag agatttcaac catttcaaca atttggccgt gatgtttctg
23161 atttcactga ttccgttcga gatcctaaaa catctgaaat attagacatt tcaccttgcg
23221 cttttggggg tgtaagtgta attacacctg gaacaaatgc ttcatctgaa gttgctgttc
23281 tatatcaaga tgttaactgc actgatgttt ctacagcaat tcatgcagat caactcacac
23341 cagcttggcg catatattct actggaaaca atgtattcca gactcaagca ggctgtctta
23401 taggagctga gcatgtcgac acttcttatg agtgcgacat tcctattgga gctggcattt
23461 gtgctagtta ccatacagtt tctttattac gtagtactag ccaaaaatct attgtggctt
23521 atactatgtc tttaggtgct gatagttcaa ttgcttactc taataacacc attgctatac
23581 ctactaactt ttcaattagc attactacag aagtaatgcc tgtttctatg gctaaaacct
23641 ccgtagattg taatatgtac atctgcggag attctactga atgtgctaat ttgcttctcc
23701 aatatggtag cttttgcaca caactaaatc gtgcactctc aggtattgct gctgaacagg
23761 atcgcaacac acgtgaagtg ttcgctcaag tcaaacaaat gtacaaaacc ccaactttga
23821 aatattttgg tggttttaat ttttcacaaa tattacctga ccctctaaag ccaactaaga
23881 ggtcttttat tgaggacttg ctctttaata aggtgacact cgctgatgct ggcttcatga
23941 agcaatatgg cgaatgccta ggtgatatta atgctagaga tctcatttgt gcgcagaagt
24001 tcaatggact tacagtgttg ccacctctgc tcactgatga tatgattgct gcctacactg
```

-continued 24061 ctgctctagt tagtggtact gccactgctg gatggacatt tggtgctggc gctgctcttc 24121 aaataccttt tgctatgcaa atggcatata ggttcaatgg cattggagtt acccaaaatg 24181 ttctctatga gaaccaaaaa caaatcgcca accaatttaa caaggcgatt agtcaaattc 24241 aagaatcact tacaacaaca tcaactgcat tgggcaagct gcaagacgtt gttaaccaga 24301 atgctcaagc attaaacaca cttgttaaac aacttagctc taattttggt gcaatttcaa 24361 gtgtgctaaa tgatatcctt tcgcgacttg ataaagtcga ggcggaggta caaattgaca 24421 ggttaattac aggcagactt caaagccttc aaacctatgt aacacaacaa ctaatcaggg 24481 ctgctgaaat cagggcttct gctaatcttg ctgctactaa aatgtctgag tgtgttcttg 24541 gacaatcaaa aagagttgac ttttgtggaa agggctacca ccttatgtcc ttcccacaag 24601 cagccccgca tggtgttgtc ttcctacatg tcacgtatgt gccatcccag gagaggaact 24661 tcaccacagc gccagcaatt tgtcatgaag gcaaagcata cttccctcgt gaaggtgttt 24721 ttgtgtttaa tggcacttct tggtttatta cacagaggaa cttcttttct ccacaaataa 24781 ttactacaga caatacattt gtctcaggaa attgtgatgt cgttattggc atcattaaca 24841 acacagttta tgatcctctg caacctgagc ttgactcatt caaagaagag ctggacaagt 24901 acttcaaaaa tcatacatca ccagatgttg atcttggcga catttcaggc attaacgctt 24961 ctgtcgtcaa cattcaaaaa gaaattgacc gcctcaatga ggtcgctaaa aatttaaatg 25021 aatcactcat tgaccttcaa gaattgggaa aatatgagca atatattaaa tggccttggt 25081 atgtttggct cggcttcatt gctggactaa ttgccatcgt catggttaca atcttgcttt 25141 gttgcatgac tagttgttgc agttgcctca agggtgcatg ctcttgtggt tcttgctgca 25201 agtttgatga ggatgactct gagccagttc tcaagggtgt caaattacat tacacataaa 25261 cgaacttatg gatttgttta tgagattttt tactcttaga tcaattactg cacagccagt 25321 aaaaattgac aatgcttctc ctgcaagtac tgttcatgct acagcaacga taccgctaca 25381 agcctcactc cctttcggat ggcttgttat tggcgttgca tttcttgctg tttttcagag 25441 cgctaccaaa ataattgcgc tcaataaaag atggcagcta gccctttata agggcttcca 25501 gttcatttgc aatttactgc tgctatttgt taccatctat tcacatcttt tgcttgtcgc 25561 tgcaggtatg gaggcgcaat tttgtacct ctatgccttg atatattttc tacaatgcat 25621 caacgcatgt agaattatta tgagatgttg gctttgttgg aagtgcaaat ccaagaaccc 25681 attactttat gatgccaact actttgtttg ctggcacaca cataactatg actactgtat 25741 accatataac agtgtcacag atacaattgt cgttactgaa ggtgacggca tttcaacacc 25801 aaaactcaaa gaagactacc aaattggtgg ttattctgag gataggcact caggtgttaa 25861 agactatgtc gttgtacatg gctatttcac cgaagtttac taccagcttg agtctacaca 25921 aattactaca gacactggta ttgaaaatgc tacattcttc atctttaaca agcttgttaa 25981 agacccaccg aatgtgcaaa tacacacaat cgacggctct tcaggagttg ctaatccagc 26041 aatggatcca atttatgatg agccgacgac gactactagc gtgcctttgt aagcacaaga 26101 aagtgagtac gaacttatgt actcattcgt ttcggaagaa acaggtacgt taatagttaa 26161 tagcgtactt ctttttcttg ctttcgtggt attcttgcta gtcacactag ccatccttac 26221 tgcgcttcga ttgtgtgcgt actgctgcaa tattgttaac gtgagtttag taaaaccaac 26281 ggtttacgtc tactcgcgtg ttaaaaatct gaactcttct gaaggagttc ctgatcttct 26341 ggtctaaacg aactaactat tattattatt ctgtttggaa ctttaacatt gcttatcatg 26401 gcagacaacg gtactattac cgttgaggag cttaaacaac tcctggaaca atggaaccta 26461 gtaataggtt tcctattcct agcctggatt atgttactac aatttgccta ttctaatcgg -continued 26521 aacaggtttt tgtacataat aaagcttgtt ttcctctggc tcttgtggcc agtaacactt 26581 gcttgttttg tgcttgctgc tgtctacaga attaattggg tgactggcgg gattgcgatt 26641 gcaatggctt gtattgtagg cttgatgtgg cttagctact tcgttgcttc cttcaggctg 26701 tttgctcgta cccgctcaat gtggtcattc aacccagaaa caaacattct tctcaatgtg 26761 cctctccggg ggacaattgt gaccagaccg ctcatggaaa gtgaacttgt cattggtgct 26821 gtgatcattc gtggtcactt gcgaatggcc ggacactccc tagggcgctg tgacattaag 26881 gacctgccaa aagagatcac tgtggctaca tcacgaacgc tttcttatta caaattagga 26941 gcgtcgcagc gtgtaggcac tgattcaggt tttgctgcat acaaccgcta ccgtattgga 27001 aactataaat taaatacaga ccacgccggt agcaacgaca atattgcttt gctagtacag 27061 taagtgacaa cagatgtttc atcttgttga cttccaggtt acaatagcag agatattgat 27121 tatcattatg aggactttca ggattgctat ttggaatctt gacgttataa taagttcaat 27181 agtgagacaa ttatttaagc ctctaactaa gaagaattat tcggagttag atgatgaaga 27241 acctatggag ttagattatc cataaaacga acatgaaaat tattctcttc ctgacattga 27301 ttgtatttac atcttgcgag ctatatcact atcaggagtg tgttagaggt acgactgtac 27361 tactaaaaga accttgccca tcaggaacat acgagggcaa ttcaccattt caccctcttg 27421 ctgacaataa atttgcacta acttgcacta gcacacactt tgcttttgct tgtgctgacg 27481 gtactcgaca tacctatcag ctgcgtgcaa gatcagtttc accaaaactt ttcatcagac 27541 aagaggaggt tcaacaagag ctctactcgc cactttttct cattgttgct gctctagtat 27601 ttttaatact ttgcttcacc attaagagaa agacagaatg aatgagctca ctttaattga 27661 cttctatttg tgctttttag cctttctgct attccttgtt ttaataatgc ttattatatt 27721 ttggttttca ctcgaaatcc aggatctaga agaaccttgt accaaagtct aaacgaacat 27781 gaaacttctc attgttttga cttgtatttc tctatgcagt tgcatatgca ctgtagtaca 27841 gcgctgtgca tctaataaac ctcatgtgct tgaagatcct tgtaaggtac aacactaggg 27901 gtaatactta tagcactgct tggctttgtg ctctaggaaa ggttttacct tttcatagat 27961 ggcacactat ggttcaaaca tgcacaccta atgttactat caactgtcaa gatccagctg 28021 gtggtgcgct tatagctagg tgttggtacc ttcatgaagg tcaccaaact gctgcattta 28081 gagacgtact tgttgtttta aataaacgaa caaattaaaa tgtctgataa tggaccccaa 28141 tcaaaccaac gtagtgcccc ccgcattaca tttggtggac ccacagattc aactgacaat 28201 aaccagaatg gaggacgcaa tggggcaagg ccaaaacagc gccgacccca aggtttaccc 28261 aataatactg cgtcttggtt cacagctctc actcagcatg gcaaggagga acttagattc 28321 cctcgaggcc agggcgttcc aatcaacacc aatagtggtc cagatgacca aattggctac 28381 taccgaagag ctacccgacg agttcgtggt ggtgacggca aaatgaaaga gctcagcccc 28441 agatggtact tctattacct aggaactggc ccagaagctt cacttcccta cggcgctaac 28501 aaagaaggca tcgtatgggt tgcaactgag ggagccttga atacacccaa agaccacatt 28561 ggcacccgca atcctaataa caatgctgcc accgtgctac aacttcctca aggaacaaca 28621 ttgccaaaag gcttctacgc agagggaagc agaggcggca gtcaagcctc ttctcgctcc 28681 tcatcacgta gtcgcggtaa ttcaagaaat tcaactcctg gcagcagtag gggaaattct 28741 cctgctcgaa tggctagcgg aggtggtgaa actgccctcg cgctattgct gctagacaga 28801 ttgaaccagc ttgagagcaa agtttctggt aaaggccaac aacaacaagg ccaaactgtc 28861 actaagaaat ctgctgctga ggcatctaaa aagcctcgcc aaaaacgtac tgccacaaaa -continued

```
28921 cagtacaacg tcactcaagc atttgggaga cgtggtccag aacaaaccca aggaaatttc

28981 ggggaccaag acctaatcag acaaggaact gattacaaac attggccgca aattgcacaa

29041 tttgctccaa gtgcctctgc attctttgga atgtcacgca ttggcatgga agtcacacct

29101 tcgggaacat ggctgactta tcatggagcc attaaattgg atgacaaaga tccacaattc

29161 aaagacaacg tcatactgct gaacaagcac attgacgcat acaaaacatt cccaccaaca

29221 gagcctaaaa aggacaaaaa gaaaaagact gatgaagctc agcctttgcc gcagagacaa

29281 aagaagcagc ccactgtgac tcttcttcct gcggctgaca tggatgattt ctccagacaa

29341 cttcaaaatt ccatgagtgg agcttctgct gattcaactc aggcataaac actcatgatg

29401 accacacaag gcagatgggc tatgtaaacg ttttcgcaat tccgtttacg atacatagtc

29461 tactcttgtg cagaatgaat tctcgtaact aaacagcaca agtaggttta gttaacttta

29521 atctcacata gcaatcttta atcaatgtgt aacattaggg aggacttgaa agagccacca

29581 cattttcatc gaggccacgc ggagtacgat cgagggtaca gtgaataatg ctagggagag

29641 ctgcctatat ggaagagccc taatgtgtaa aattaatttt agtagtgcta tccccatgtg

29701 attttaatag cttcttagga gaatgacaaa aaaaaaaaaa aaaaaaaaaa a.
```

GenBank Accession No. GenBank: JX869059.2, which is specifically incorporated by reference herein in its entirety, provides the following (DNA) genomic sequence for MERS-CoV (Human betacoronavirus 2c EMC/2012, complete genome):

(SEQ ID NO: 4)

```
   1 gatttaagtg aatagcttgg ctatctcact tcccctcgtt ctcttgcaga actttgattt

  61 taacgaactt aaataaaagc cctgttgttt agcgtatcgt tgcacttgtc tggtgggatt

 121 gtggcattaa tttgcctgct catctaggca gtggacatat gctcaacact gggtataatt

 181 ctaattgaat actatttttc agttagagcg tcgtgtctct tgtacgtctc ggtcacaata

 241 cacggtttcg tccggtgcgt ggcaattcgg ggcacatcat gtctttcgtg gctggtgtga

 301 ccgcgcaagg tgcgcgcggt acgtatcgag cagcgctcaa ctctgaaaaa catcaagacc

 361 atgtgtctct aactgtgcca ctctgtggtt caggaaacct ggttgaaaaa ctttcaccat

 421 ggttcatgga tggcgaaaat gcctatgaag tggtgaaggc catgttactt aaaaaggagc

 481 cacttctcta tgtgcccatc cggctggctg gacacactag acacctccca ggtcctcgtg

 541 tgtacctggt tgagaggctc attgcttgtg aaaatccatt catggttaac caattggctt

 601 atagctctag tgcaaatggc agcctggttg gcacaacttt gcagggcaag cctattggta

 661 tgttcttccc ttatgacatc gaacttgtca caggaaagca aaatattctc ctgcgcaagt

 721 atggccgtgg tggttatcac tacaccccat tccactatga gcgagacaac acctcttgcc

 781 ctgagtggat ggacgatttt gaggcggatc ctaaaggcaa atatgcccag aatctgctta

 841 agaagttgat tggcggtgat gtcactccag ttgaccaata catgtgtggc gttgatggaa

 901 aacccattag tgcctacgca tttttaatgg ccaaggatgg aataaccaaa ctggctgatg

 961 ttgaagcgga cgtcgcagca cgtgctgatg acgaaggctt catcacatta aagaacaatc

1021 tatatagatt ggtttggcat gttgagcgta aagacgttcc atatcctaag caatctattt

1081 ttactattaa tagtgtggtc caaaaggatg gtgttgaaaa cactcctcct cactatttta

1141 ctcttggatg caaaatttta acgctcaccc cacgcaacaa gtggagtggc gtttctgact

1201 tgtccctcaa acaaaaactc ctttacacct tctatggtaa ggagtcactt gagaacccaa

1261 cctacattta ccactccgca ttcattgagt gtggaagttg tggtaatgat tcctggctta
```

-continued 1321 cagggaatgc tatccaaggg tttgcctgtg gatgtggggc atcatataca gctaatgatg
1381 tcgaagtcca atcatctggc atgattaagc caaatgctct tctttgtgct acttgcccct
1441 ttgctaaggg tgatagctgt tcttctaatt gcaaacattc agttgctcag ttggttagtt
1501 acctttctga acgctgtaat gttattgctg attctaagtc cttcacactt atctttggtg
1561 gcgtagctta cgcctacttt ggatgtgagg aaggtactat gtactttgtg cctagagcta
1621 agtctgttgt ctcaaggatt ggagactcca tctttacagg ctgtactggc tcttggaaca
1681 aggtcactca aattgctaac atgttcttgg aacagactca gcattccctt aactttgtgg
1741 gagagttcgt tgtcaacgat gttgtcctcg caattctctc tggaaccaca actaatgttg
1801 acaaaatacg ccagcttctc aaaggtgtca cccttgacaa gttgcgtgat tatttagctg
1861 actatgacgt agcagtcact gccggcccat tcatggataa tgctattaat gttggtggta
1921 caggattaca gtatgccgcc attactgcac cttatgtagt tctcactggc ttaggtgagt
1981 cctttaagaa agttgcaacc ataccgtata aggtttgcaa ctctgttaag gatactctgg
2041 cttattatgc tcacagcgtg ttgtacagag tttttcctta tgacatggat tctggtgtgt
2101 catcctttag tgaactactt tttgattgcg ttgatctttc agtagcttct acctattttt
2161 tagtccgcat cttgcaagat aagactggcg actttatgtc tacaattatt acttcctgcc
2221 aaactgctgt tagtaagctt ctagatacat gttttgaagc tacagaagca acatttaact
2281 tcttgttaga tttggcagga ttgttcagaa tctttctccg caatgcctat gtgtacactt
2341 cacaagggtt tgtggtggtc aatggcaaag tttctacact tgtcaaacaa gtgttagact
2401 tgcttaataa gggtatgcaa cttttgcata caaaggtctc ctgggctggt tctaaaatca
2461 ttgctgttat ctacagcggc agggagtctc taatattccc atcgggaacc tattactgtg
2521 tcaccactaa ggctaagtcc gttcaacaag atcttgacgt tattttgcct ggtgagtttt
2581 ccaagaagca gttaggactg ctccaaccta ctgacaattc tacaactgtt agtgttactg
2641 tatccagtaa catggttgaa actgttgtgg gtcaacttga gcaaactaat atgcatagtc
2701 ctgatgttat agtaggtgac tatgtcatta ttagtgaaaa attgtttgtg cgtagtaagg
2761 aagaagacgg atttgccttc taccctgctt gcactaatgg tcatgctgta ccgactctct
2821 ttagacttaa gggaggtgca cctgtaaaaa aagtagcctt tggcggtgat caagtacatg
2881 aggttgctgc tgtaagaagt gttactgtcg agtacaacat tcatgctgta ttagacacac
2941 tacttgcttc ttctagtctt agaacctttg ttgtagataa gtctttgtca attgaggagt
3001 ttgctgacgt agtaaaggaa caagtctcag acttgcttgt taaattactg cgtggaatgc
3061 cgattccaga ttttgattta gacgatttta ttgacgcacc atgctattgc tttaacgctg
3121 agggtgatgc atcctggtct tctactatga tcttctctct tcaccccgtc gagtgtgacg
3181 aggagtgttc tgaagtagag gcttcagatt tagaagaagg tgaatcagag tgcatttctg
3241 agacttcaac tgaacaagtt gacgtttctc atgagacttc tgacgacgag tgggctgctg
3301 cagttgatga agcgttccct ctcgatgaag cagaagatgt tactgaatct gtgcaagaag
3361 aagcacaacc agtagaagta cctgttgaag atattgcgca ggttgtcata gctgacacct
3421 tacaggaaac tcctgttgtg cctgatactg ttgaagtccc accgcaagtg gtgaaacttc
3481 cgtctgcacc tcagactatc cagcccgagg taaaagaagt tgcacctgtc tatgaggctg
3541 ataccgaaca gacacagaat gttactgtta aacctaagag gttacgcaaa aagcgtaatg
3601 ttgacccttt gtccaatttt gaacataagg ttattacaga gtgcgttacc atagttttag
3661 gtgacgcaat tcaagtagcc aagtgctatg gggagtctgt gttagttaat gctgctaaca -continued 3721 cacatcttaa gcatggcggt ggtatcgctg gtgctattaa tgcggcttca aaaggggctg 3781 tccaaaaaga gtcagatgag tatattctgg ctaaagggcc gttacaagta ggagattcag 3841 ttctcttgca aggccattct ctagctaaga atatcctgca tgtcgtaggc ccagatgccc 3901 gcgctaaaca ggatgtttct ctccttagta agtgctataa ggctatgaat gcatatcctc 3961 ttgtagtcac tcctcttgtt tcagcaggca tatttggtgt aaaaccagct gtgtcttttg 4021 attatcttat tagggaggct aagactagag ttttagtcgt cgttaattcc caagatgtct 4081 ataagagtct taccatagtt gacattccac agagtttgac tttttcatat gatgggttac 4141 gtggcgcaat acgtaaagct aaagattatg gttttactgt ttttgtgtgc acagacaact 4201 ctgctaacac taaagttctt aggaacaagg gtgttgatta tactaagaag tttcttacag 4261 ttgacggtgt gcaatattat tgctacacgt ctaaggacac tttagatgat atcttacaac 4321 aggctaataa gtctgttggt attatatcta tgcctttggg atatgtgtct catggtttag 4381 acttaatgca agcagggagt gtcgtgcgta gagttaacgt gccctacgtg tgtctcctag 4441 ctaataaaga gcaagaagct attttgatgt ctgaagacgt taagttaaac ccttcagaag 4501 attttataaa gcacgtccgc actaatggtg gttacaattc ttggcattta gtcgagggtg 4561 aactattggt gcaagactta cgcttaaata agctcctgca ttggtctgat caaaccatat 4621 gctacaagga tagtgtgttt tatgttgtaa agaatagtac agcttttcca tttgaaacac 4681 tttcagcatg tcgtgcgtat ttggattcac gcacgacaca gcagttaaca atcgaagtct 4741 tagtgactgt cgatggtgta aattttagaa cagtcgttct aaataataag aacacttata 4801 gatcacagct tggatgcgtt ttctttaatg gtgctgatat ttctgacacc attcctgatg 4861 agaaacagaa tggtcacagt ttatatctag cagacaattt gactgctgat gaaacaaagg 4921 cgcttaaaga gttatatggc cccgttgatc ctactttctt acacagattc tattcactta 4981 aggctgcagt ccatgggtgg aagatggttg tgtgtgataa ggtacgttct ctcaaattga 5041 gtgataataa ttgttatctt aatgcagtta ttatgacact tgatttattg aaggacatta 5101 aatttgttat acctgctcta cagcatgcat ttatgaaaca taagggcggt gattcaactg 5161 acttcatagc cctcattatg gcttatggca attgcacatt tggtgctcca gatgatgcct 5221 ctcggttact tcataccgtg cttgcaaagg ctgagttatg ctgttctgca cgcatggttt 5281 ggagagagtg gtgcaatgtc tgtggcataa aagatgttgt tctacaaggc ttaaaagctt 5341 gttgttacgt gggtgtgcaa actgttgaag atctgcgtgc tcgcatgaca tatgtatgcc 5401 agtgtggtgg tgaacgtcat cggcaattag tcgaacacac cacccccctgg ttgctgctct 5461 caggcacacc aaatgaaaaa ttggtgacaa cctccacggc gcctgatttt gtagcattta 5521 atgtctttca gggcattgaa acggctgttg gccattatgt tcatgctcgc ctgaagggtg 5581 gtcttatttt aaagtttgac tctggcaccg ttagcaagac ttcagactgg aagtgcaagg 5641 tgacagatgt acttttcccc ggccaaaaat acagtagcga ttgtaatgtc gtacggtatt 5701 ctttggacgg taatttcaga acagaggttg atcccgacct atctgctttc tatgttaagg 5761 atggtaaata ctttacaagt gaaccacccg taacatattc accagctaca attttagctg 5821 gtagtgtcta cactaatagc tgccttgtat cgtctgatgg acaacctggc ggtgatgcta 5881 ttagtttgag ttttaataac cttttagggt ttgattctag taaaccagtc actaagaaat 5941 acacttactc cttcttgcct aaagaagacg gcgatgtgtt gttggctgag tttgacactt 6001 atgaccctat ttataagaat ggtgccatgt ataaaggcaa accaattctt tgggtcaata 6061 aagcatctta tgatactaat cttaataagt tcaatagagc tagtttgcgt caaatttttg 6121 acgtagcccc cattgaactc gaaaataaat tcacaccttt gagtgtggag tctacaccag -continued 6181 ttgaacctcc aactgtagat gtggtagcac ttcaacagga aatgacaatt gtcaaatgta
6241 agggtttaaa taaacctttc gtgaaggaca atgtcagttt cgttgctgat gattcaggta
6301 ctcccgttgt tgagtatctg tctaaagaag acctacatac attgtatgta gaccctaagt
6361 atcaagtcat tgtcttaaaa gacaatgtac tttcttctat gcttagattg cacaccgttg
6421 agtcaggtga tattaacgtt gttgcagctt ccggatcttt gacacgtaaa gtgaagttac
6481 tatttagggc ttcattttat ttcaaagaat ttgctacccg cactttcact gctaccactg
6541 ctgtaggtag ttgtataaag agtgtagtgc ggcatctagg tgttactaaa ggcatattga
6601 caggctgttt tagttttgcc aagatgttat ttatgcttcc actagcttac tttagtgatt
6661 caaaactcgg caccacagag gttaaagtga gtgctttgaa aacagccggc gttgtgacag
6721 gtaatgttgt aaaacagtgt tgcactgctg ctgttgattt aagtatggat aagttgcgcc
6781 gtgtggattg gaaatcaacc ctacggttgt tacttatgtt atgcacaact atggtattgt
6841 tgtcttctgt gtatcacttg tatgtcttca atcaggtctt atcaagtgat gttatgtttg
6901 aagatgccca aggtttgaaa aagttctaca aagaagttag agcttaccta ggaatctctt
6961 ctgcttgtga cggtcttgct tcagcttata gggcgaattc ctttgatgta cctacattct
7021 gcgcaaaccg ttctgcaatg tgtaattggt gcttgattag ccaagattcc ataactcact
7081 acccagctct taagatggtt caaacacatc ttagccacta tgttcttaac atagattggt
7141 tgtggtttgc atttgagact ggtttggcat acatgctcta tacctcggcc ttcaactggt
7201 tgttgttggc aggtacattg cattatttct ttgcacagac ttccatattt gtagactggc
7261 ggtcatacaa ttatgctgtg tctagtgcct tctggttatt cacccacatt ccaatggcgg
7321 gtttggtacg aatgtataat ttgttagcat gcctttggct tttacgcaag ttttatcagc
7381 atgtaatcaa tggttgcaaa gatacggcat gcttgctctg ctataagagg aaccgactta
7441 ctagagttga agcttctacc gttgtctgtg gtggaaaacg tacgttttat atcacagcaa
7501 atggcggtat ttcattctgt cgtaggcata attggaattg tgtggattgt gacactgcag
7561 gtgtggggaa taccttcatc tgtgaagaag tcgcaaatga cctcactacc gccctacgca
7621 ggcctattaa cgctacggat agatcacatt attatgtgga ttccgttaca gttaaagaga
7681 ctgttgttca gtttaattat cgtagagacg gtcaaccatt ctacgagcgg tttcccctct
7741 gcgcttttac aaatctagat aagttgaagt tcaaagaggt ctgtaaaact actactggta
7801 tacctgaata caactttatc atctacgact catcagatcg tggccaggaa agtttagcta
7861 ggtctgcatg tgtttattat tctcaagtct tgtgtaaatc aattcttttg gttgactcaa
7921 gtttggttac ttctgttggt gattctagtg aaatcgccac taaaatgttt gattcctttg
7981 ttaatagttt cgtctcgctg tataatgtca cacgcgataa gttggaaaaa cttatctcta
8041 ctgctcgtga tggcgtaagg cgaggcgata acttccatag tgtcttaaca acattcattg
8101 acgcagcacg aggccccgca ggtgtggagt ctgatgttga gaccaatgaa attgttgact
8161 ctgtgcagta tgctcataaa catgacatac aaattactaa tgagagctac aataattatg
8221 taccctcata tgttaaacct gatagtgtgt ctaccagcga tttaggtagt ctcattgatt
8281 gtaatgcggc ttcagttaac caaattgtct tgcgtaattc taatggtgct tgcatttgga
8341 acgctgctgc atatatgaaa ctctcggatg cacttaaacg acagattcgc attgcatgcc
8401 gtaagtgtaa tttagctttc cggttaacca cctcaaagct acgcgctaat gataatatct
8461 tatcagttag attcactgct aacaaaattg ttggtggtgc tcctacatgg tttaatgcgt
8521 tgcgtgactt tacgttaaag ggttatgttc ttgctaccat tattgtgttt ctgtgtgctg -continued 8581 tactgatgta tttgtgttta cctacatttt ctatggcacc tgttgaattt tatgaagacc 8641 gcatcttgga ctttaaagtt cttgataatg gtatcattag ggatgtaaat cctgatgata 8701 agtgctttgc taataagcac cggtccttca cacaatggta tcatgagcat gttggtggtg 8761 tctatgacaa ctctatcaca tgcccattga cagttgcagt aattgctgga gttgctggtg 8821 ctcgcattcc agacgtacct actacattgg cttgggtgaa caatcagata attttctttg 8881 tttctcgagt ctttgctaat acaggcagtg tttgctacac tcctatagat gagataccct 8941 ataagagttt ctctgatagt ggttgcattc ttccatctga gtgcactatg tttagggatg 9001 cagagggccg tatgacacca tactgccatg atcctactgt tttgcctggg gcttttgcgt 9061 acagtcagat gaggcctcat gttcgttacg acttgtatga tggtaacatg tttattaaat 9121 ttcctgaagt agtatttgaa agtacactta ggattactag aactctgtca actcagtact 9181 gccggttcgg tagttgtgag tatgcacaag agggtgtttg tattaccaca aatggctcgt 9241 gggccatttt taatgaccac catcttaata gacctggtgt ctattgtggc tctgatttta 9301 ttgacattgt caggcggtta gcagtatcac tgttccagcc tattacttat ttccaattga 9361 ctacctcatt ggtcttgggt ataggtttgt gtgcgttcct gactttgctc ttctattata 9421 ttaataaagt aaaacgtgct tttgcagatt acacccagtg tgctgtaatt gctgttgttg 9481 ctgctgttct taatagcttg tgcatctgct ttgttacctc tataccattg tgtatagtac 9541 cttacactgc attgtactat tatgctacat tctattttac taatgagcct gcatttatta 9601 tgcatgtttc ttggtacatt atgttcgggc ctatcgttcc catatggatg acctgcgtct 9661 atacagttgc aatgtgcttt agacacttct tctgggtttt agcttatttt agtaagaaac 9721 atgtagaagt ttttactgat ggtaagctta attgtagttt ccaggacgct gcctctaata 9781 tctttgttat taacaaggac acttatgcag ctcttagaaa ctctttaact aatgatgcct 9841 attcacgatt tttggggttg tttaacaagt ataagtactt ctctggtgct atggaaacag 9901 ccgcttatcg tgaagctgca gcatgtcatc ttgctaaagc cttacaaaca tacagcgaga 9961 ctggtagtga tcttctttac caaccaccca actgtagcat aacctctggc gtgttgcaaa 10021 gcggtttggt gaaaatgtca catcccagtg gagatgttga ggcttgtatg gttcaggtta 10081 cctgcggtag catgactctt aatggtcttt ggcttgacaa cacagtctgg tgcccacgac 10141 acgtaatgtg cccggctgac cagttgtctg atcctaatta tgatgccttg ttgatttcta 10201 tgactaatca tagtttcagt gtgcaaaaac acattggcgc tccagcaaac ttgcgtgttg 10261 ttggtcatgc catgcaaggc actcttttga agttgactgt cgatgttgct aaccctagca 10321 ctccagccta cacttttaca acagtgaaac ctggcgcagc atttagtgtg ttagcatgct 10381 ataatggtcg tccgactggt acattcactg ttgtaatgcg ccctaactac acaattaagg 10441 gttcctttct gtgtggttct tgtggtagtg ttggttacac caaggagggt agtgtgatca 10501 atttctgtta catgcatcaa atggaacttg ctaatggtac acataccggt tcagcatttg 10561 atggtactat gtatggtgcc tttatggata aacaagtgca ccaagttcag ttaacagaca 10621 aatactgcag tgttaatgta gtagcttggc tttacgcagc aatacttaat ggttgcgctt 10681 ggtttgtaaa acctaatcgc actagtgttg tttcttttaa tgaatgggct cttgccaacc 10741 aattcactga atttgttggc actcaatccg ttgacatgtt agctgtcaaa acaggcgttg 10801 ctattgaaca gctgctttat gcgatccaac aactgtatac tgggttccag ggaaagcaaa 10861 tccttggcag taccatgttg gaagatgaat tcacacctga ggatgttaat atgcagatta 10921 tgggtgtggt tatgcagagt ggtgtgagaa aagttacata tggtactgcg cattggttgt 10981 ttgcgaccct tgtctcaacc tatgtgataa tcttacaagc cactaaattt actttgtgga -continued 11041 actacttgtt tgagactatt cccacacagt tgttcccact cttatttgtg actatggcct
11101 tcgttatgtt gttggttaaa cacaaacaca ccttttttgac acttttcttg ttgcctgtgg
11161 ctatttgttt gacttatgca aacatagtct acgagcccac tactcccatt tcgtcagcgc
11221 tgattgcagt tgcaaattgg cttgcccccca ctaatgctta tatgcgcact acacatactg
11281 atattggtgt ctacattagt atgtcacttg tattagtcat tgtagtgaag agattgtaca
11341 acccatcact ttctaacttt gcgttagcat tgtgcagtgg tgtaatgtgg ttgtacactt
11401 atagcattgg agaagcctca agccccattg cctatctggt ttttgtcact acactcacta
11461 gtgattatac gattacagtc tttgttactg tcaaccttgc aaaagtttgc acttatgcca
11521 tctttgctta ctcaccacag cttacacttg tgtttccgga agtgaagatg atacttttat
11581 tatacacatg tttaggtttc atgtgtactt gctattttgg tgtcttctct cttttgaacc
11641 ttaagcttag agcacctatg ggtgtctatg actttaaggt ctcaacacaa gagttcagat
11701 tcatgactgc taacaatcta actgcaccta gaaattcttg ggaggctatg gctctgaact
11761 ttaagttaat aggtattggc ggtacacctt gtataaaggt tgctgctatg cagtctaaac
11821 ttacagatct taaatgcaca tctgtggttc tcctctctgt gctccaacag ttacacttag
11881 aggctaatag tagggcctgg gctttctgtg ttaaatgcca taatgatata ttggcagcaa
11941 cagaccccag tgaggctttc gagaaattcg taagtctctt tgctacttta atgacttttt
12001 ctggtaatgt agatcttgat gcgttagcta gtgatatttt tgacactcct agcgtacttc
12061 aagctactct ttctgagttt tcacacttag ctacctttgc tgagttggaa gctgcgcaga
12121 aagcctatca ggaagctatg gactctggtg acacctcacc acaagttctt aaggctttgc
12181 agaaggctgt taatatagct aaaaacgcct atgagaagga taaggcagtg gcccgtaagt
12241 tagaacgtat ggctgatcag gctatgactt ctatgtataa gcaagcacgt gctgaagaca
12301 agaaagcaaa aattgtcagt gctatgcaaa ctatgttgtt tggtatgatt aagaagctcg
12361 acaacgatgt tcttaatggt atcatttcta acgctaggaa tggttgtata cctcttagtg
12421 tcatcccact gtgtgcttca aataaacttc gcgttgtaat tcctgacttc accgtctgga
12481 atcaggtagt cacatatccc tcgcttaact acgctggggc tttgtgggac attacagtta
12541 taaacaatgt ggacaatgaa attgttaagt cttcagatgt tgtagacagc aatgaaaatt
12601 taacatggcc acttgtttta gaatgcacta gggcatccac ttctgccgtt aagttgcaaa
12661 ataatgagat caaaccttca ggtctaaaaa ccatggttgt gtctgcgggt caagagcaaa
12721 ctaactgtaa tactagttcc ttagcttatt acgaacctgt gcagggtcgt aaaatgctga
12781 tggctcttct ttctgataat gcctatctca aatgggcgcg tgttgaaggt aaggacggat
12841 ttgtcagtgt agagctacaa cctccttgca aattcttgat tgcgggacca aaaggacctg
12901 aaatccgata tctctatttt gttaaaaatc ttaacaacct tcatcgcggg caagtgttag
12961 ggcacattgc tgcgactgtt agattgcaag ctggttctaa caccgagttt gcctctaatt
13021 cctcggtgtt gtcacttgtt aacttcaccg ttgatcctca aaaagcttat ctcgatttcg
13081 tcaatgcggg aggtgcccca ttgacaaatt gtgttaagat gcttactcct aaaactggta
13141 caggtatagc tatatctgtt aaaccagaga gtacagctga tcaagagact tatggtggag
13201 cttcagtgtg tctctattgc cgtgcgcata tagaacatcc tgatgtctct ggtgtttgta
13261 aatataaggg taagtttgtc caaatccctg ctcagtgtgt ccgtgaccct gtgggatttt
13321 gtttgtcaaa tacccccctgt aatgtctgtc aatattggat tggatatggg tgcaattgtg
13381 actcgcttag gcaagcagca ctgccccaat ctaaagattc caatttttta aacgagtccg -continued 13441 gggttctatt gtaaatgccc gaatagaacc ctgttcaagt ggtttgtcca ctgatgtcgt 13501 ctttagggca tttgacatct gcaactataa ggctaaggtt gctggtattg gaaaatacta 13561 caagactaat acttgtaggt ttgtagaatt agatgaccaa gggcatcatt tagactccta 13621 ttttgtcgtt aagaggcata ctatggagaa ttatgaacta gagaagcact gttacgactt 13681 gttacgtgac tgtgatgctg tagctcccca tgatttcttc atctttgatg tagacaaagt 13741 taaaacacct catattgtac gtcagcgttt aactgagtac actatgatgg atcttgtata 13801 tgccctgagg cactttgatc aaaatagcga agtgcttaag gctatcttag tgaagtatgg 13861 ttgctgtgat gttacctact ttgaaaataa actctggttt gattttgttg aaaatcccag 13921 tgttattggt gtttatcata aacttggaga acgtgtacgc caagctatct taaacactgt 13981 taaattttgt gaccacatgg tcaaggctgg tttagtcggt gtgctcacac tagacaacca 14041 ggaccttaat ggcaagtggt atgattttgg tgacttcgta atcactcaac ctggttcagg 14101 agtagctata gttgatagct actattctta tttgatgcct gtgctctcaa tgaccgattg 14161 tctggccgct gagacacata gggattgtga ttttaataaa ccactcattg agtggccact 14221 tactgagtat gattttactg attataaggt acaactcttt gagaagtact ttaaatattg 14281 ggatcagacg tatcacgcaa attgcgttaa ttgtactgat gaccgttgtg tgttacattg 14341 tgctaatttc aatgtattgt ttgctatgac catgcctaag acttgtttcg gacccatagt 14401 ccgaaagatc tttgttgatg gcgtgccatt tgtagtatct tgtggttatc actacaaaga 14461 attaggttta gtcatgaata tggatgttag tctccataga cataggctct ctcttaagga 14521 gttgatgatg tatgccgctg atccagccat gcacattgcc tcctctaacg cttttcttga 14581 tttgaggaca tcatgtttta gtgtcgctgc acttacaact ggtttgactt ttcaaactgt 14641 gcggcctggc aattttaacc aagacttcta tgatttcgtg gtatctaaag gtttctttaa 14701 ggagggctct tcagtgacgc tcaaacattt tttctttgct caagatggta atgctgctat 14761 tacagattat aattactatt cttataatct gcctactatg tgtgacatca aacaaatgtt 14821 gttctgcatg gaagttgtaa acaagtactt cgaaatctat gacggtggtt gtcttaatgc 14881 ttctgaagtg gttgttaata atttagacaa gagtgctggc catcctttta ataagtttgg 14941 caaagctcgt gtctattatg agagcatgtc ttaccaggag caagatgaac tttttgccat 15001 gacaaagcgt aacgtcattc ctaccatgac tcaaatgaat ctaaaatatg ctattagtgc 15061 taagaataga gctcgcactg ttgcaggcgt gtccatactt agcacaatga ctaatcgcca 15121 gtaccatcag aaaatgctta agtccatggc tgcaactcgt ggagcgactt gcgtcattgg 15181 tactacaaag ttctacggtg gctgggattt catgcttaaa acattgtaca aagatgttga 15241 taatccgcat cttatgggtt gggattaccc taagtgtgat agagctatgc ctaatatgtg 15301 tagaatcttc gcttcactca tattagctcg taaacatggc acttgttgta ctacaaggga 15361 cagattttat cgcttggcaa atgagtgtgc tcaggtgcta agcgaatatg ttctatgtgg 15421 tggtggttac tacgtcaaac ctggaggtac cagtagcgga gatgccacca ctgcatatgc 15481 caatagtgtc tttaacattt tgcaggcgac aactgctaat gtcagtgcac ttatgggtgc 15541 taatggcaac aagattgttg acaaagaagt taaagacatg cagtttgatt tgtatgtcaa 15601 tgtttacagg agcactagcc cagaccccaa atttgttgat aaatactatg cttttcttaa 15661 taagcacttt tctatgatga tactgtctga tgacggtgtc gtttgctata atagtgatta 15721 tgcagctaag ggttacattg ctggaataca gaattttaag gaaacgctgt attatcagaa 15781 caatgtcttt atgtctgaag ctaaatgctg ggtggaaacc gatctgaaga aagggccaca 15841 tgaattctgt tcacagcata cgctttatat taaggatggc gacgatggtt acttccttcc -continued 15901 ttatccagac ccttcaagaa ttttgtctgc cggttgcttt gtagatgata tcgttaagac
15961 tgacggtaca ctcatggtag agcggtttgt gtctttggct atagatgctt accctctcac
16021 aaagcatgaa gatatagaat accagaatgt attctgggtc tacttacagt atatagaaaa
16081 actgtataaa gaccttacag gacacatgct tgacagttat tctgtcatgc tatgtggtga
16141 taattctgct aagttttggg aagaggcatt ctatagagat ctctatagtt cgcctaccac
16201 tttgcaggct gtcggttcat gcgttgtatg ccattcacag acttccctac gctgtgggac
16261 atgcatccgt agaccatttc tctgctgtaa atgctgctat gatcatgtta tagcaactcc
16321 acataagatg gttttgtctg tttctcctta cgtttgtaat gcccctggtt gtggcgtttc
16381 agacgttact aagctatatt taggtggtat gagctacttt tgtgtagatc atagacctgt
16441 gtgtagtttt ccactttgcg ctaatggtct tgtattcggc ttatacaaga atatgtgcac
16501 aggtagtcct tctatagttg aatttaatag gttggctacc tgtgactgga ctgaaagtgg
16561 tgattacacc cttgccaata ctacaacaga accactcaaa ctttttgctg ctgagacttt
16621 acgtgccact gaagaggcgt ctaagcagtc ttatgctatt gccaccatca aagaaattgt
16681 tggtgagcgc caactattac ttgtgtggga ggctggcaag tccaaaccac cactcaatcg
16741 taattatgtt tttactggtt atcatataac caaaaatagt aaagtgcagc tcggtgagta
16801 cattttcgag cgcattgatt atagtgatgc tgtatcctac aagtctagta caacgtataa
16861 actgactgta ggtgacatct tcgtacttac ctctcactct gtggctacct tgacggcgcc
16921 cacaattgtg aatcaagaga ggtatgttaa aattactggg ttgtacccaa ccattacggt
16981 acctgaagag ttcgcaagtc atgttgccaa cttccaaaaa tcaggttata gtaaatatgt
17041 cactgttcag ggaccacctg gcactggcaa aagtcatttt gctatagggt tagcgattta
17101 ctaccctaca gcacgtgttg tttatacagc atgttcacac gcagctgttg atgctttgtg
17161 tgaaaaagct tttaaatatt tgaacattgc taaatgttcc cgtatcattc ctgcaaaggc
17221 acgtgttgag tgctatgaca ggtttaaagt taatgagaca aattctcaat atttgtttag
17281 tactattaat gctctaccag aaacttctgc cgatattctg gtggttgatg aggttagtat
17341 gtgcactaat tatgatcttt caattattaa tgcacgtatt aaagctaagc acattgtcta
17401 tgtaggagat ccagcacagt tgccagctcc taggactttg ttgactagag gcacattgga
17461 accagaaaat ttcaatagtg tcactagatt gatgtgtaac ttaggtcctg acatattttt
17521 aagtatgtgc tacaggtgtc ctaaggaaat agtaagcact gtgagcgctc ttgtctacaa
17581 taataaattg ttagccaaga aggagctttc aggccagtgc tttaaaatac tctataaggg
17641 caatgtgacg catgatgcta gctctgccat taatagacca caactcacat ttgtgaagaa
17701 ttttattact gccaatccgg catggagtaa ggcagtcttt atttcgcctt acaattcaca
17761 gaatgctgtg tctcgttcaa tgctgggtct taccactcag actgttgatt cctcacaggg
17821 ttcagaatac cagtacgtta tcttctgtca aacagcagat acggcacatg ctaacaacat
17881 taacagattt aatgttgcaa tcactcgtgc ccaaaaaggt attctttgtg ttatgacatc
17941 tcaggcactc tttgagtcct tagagtttac tgaattgtct tttactaatt acaagctcca
18001 gtctcagatt gtaactggcc tttttaaaga ttgctctaga gaaacttctg gcctctcacc
18061 tgcttatgca ccaacatatg ttagtgttga tgacaagtat aagacgagtg atgagctttg
18121 cgtgaatctt aatttacccg caaatgtccc atactctcgt gttatttcca ggatgggctt
18181 taaactcgat gcaacagttc ctggatatcc taagcttttc attactcgtg aagaggctgt
18241 aaggcaagtt cgaagctgga taggcttcga tgttgagggt gctcatgctt cccgtaatgc -continued 18301 atgtggcacc aatgtgcctc tacaattagg attttcaact ggtgtgaact ttgttgttca 18361 gccagttggt gttgtagaca ctgagtgggg taacatgtta acgggcattg ctgcacgtcc 18421 tccaccaggt gaacagttta agcacctcgt gcctcttatg cataaggggg ctgcgtggcc 18481 tattgttaga cgacgtatag tgcaaatgtt gtcagacact ttagacaaat tgtctgatta 18541 ctgtacgttt gtttgttggg ctcatggctt tgaattaacg tctgcatcat acttttgcaa 18601 gataggtaag gaacagaagt gttgcatgtg caatagacgc gctgcagcgt actcttcacc 18661 tctgcaatct tatgcctgct ggactcattc ctgcggttat gattatgtct acaacccttt 18721 ctttgtcgat gttcaacagt ggggttatgt aggcaatctt gctactaatc acgatcgtta 18781 ttgctctgtc catcaaggag ctcatgtggc ttctaatgat gcaataatga ctcgttgttt 18841 agctattcat tcttgtttta tagaacgtgt ggattgggat atagagtatc cttatatctc 18901 acatgaaaag aaattgaatt cctgttgtag aatcgttgag cgcaacgtcg tacgtgctgc 18961 tcttcttgcc ggttcatttg acaaagtcta tgatattggc aatcctaaag gaattcctat 19021 tgttgatgac cctgtggttg attggcatta ttttgatgca cagcccttga ccaggaaggt 19081 acaacagctt ttctatacag aggacatggc ctcaagattt gctgatgggc tctgcttatt 19141 ttggaactgt aatgtaccaa aatatcctaa taatgcaatt gtatgcaggt ttgacacacg 19201 tgtgcattct gagttcaatt tgccaggttg tgatggcggt agtttgtatg ttaacaagca 19261 cgcttttcat acaccagcat atgatgtgag tgcattccgt gatctgaaac ctttaccatt 19321 cttttattat tctactacac catgtgaagt gcatggtaat ggtagtatga tagaggatat 19381 tgattatgta ccccctaaaat ctgcagtctg tattacagct tgtaatttag gggcgctgt 19441 ttgtaggaag catgctacag agtacagaga gtatatggaa gcatataatc ttgtctctgc 19501 atcaggtttc cgcctttggt gttataagac ctttgatatt tataatctct ggtctacttt 19561 tacaaaagtt caaggtttgg aaaacattgc ttttaatgtt gttaaacaag gccattttat 19621 tggtgttgag ggtgaactac ctgtagctgt agtcaatgat aagatcttca ccaagagtgg 19681 cgttaatgac atttgtatgt ttgagaataa aaccactttg cctactaata tagcttttga 19741 actctatgct aagcgtgctg tacgctcgca tcccgatttc aaattgctac acaatttaca 19801 agcagacatt tgctacaagt tcgtcctttg ggattatgaa cgtagcaata tttatggtac 19861 tgctactatt ggtgtatgta agtacactga tattgatgtt aattcagctt tgaatatatg 19921 ttttgacata cgcgataatt gttcattgga gaagttcatg tctactccca atgccatctt 19981 tatttctgat agaaaaatca agaaataccc ttgtatggta ggtcctgatt atgcttactt 20041 caatggtgct atcatccgtg atagtgatgt tgttaaacaa ccagtgaagt tctacttgta 20101 taagaaagtc aataatgagt ttattgatcc tactgagtgt atttacactc agagtcgctc 20161 ttgtagtgac ttcctacccc tttctgacat ggagaaagac tttctatctt ttgatagtga 20221 tgttttcatt aagaagtatg gcttggaaaa ctatgctttt gagcacgtag tctatggaga 20281 cttctctcat actacgttag gcggtcttca cttgcttatt ggtttataca agaagcaaca 20341 ggaaggtcat attattatgg aagaaatgct aaaaggtagc tcaactattc ataactattt 20401 tattactgag actaacacag cggcttttaa ggcggtgtgt tctgttatag atttaaagct 20461 tgacgacttt gttatgattt taaagagtca agaccttggc gtagtatcca aggttgtcaa 20521 ggttcctatt gacttaacaa tgattgagtt tatgttatgg tgtaaggatg gacaggttca 20581 aaccttctac cctcgactcc aggcttctgc agattggaaa cctggtcatg caatgccatc 20641 cctctttaaa gttcaaaatg taaaccttga acgttgtgag cttgctaatt acaagcaatc 20701 tattcctatg cctcgcggtg tgcacatgaa catcgctaaa tatatgcaat tgtgccagta -continued 20761 tttaaatact tgcacattag ccgtgcctgc caatatgcgt gttatacatt ttggcgctgg 20821 ttctgataaa ggtatcgctc ctggtacctc agttttacga cagtggcttc ctacagatgc 20881 cattattata gataatgatt taaatgagtt cgtgtcagat gctgacataa ctttatttgg 20941 agattgtgta actgtacgtg tcggccaaca agtggatctt gttatttccg acatgtatga 21001 tcctactact aagaatgtaa caggtagtaa tgagtcaaag gctttattct ttacttacct 21061 gtgtaacctc attaataata atcttgctct tggtgggtct gttgctatta aaataacaga 21121 acactcttgg agcgttgaac tttatgaact tatgggaaaa tttgcttggt ggactgtttt 21181 ctgcaccaat gcaaatgcat cctcatctga aggattcctc ttaggtatta attacttggg 21241 tactattaaa gaaaatatag atggtggtgc tatgcacgcc aactatatat tttggagaaa 21301 ttccactcct atgaatctga gtacttactc acttttgat ttatccaagt ttcaattaaa 21361 attaaaagga acaccagttc ttcaattaaa ggagagtcaa attaacgaac tcgtaatatc 21421 tctcctgtcg cagggtaagt tacttatccg tgacaatgat acactcagtg tttctactga 21481 tgttcttgtt aacacctaca gaaagttacg ttgatgtagg gccagattct gttaagtctg 21541 cttgtattga ggttgatata caacagactt tctttgataa aacttggcct aggccaattg 21601 atgtttctaa ggctgacggt attatatacc ctcaaggccg tacatattct aacataacta 21661 tcacttatca aggtcttttt ccctatcagg gagaccatgg tgatatgtat gtttactctg 21721 caggacatgc tacaggcaca actccacaaa agttgtttgt agctaactat tctcaggacg 21781 tcaaacagtt tgctaatggg tttgtcgtcc gtataggagc agctgccaat tccactggca 21841 ctgttattat tagcccatct accagcgcta ctatacgaaa aatttaccct gcttttatgc 21901 tgggttcttc agttggtaat ttctcagatg gtaaaatggg ccgcttcttc aatcatactc 21961 tagttctttt gcccgatgga tgtggcactt tacttagagc tttttattgt attctagagc 22021 ctcgctctgg aaatcattgt cctgctggca attcctatac ttcttttgcc acttatcaca 22081 ctcctgcaac agattgttct gatggcaatt acaatcgtaa tgccagtctg aactctttta 22141 aggagtattt taatttacgt aactgcacct ttatgtacac ttataacatt accgaagatg 22201 agattttaga gtggtttggc attacacaaa ctgctcaagg tgttcacctc ttctcatctc 22261 ggtatgttga tttgtacggc ggcaatatgt ttcaatttgc caccttgcct gtttatgata 22321 ctattaagta ttattctatc attcctcaca gtattcgttc tatccaaagt gatagaaaag 22381 cttgggctgc cttctacgta tataaacttc aaccgttaac tttcctgttg gatttttctg 22441 ttgatggtta tatacgcaga gctatagact gtggttttaa tgatttgtca caactccact 22501 gctcatatga atccttcgat gttgaatctg gagtttattc agtttcgtct ttcgaagcaa 22561 aaccttctgg ctcagttgtg gaacaggctg aaggtgttga atgtgatttt tcacctcttc 22621 tgtctggcac acctcctcag gtttataatt tcaagcgttt ggtttttacc aattgcaatt 22681 ataatcttac caaattgctt tcactttttt ctgtgaatga ttttacttgt agtcaaatat 22741 ctccagcagc aattgctagc aactgttatt cttcactgat tttggattac ttttcatacc 22801 cacttagtat gaaatccgat ctcagtgtta gttctgctgg tccaatatcc cagtttaatt 22861 ataaacagtc cttttctaat cccacatgtt tgattttagc gactgttcct cataacctta 22921 ctactattac taagcctctt aagtacagct atattaacaa gtgctctcgt cttctttctg 22981 atgatcgtac tgaagtacct cagttagtga acgctaatca atactcaccc tgtgtatcca 23041 ttgtcccatc cactgtgtgg gaagacggtg attattatag gaaacaacta tctccacttg 23101 aaggtggtgg ctggcttgtt gctagtggct caactgttgc catgactgag caattacaga -continued

```
23161 tgggctttgg tattacagtt caatatggta cagacaccaa tagtgtttgc cccaagcttg
23221 aatttgctaa tgacacaaaa attgcctctc aattaggcaa ttgcgtggaa tattccctct
23281 atggtgtttc gggccgtggt gtttttcaga attgcacagc tgtaggtgtt cgacagcagc
23341 gctttgttta tgatgcgtac cagaatttag ttggctatta ttctgatgat ggcaactact
23401 actgtttgcg tgcttgtgtt agtgttcctg tttctgtcat ctatgataaa gaaactaaaa
23461 cccacgctac tctatttggt agtgttgcat gtgaacacat ttcttctacc atgtctcaat
23521 actcccgttc tacgcgatca atgcttaaac ggcgagattc tacatatggc ccccttcaga
23581 cacctgttgg ttgtgtccta ggacttgtta attcctcttt gttcgtagag gactgcaagt
23641 tgcctcttgg tcaatctctc tgtgctcttc ctgacacacc tagtactctc acacctcgca
23701 gtgtgcgctc tgttccaggt gaaatgcgct tggcatccat tgcttttaat catcctattc
23761 aggttgatca acttaatagt agttatttta aattaagtat acccactaat tttttcctttg
23821 gtgtgactca ggagtacatt cagacaacca ttcagaaagt tactgttgat tgtaaacagt
23881 acgtttgcaa tggtttccag aagtgtgagc aattactgcg cgagtatggc cagttttgtt
23941 ccaaaataaa ccaggctctc catggtgcca atttacgcca ggatgattct gtacgtaatt
24001 tgtttgcgag cgtgaaaagc tctcaatcat ctcctatcat accaggtttt ggaggtgact
24061 ttaatttgac acttctagaa cctgtttcta tatctactgg cagtcgtagt gcacgtagtg
24121 ctattgagga tttgctattt gacaaagtca ctatagctga tcctggttat atgcaaggtt
24181 acgatgattg catgcagcaa ggtccagcat cagctcgtga tcttatttgt gctcaatatg
24241 tggctggtta caaagtatta cctcctctta tggatgttaa tatggaagcc gcgtatactt
24301 catctttgct tggcagcata gcaggtgttg gctggactgc tggcttatcc tcctttgctg
24361 ctattccatt tgcacagagt atcttttata ggttaaacgg tgttggcatt actcaacagg
24421 ttctttcaga gaaccaaaag cttattgcca ataagtttaa tcaggctctg ggagctatgc
24481 aaacaggctt cactacaact aatgaagctt ttcagaaggt tcaggatgct gtgaacaaca
24541 atgcacaggc tctatccaaa ttagctagcg agctatctaa tacttttggt gctatttccg
24601 cctctattgg agacatcata caacgtcttg atgttctcga acaggacgcc caaatagaca
24661 gacttattaa tggccgtttg acaacactaa atgcttttgt tgcacagcag cttgttcgtt
24721 ccgaatcagc tgctctttcc gctcaattgg ctaaagataa agtcaatgag tgtgtcaagg
24781 cacaatccaa gcgttctgga ttttgcggtc aaggcacaca tatagtgtcc tttgttgtaa
24841 atgcccctaa tggcctttac ttcatgcatg ttggttatta ccctagcaac cacattgagg
24901 ttgtttctgc ttatggtctt tgcgatgcag ctaaccctac taattgtata gcccctgtta
24961 atggctactt tattaaaact aataacacta ggattgttga tgagtggtca tatactggct
25021 cgtccttcta tgcacctgag cccattacct cccttaatac taagtatgtt gcaccacagg
25081 tgacatacca aaacatttct actaacctcc ctcctcctct tctcggcaat tccaccggga
25141 ttgacttcca agatgagttg gatgagtttt tcaaaaatgt tagcaccagt atacctaatt
25201 ttggttccct aacacagatt aatactacat tactcgatct tacctacgag atgttgtctc
25261 ttcaacaagt tgttaaagcc cttaatgagt cttacataga ccttaaagag cttggcaatt
25321 atacttatta caacaaatgg ccgtggtaca tttggcttgg tttcattgct gggcttgttg
25381 ccttagctct atgcgtcttc ttcatactgt gctgcactgg ttgtggcaca aactgtatgg
25441 gaaaacttaa gtgtaatcgt tgttgtgata gatacgagga atacgacctc gagccgcata
25501 aggttcatgt tcactaatta acgaactatt aatgagagtt caaagaccac ccactctctt
25561 gttagtgttt tcactctctc ttttggtcac tgcatcctca aaacctctct atgtacctga
```

-continued 25621 gcattgtcag aattattctg gttgcatgct tagggcttgt attaaaactg cccaagctga 25681 tacagctggt ctttatacaa attttcgaat tgacgtccca tctgcagaat caactggtac 25741 tcaatcagtt tctgtcgatc ttgagtcaac ttcaactcat gatggtccta ccgaacatgt 25801 tactagtgtg aatctttttg acgttggtta ctcagttaat taacgaactc tatggattac 25861 gtgtctctgc ttaatcaaat ttggcagaag taccttaact caccgtatac tacttgtttg 25921 tacatcccta aacccacagc taagtataca cctttagttg gcacttcatt gcaccctgtg 25981 ctgtggaact gtcagctatc ctttgctggt tatactgaat ctgctgttaa ttctacaaaa 26041 gctttggcca aacaggacgc agctcagcga atcgcttggt tgctacataa ggatggagga 26101 atccctgatg gatgttccct ctacctccgg cactcaagtt tattcgcgca aagcgaggaa 26161 gaggagccat tctccaacta agaaactgcg ctacgttaag cgtagatttt ctcttctgcg 26221 ccatgaagac cttagtgtta ttgtccaacc aacacactat gtcagggtta cattttcaga 26281 ccccaacatg tggtatctac gttcgggtca tcatttacac tcagttcaca attggcttaa 26341 accttatggc ggccaacctg tttctgagta ccatattact ctagctttgc taaatctcac 26401 tgatgaagat ttagctagag atttttcacc cattgcgctc tttttgcgca atgtcagatt 26461 tgagctacat gagttcgcct tgctgcgcaa aactcttgtt cttaatgcat cagagatcta 26521 ctgtgctaac atacatagat ttaagcctgt gtatagagtt aacacggcaa tccctactat 26581 taaggattgg cttctcgttc agggattttc cctttaccat agtggcctcc ctttacatat 26641 gtcaatctct aaattgcatg cactggatga tgttactcgc aattacatca ttacaatgcc 26701 atgctttaga acttaccctc aacaaatgtt tgttactcct ttggccgtag atgttgtctc 26761 catacggtct tccaatcagg gtaataaaca aattgttcat tcttatccca ttttacatca 26821 tccaggattt taacgaacta tggctttctc ggcgtcttta tttaaacccg tccagctagt 26881 cccagtttct cctgcatttc atcgcattga gtctactgac tctattgttt tcacatacat 26941 tcctgctagc ggctatgtag ctgctttagc tgtcaatgtg tgtctcattc ccctattatt 27001 actgctacgt caagatactt gtcgtcgcag cattatcaga actatggttc tctatttcct 27061 tgttctgtat aactttttat tagccattgt actagtcaat ggtgtacatt atccaactgg 27121 aagttgcctg atagccttct tagttatcct cataatactt tggtttgtag atagaattcg 27181 tttctgtctc atgctgaatt cctacattcc actgtttgac atgcgttccc actttattcg 27241 tgttagtaca gtttcttctc atggtatggt ccctgtaata cacaccaaac cattatttat 27301 tagaaacttc gatcagcgtt gcagctgttc tcgttgtttt tatttgcact cttccactta 27361 tatagagtgc acttatatta gccgttttag taagattagc ctagtttctg taactgactt 27421 ctccttaaac ggcaatgttt ccactgtttt cgtgcctgca acgcgcgatt cagttcctct 27481 tcacataatc gccccgagct cgcttatcgt ttaagcagct ctgcgctact atgggtcccg 27541 tgtagaggct aatccattag tctctctttg gacatatgga aaacgaacta tgttaccctt 27601 tgtccaagaa cgaatagggt tgttcatagt aaactttttc atttttaccg tagtatgtgc 27661 tataacactc ttggtgtgta tggctttcct tacggctact agattatgtg tgcaatgtat 27721 gacaggcttc aataccctgt tagttcagcc cgcattatac ttgtataata ctggacgttc 27781 agtctatgta aaattccagg atagtaaacc ccctctacca cctgacgagt gggtttaacg 27841 aactccttca taatgtctaa tatgacgcaa ctcactgagg cgcagattat tgccattatt 27901 aaagactgga actttgcatg gtccctgatc tttctcttaa ttactatcgt actacagtat 27961 ggataccccat cccgtagtat gactgtctat gtctttaaaa tgtttgtttt atggctccta -continued

```
28021 tggccatctt ccatggcgct atcaatattt agcgccgttt atccaattga tctagcttcc
28081 cagataatct ctggcattgt agcagctgtt tcagctatga tgtggatttc ctactttgtg
28141 cagagtatcc ggctgtttat gagaactgga tcatggtggt cattcaatcc tgagactaat
28201 tgccttttga acgttccatt tggtggtaca actgtcgtac gtccactcgt agaggactct
28261 accagtgtaa ctgctgttgt aaccaatggc cacctcaaaa tggctggcat gcatttcggt
28321 gcttgtgact acgacagact tcctaatgaa gtcaccgtgg ccaaacccaa tgtgctgatt
28381 gctttaaaaa tggtgaagcg gcaaagctac ggaactaatt ccggcgttgc catttaccat
28441 agatataagg caggtaatta caggagtccg cctattacgg cggatattga acttgcattg
28501 cttcgagctt aggctcttta gtaagagtat cttaattgat tttaacgaat ctcaatttca
28561 ttgttatggc atcccctgct gcacctcgtg ctgtttcctt tgccgataac aatgatataa
28621 caaatacaaa cctatctcga ggtagaggac gtaatccaaa accacgagct gcaccaaata
28681 acactgtctc ttggtacact gggcttaccc aacacgggaa agtccctctt acctttccac
28741 ctgggcaggg tgtacctctt aatgccaatt ctacccctgc gcaaaatgct gggtattggc
28801 ggagacagga cagaaaaatt aataccggga atggaattaa gcaactggct cccaggtggt
28861 acttctacta cactggaact ggacccgaag cagcactccc attccgggct gttaaggatg
28921 gcatcgtttg ggtccatgaa gatggcgcca ctgatgctcc ttcaactttt gggacgcgga
28981 accctaacaa tgattcagct attgttacac aattcgcgcc cggtactaag cttcctaaaa
29041 acttccacat tgaggggact ggaggcaata gtcaatcatc ttcaagagcc tctagcttaa
29101 gcagaaactc ttccagatct agttcacaag gttcaagatc aggaaactct acccgcggca
29161 cttctccagg tccatctgga atcggagcag taggaggtga tctactttac cttgatcttc
29221 tgaacagact acaagccctt gagtctggca aagtaaagca atcgcagcca aaagtaatca
29281 ctaagaaaga tgctgctgct gctaaaaata agatgcgcca caagcgcact tccaccaaaa
29341 gtttcaacat ggtgcaagct tttggtcttc gcggaccagg agacctccag ggaaactttg
29401 gtgatcttca attgaataaa ctcggcactg aggacccacg ttggccccaa attgctgagc
29461 ttgctcctac agccagtgct tttatgggta tgtcgcaatt taaacttacc catcagaaca
29521 atgatgatca tggcaaccct gtgtacttcc ttcggtacag tggagccatt aaacttgacc
29581 caaagaatcc caactacaat aagtggttgg agcttcttga gcaaaatatt gatgcctaca
29641 aaaccttccc taagaaggaa aagaaacaaa aggcaccaaa agaagaatca acagaccaaa
29701 tgtctgaacc tccaaaggag cagcgtgtgc aaggtagcat cactcagcgc actcgcaccc
29761 gtccaagtgt tcagcctggt ccaatgattg atgttaacac tgattagtgt cactcaaagt
29821 aacaagatcg cggcaatcgt ttgtgtttgg caaccccatc tcaccatcgc ttgtccactc
29881 ttgcacagaa tggaatcatg ttgtaattac agtgcaataa ggtaattata acccatttaa
29941 ttgatagcta tgctttatta aagtgtgtag ctgtagagag aatgttaaag actgtcacct
30001 ctgcttgatt gcaagtgaac agtgcccccc gggaagagct ctacagtgtg aaatgtaaat
30061 aaaaaatagc tattattcaa ttagattagg ctaattagat gatttgcaaa aaaaaaaaa.
```

The disclosed compositions and methods can be further understood through the following numbered paragraphs.

1. A method of treating a subject for a coronavirus infection comprising administering the subject an effective amount of probenecid, a metabolite or analog thereof, or a pharmaceutically acceptable salt thereof.

2. The method of paragraph 1, wherein the method comprises administering the subject probenecid.

3. The method of paragraphs 1 or 2, wherein the probenecid, metabolite or analog thereof, or pharmaceutically acceptable salt thereof is in a pharmaceutical composition further comprising a pharmaceutically acceptable carrier and/or excipient.

4. The method of any one of paragraphs 1-3, wherein the probenecid, metabolite or analog thereof, or pharmaceutically acceptable salt thereof is administered systemically.

5. The method of any one of paragraphs 1-4, wherein the probenecid, metabolite or analog thereof, or pharmaceutically acceptable salt thereof is administered orally, parenterally, topically or mucosally.

6. The method of any one of paragraphs 1-4, wherein the probenecid, metabolite or analog thereof, or pharmaceutically acceptable salt thereof is administered orally.

7. The method of any one of paragraphs 1-4, wherein the probenecid, metabolite or analog thereof, or pharmaceutically acceptable salt thereof is administered to the lungs (e.g., pulmonary administration).

8. The method of any one of paragraphs 1-4, wherein the probenecid, metabolite or analog thereof, or pharmaceutically acceptable salt thereof is administered intranasally.

9. The method of any one of paragraph 1-8, wherein the probenecid, metabolite or analog thereof, or pharmaceutically acceptable salt thereof is administered in an effective amount to reduce viral replication.

10. The method of any one of paragraph 1-9, wherein the probenecid, metabolite or analog thereof, or pharmaceutically acceptable salt thereof is administered in an effective amount to reduce one or more symptoms of disease, disorder, or illness associated with virus.

11. The method of any one of paragraphs 1-10, wherein the symptoms include fever, congestion in the nasal sinuses and/or lungs, runny or stuffy nose, cough, sneezing, sore throat, body aches, fatigue, shortness of breath, chest tightness, wheezing when exhaling, chills, muscle aches, headache, diarrhea, tiredness, nausea, vomiting, and combinations thereof.

12. The method of any one of paragraphs 1-11, wherein the virus is a Severe acute respiratory syndrome-related coronavirus, a Bat Hp-betacoronavirus Zhejiang2013, a *Rousettus* bat coronavirus GCCDC1, a *Rousettus* bat coronavirus HKU9, a Eidolon bat coronavirus C704, a *Pipistrellus* bat coronavirus HKU5, a *Tylonycteris* bar coronavirus HKU4, a Middle East respiratory syndrome-related coronavirus, a Hedgehog coronavirus, a murine coronavirus, a Human coronavirus HKU1, a China *Rattus* coronavirus HKU24, a Betacoronavirus 1, a *Myodes* coronavirus 2JL14, a Human coronavirus NL63, a Human coronavirus 229E, or a Human coronavirus OC43.

13. The method of paragraph 12, wherein the virus is a Severe acute respiratory syndrome-related coronavirus.

14. The method of paragraph 13, wherein the Severe acute respiratory syndrome-related coronavirus is SARS-CoV-2, SARS-CoV, SARSr-CoV RaTG13, SARS-CoV PC4-227, or SARSr-CoV BtKY72.

15. The method of paragraph 14, wherein the Severe acute respiratory syndrome-related coronavirus is SARS-CoV-2.

16. The method of paragraph 15, wherein the SARS-CoV-2 comprises a genome encoded by a nucleic acid sequence comprising at least 85%, 86%, 87%, 88%, 89%, 90%, 91%, 92%, 93%, 94%, 95%, 96%, 97%, 98%, 99%, or 100% sequence identity SEQ ID NO:1 or 2.

17. The method of paragraph 14, wherein the Severe acute respiratory syndrome-related coronavirus is SARS-CoV.

18. The method of paragraph 17, wherein the SAR-CoV comprises a genome encoded by a nucleic acid sequence comprising at least 85%, 86%, 87%, 88%, 89%, 90%, 91%, 92%, 93%, 94%, 95%, 96%, 97%, 98%, 99%, or 100% sequence identity SEQ ID NO:3.

19. The method of paragraph 12, wherein the virus is a Middle East respiratory syndrome-related coronavirus.

20. The method of paragraph 19, wherein the Middle East respiratory syndrome-related coronavirus is MERS-CoV.

21. The method of 20, wherein the MERS-CoV comprises a genome encoded by a nucleic acid sequence comprising at least 85%, 86%, 87%, 88%, 89%, 90%, 91%, 92%, 93%, 94%, 95%, 96%, 97%, 98%, 99%, or 100% sequence identity SEQ ID NO:4.

22. The method of any one of paragraphs 1-21, wherein the subject has been exposed to the coronavirus.

23. The method of paragraph 22, wherein the subject is presently suffering from an infection of the coronavirus.

24. The method of paragraph 23, wherein the subject has COVID-19.

25. The method of any one of paragraphs 1-20, wherein the subject has been exposed to the coronavirus, but is asymptomatic.

26. A method of treating a subject for SAR-CoV-2 infection comprising administering the subject an effective amount of probenecid or a pharmaceutically acceptable salt thereof.

27. The method of paragraph 26, wherein the subject has COVID-19.

28. A prophylactic method comprising administering to a subject that has not be exposed to a coronavirus, an effective amount of probenecid, metabolite or analog thereof, or a pharmaceutically acceptable salt thereof, to reduce viral infection in the subject upon exposure to the virus relative to viral infection in the absence of treatment.

29. The method of paragraph 28, wherein the coronavirus is SAR-CoV-2.

30. The method of any one of paragraphs 1-29, wherein the subject is administered 10 mg-1,000 mg or 50 mg-500 mg of probenecid, a metabolite or analog thereof, or a pharmaceutically acceptable salt thereof 1 to 5 times per day until symptoms are reduced, the infection clears, or a combination thereof.

31. The method of any one of paragraphs 1-30, wherein the subject is treated by pulse dosing.

32. The method of paragraph 31, wherein the pulse dosing comprises a 1-5 bolus doses of 1,000 mg to 5,000 mg probenecid, a metabolite or analog thereof, or a pharmaceutically acceptable salt thereof.

33. The method of paragraph 32, wherein the bolus dose(s) is followed by a drug holiday until the serum levels of the probenecid, metabolite or analog thereof, or a pharmaceutically acceptable salt thereof are about 0.

34. The method of any one of paragraphs 31-33, wherein the probenecid, metabolite or analog thereof, or a pharmaceutically acceptable salt thereof is administered orally or by infusion.

35. A pharmaceutical composition comprising an effective amount of probenecid, metabolite or analog thereof, or a pharmaceutically acceptable salt thereof for use in the method of any one of paragraphs 1-34.

EXAMPLE

Example 1: Probenecid Reduces SARS-CoV-2 Plaque Formation In Vitro

Materials and Methods

Plaque Reduction Assay

Prophylactic Treatment

Vero E6 cells were plated in a 12 well plates at $5\times10^5$ cells/well and incubated overnight.

Cells were washed 1× with PBS and probenecid at 0.1 μM, 1 μM, 2.5 μM, or 5 μM was added to the wells in culture media and incubated for 24 hours (FIG. 1). All wells were normalized to 0.05% DMSO. Each concentration was completed in duplicate.

Following pre-treatment, media was discarded and cells were replenished with media containing probenecid (as above) and SARS-CoV-2 (stock grown from Isolate USA-WA1/2020, BEI Resources Catalogue Ref. Number NR-52281). The complete genome of SARS-CoV-2, USA-WA1/2020 has been sequenced (the isolate—GenBank Accession Number: MN985325 and after one passage in Vero cells—GenBank Accession Number: MT020880 and after four passages in Vero cells—GenBank Accession Number: MT246667).

Cells were infected at a MOI of 0.01 for 4 days. Post-infection cells were fixed and stained to visualize plaques. Plaques were quantified manually (FIG. 1).

Figure 2:
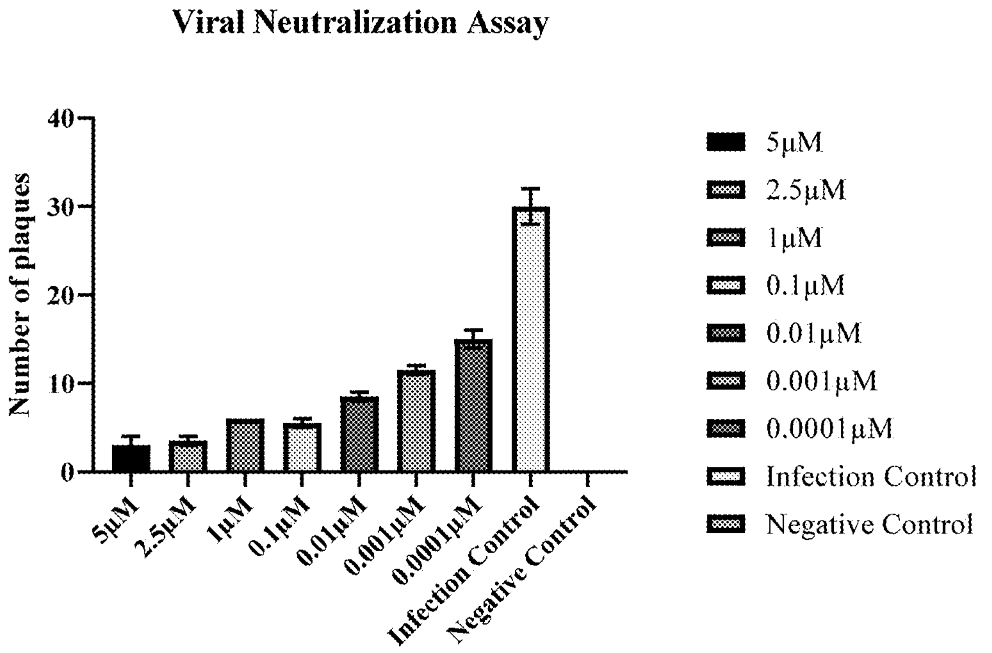
FIG. 2 is a bar graph showing (left-to-right) the effect of probenecid pre-treatment (5 μM, 2.5 μM, 1 μM, 0.1 μM, 0.01 μM, 0.001 μM, or 0.0001 μM) compared to controls (DMSO (infected), DMSO (only)) on viral replication using a plaque reduction assay.

In another experiment, probenecid at 0.0001 μM, 0.001 μM, 0.01 μM, 0.1 μM, 1 μM, 2.5 μM, or 5 μM (FIG. 2) was added. Vero E6 cells were plated in a 6 well plate at 8E5 cells/well and incubated overnight. Cells were washed once with PBS and the compound was added to the wells in culture media and incubated for 24 hours. All wells were normalized to 0.05% DMSO. Each concentration was completed in duplicate. Following pre-treatment, media was discarded and cells were replenished with media containing drug (as above) and SARS-CoV-2. Cells were infected at a MOI of 0.01 for 4 days. Post-infection the cells were fixed and stained to visualize plaques. Plaques were quantified (FIG. 2).

Therapeutic Treatment

Figure 3:
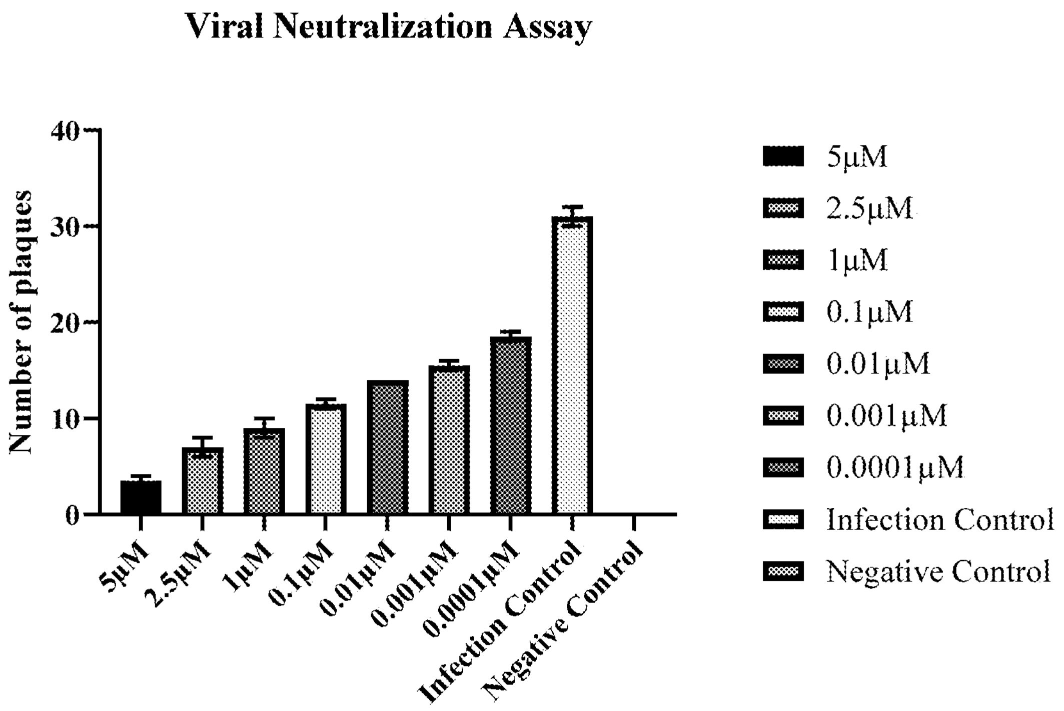
FIG. 3 is a bar graph showing (left-to-right) the effect of probenecid post-treatment (5 μM, 2.5 μM, 1 μM, 0.1 μM, 0.01 μM, 0.001 μM, or 0.0001 μM) compared to controls (DMSO (infected), DMSO (only)) on viral replication using a plaque reduction assay.

Vero E6 cells were plated in a 6 well plate at 8E5 cells/well and incubated overnight. Cells were washed once with PBS and infected with virus at a MOI of 0.01 for 1 hour. Following 1 hour infection probenecid at 0.0001 μM, 0.001 μM, 0.01 μM, 0.1 μM, 1 μM, 2.5 μM, or 5 μM was added to the wells in overlay media and incubated 4 days. Post-infection the cells were fixed and stained to visualize plaques. Plaques were quantified (FIG. 3).

Results

The effect of probenecid on viral replication was investigated using an in vitro plaque formation assay.

Probenecid pre-treatment resulted in a dose dependent reduction in plaque formation for concentrations tested (5 μM-0.1 μM) in two independent experiments. 5 μM-0.1 μM reduced plaque formation from ~89% to 72% (FIG. 1), respectively, compared to DMSO treated infected control.

In another experiment, probenecid pre-treatment resulted in a dose dependent reduction in plaque formation for concentrations tested (5 μM-0.0001 μM) in two independent experiments. 5 μM-0.0001 μM reduced plaque formation from ~93% to 50%, respectively, (FIG. 2), compared to DMSO treated infected control.

In another experiment, probenecid post-treatment resulted in a dose dependent reduction in plaque formation for concentrations tested (5 μM-0.0001 μM). 5 μM-0.0001 μM reduced plaque ~90% to 40% (FIG. 3), respectively, compared to DMSO treated infected control.

These results show that probenecid significantly reduces viral titer/plaque formation with 24 hour pretreatment at the concentrations tested. These results also show that probenecid significantly reduces viral titer/plaque formation with post-treatment at the concentrations tested.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

We claim:

1. A method of treating a subject for a Severe acute respiratory syndrome coronavirus 2 (SARS-CoV-2) infection comprising administering to a subject in need thereof an effective amount of probenecid or a pharmaceutically acceptable salt thereof.

2. The method of claim 1, wherein the probenecid or pharmaceutically acceptable salt thereof is in a pharmaceutical composition further comprising a pharmaceutically acceptable carrier and/or excipient.

3. The method of claim 1, wherein the probenecid or pharmaceutically acceptable salt thereof is administered systemically.

4. The method of claim 1, wherein the probenecid or pharmaceutically acceptable salt thereof is administered orally, parenterally, topically, or mucosally.

5. The method of claim 4, wherein the probenecid or pharmaceutically acceptable salt thereof is administered mucosally to the lungs, nasal mucosa, or combination thereof.

6. The method of claim 1, wherein the probenecid or pharmaceutically acceptable salt thereof is administered in an effective amount to reduce viral replication.

7. The method of claim 1, wherein the probenecid or pharmaceutically acceptable salt thereof is administered in an effective amount to reduce one or more symptoms of a disease, disorder, or illness associated with the SARS-CoV-2.

8. The method of claim 7, wherein the symptoms include fever, congestion in the nasal sinuses and/or lungs, runny or stuffy nose, cough, sneezing, sore throat, body aches, fatigue, shortness of breath, chest tightness, wheezing when exhaling, chills, muscle aches, headache, diarrhea, tiredness, nausea, vomiting, and combinations thereof.

9. The method of claim 1, wherein the SARS-CoV-2 comprises a genome encoded by a nucleic acid sequence comprising at least 85%, 86%, 87%, 88%, 89%, 90%, 91%, 92%, 93%, 94%, 95%, 96%, 97%, 98%, 99%, or 100% sequence identity SEQ ID NO:1 or 2.

10. The method of claim 1, wherein the subject has COVID-19.

11. The method of claim 1, wherein the subject has been exposed to the SARS-CoV-2, but is asymptomatic.

12. The method of claim 1, wherein the subject is administered 10 mg-1,000 mg or 50 mg-500 mg of probenecid or a pharmaceutically acceptable salt thereof.

13. The method of claim 1, wherein the subject is treated by pulse dosing.

14. The method of claim 13, wherein the pulse dosing comprises a 1-5 bolus doses of 1,000 mg to 5,000 mg probenecid or a pharmaceutically acceptable salt thereof.

15. The method of claim 14, wherein the bolus dose(s) is followed by a drug holiday.

16. The method of claim 13, wherein the probenecid or pharmaceutically acceptable salt thereof is administered orally or by infusion.

17. A method of reducing replication of Severe acute respiratory syndrome coronavirus 2 (SARS-CoV-2) in a subject infected with SARS-CoV-2 comprising administering the subject an effective amount of probenecid or a pharmaceutically acceptable salt thereof.

18. The method of claim 17, wherein the subject is administered 10 mg-1,000 mg or 50 mg-500 mg of probenecid or a pharmaceutically acceptable salt thereof.

19. The method of claim 1, wherein the subject is a human.

20. The method of claim 1, wherein the probenecid or pharmaceutically acceptable salt thereof is administered in a dose of 250 mg to 1,000 mg once or twice a day.

21. The method of claim 20, wherein the probenecid or pharmaceutically acceptable salt thereof is administered in a dose of 500 mg twice a day.

22. The method of claim 21, wherein the probenecid or pharmaceutically acceptable salt thereof is administered to the subject for two weeks.

23. The method of claim 1, wherein the probenecid or pharmaceutically acceptable salt thereof is administered orally.

24. The method of claim 1, wherein the subject is a human and the probenecid or pharmaceutically acceptable salt thereof is administered orally in a dose of 250 mg to 1,000 mg once or twice a day.

25. The method of claim 1, wherein the probenecid or pharmaceutically acceptable salt thereof reduces viral titer in the subject relative to untreated control subjects.

* * * * *